United States Patent
Hong

(10) Patent No.: US 11,450,814 B2
(45) Date of Patent: Sep. 20, 2022

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventor: Jin-Ri Hong, Gyeonggi-do (KR)

(73) Assignee: Rohm and Haas Electronic Materials Korea Ltd.

( * ) Notice: Subject to any disclaimer, the term of this patent is extended or adjusted under 35 U.S.C. 154(b) by 387 days.

(21) Appl. No.: 16/640,425

(22) PCT Filed: Sep. 20, 2018

(86) PCT No.: PCT/KR2018/011129
§ 371 (c)(1),
(2) Date: Feb. 20, 2020

(87) PCT Pub. No.: WO2019/059672
PCT Pub. Date: Mar. 28, 2019

(65) Prior Publication Data
US 2020/0212311 A1    Jul. 2, 2020

(30) Foreign Application Priority Data

Sep. 25, 2017  (KR) .................. 10-2017-0123714
Aug. 30, 2018  (KR) .................. 10-2018-0102966

(51) Int. Cl.
| | | |
|---|---|---|
| H01L 51/00 | (2006.01) |
| C07D 209/88 | (2006.01) |
| C09K 11/06 | (2006.01) |
| H01L 51/50 | (2006.01) |

(52) U.S. Cl.
CPC ........ H01L 51/0072 (2013.01); C07D 209/88 (2013.01); C09K 11/06 (2013.01); H01L 51/0059 (2013.01); H01L 51/0067 (2013.01); H01L 51/0073 (2013.01); H01L 51/0074 (2013.01); C09K 2211/1022 (2013.01); H01L 51/5056 (2013.01)

(58) Field of Classification Search
CPC ............ H01L 51/0072; H01L 51/0067; H01L 51/0059; C09K 11/06; C07D 209/88
See application file for complete search history.

(56) References Cited

U.S. PATENT DOCUMENTS

| | | | |
|---|---|---|---|
| 8,993,128 B2 * | 3/2015 | Lee ...................... | C07D 221/18 |
| | | | 544/333 |
| 10,109,801 B2 | 10/2018 | Lee et al. | |
| 2018/0351113 A1 * | 12/2018 | Ahn ..................... | H01L 51/0067 |
| 2019/0259947 A1 * | 8/2019 | Lee ..................... | H01L 51/0058 |
| 2019/0273209 A1 * | 9/2019 | Lee ..................... | H01L 51/5088 |
| 2019/0288222 A1 * | 9/2019 | Moon .................... | H01L 51/50 |
| 2020/0119275 A1 * | 4/2020 | Oh ....................... | H01L 51/0067 |
| 2020/0152885 A1 * | 5/2020 | Kim ..................... | C07D 401/10 |
| 2020/0172558 A1 * | 6/2020 | Joo ..................... | H01L 51/0072 |
| 2020/0203629 A1 * | 6/2020 | Jung .................... | H01L 51/0072 |

FOREIGN PATENT DOCUMENTS

| | | |
|---|---|---|
| JP | 2010-254635 A | 11/2010 |
| WO | 2014021569 A1 | 2/2014 |
| WO | 2014021572 A1 | 2/2014 |

OTHER PUBLICATIONS

Moriwaki, K., "Photochemical Reaction of 1,3,5-Tris(diphenylamino)benzene", J. Photopolym. Sci. Technol., vol. 12, No. 5, 1999, pp. 777-780.

Yoshikawa, S., "Photocyclization Reaction of 1,3,5-Tris(diphenylamino)benzene", J. Photopolym. Sci. Technol., vol. 7, No. 1, 1994, pp. 83-84.

* cited by examiner

*Primary Examiner* — Douglas M Menz
(74) *Attorney, Agent, or Firm* — G. Creston Campbell

(57) ABSTRACT

The present disclosure relates to an organic electroluminescent compound represented by formula 1 and an organic electroluminescent device comprising the same. By comprising the organic electroluminescent compound of the present disclosure, an organic electroluminescent device having improved driving voltage, luminous efficiency, and/or lifespan characteristics can be provided.

10 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

An electroluminescent device (EL device) is a self-light-emitting device which has advantages in that it provides a wider viewing angle, a greater contrast ratio, and a faster response time. The first organic EL device was developed by Eastman Kodak in 1987, by using small aromatic diamine molecules, and aluminum complexes as materials for forming a light-emitting layer [Appl. Phys. Lett. 51, 913, 1987].

In order to enhance the efficiency and stability of an organic EL device, it has a structure of a multilayer comprising a hole injection layer, a hole transport layer, a light-emitting layer, an electron transport layer, and an electron injection layer. The selection of a compound comprised in the hole transport layer is known as one of the methods for improving the characteristics of a device such as hole transport efficiency to the light-emitting layer, luminous efficiency, lifespan, etc.

In this regard, copper phthalocyanine (CuPc), 4,4'-bis[N-(1-naphthyl)-N-phenylamino]biphenyl (NPB), N,N'-diphenyl-N,N'-bis(3-methylphenyl)-(1,1't-biphenyl)-4,4'-diamine (TPD), 4,4',4"-tris(3-methylphenylphenylamino)triphenylamine (MTDATA), etc., were used as a hole injection and transport material in an organic EL device. However, an organic EL device using these materials is problematic in quantum efficiency and lifespan. It is because, when an organic EL device is driven under high current, thermal stress occurs between an anode and the hole injection layer. Thermal stress significantly reduces the lifespan of the device. Further, since the organic material used in the hole injection layer has very high hole mobility, the hole-electron charge balance may be broken and quantum yield (cd/A) may decrease.

Therefore, a hole transport layer for improving performance of an organic EL device still needs to be developed.

Korean Patent No. 10-1512059 discloses a carbazole derivative substituted with an arylamino. However, this compound is not sufficiently satisfactory to be used in the hole transport zone.

DISCLOSURE OF THE INVENTION

Problems to be Solved

The objective of the present disclosure is to provide an organic electroluminescent device having improved driving voltage, luminous efficiency, and/or lifespan characteristics.

Solution to Problems

The present inventors found that an exciton recombination in the light-emitting layer can increase by controlling the hole mobility and the charge balance of holes and electrons when a (hetero)arylamino substituent is bonded at a specific position in an organic electroluminescent compound having a carbazole structure. More specifically, the above objective can be achieved by an organic electroluminescent compound represented by the following formula 1 in which the (hetero)arylamino substituent is bonded at 2- and 4-positions:

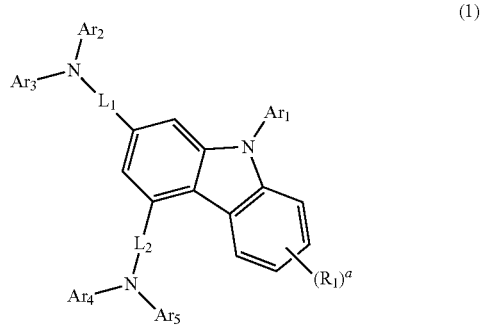

(1)

wherein $Ar_1$ to $Ar_5$ each independently represent hydrogen, deuterium, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or $Ar_2$ and $Ar_3$, and $Ar_4$ and $Ar_5$ may independently be linked to form a ring;

$L_1$ and $L_2$ each independently represent a single bond, a substituted or unsubstituted (C6-C30)arylene, or a substituted or unsubstituted (3- to 30-membered) heteroarylene;

$R_1$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl (C6-C30)arylsilyl, a substituted or unsubstituted (C1-C30) alkyldi(C6-C30)arylsilyl, a substituted or unsubstituted tri (C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to each other to form a ring; and a represents an integer of 1 to 4, where a is 2 or more, each of $R_1$ may be the same or different.

Effects of the Invention

By using the organic electroluminescent compound of the present disclosure, an organic electroluminescent device having improved driving voltage, luminous efficiency, and/or lifespan characteristics can be provided.

EMBODIMENTS OF THE INVENTION

Hereinafter, the present disclosure will be described in detail. However, the following description is intended to explain the disclosure, and is not meant in any way to restrict the scope of the disclosure.

The present disclosure relates to an organic electroluminescent compound of formula 1, an organic electroluminescent material comprising the compound, and an organic electroluminescent device comprising the material.

The term "organic electroluminescent compound" in the present disclosure means a compound that may be used in an organic electroluminescent device, and may be comprised in any layer constituting an organic electroluminescent device, as necessary.

The term "organic electroluminescent material" in the present disclosure means a material that may be used in an organic electroluminescent device, and may comprise at least one compound. The organic electroluminescent material may be comprised in any layer constituting an organic electroluminescent device, as necessary. For example, the organic electroluminescent material may be a hole injection material, a hole transport material, a hole auxiliary material, a light-emitting auxiliary material, an electron blocking material, a light-emitting material, an electron buffer material, a hole blocking material, an electron transport material, or an electron injection material.

The organic electroluminescent material of the present disclosure may comprise at least one compound represented by formula 1. The compound represented by formula 1 may be comprised in at least one layer constituting an organic electroluminescent device, and may be comprised in at least one layer constituting a hole transport zone, but is not limited thereto. When the compound of formula 1 is comprised in a hole transport layer, a hole auxiliary layer, or a light-emitting auxiliary layer, it may be comprised as a hole transport material, a hole auxiliary material, or a light-emitting auxiliary material.

Herein, "(C1-C30)alkyl" is meant to be a linear or branched alkyl having 1 to 30 carbon atoms constituting the chain, in which the number of carbon atoms is preferably 1 to 10, more preferably 1 to 6, and includes methyl, ethyl, n-propyl, isopropyl, n-butyl, isobutyl, tert-butyl, etc. "(C2-C30)alkenyl" is meant to be a linear or branched alkenyl having 2 to 30 carbon atoms constituting the chain, in which the number of carbon atoms is preferably 2 to 20, more preferably 2 to 10, and includes vinyl, 1-propenyl, 2-propenyl, 1-butenyl, 2-butenyl, 3-butenyl, 2-methylbut-2-enyl, etc. "(C2-C30)alkynyl" is a linear or branched alkynyl having 2 to 30 carbon atoms constituting the chain, in which the number of carbon atoms is preferably 2 to 20, more preferably 2 to 10, and includes ethynyl, 1-propynyl, 2-propynyl, 1-butynyl, 2-butynyl, 3-butynyl, 1-methylpent-2-ynyl, etc. "(C3-C30)cycloalkyl" is a mono- or polycyclic hydrocarbon having 3 to 30 ring backbone atoms, in which the number of carbon atoms is preferably 3 to 20, more preferably 3 to 7, and includes cyclopropyl, cyclobutyl, cyclopentyl, cyclohexyl, etc. "(3- to 7-membered)heterocycloalkyl" is a cycloalkyl having at least one heteroatom selected from the group consisting of B, N, O, S, Si, and P, preferably O, S, and N, and 3 to 7 ring backbone atoms, and includes tetrahydrofuran, pyrrolidine, thiolan, tetrahydropyran, etc. "(C6-C30)aryl(ene)" is a monocyclic or fused ring radical derived from an aromatic hydrocarbon having 6 to 30 ring backbone carbon atoms, in which the number of ring backbone carbon atoms is preferably 6 to 20, more preferably 6 to 15, includes an aryl having a spiro structure, and includes phenyl, biphenyl, terphenyl, naphthyl, binaphthyl, phenylnaphthyl, naphthylphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, etc. "(3- to 30-membered)heteroaryl(ene)" is an aryl group having at least one, preferably 1 to 4 heteroatoms selected from the group consisting of B, N, O, S, Si, and P, and 3 to 30 ring backbone atoms, in which the number of ring backbone atoms is preferably 5 to 20, more preferably 5 to 15; is a monocyclic ring, or a fused ring condensed with at least one benzene ring; may be partially saturated; may be one formed by linking at least one heteroaryl or aryl group to a heteroaryl group via a single bond(s); and includes a monocyclic ring-type heteroaryl including furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, pyridazinyl, etc., and a fused ring-type heteroaryl including benzofuranyl, benzothiophenyl, isobenzofuranyl, dibenzofuranyl, dibenzothiophenyl, benzonaphthothiophenyl, benzimidazolyl, benzothiazolyl, benzoisothiazolyl, benzoisoxazolyl, benzoxazolyl, isoindolyl, indolyl, indazolyl, benzothiadiazolyl, quinolyl, isoquinolyl, cinnolinyl, quinazolinyl, quinoxalinyl, carbazolyl, phenoxazinyl, phenanthridinyl, benzodioxolyl, etc. "Halogen" includes F, Cl, Br, and I.

Herein, "substituted" in the expression "substituted or unsubstituted" means that a hydrogen atom in a certain functional group is replaced with another atom or functional group, i.e., a substituent. The substituents of the substituted alkyl, the substituted aryl(ene), the substituted heteroaryl (ene), the substituted cycloalkyl, the substituted alkoxy, the substituted trialkylsilyl, the substituted dialkylarylsilyl, the substituted alkyldiarylsilyl, the substituted triarylsilyl, the substituted mono- or di- alkylamino, the substituted mono- or di-arylamino, and the substituted alkylarylamino in $Ar_1$ to $Ar_5$, $L_1$, $L_2$, and $R_1$ in formula 1 each independently are at least one selected from the group consisting of deuterium, a halogen, a cyano, a carboxyl, a nitro, a hydroxyl, a (C1-C30)alkyl, a halo(C1-C30)alkyl, a (C2-C30) alkenyl, a (C2-C30) alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (3- to 30-membered)heteroaryl unsubstituted or substituted with a (C6-C30)aryl, a (C6-C30)aryl unsubstituted or substituted with a (3- to 30-membered) heteroaryl, a tri(C1-C30)alkylsilyl, a tri(C6-C30)arylsilyl, a di(C1-C30)alkyl(C6-C30)arylsilyl, a (C1-C30)alkyldi(C6-C30)arylsilyl, an amino, a mono- or di-(C1-C30)alkylamino, a mono- or di-(C6-C30)arylamino, a (C1-C30)alkyl(C6-C30)arylamino, a (C1-C30)alkylcarbonyl, a (C1-C30) alkoxycarbonyl, a (C6-C30)arylcarbonyl, a di(C6-C30)arylboronyl, a di(C1-C30)alkylboronyl, a (C1-C30)alkyl(C6-C30)arylboronyl, a (C6-C30)aryl(C1-C30)alkyl, and a (C1-C30)alkyl(C6-C30)aryl; and preferably each independently are a (C1-C6)alkyl and/or a (C6-C20)aryl. Specifically, the substituent may be methyl, phenyl, naphthyl, and/or biphenyl.

Formula 1 may be represented by the following formula 2 or 3:

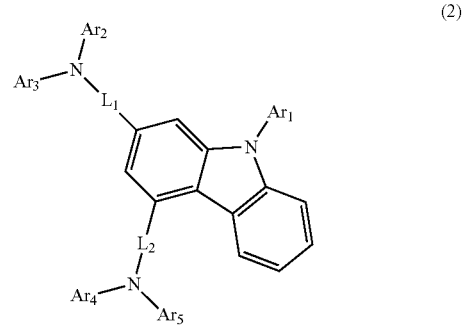

(2)

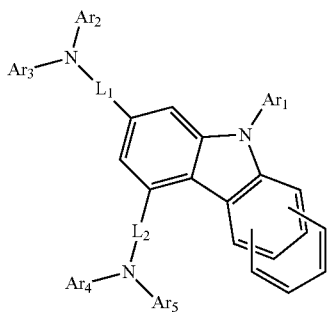

(3)

wherein Ar₁ to Ar₅, L₁, and L₂ are as defined in formula 1.

In formula 1 above, Ar₁ to Ar₅ each independently represent hydrogen, deuterium, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or Ar₂ and Ar₃, and Ar₄ and Ar₅ may independently be linked to form a ring. According to one embodiment of the present disclosure, Ar₁ to Ar₅ each independently represent a substituted or unsubstituted (C6-C30)aryl, or a substituted or unsubstituted (5- to 20-membered)heteroaryl, or Ar₂ and Ar₃, and Ar₄ and Ar₅ may independently be linked to form a ring. According to another embodiment of the present disclosure, Ar₁ to Ar₅ each independently represent a (C6-C30)aryl unsubstituted or substituted with a (C1-C6)alkyl(s) and/or a (C6-C12)aryl(s), or a (5- to 20-membered)heteroaryl unsubstituted or substituted with a (C6-C12)aryl(s), or Ar₂ and Ar₃, and Ar₄ and Ar₅ may independently be linked to form a ring. Specifically, Ar₁ may represent a phenyl, a naphthyl, a biphenyl, a phenanthrenyl, a terphenyl, a naphthylbiphenyl, a dimethylfluorenyl, a dimethylbenzofluorenyl, a dimethylfluorenyl substituted with a biphenyl, a diphenylfluorenyl, a diphenylbenzofluorenyl, a spirobifluorenyl, a pyridinyl, a phenylpyrimidinyl, a dibenzofuranyl, a benzonaphthofuranyl, a dibenzothiophenyl, a benzonaphthothiophenyl, a phenylcarbazolyl, a naphthylcarbazolyl, or a phenylbenzocarbazolyl, and Ar₂ to Ar₅ may each independently represent a phenyl, a naphthyl, a biphenyl, a terphenyl, a naphthylphenyl, a dimethylfluorenyl, a dimethylbenzofluorenyl, a diphenylfluorenyl, a diphenylbenzofluorenyl, a spirobifluorenyl, a dibenzofuranyl, a benzonaphthofuranyl, a dibenzothiophenyl, a benzonaphthothiophenyl, a phenylcarbazolyl, or a phenylbenzocarbazolyl, or Ar₂ and Ar₃, and Ar₄ and Ar₅ may independently be linked to form a carbazole ring with the nitrogen atom. Herein, "Ar₂ and Ar₃, and Ar₄ and Ar₅ may independently be linked to form a ring" means that among Ar₂ and Ar₃, and Ar₄ and Ar₅, only Ar₂ and Ar₃ may be linked to each other to form a ring, only Ar₄ and Ar₅ may be linked to each other to form a ring, or Ar₂ and Ar₃ are linked to each other and Ar₄ and Ar₅ are linked to each other to form two rings.

L₁ and L₂ each independently represent a single bond, a substituted or unsubstituted (C6-C30)arylene, or a substituted or unsubstituted (3- to 30-membered)heteroarylene. According to one embodiment of the present disclosure, L₁ and L₂ each independently represent a single bond, or a substituted or unsubstituted (C6-C12)arylene. According to another embodiment of the present disclosure, L₁ and L₂ each independently represent a single bond, or an unsubstituted (C6-C12)arylene. Specifically, L₁ and L₂ may each independently represent a single bond, a phenylene, or a naphthylene.

R₁ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino; or may be linked to each other to form a ring. According to one embodiment of the present disclosure, R₁ represents hydrogen, a substituted or unsubstituted (C6-C20)aryl, or a substituted or unsubstituted (5- to 15-membered)heteroaryl, or may be linked to each other to form a ring. According to another embodiment of the present disclosure, R₁ represents hydrogen, an unsubstituted (C6-C20)aryl, or an unsubstituted (5- to 15-membered)heteroaryl, or may be linked to each other to form a ring. Specifically, R₁ may represent hydrogen, a phenyl, a naphthyl, a phenanthrenyl, a pyridinyl, or two R₁'s may be linked to each other to form a benzene ring.

a represents an integer of 1 to 4, where a is 2 or more, each of R₁ may be the same or different. According to one embodiment of the present disclosure, a represents 1 or 2.

According to one embodiment of the present disclosure, in formula 1 above, Ar₁ to Ar₅ each independently represent a substituted or unsubstituted (C6-C30)aryl, or a substituted or unsubstituted (5- to 20-membered)heteroaryl, or Ar₂ and Ar₃, and Ar₄ and Ar₅ may independently be linked to each other to form a ring; L₁ and L₂ each independently represent a single bond, or a substituted or unsubstituted (C6-C12)arylene; R₁ represents hydrogen, a substituted or unsubstituted (C6-C20)aryl, or a substituted or unsubstituted (5- to 15-membered)heteroaryl, or may be linked to each other to form a ring; and a represents 1 or 2.

According to another embodiment of the present disclosure, in formula 1 above, Ar₁ to Ar₅ each independently represent a (C6-C30)aryl unsubstituted or substituted with a (C1-C6)alkyl(s) and/or a (C6-C12)aryl(s), or a (5- to 20-membered)heteroaryl unsubstituted or substituted with a (C6-C12)aryl(s), or Ar₂ and Ar₃, and Ar₄ and Ar₅ may independently be linked to each other to form a ring; L₁ and L₂ each independently represent a single bond, or an unsubstituted (C6-C12)arylene; R₁ represents hydrogen, an unsubstituted (C6-C20)aryl, or an unsubstituted (5- to 15-membered)heteroaryl, or two R₁'s may be linked to each other to form a ring; and a represents 1 or 2.

In the formulas of the present disclosure, when adjacent substituents are linked to each other to form a ring, the ring may be a substituted or unsubstituted (3- to 30-membered) mono- or polycyclic, alicyclic or aromatic ring, or the combination thereof, in which the ring may contain at least one heteroatom selected from nitrogen, oxygen, and sulfur.

In the formulas of the present disclosure, the heteroaryl(ene) may each independently contain at least one heteroatom selected from B, N, O, S, Si, and P. In addition, the heteroatom may be substituted with at least one substituent selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

The organic electroluminescent compound represented by formula 1 includes the following compounds, but is not limited thereto:

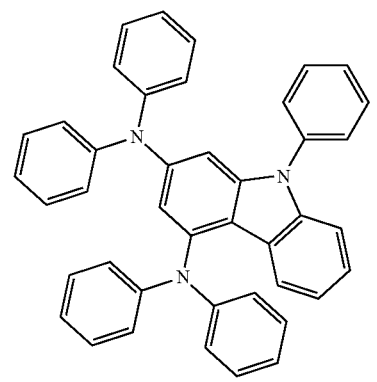

C-1

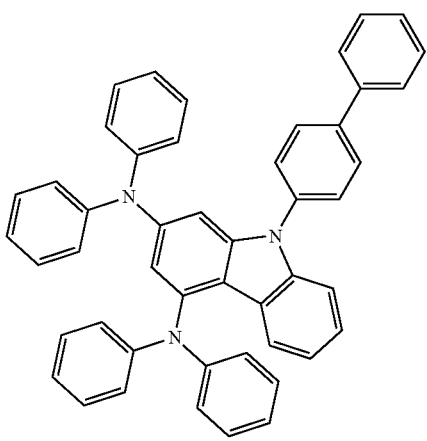

C-2

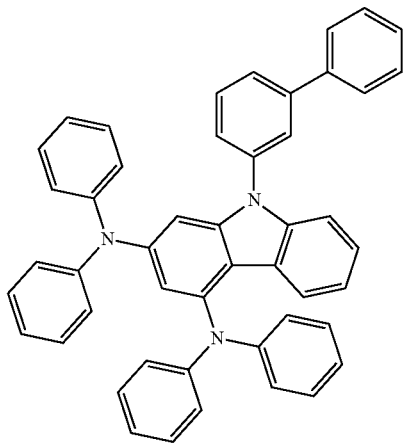

C-3

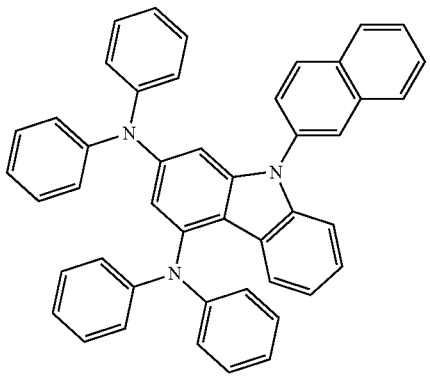

C-4

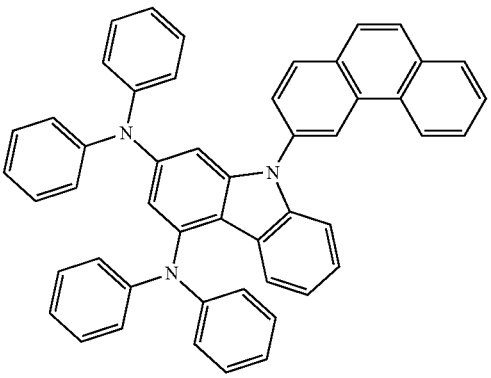

C-5

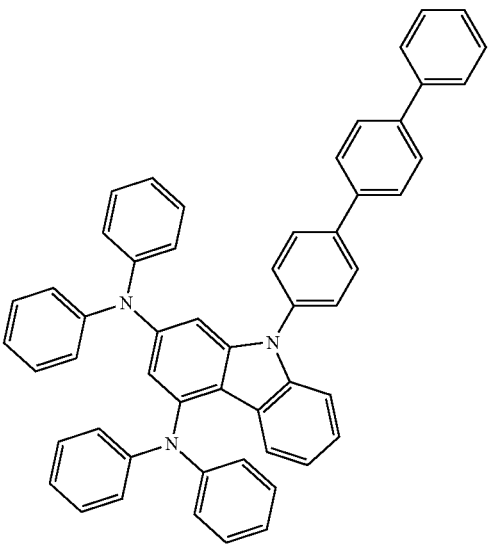

C-6

C-7
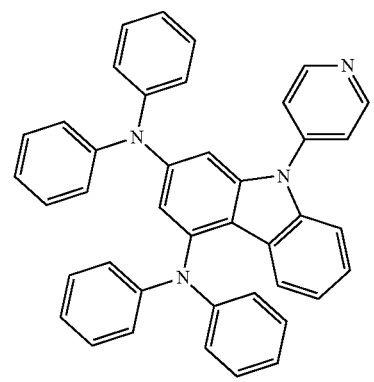
C-8
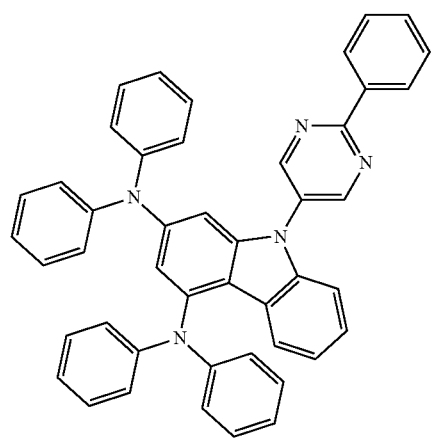
C-10
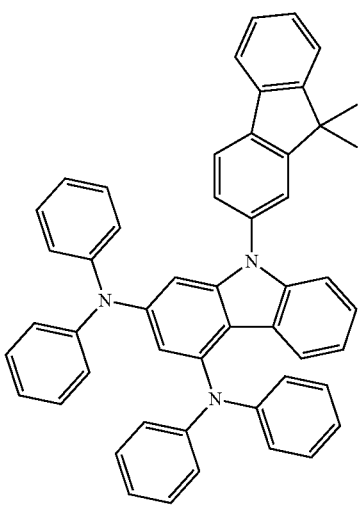
C-11
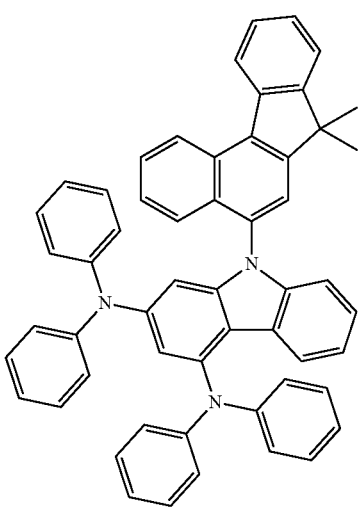
C-9
C-12
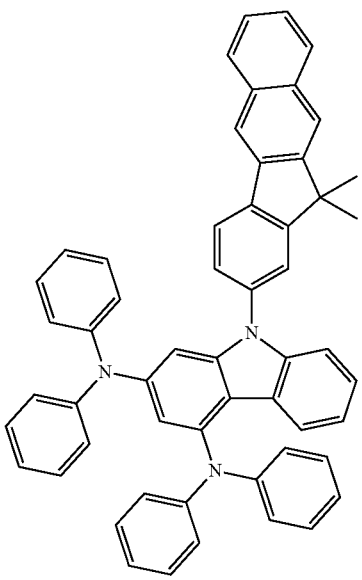

C-13
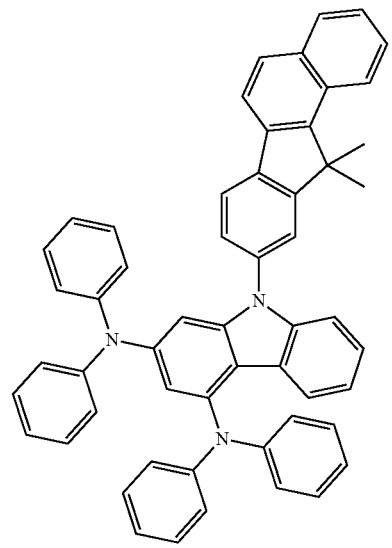
C-14
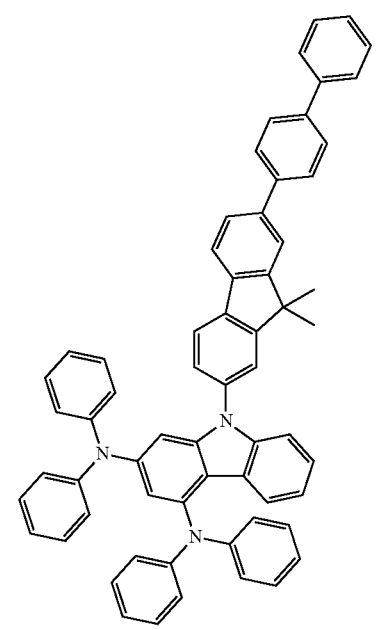
C-15
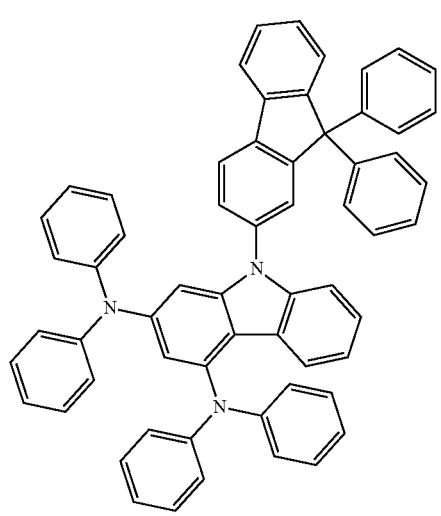
C-16
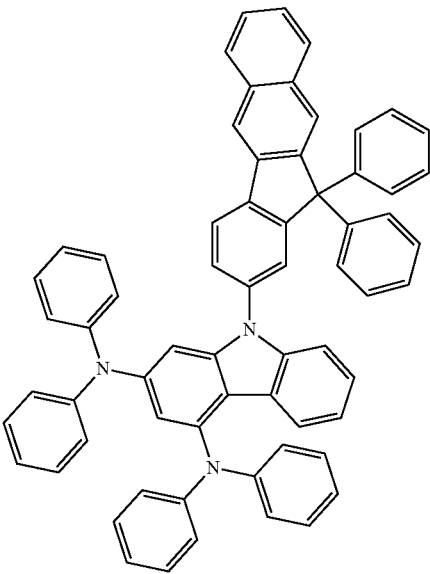
C-17
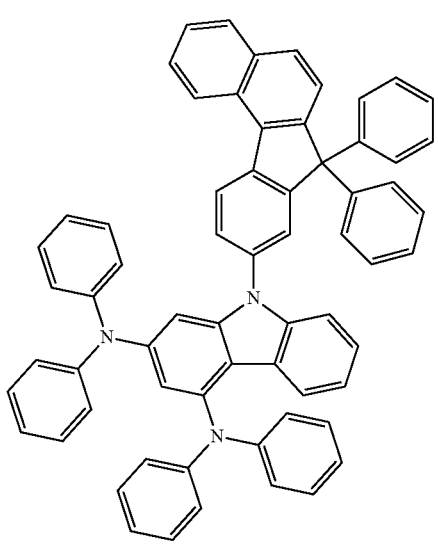
C-18
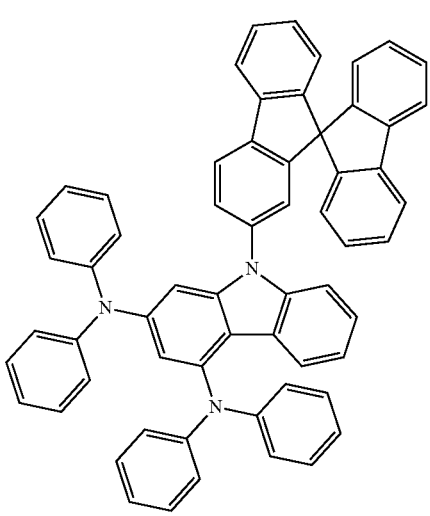

C-19
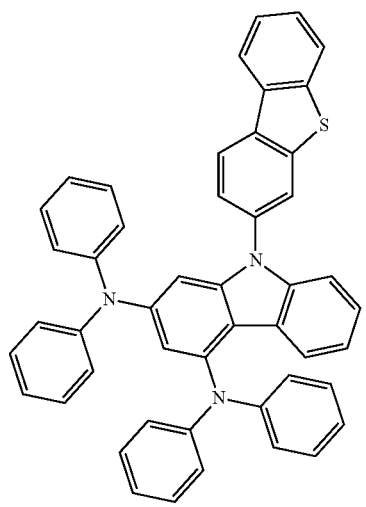
C-22
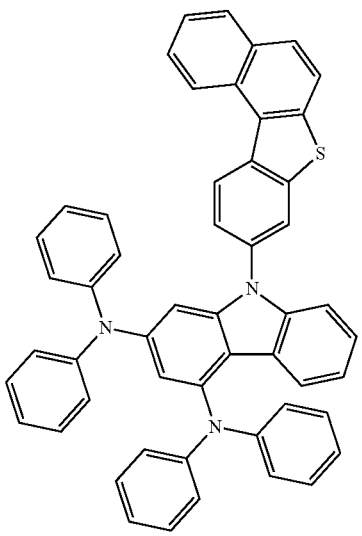
C-20
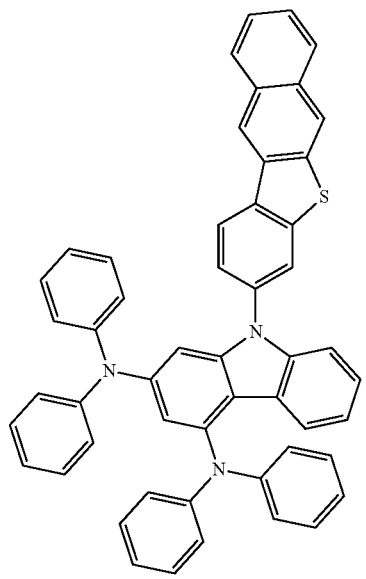
C-23
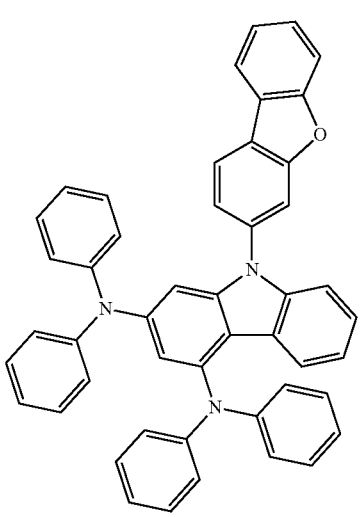
C-21
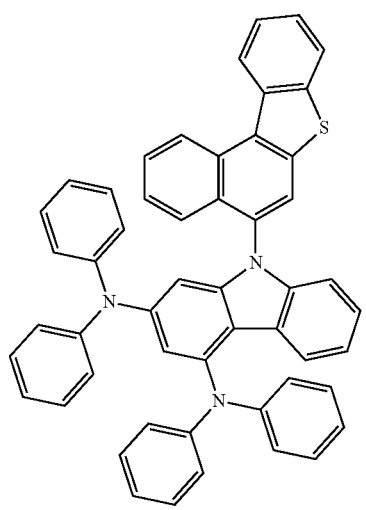
C-24
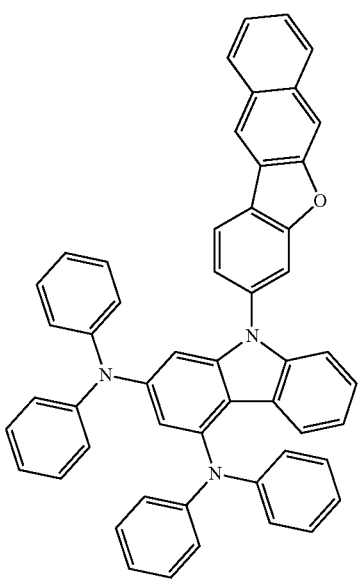

C-25
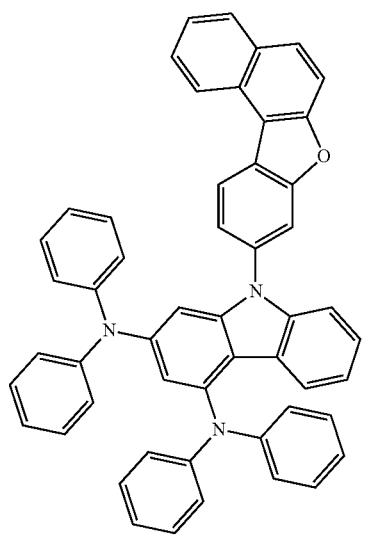
C-28
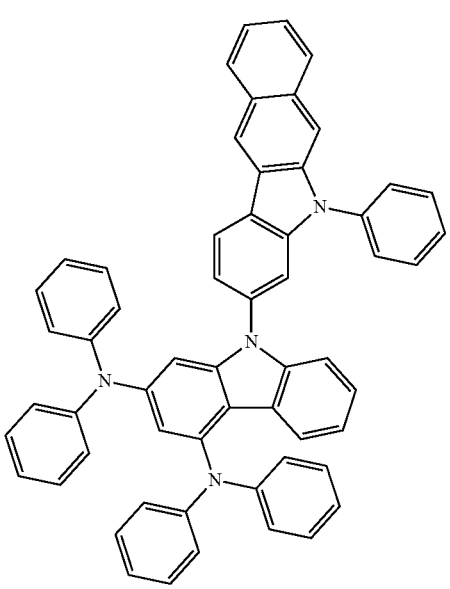
C-26
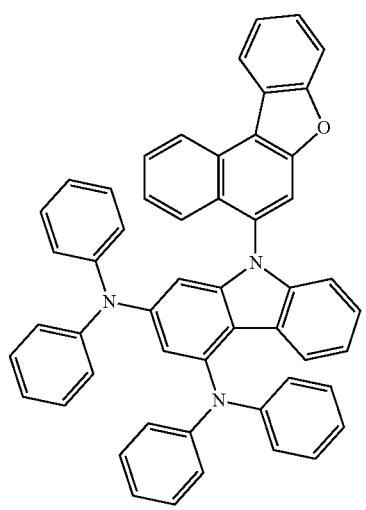
C-29
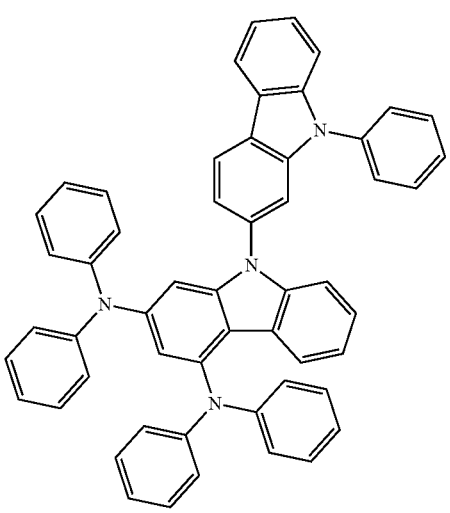
C-27
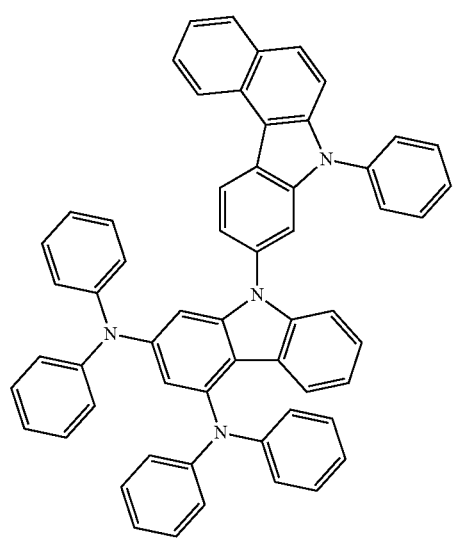
C-30
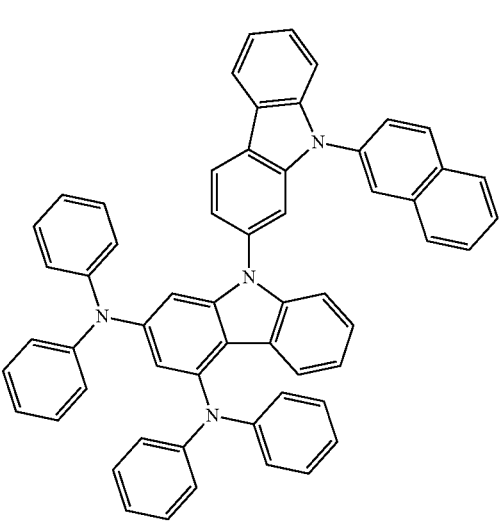

C-31
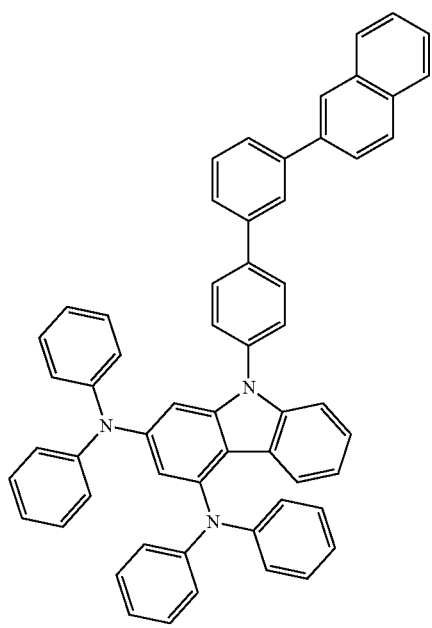
C-34
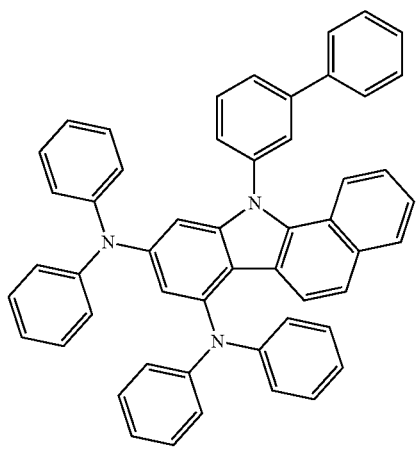
C-32
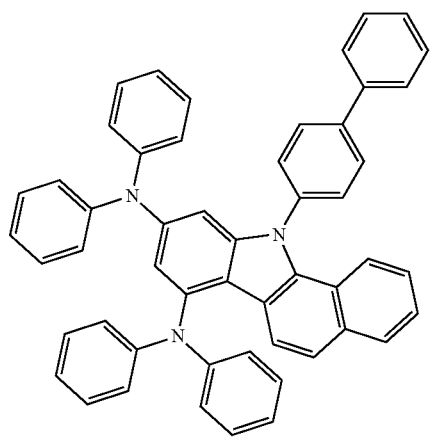
C-35
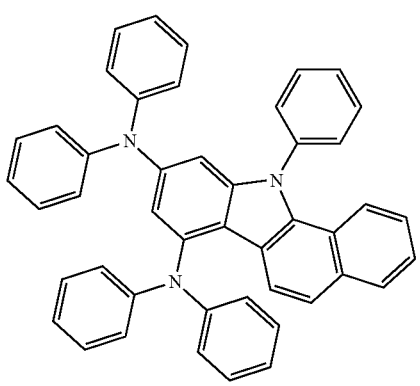
C-33
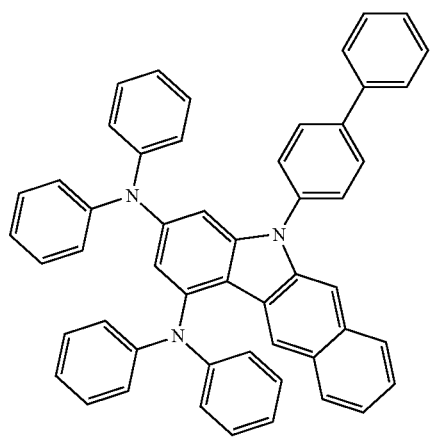
C-36
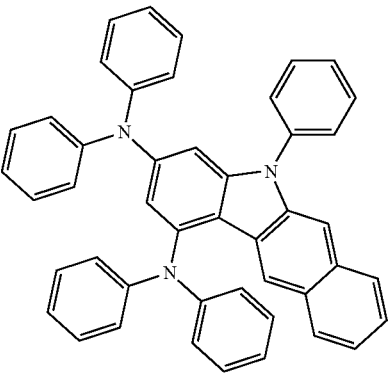

C-37
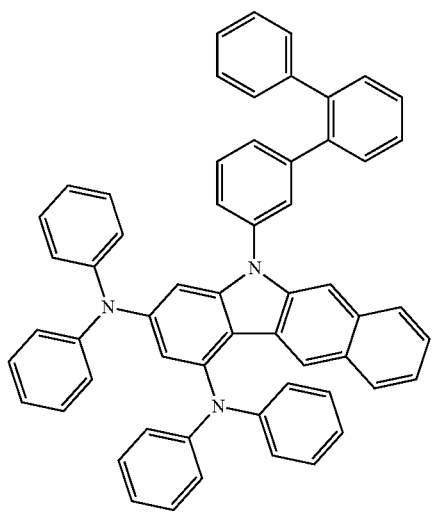
C-38
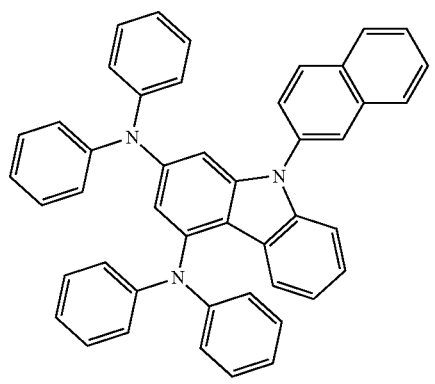
C-39
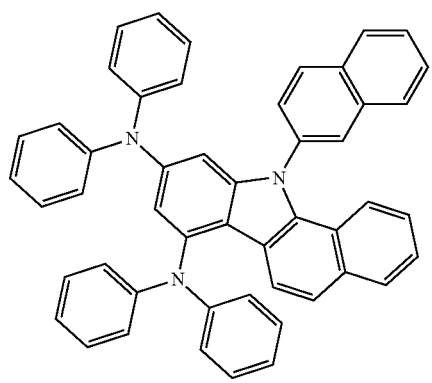
C-40
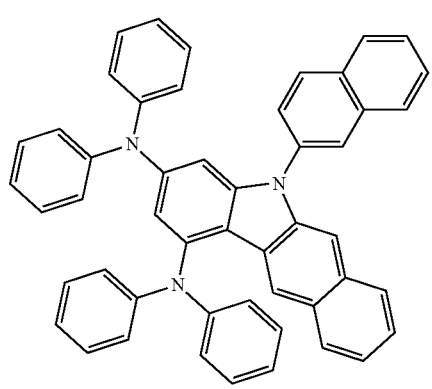
C-41
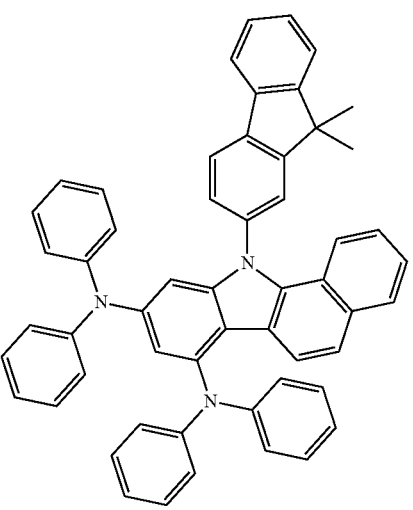
C-42
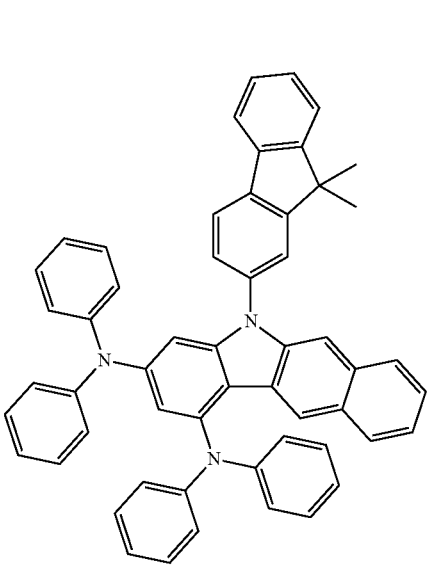
C-43
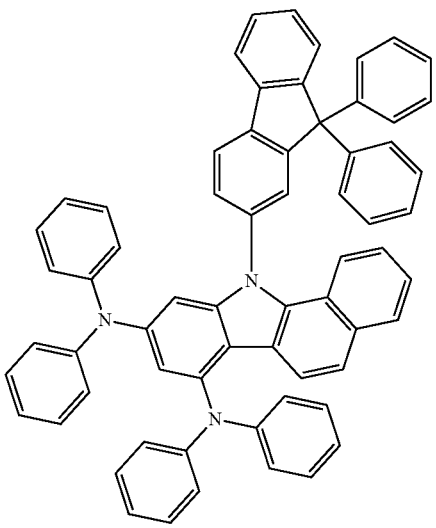

C-44
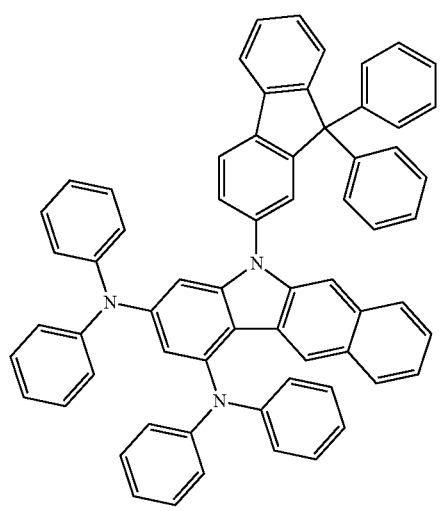
C-45
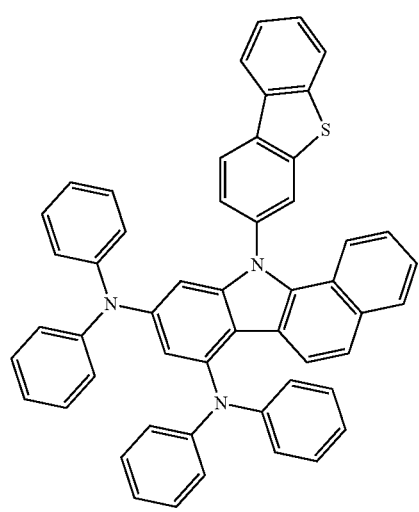
C-46
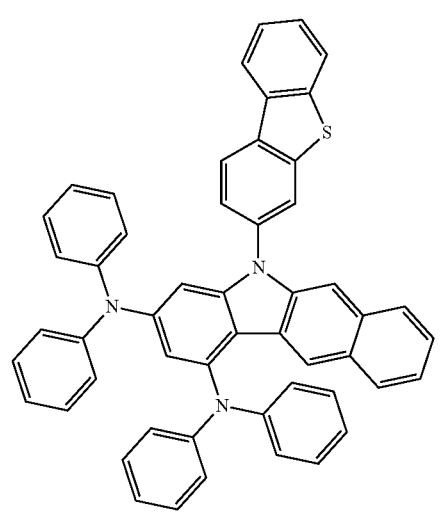
C-47
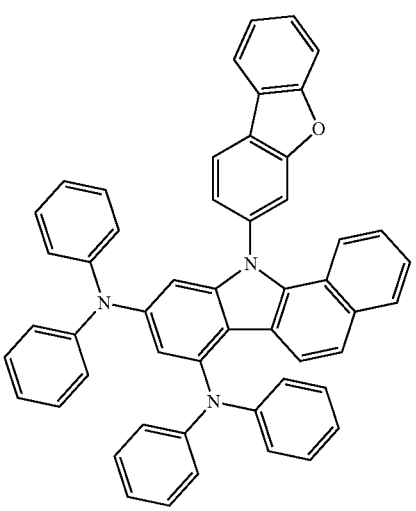
C-48
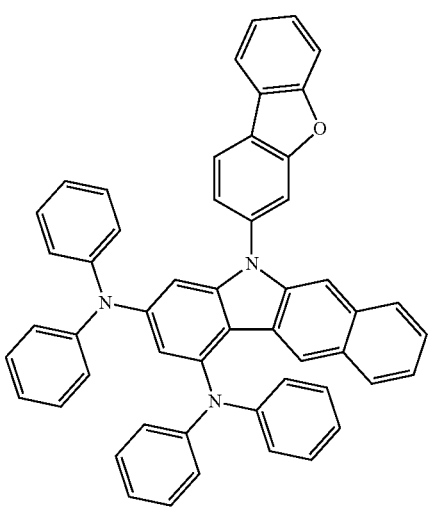
C-49
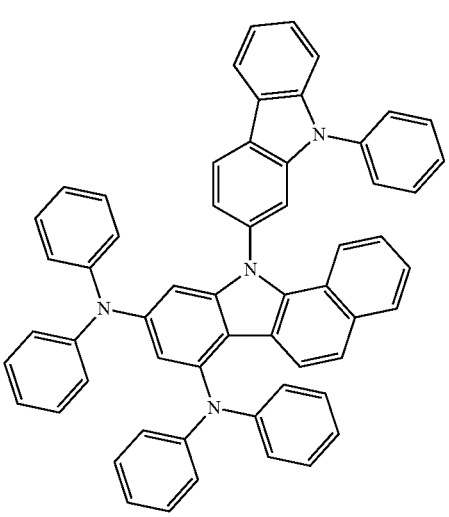

C-50
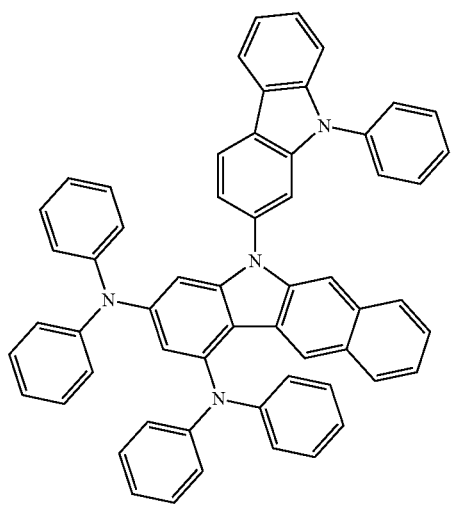
C-51
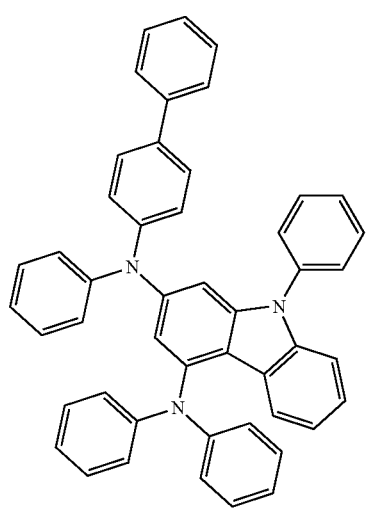
C-52
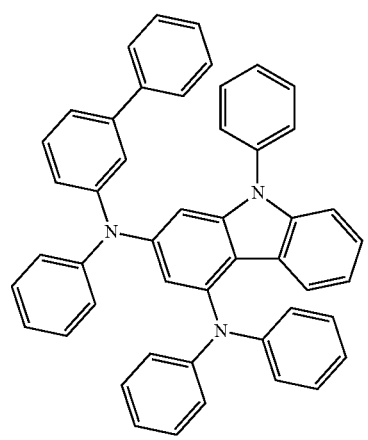
C-53
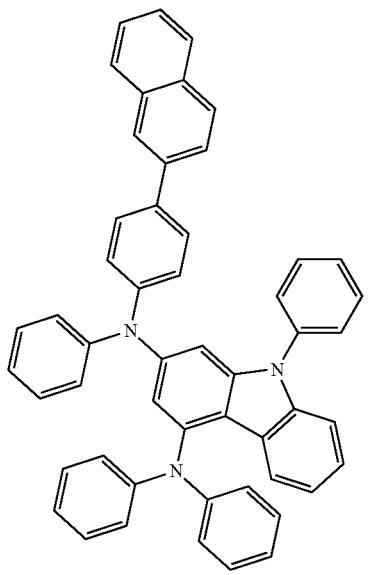
C-54
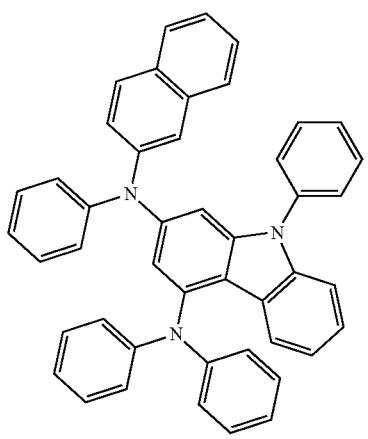
C-55
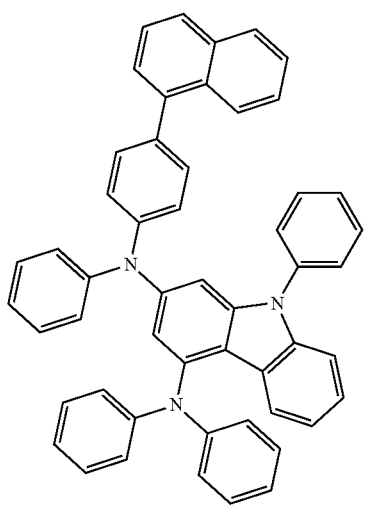

C-56
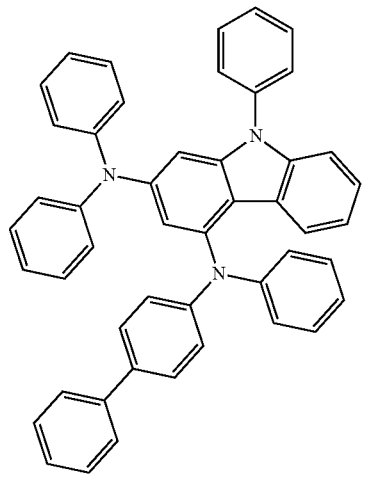
C-57
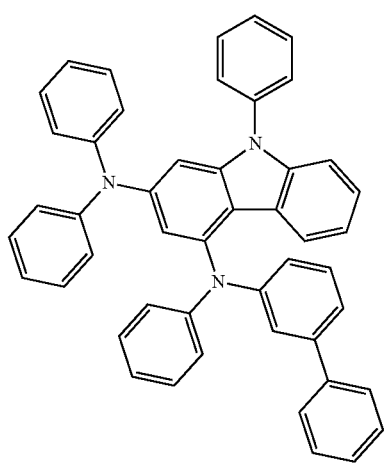
C-58
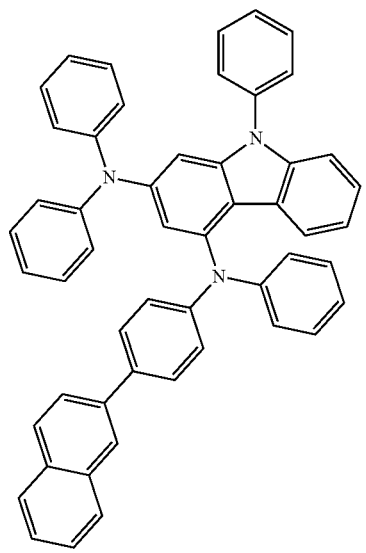
C-59
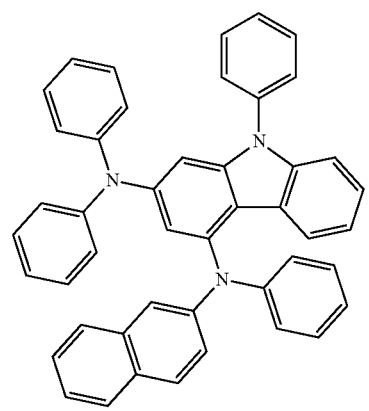
C-60
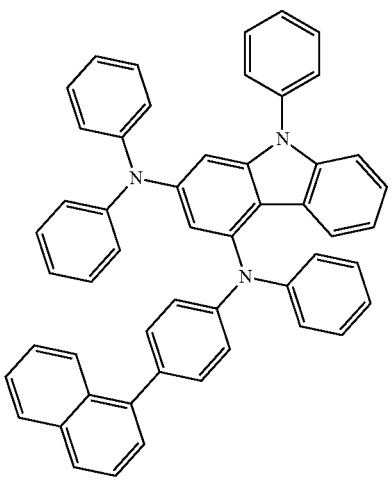
C-61
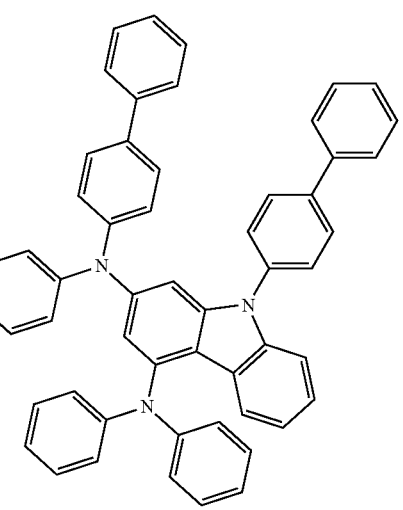

C-62
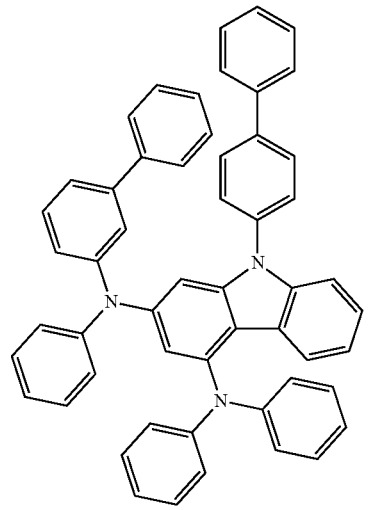
C-63
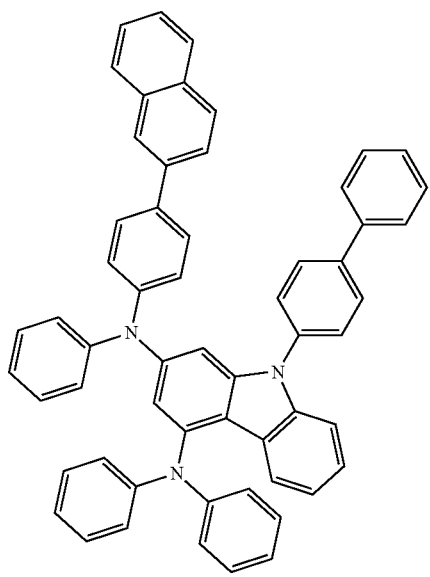
C-64
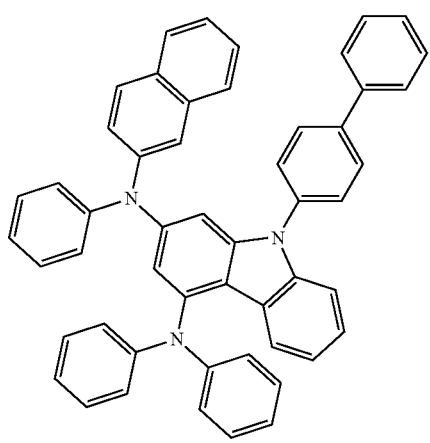
C-65
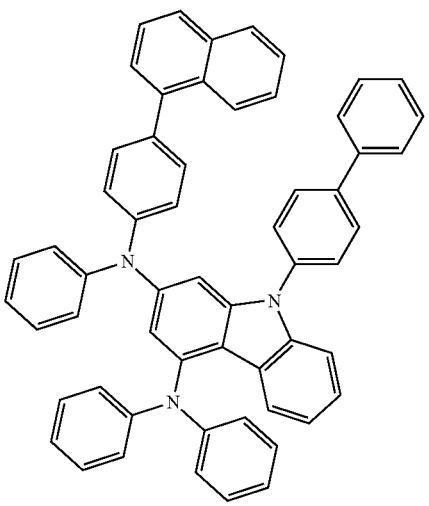
C-66
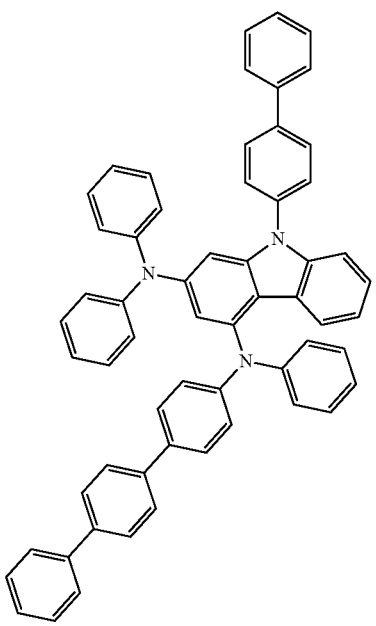

C-67
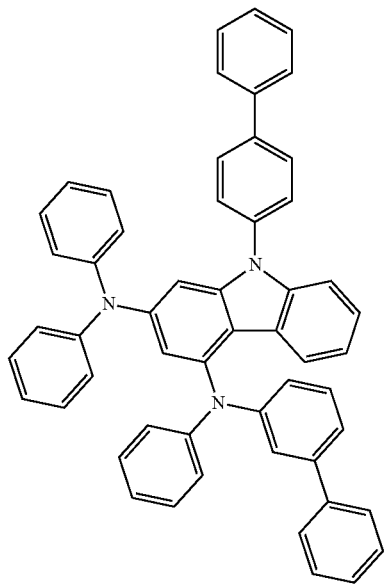
C-68
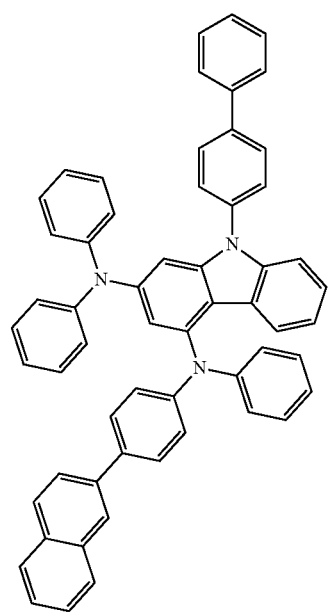
C-69
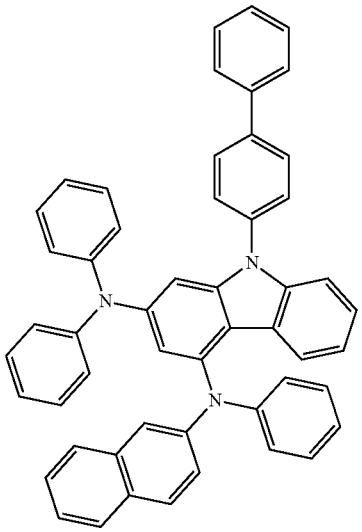
C-70
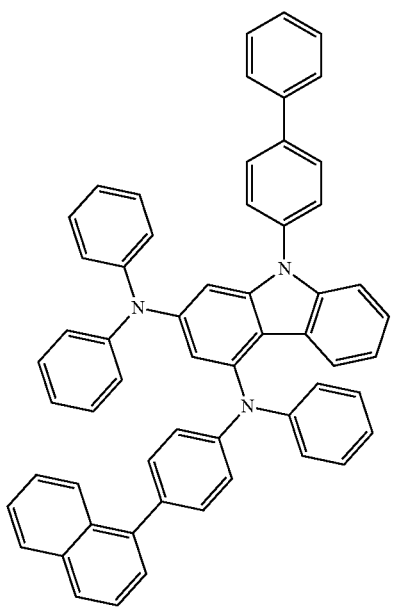
C-71
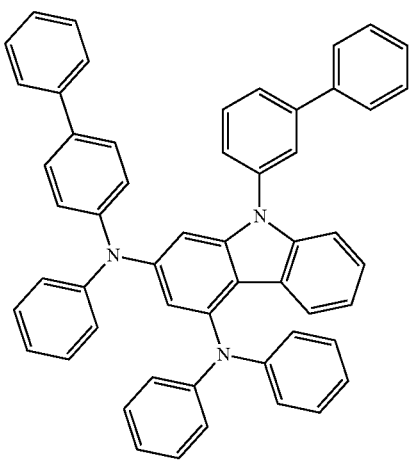

C-72
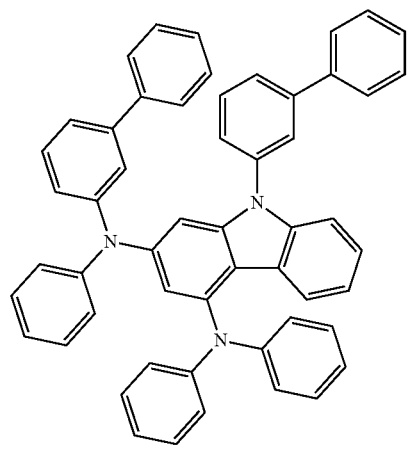
C-73
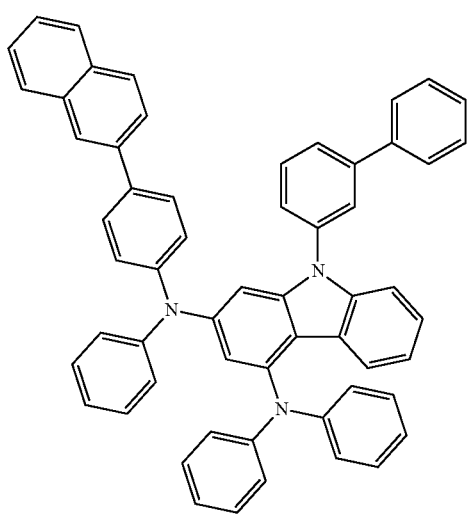
C-74
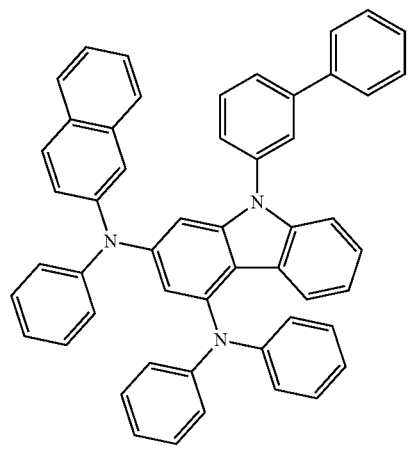
C-75
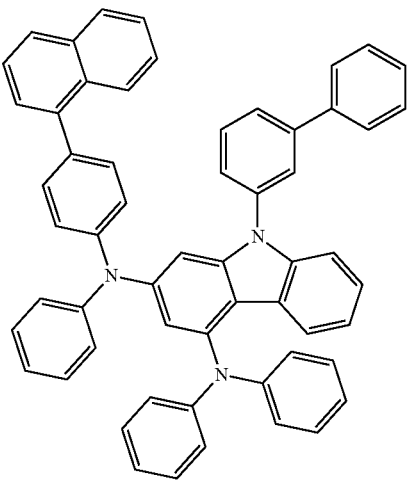
C-76
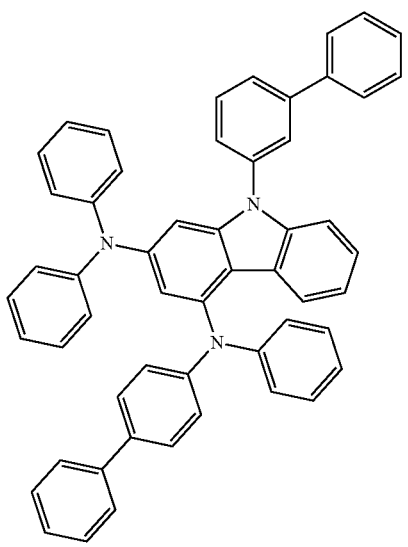
C-77
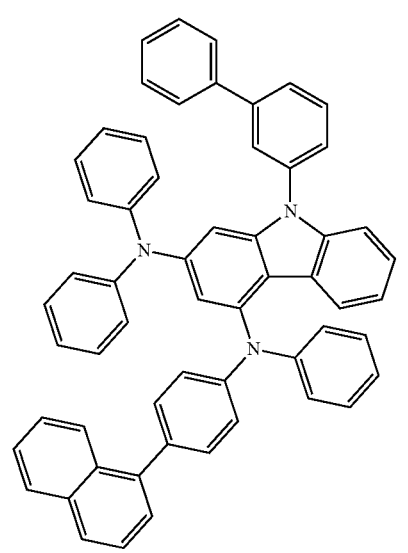

C-78
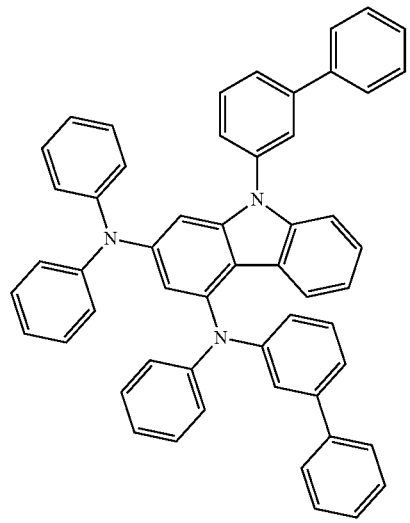
C-79
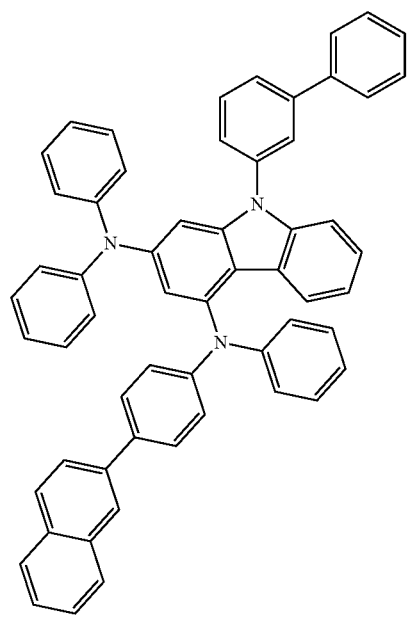
C-80
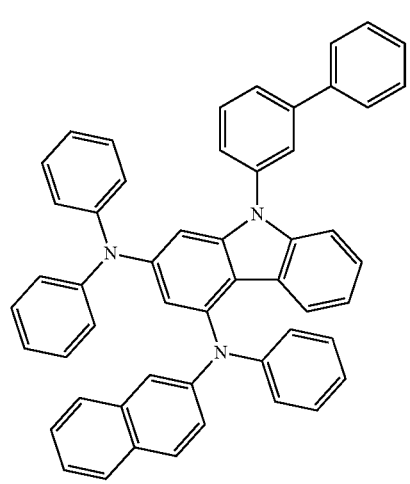
C-81
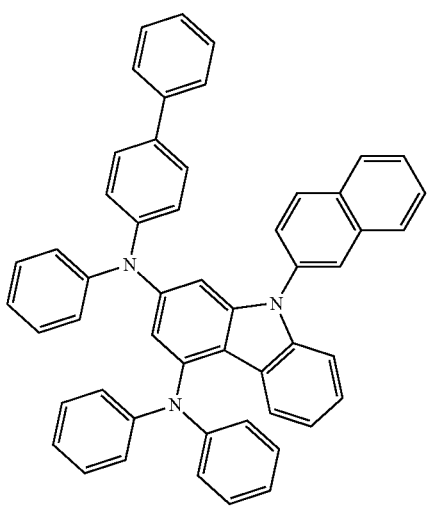
C-82
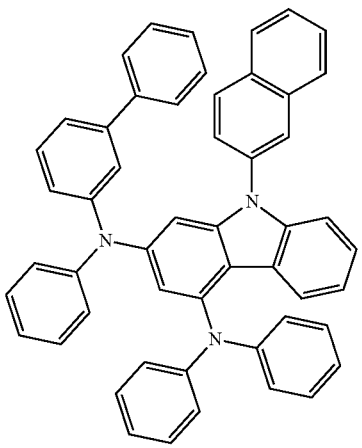
C-83
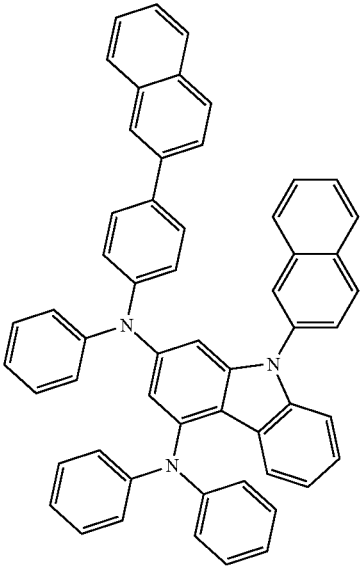

C-84
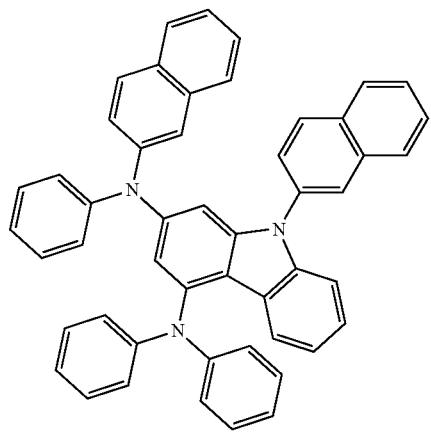
C-85
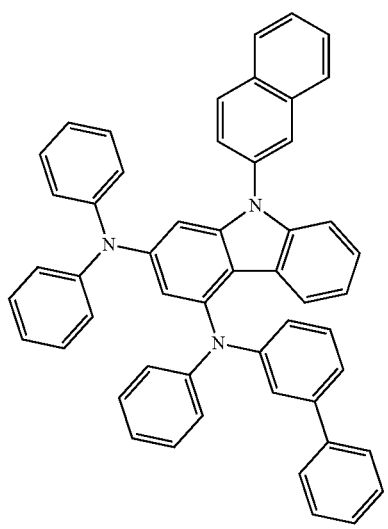
C-86
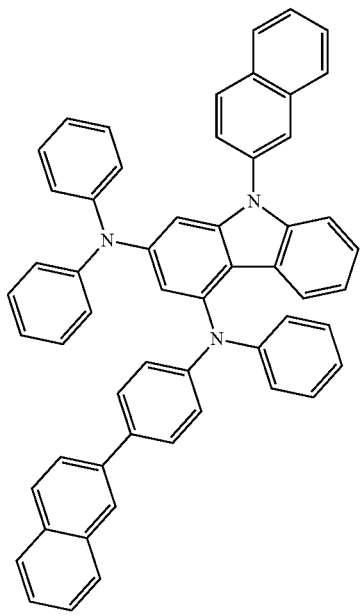
C-87
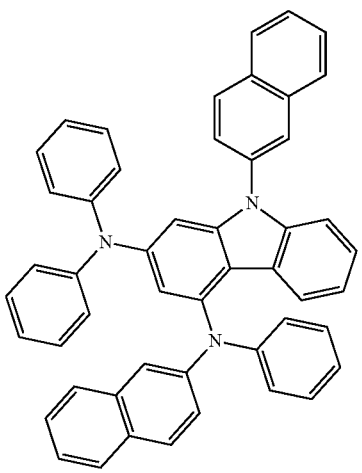
C-88
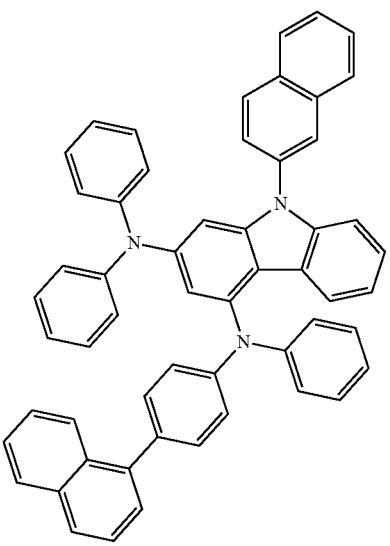
C-89
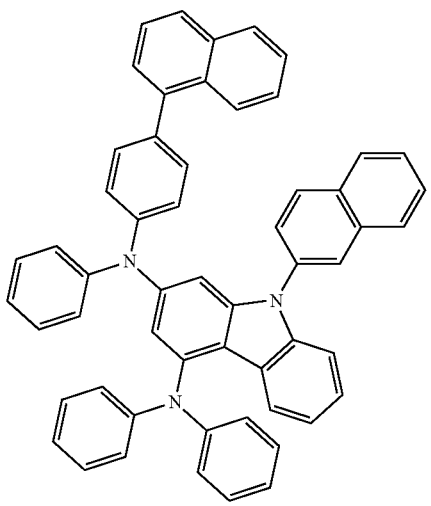

C-90
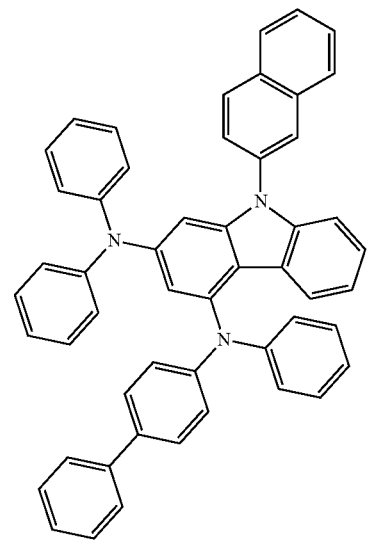
C-91
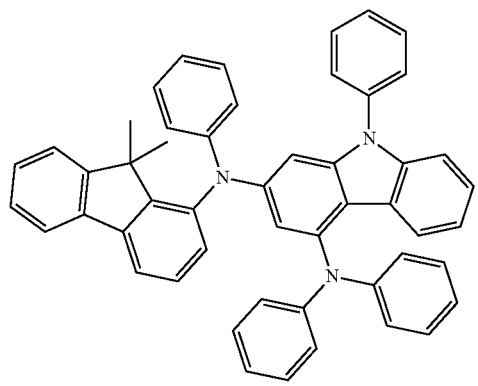
C-92
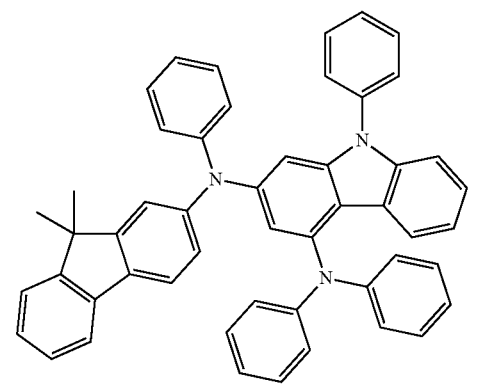
C-93
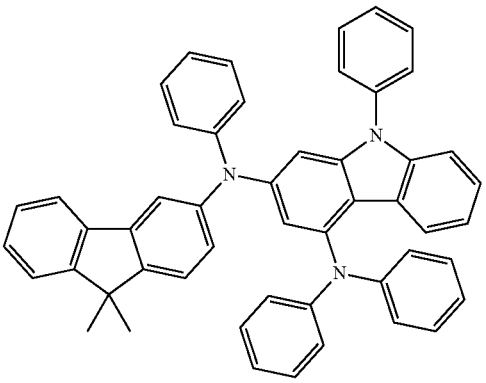
C-94
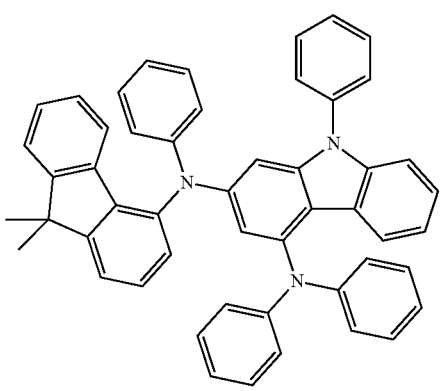
C-95
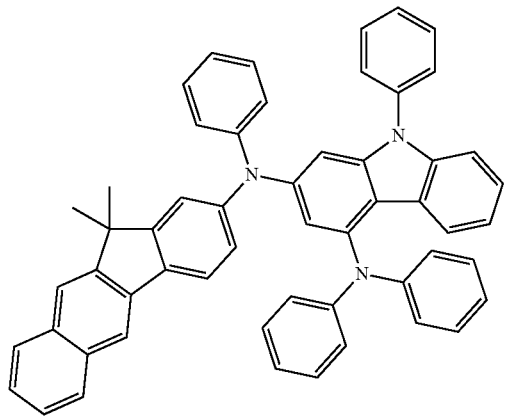
C-96
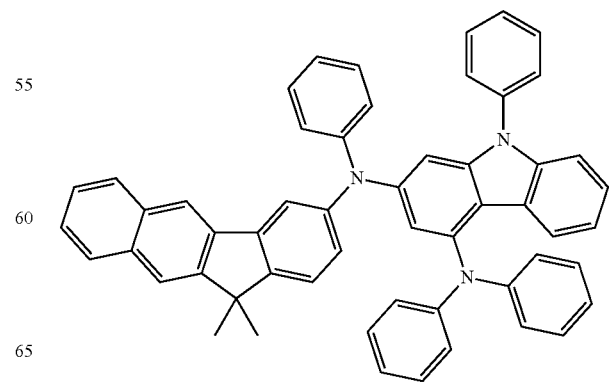

C-97
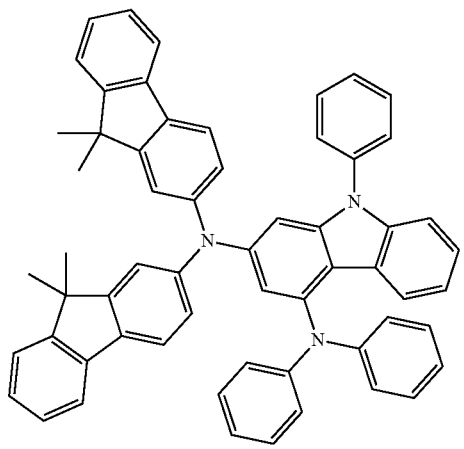
C-100
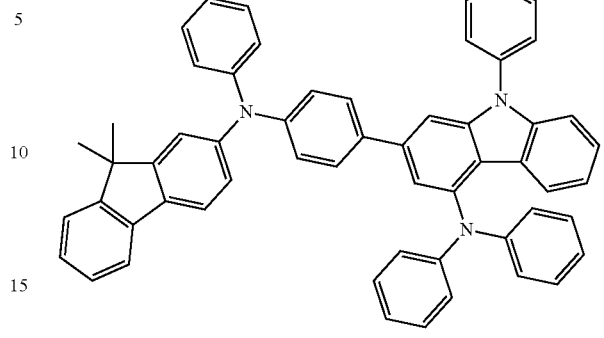
C-98
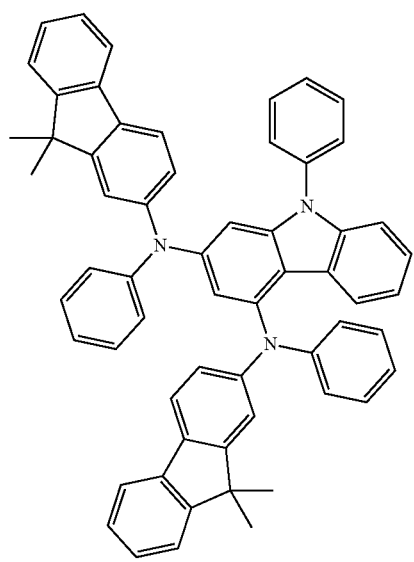
C-101
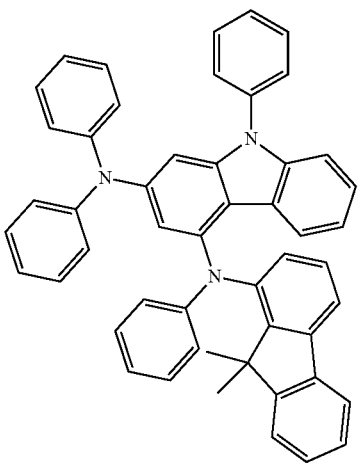
C-99
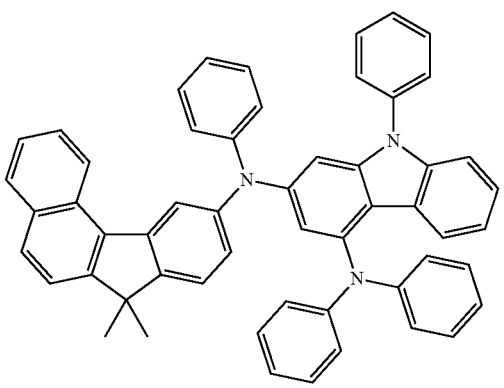
C-102
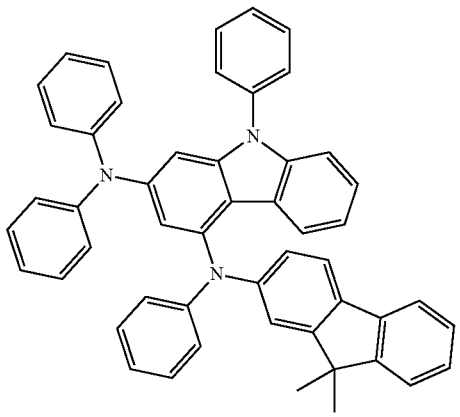

C-103
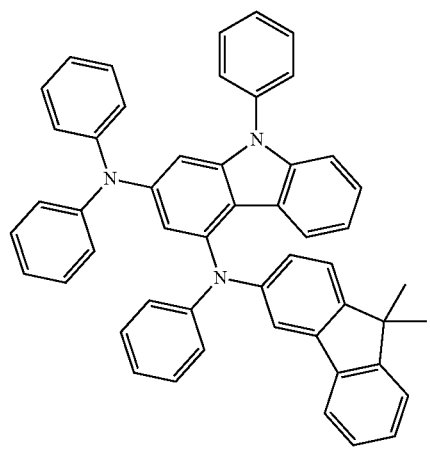
C-104
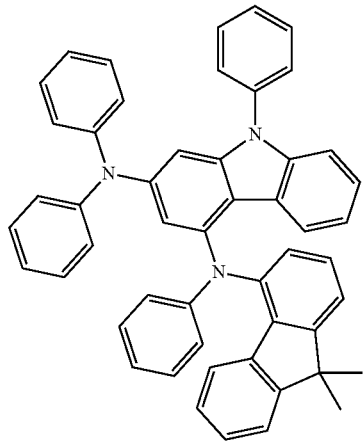
C-105
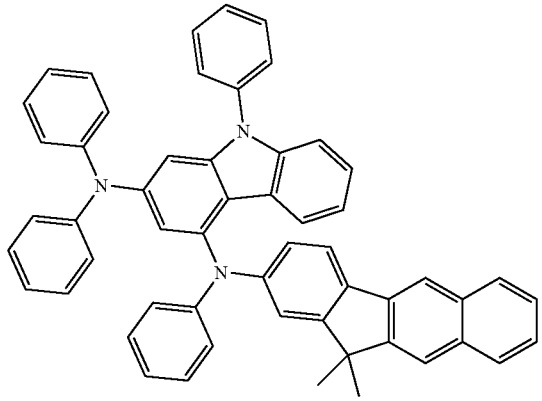
C-106
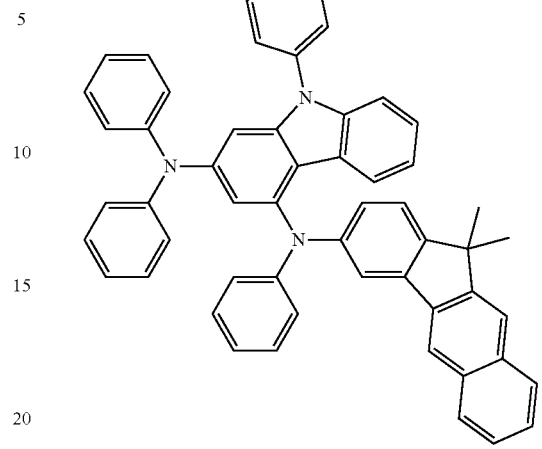
C-107
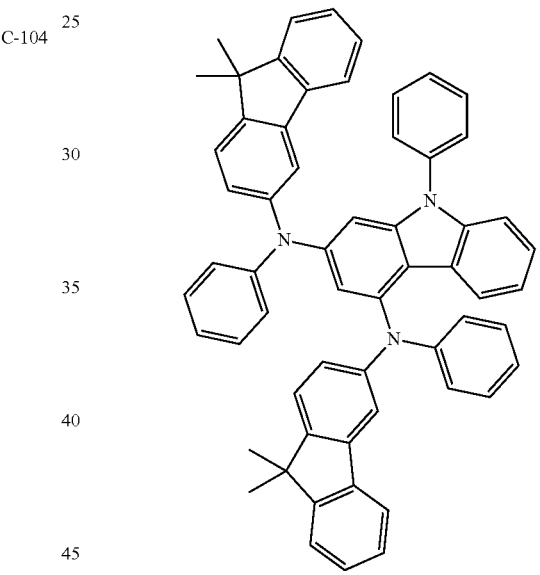
C-108
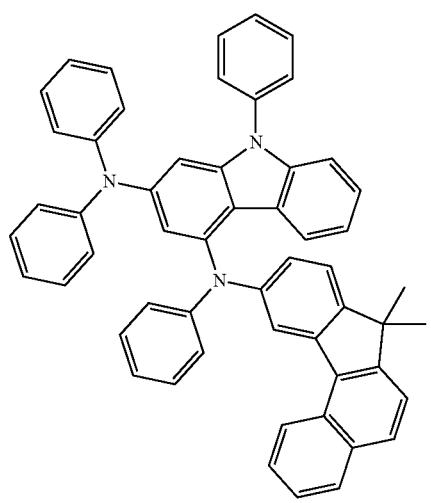

C-109
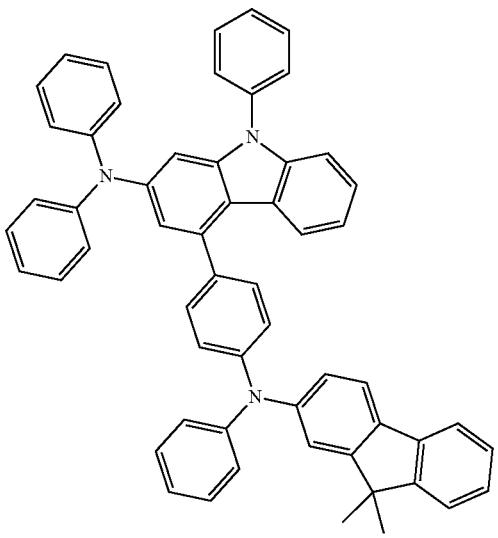
C-110
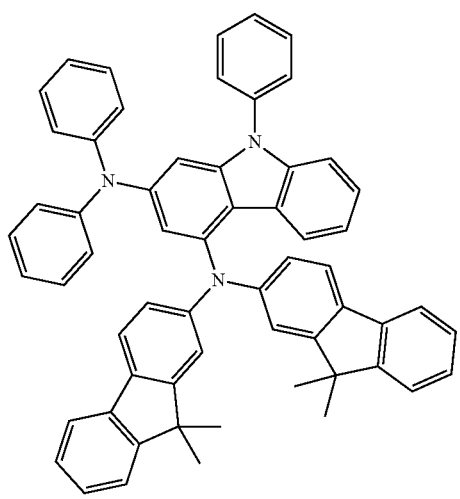
C-111
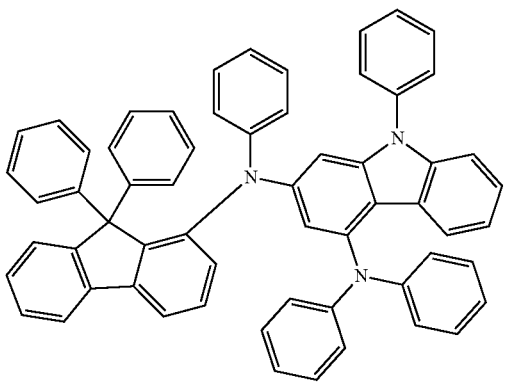
C-112
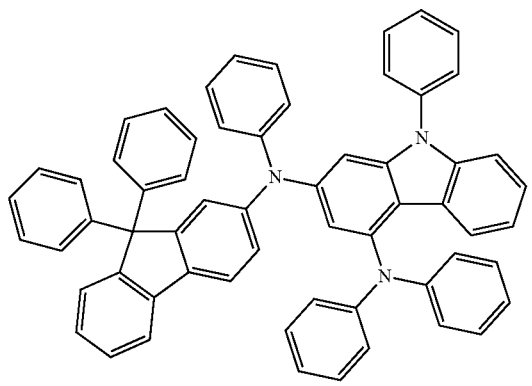
C-113
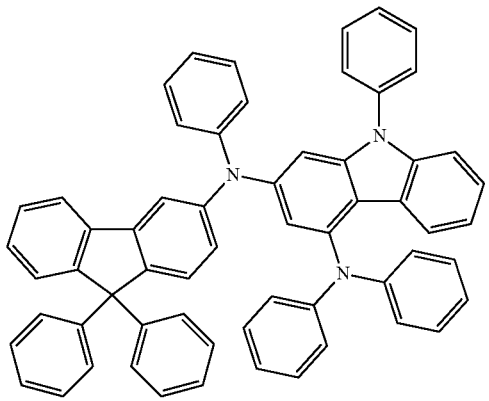
C-114
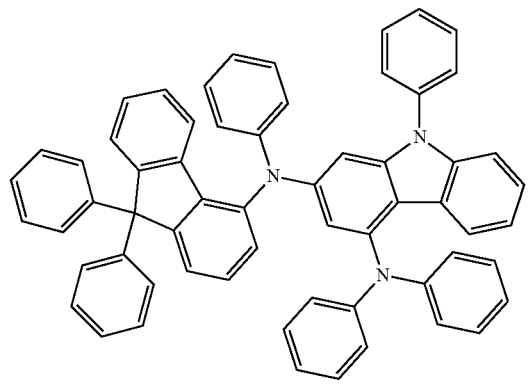

C-115
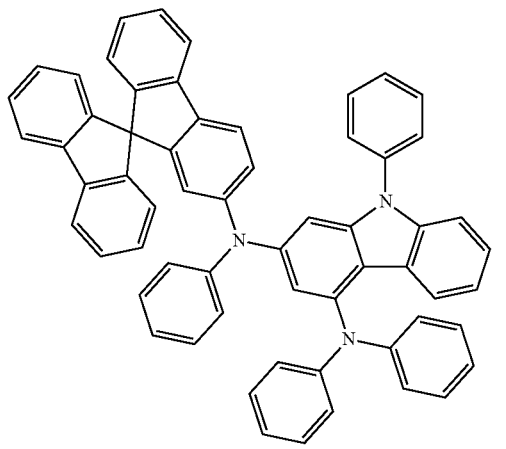
C-116
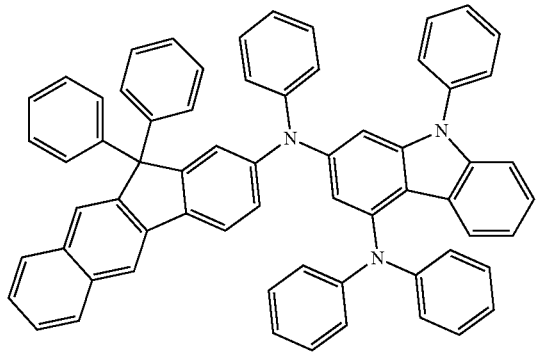
C-117
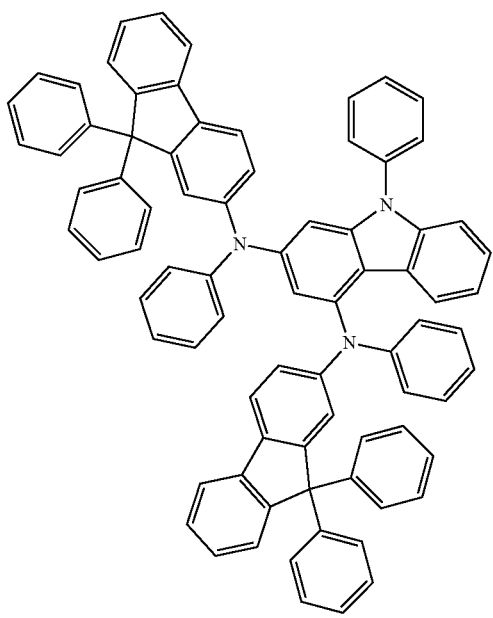
C-118
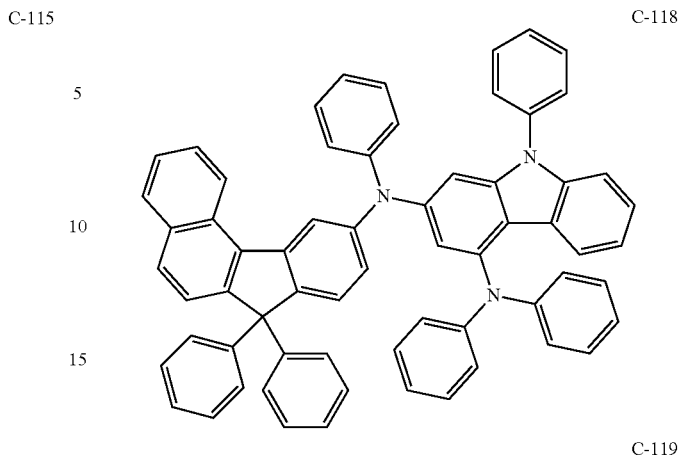
C-119
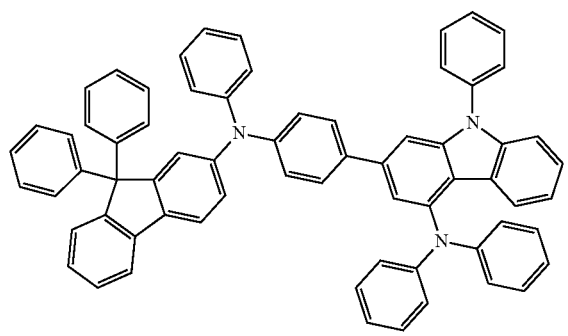
C-120
C-121
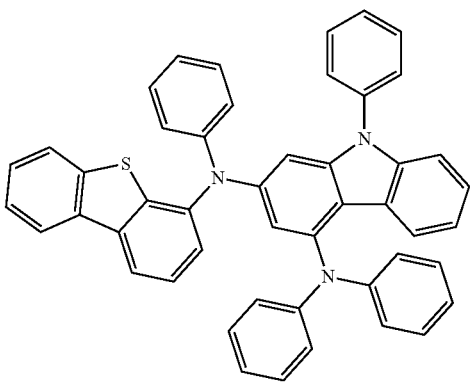

-continued
C-122
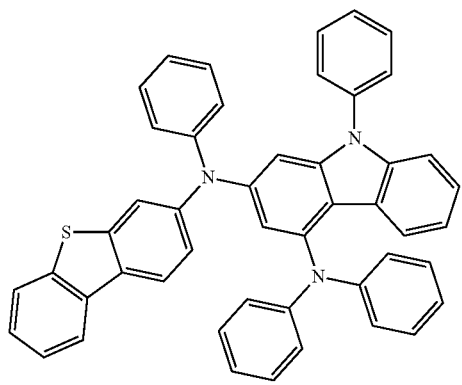
C-123
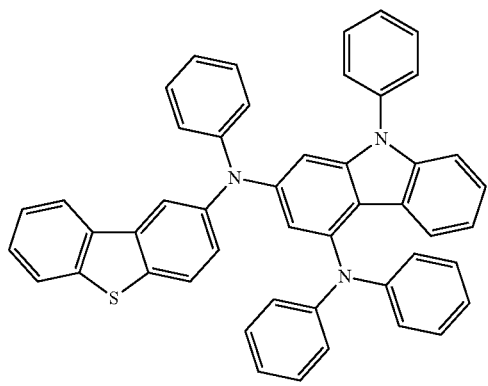
C-124
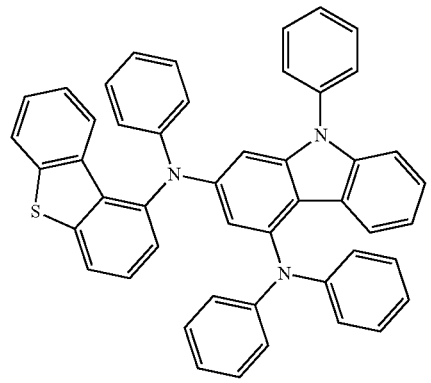
C-125
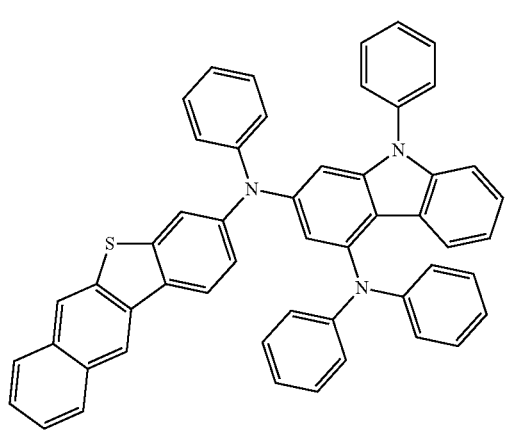
-continued
C-126
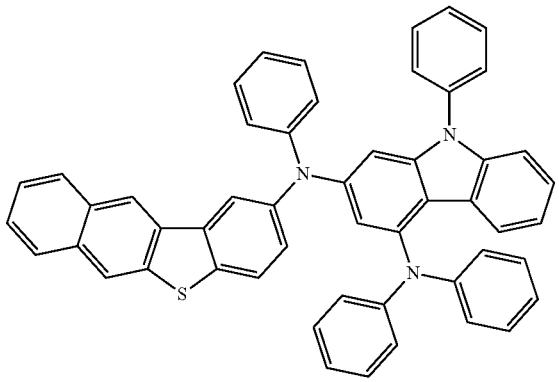
C-127
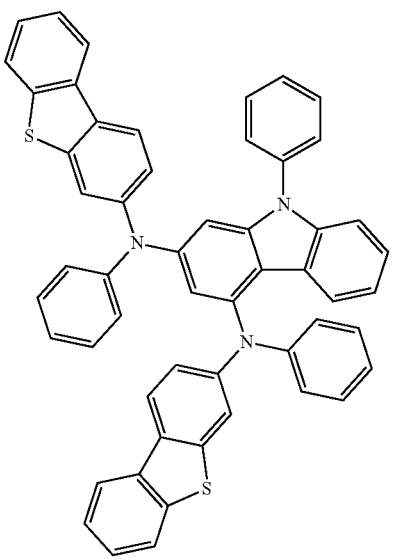
C-128
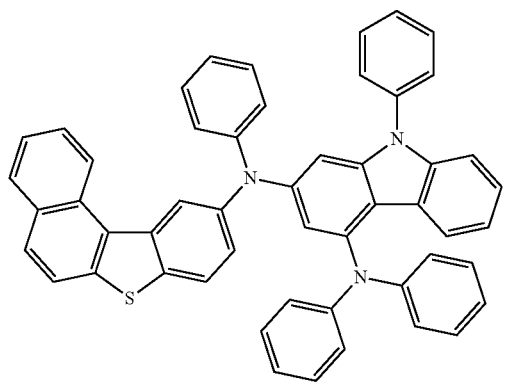

C-129
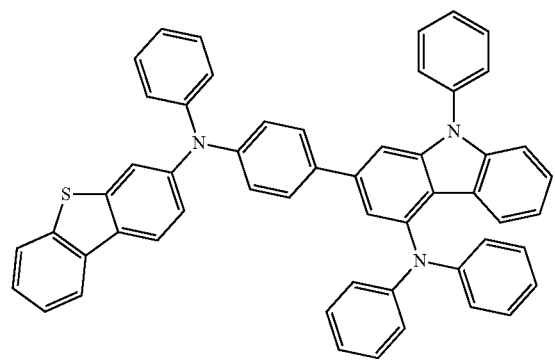
C-130
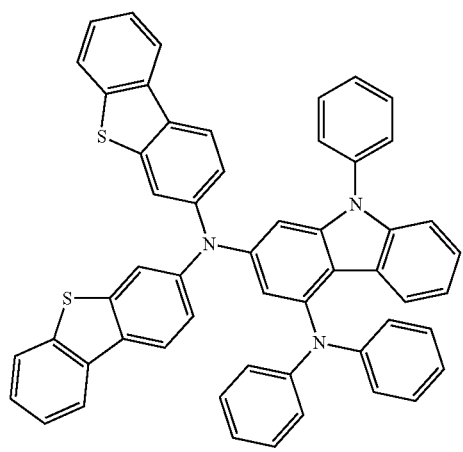
C-131
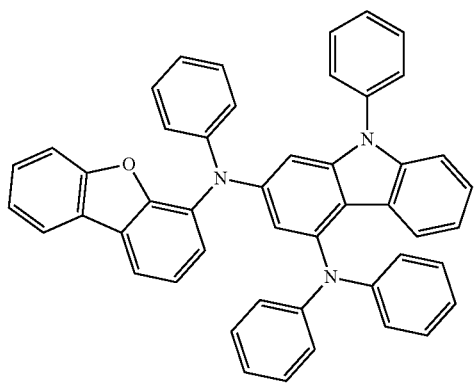
C-132
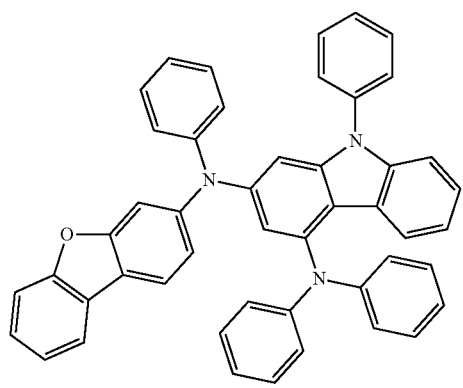
C-133
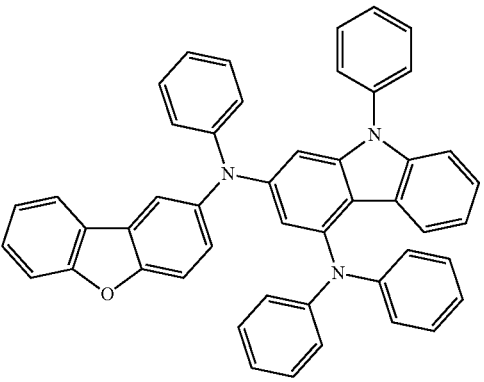
C-134
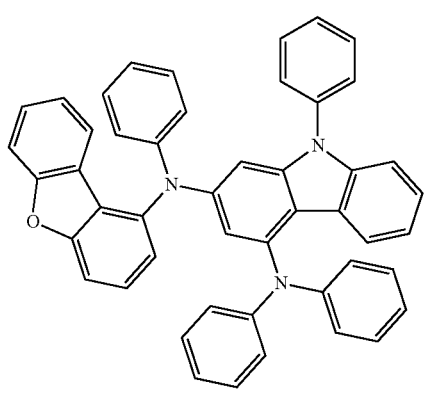
C-135
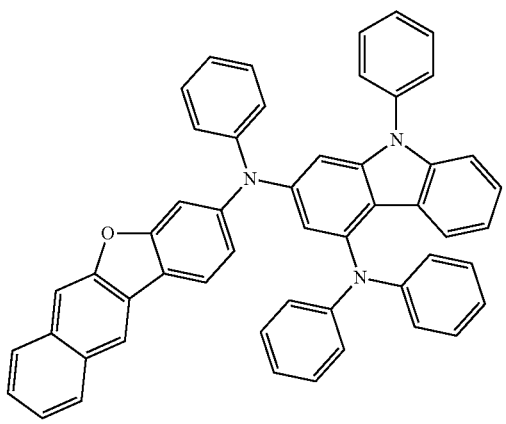
C-136
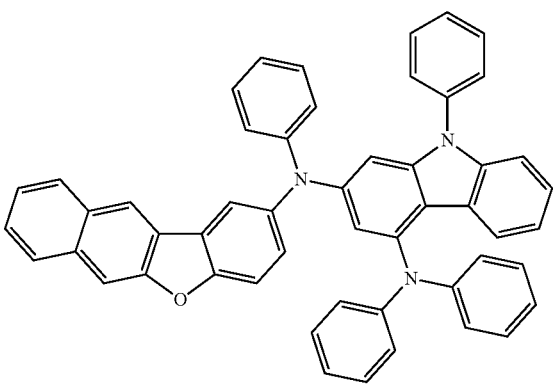

C-137
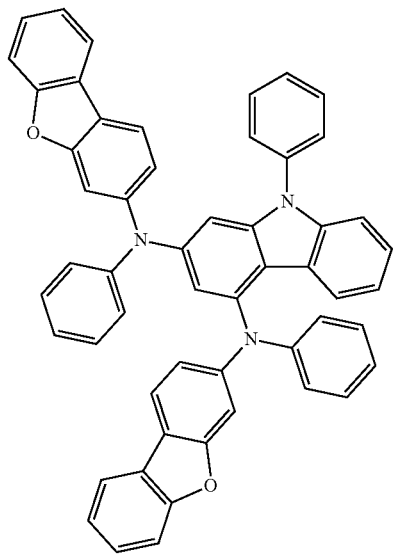
C-140
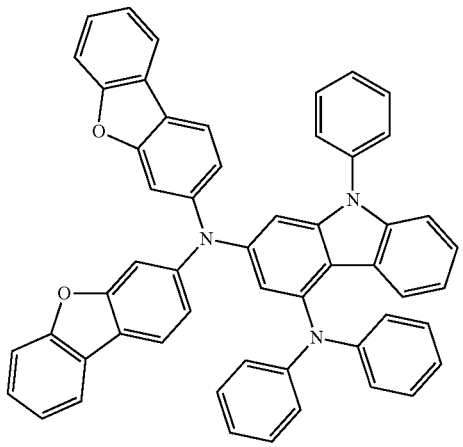
C-138
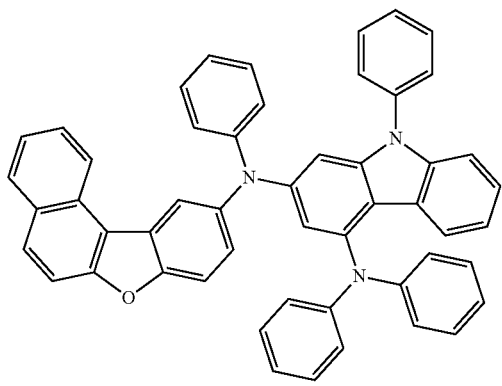
C-141
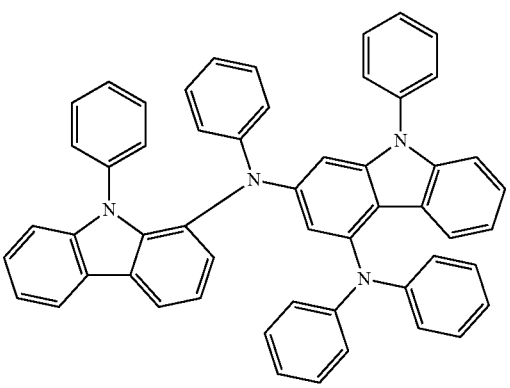
C-139
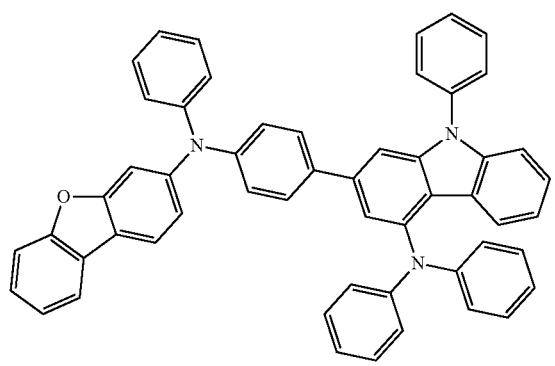
C-142
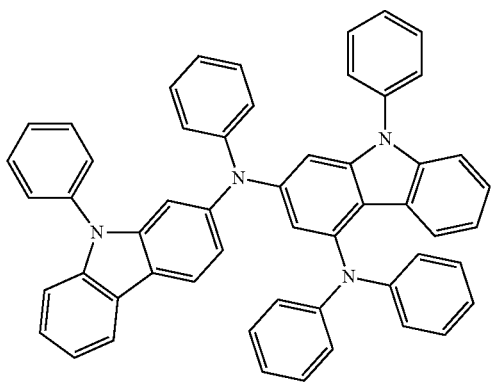

-continued
C-143
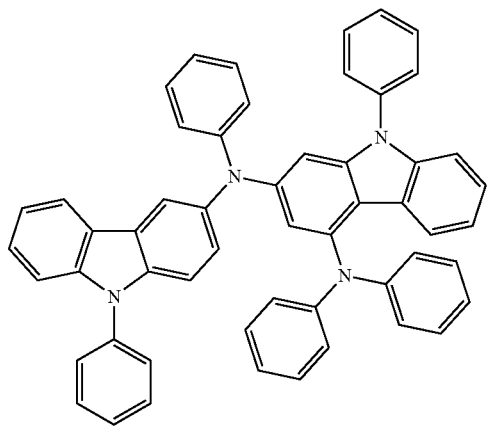
C-144
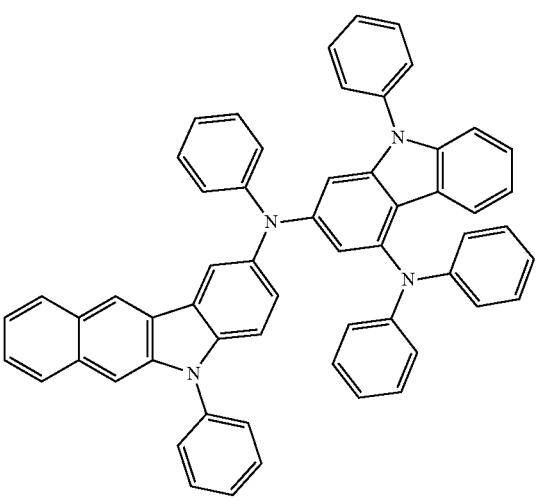
C-145
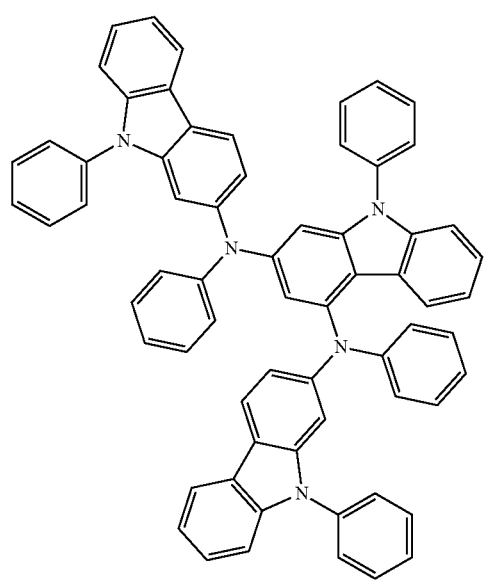
-continued
C-146
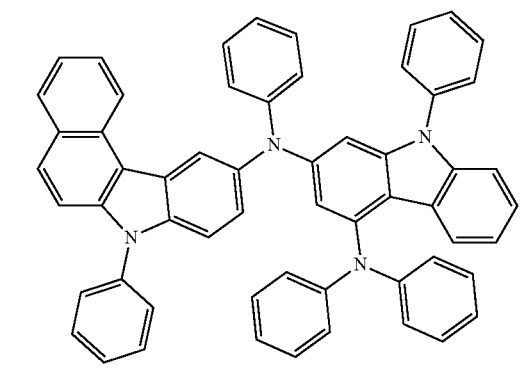
C-147
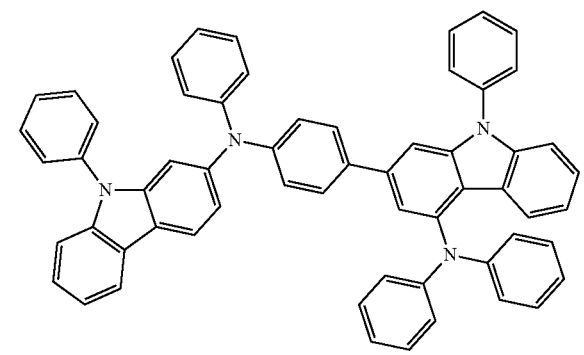
C-148
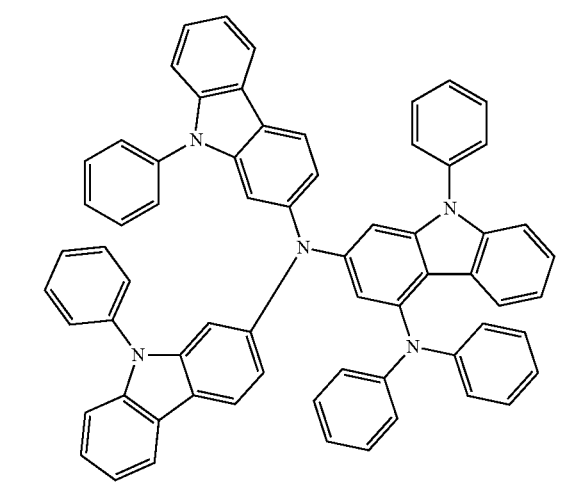
C-149
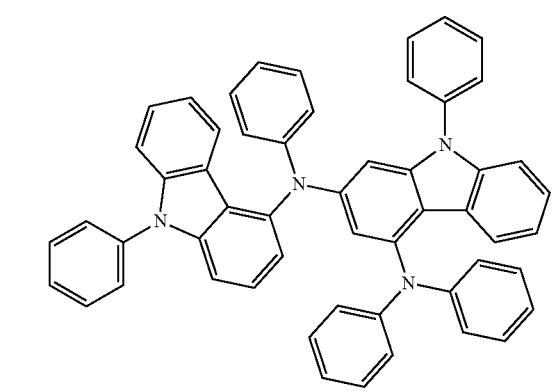

C-150
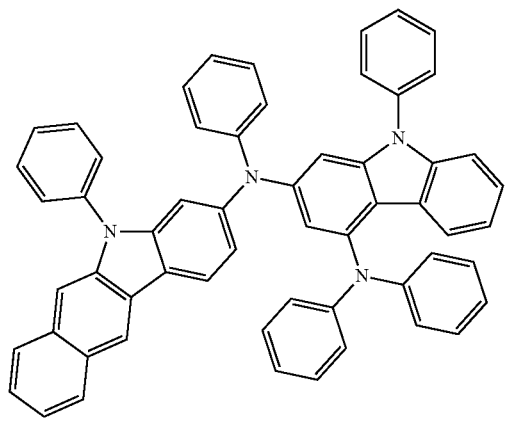
153
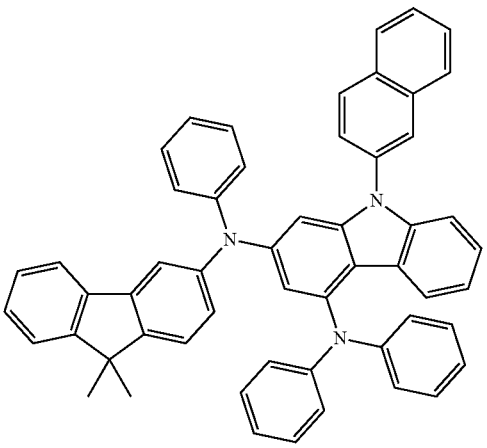
C-151
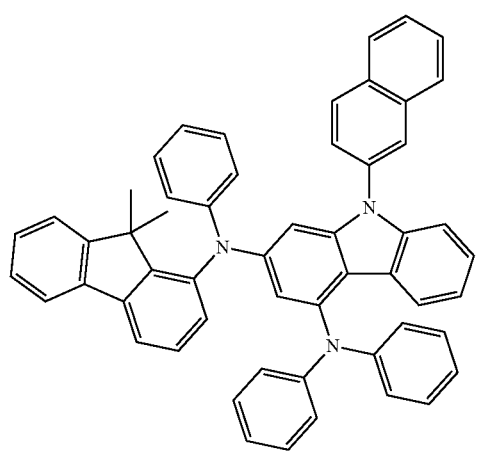
C-154
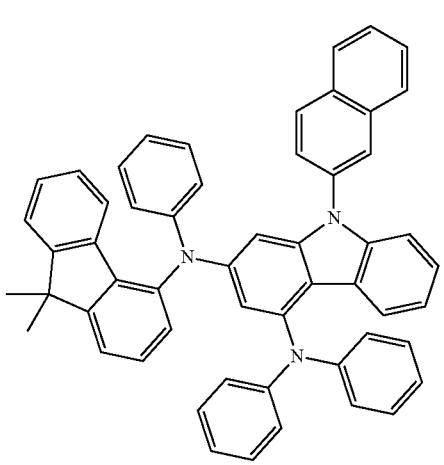
C-152
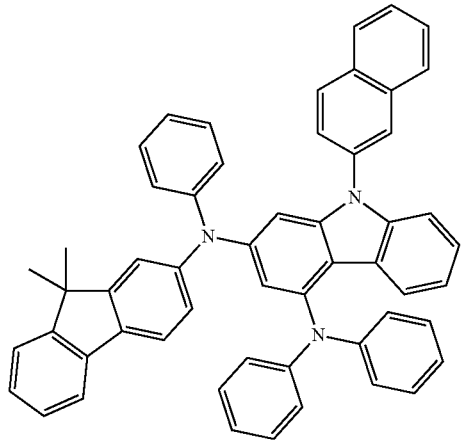
C-155
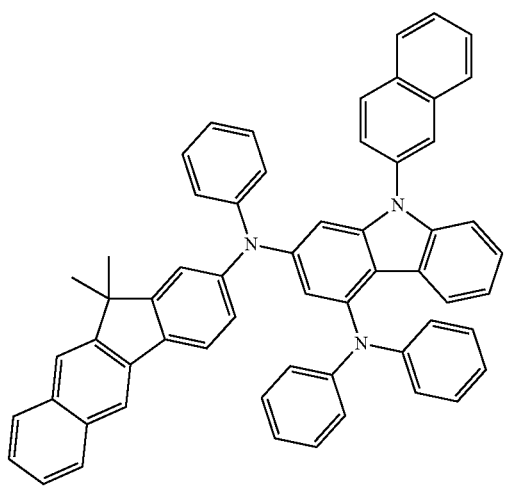

C-156
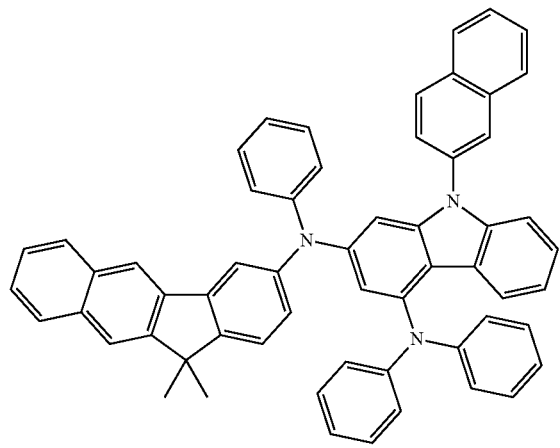
C-159
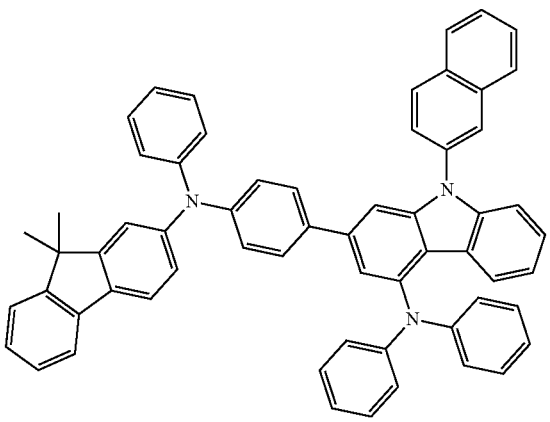
C-157
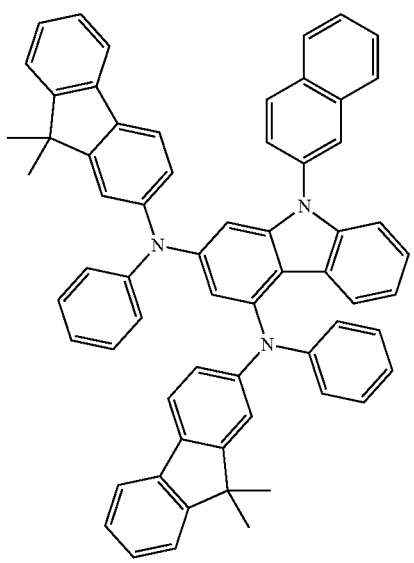
C-160
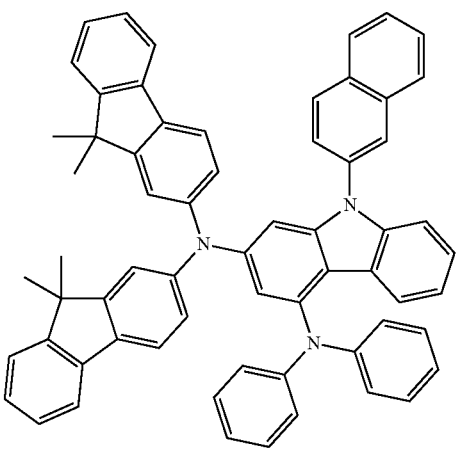
C-158
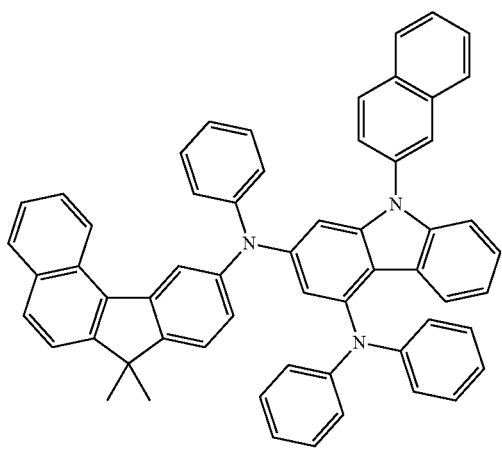
C-161
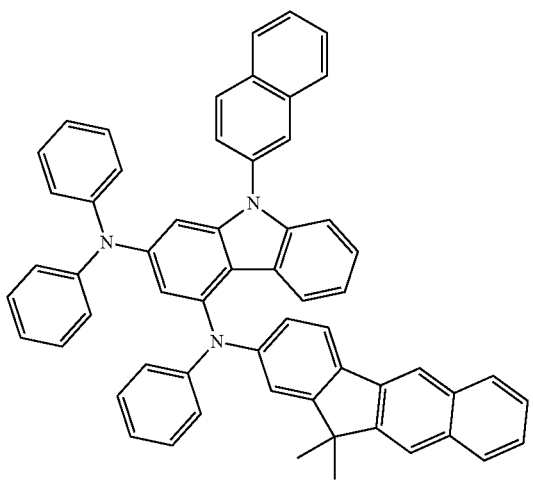

C-162
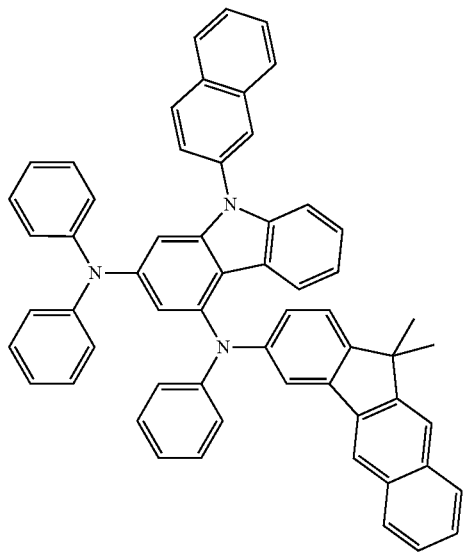
C-163
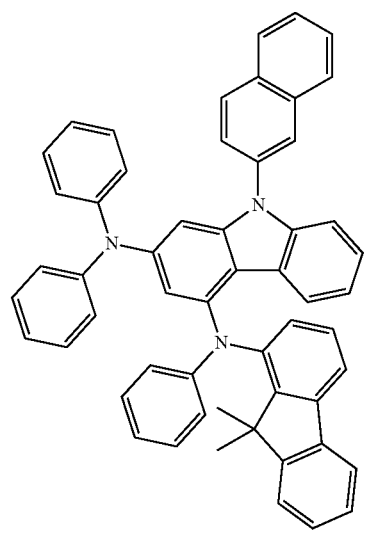
C-164
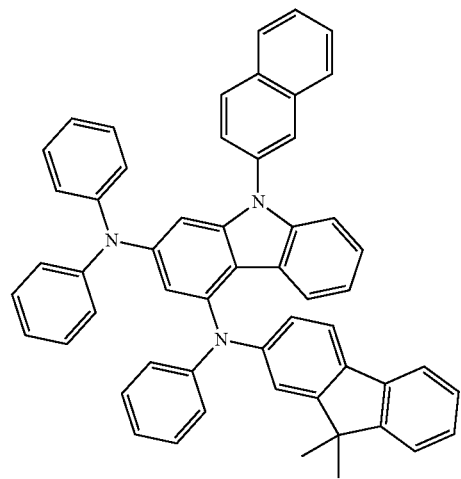
C-165
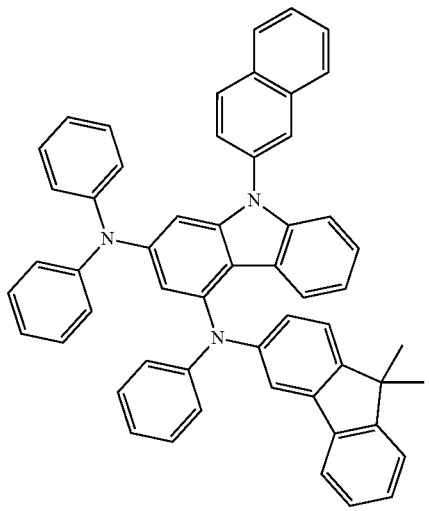
C-166
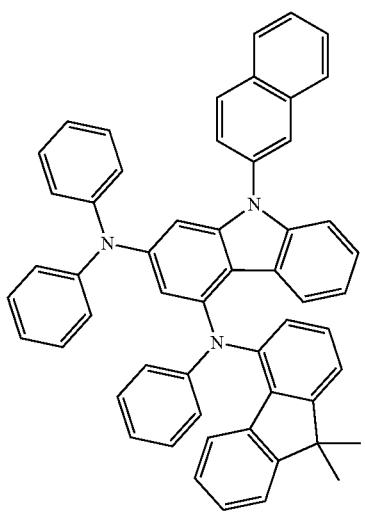
C-167
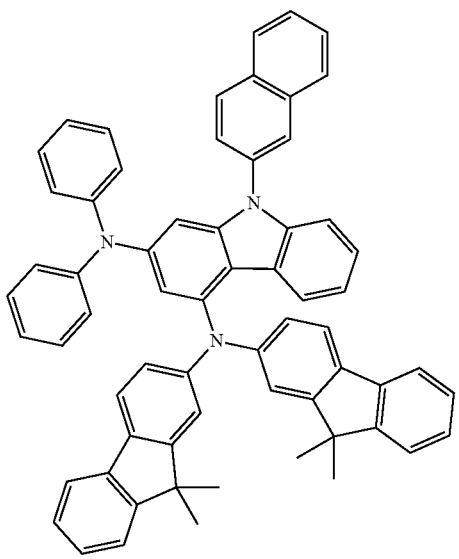

C-168
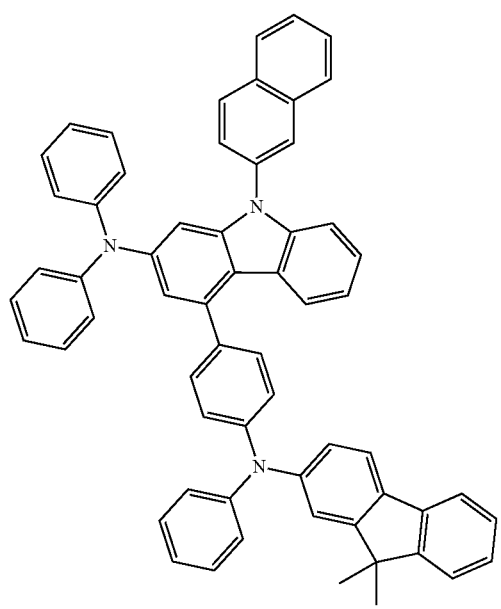
C-169
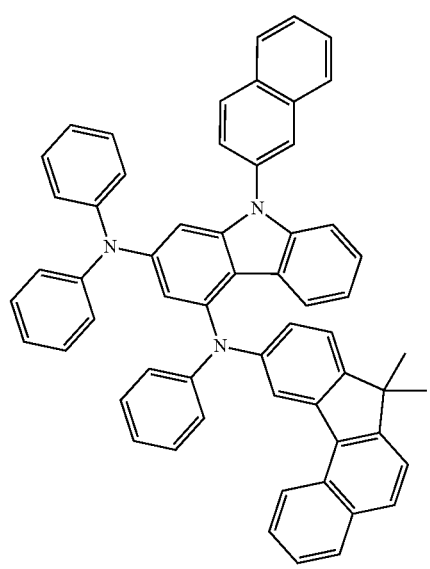
C-170
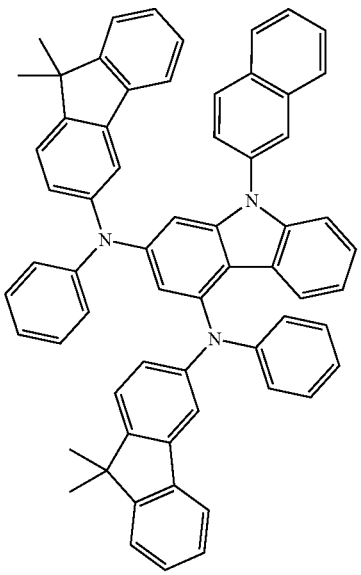
C-171
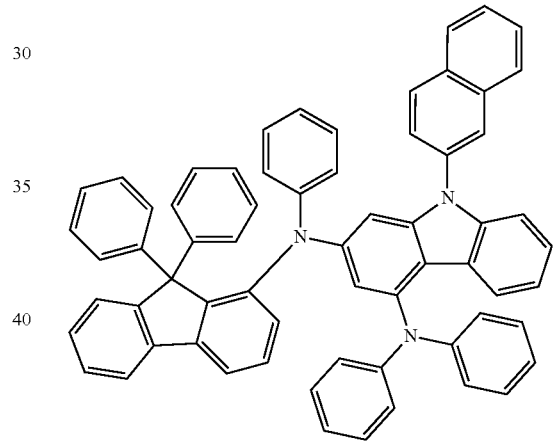
C-172
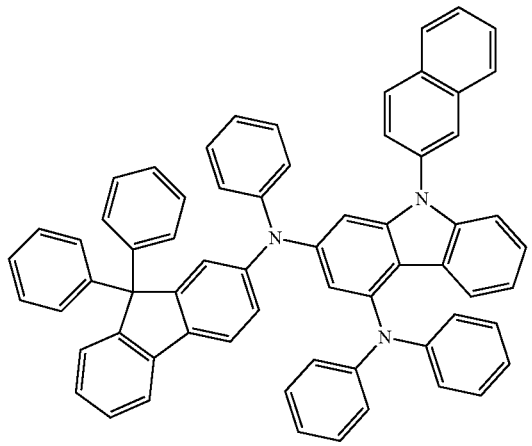

-continued
C-173
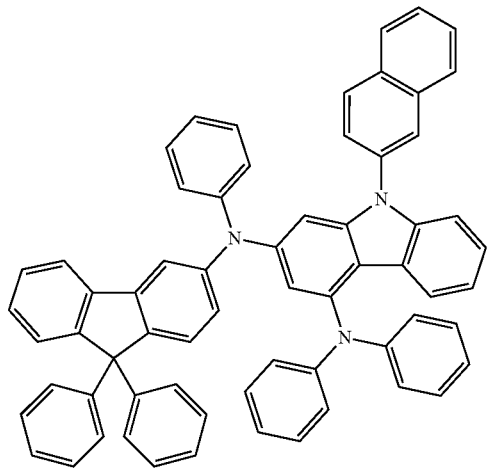
C-174
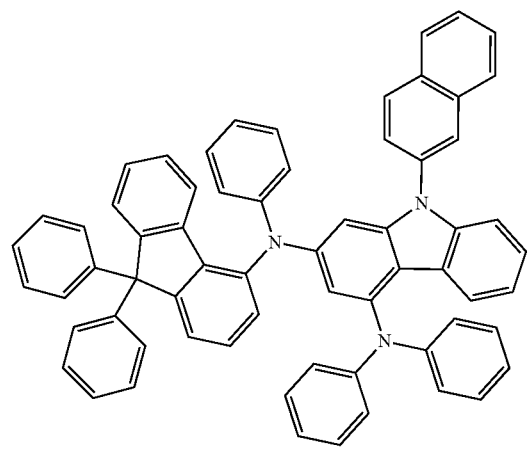
C-175
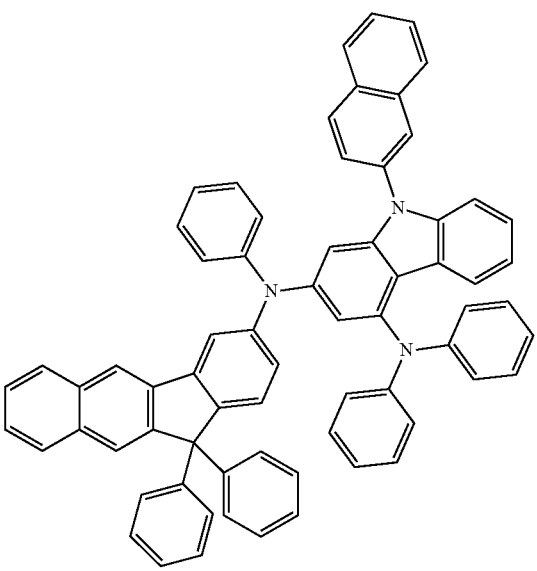
-continued
C-176
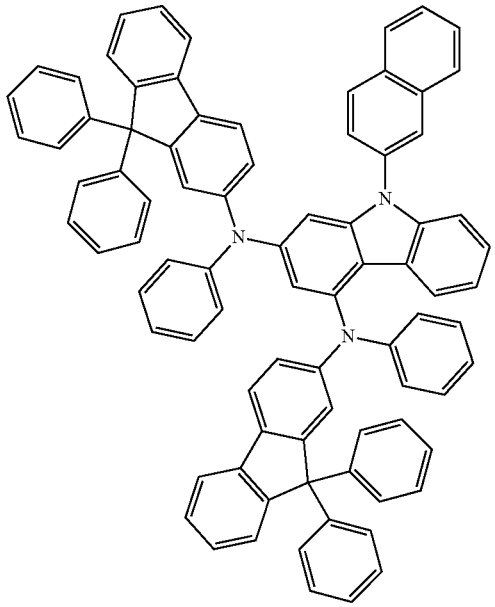
C-177
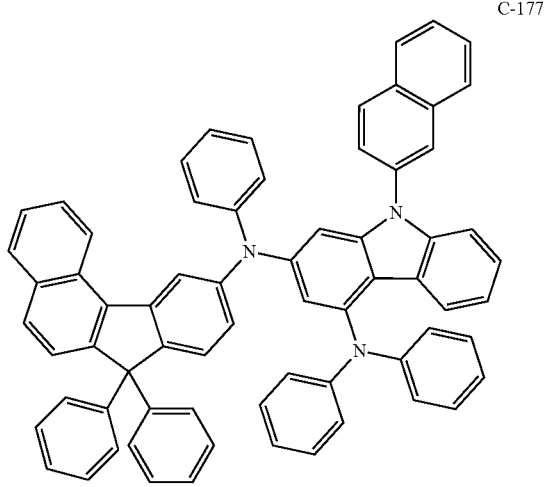
C-178
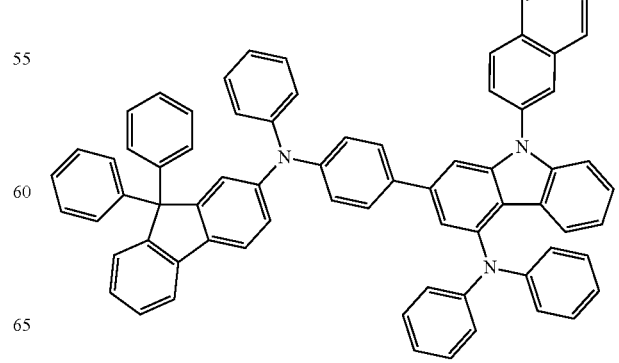

-continued
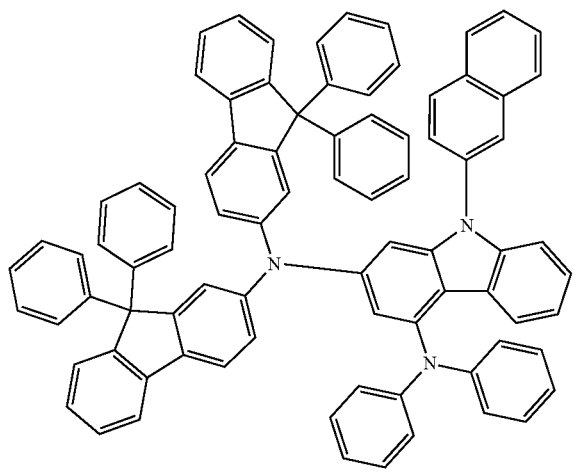
C-179
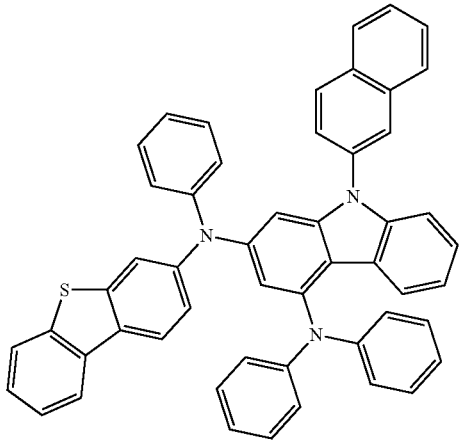
C-182
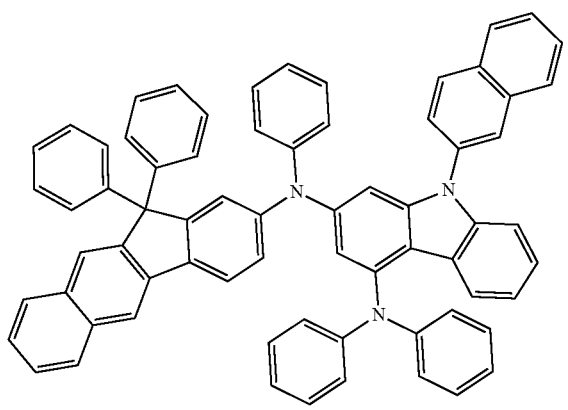
C-180
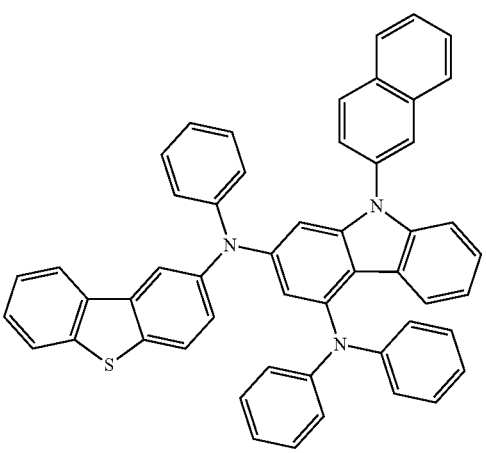
C-183
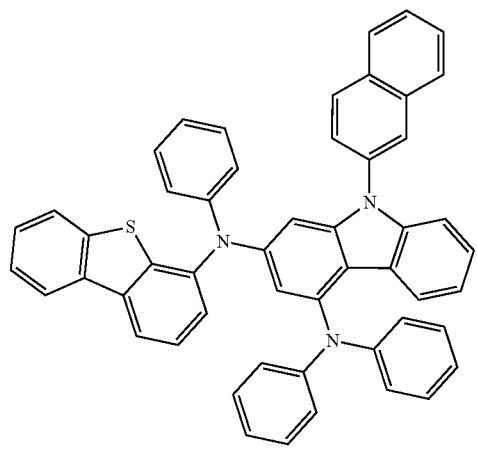
C-181

-continued
C-185
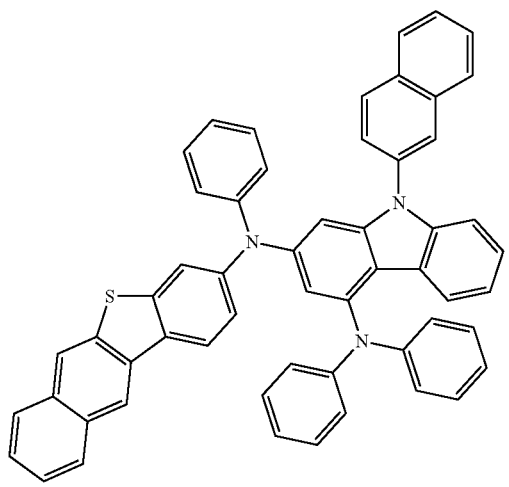
C-186
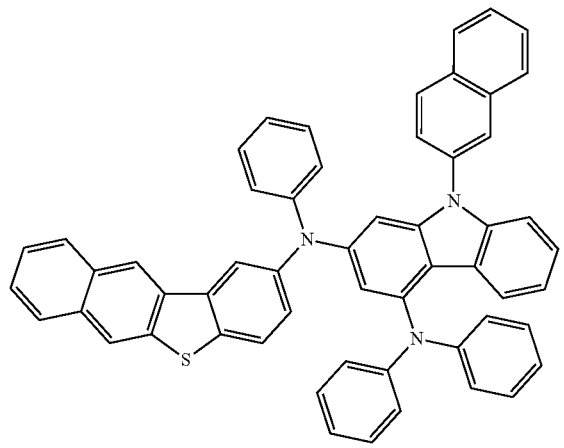
C-187
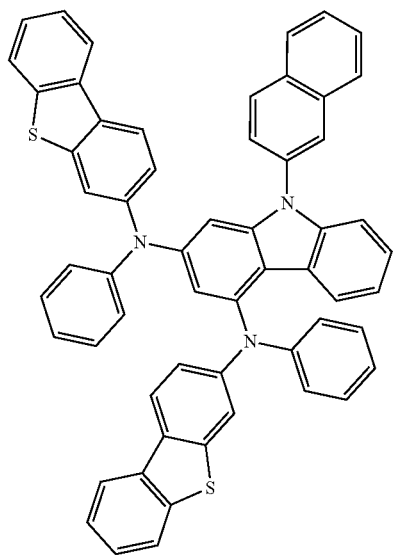
-continued
C-188
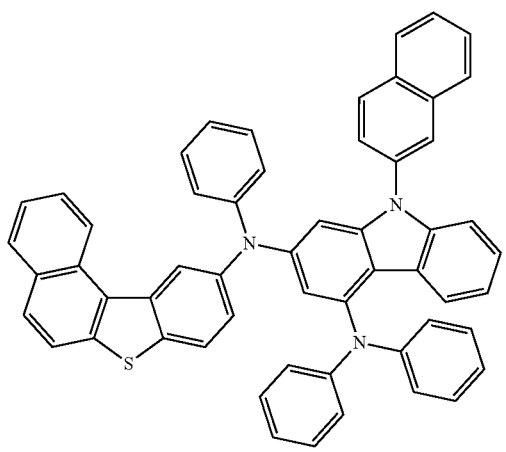
C-189
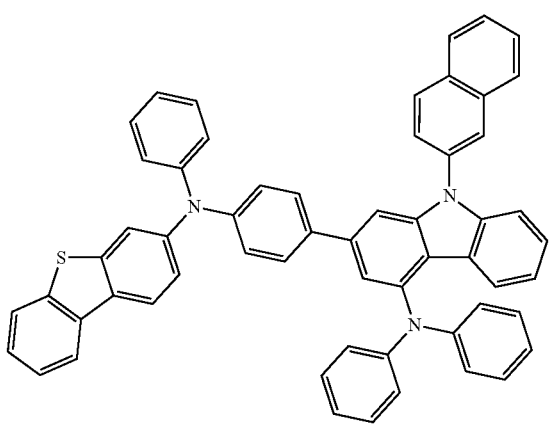
C-190
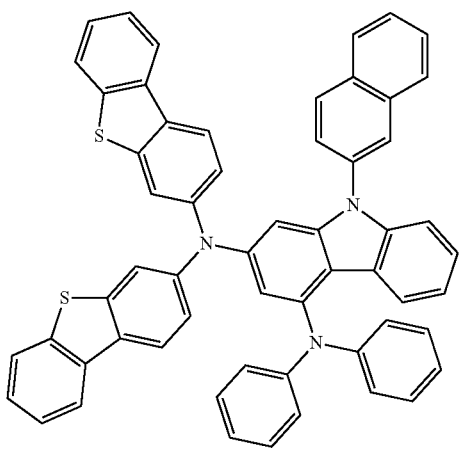

C-191
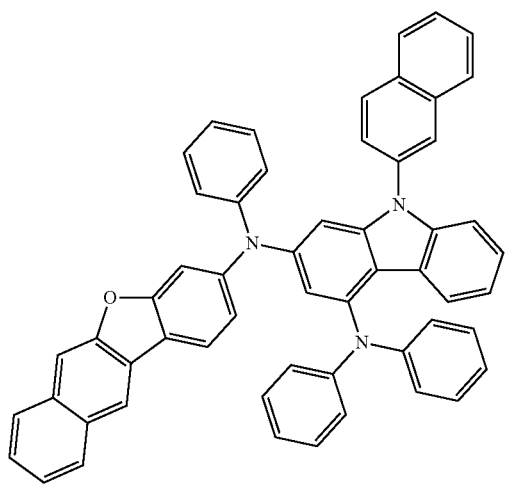
C-192
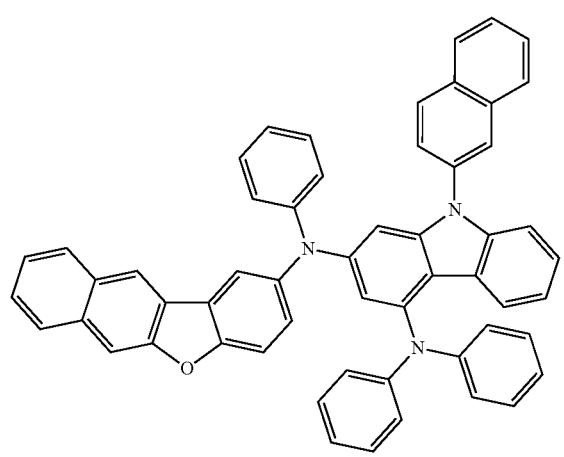
C-193
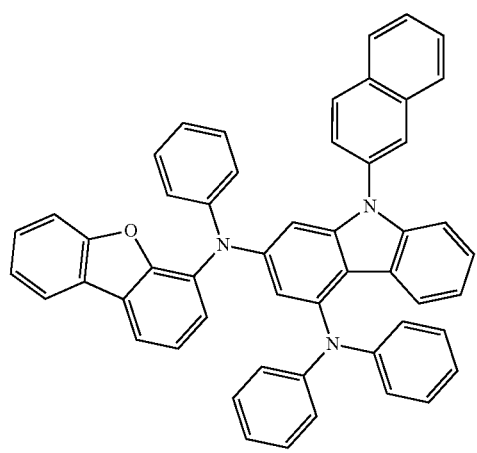
C-194
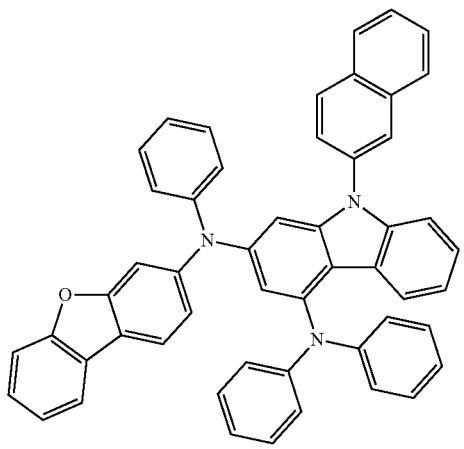
C-195
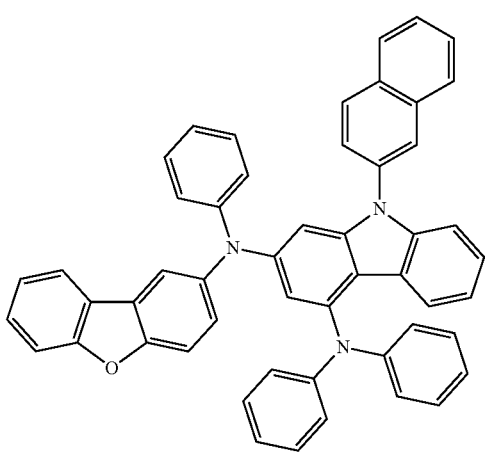
C-196
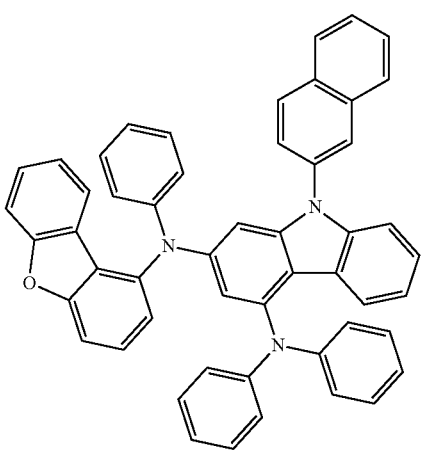

C-197
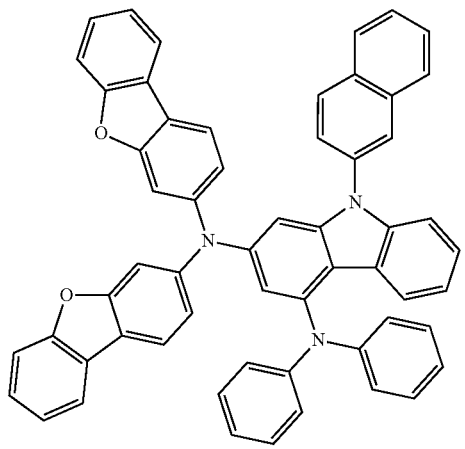
C-200
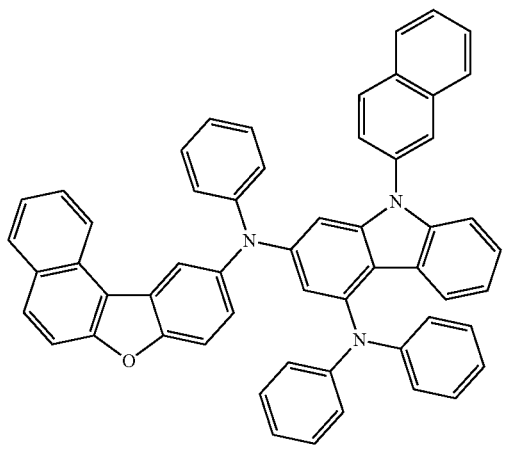
C-198
C-201
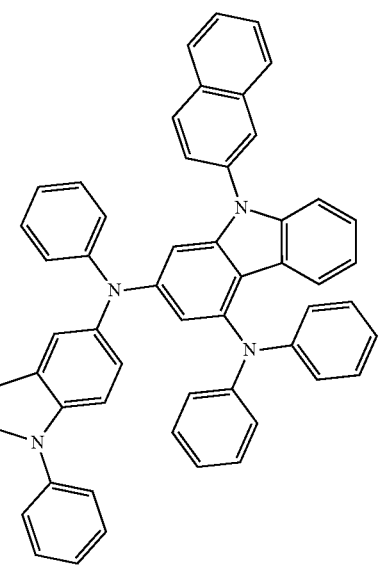
C-199
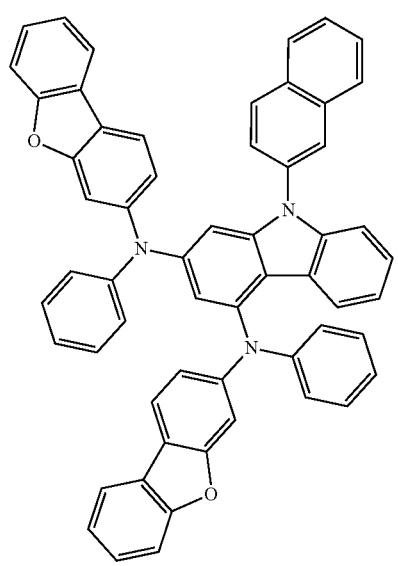
C-202
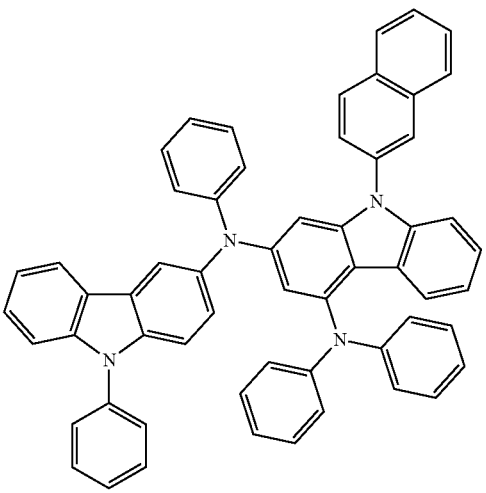

C-203
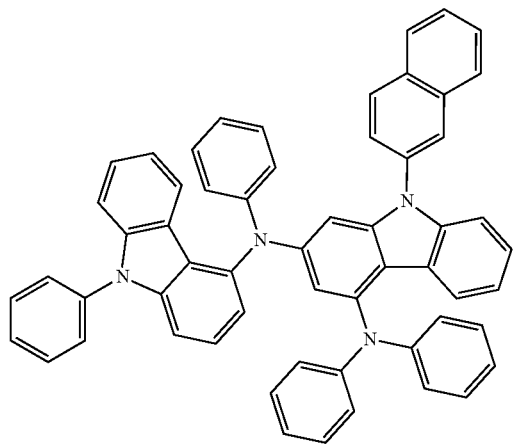
C-206
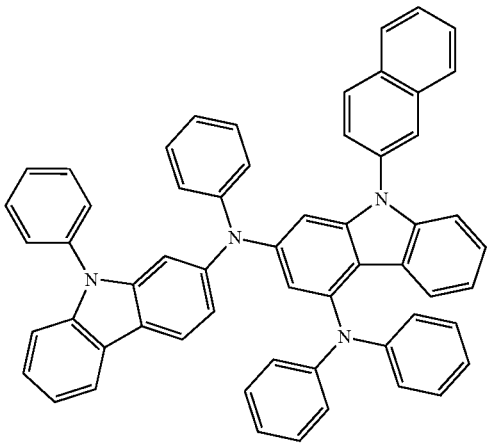
C-204
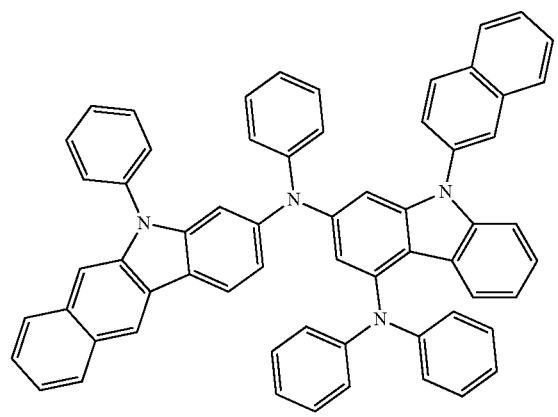
C-207
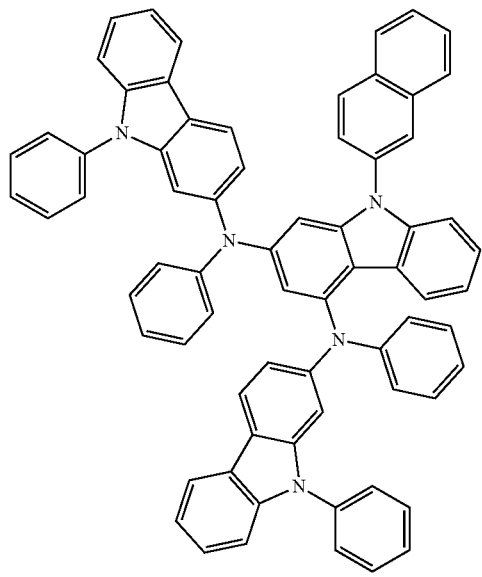
C-205
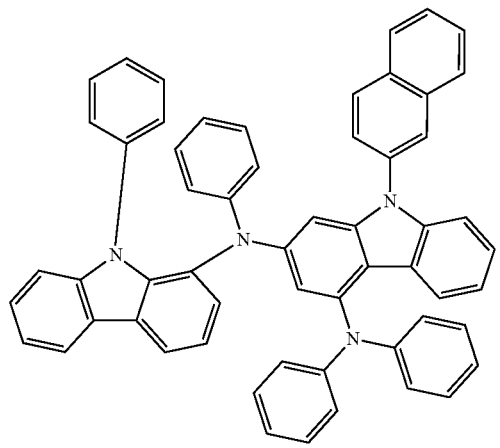
C-208
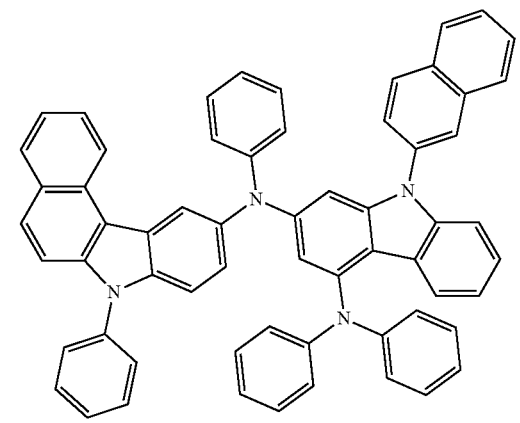

C-209
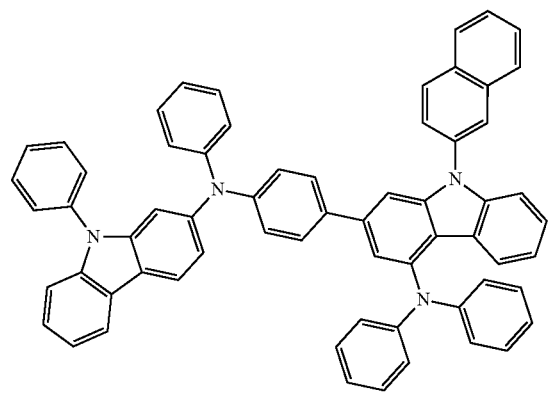
C-210
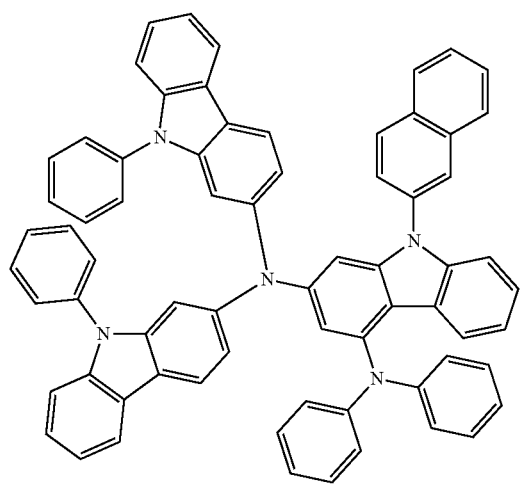
C-211
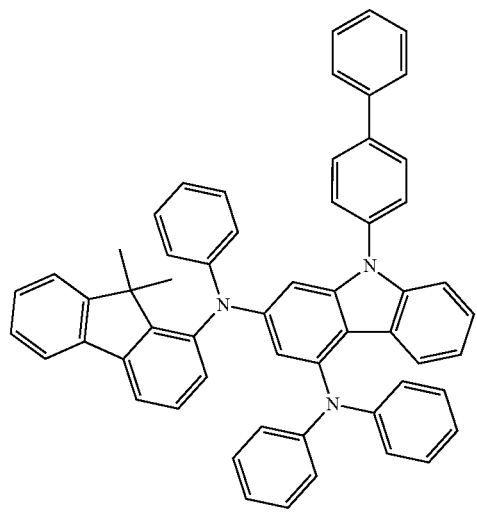
C-212
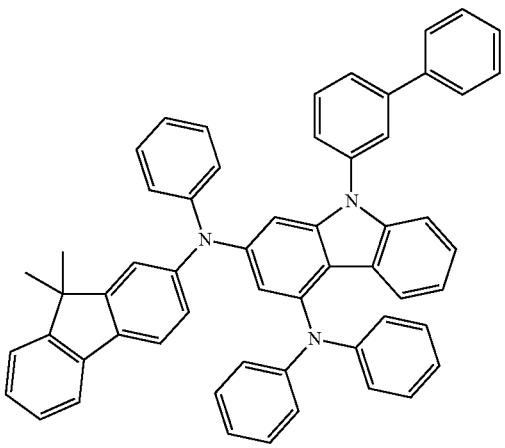
C-213
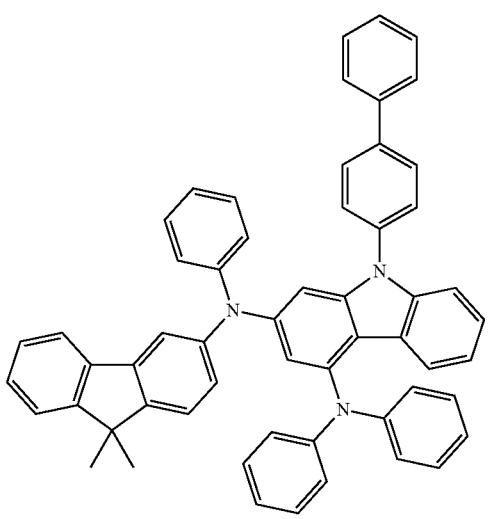
C-214
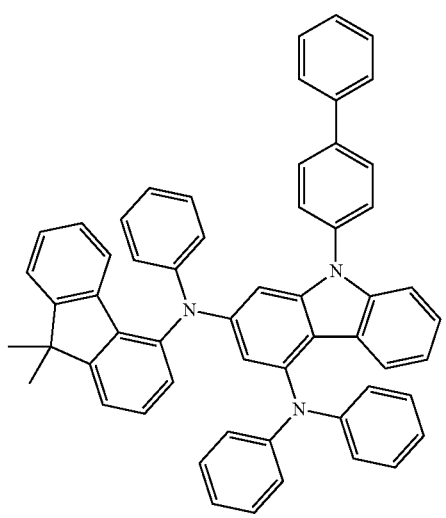

-continued
C-215
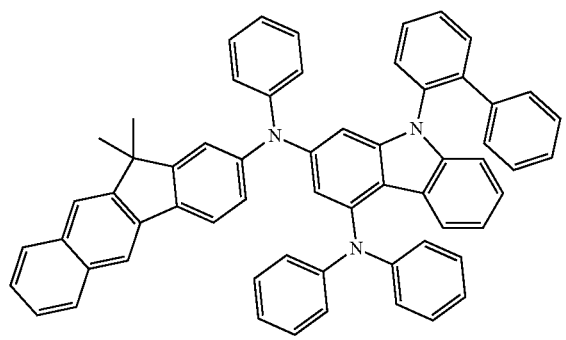
C-216
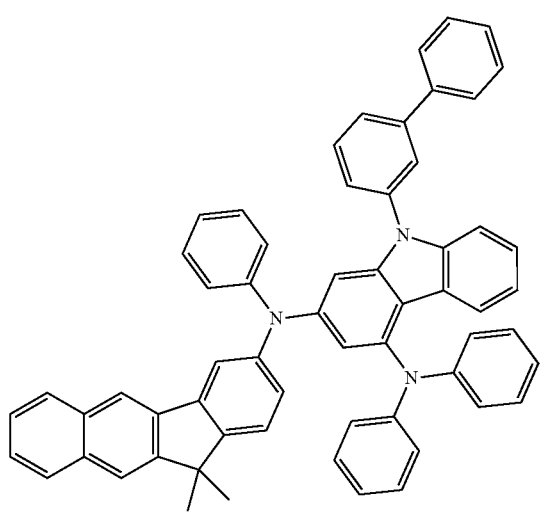
C-217
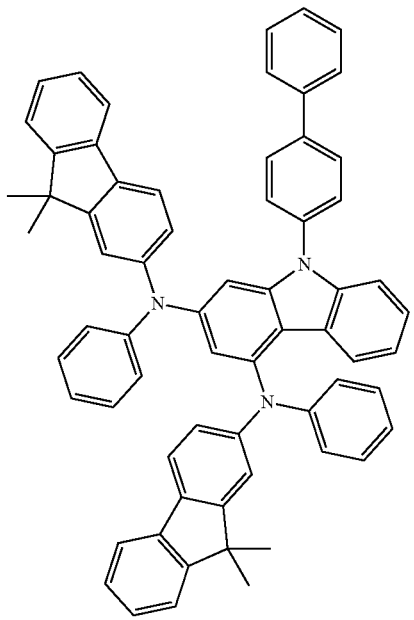
-continued
C-218
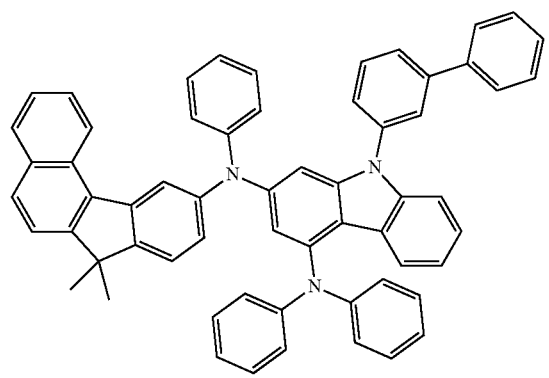
C-219
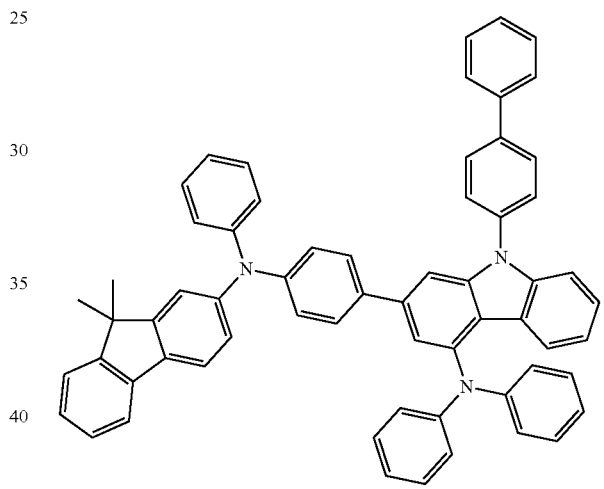
C-220
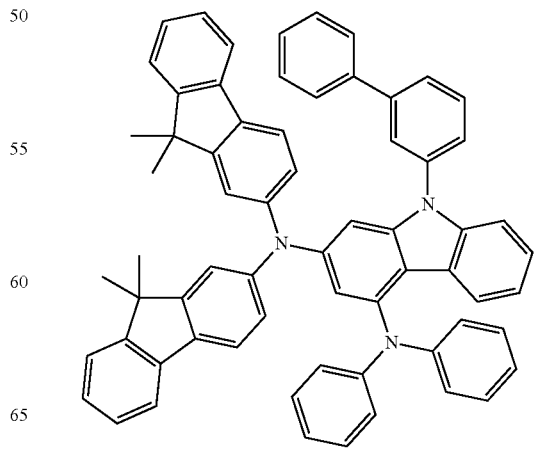

C-221
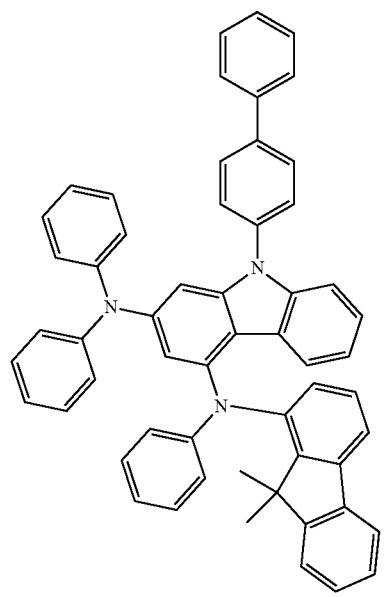
C-223
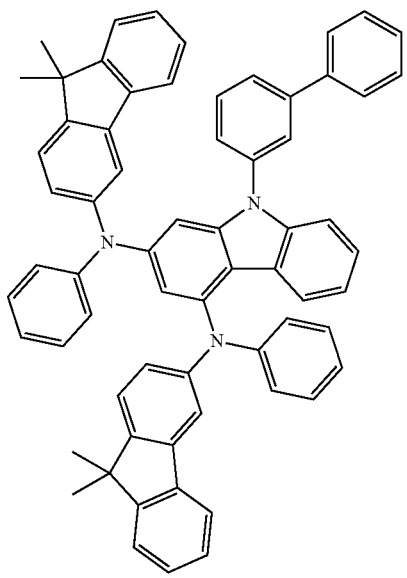
C-222
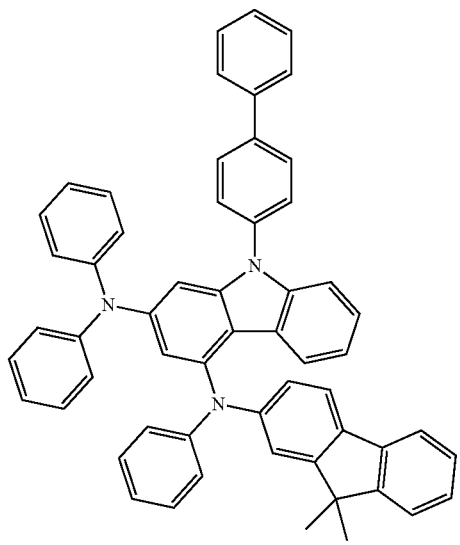
C-224
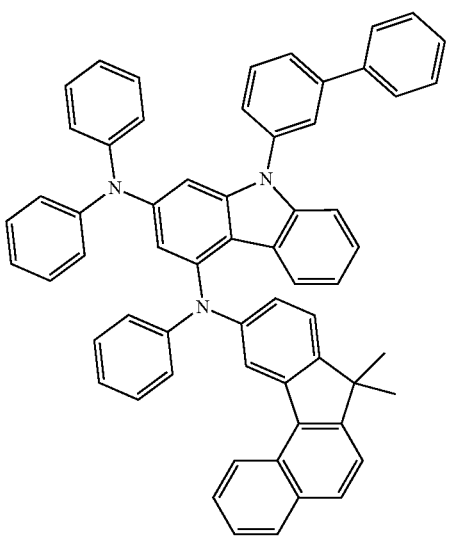

C-225
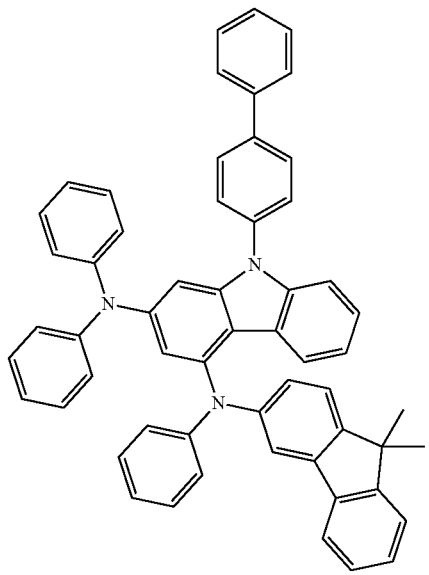
C-227
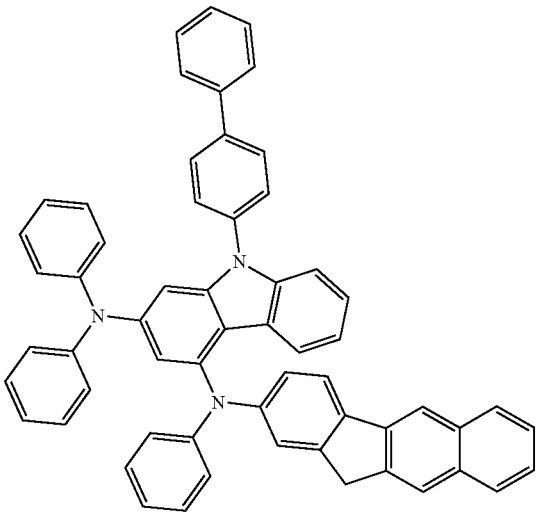
C-226
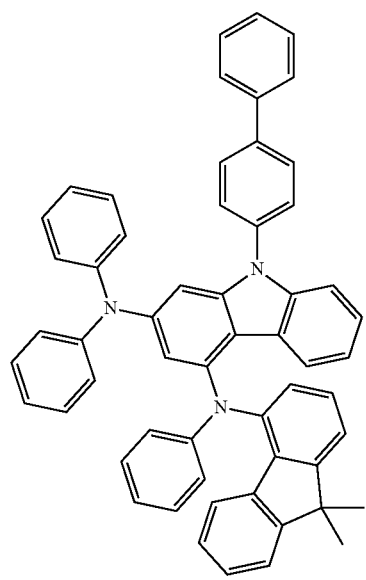
C-228
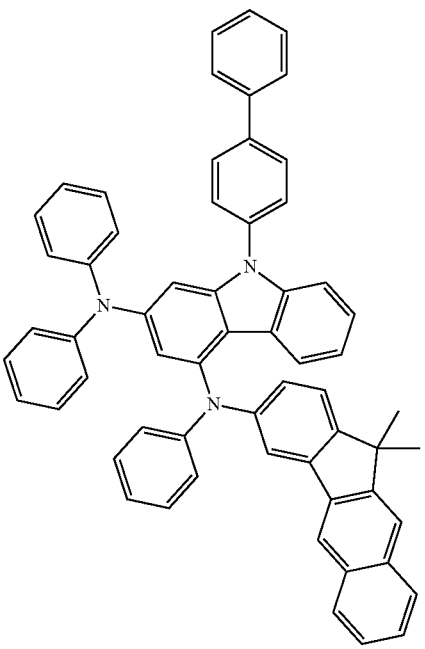

C-229
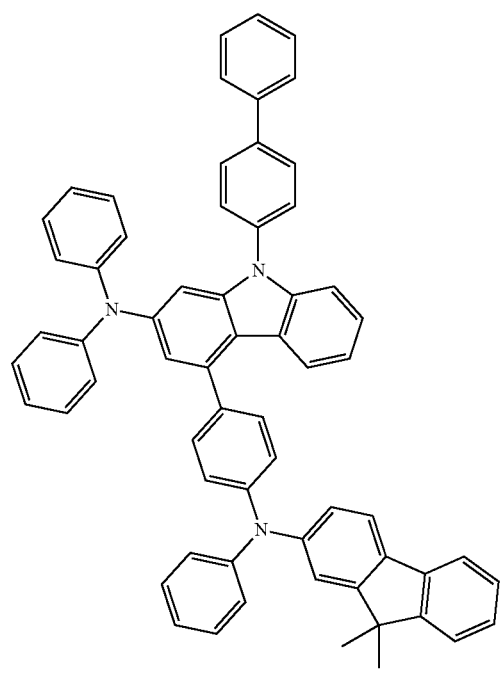
C-231
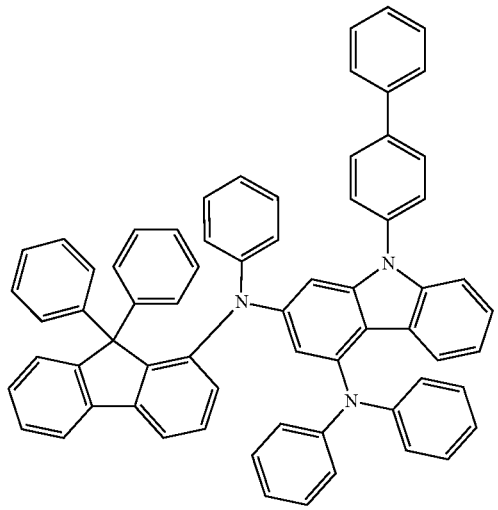
C-232
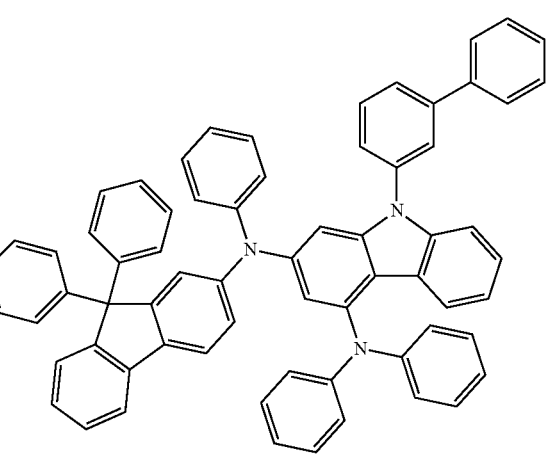
C-230
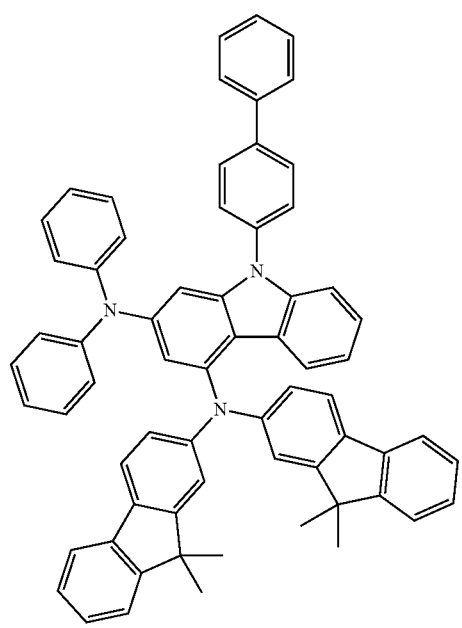
C-233
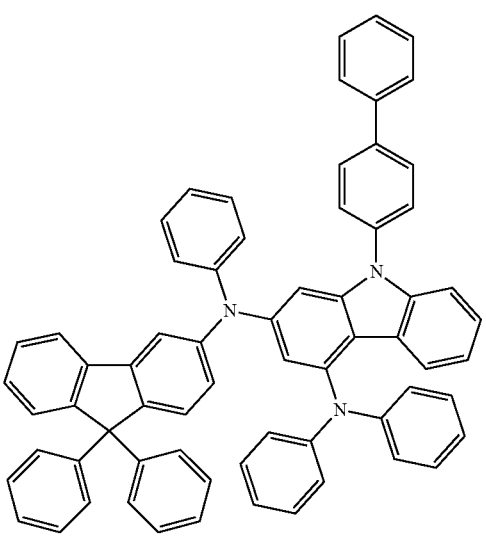

C-234
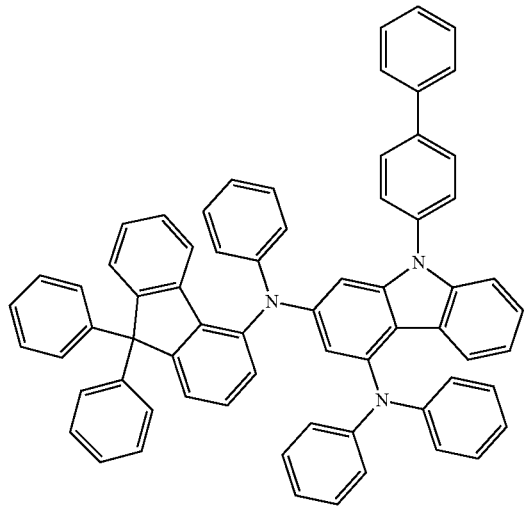
C-235
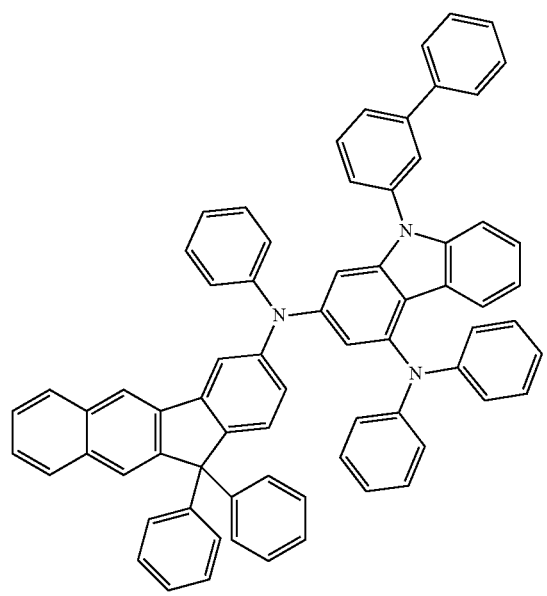
C-236
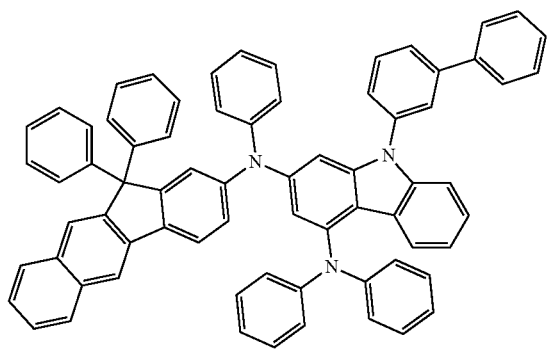
C-237
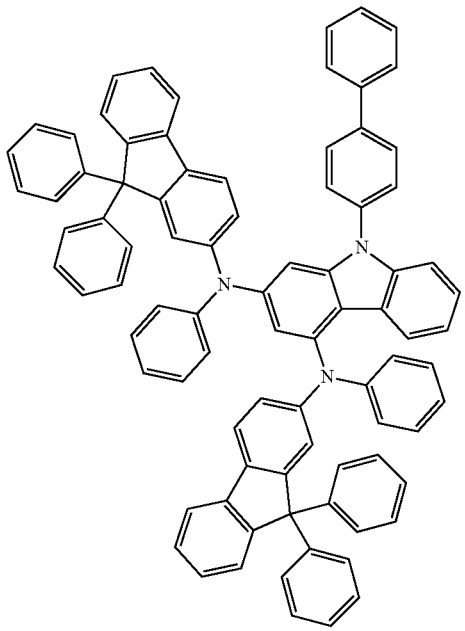
C-238
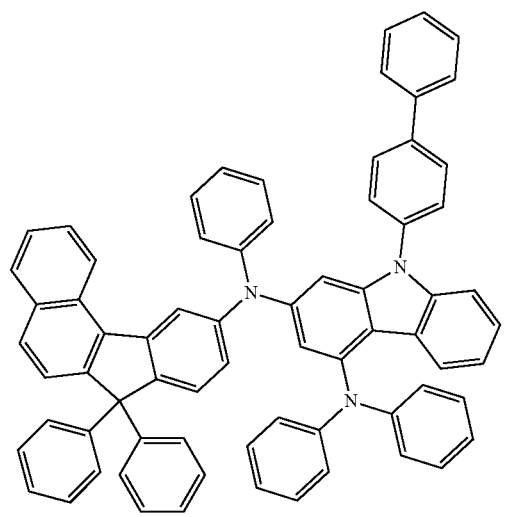
C-239
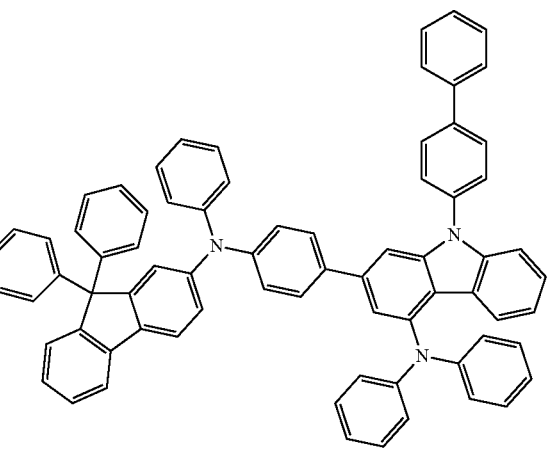

C-240
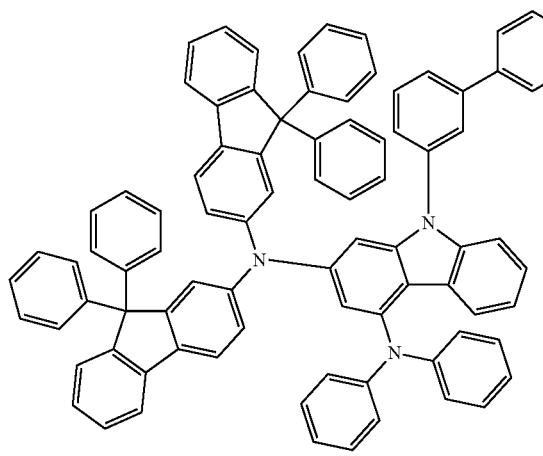
C-241
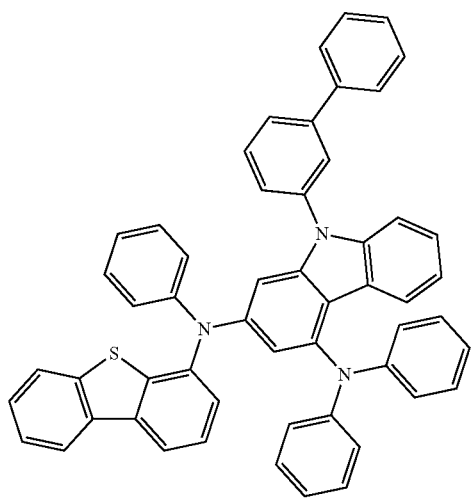
C-243
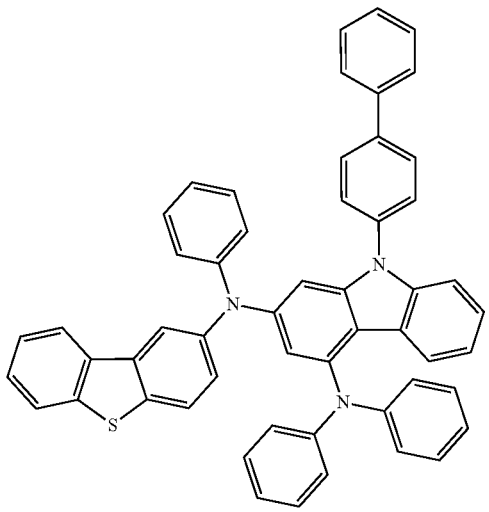
C-244
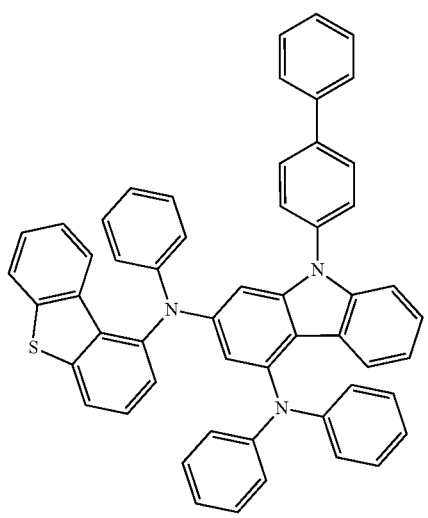
C-242
C-245
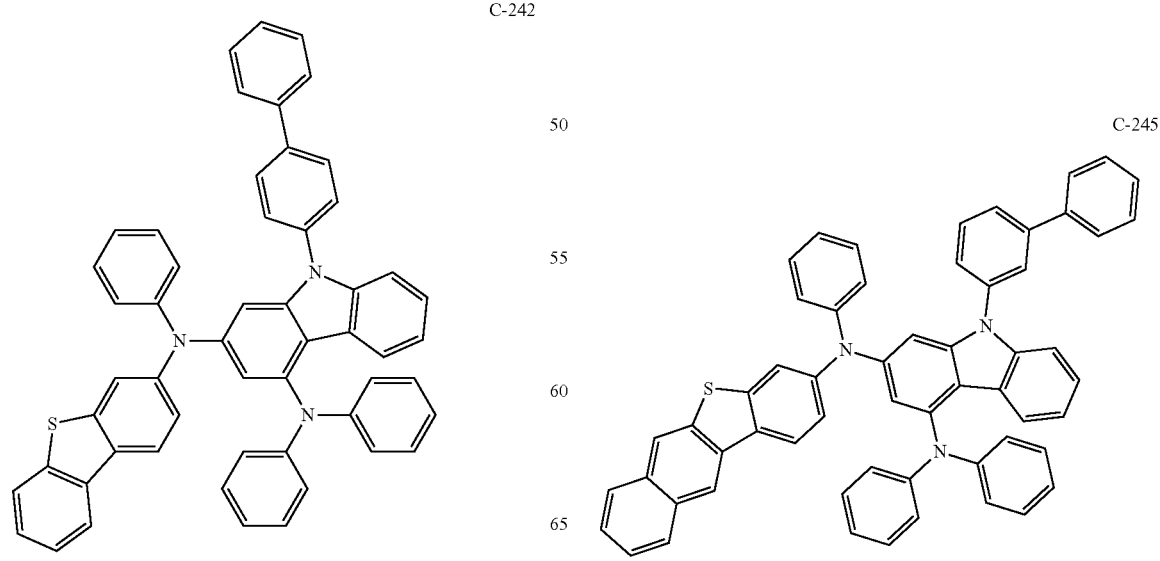

C-246
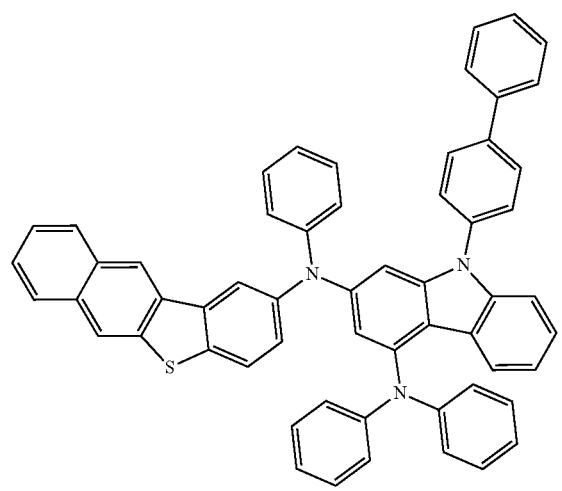
C-249
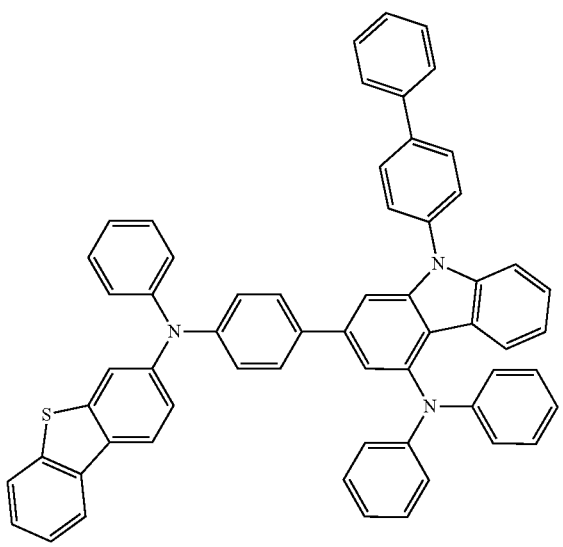
C-247
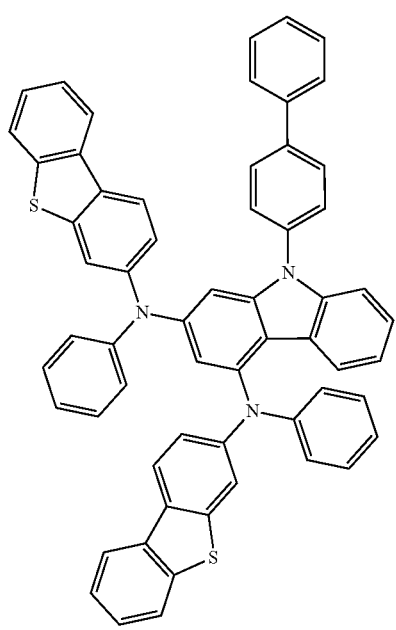
C-250
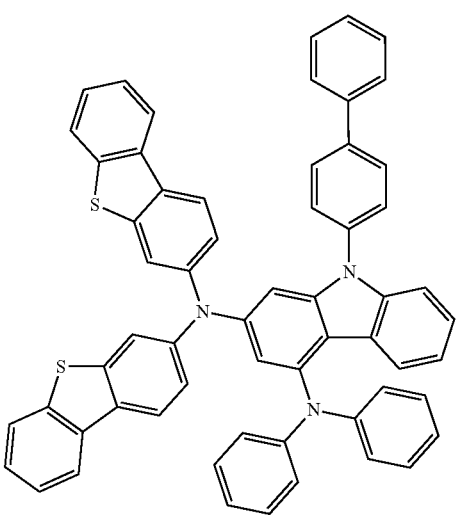
C-248
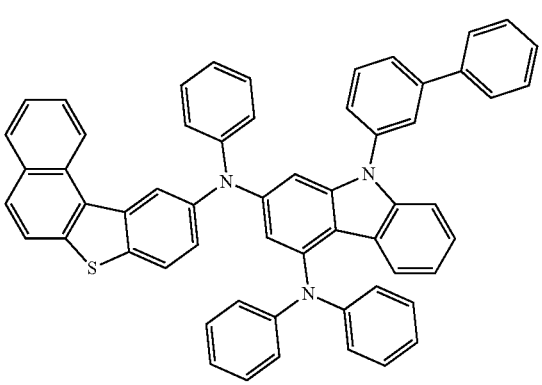
C-251
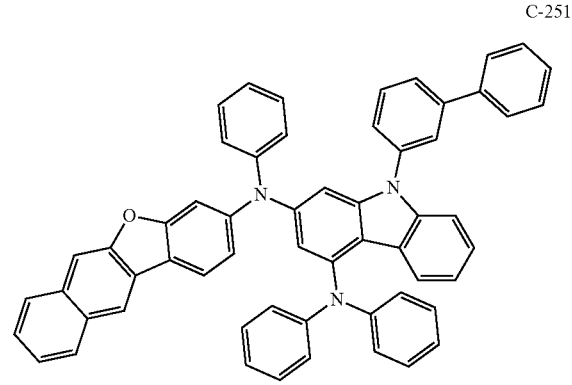

C-252
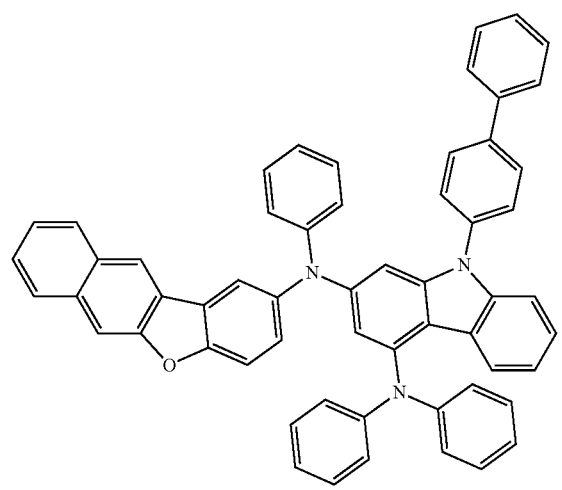
C-253
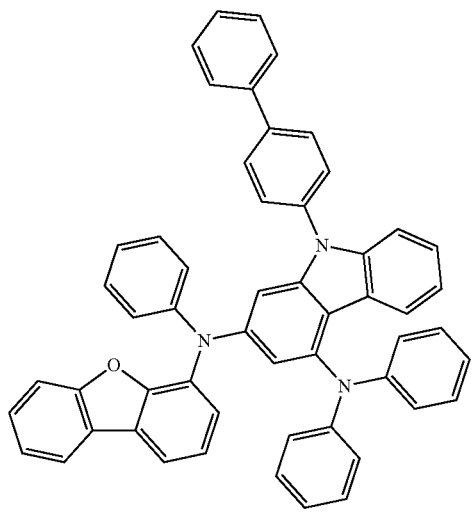
C-254
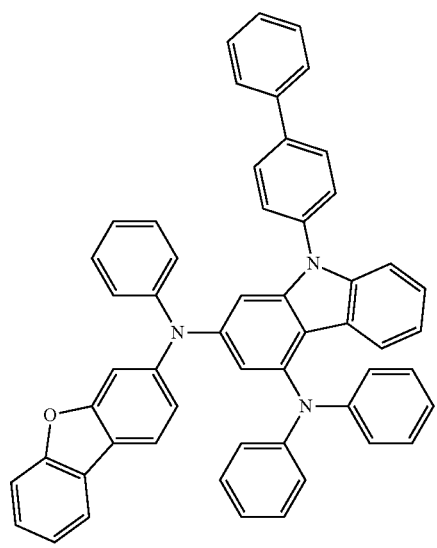
C-255
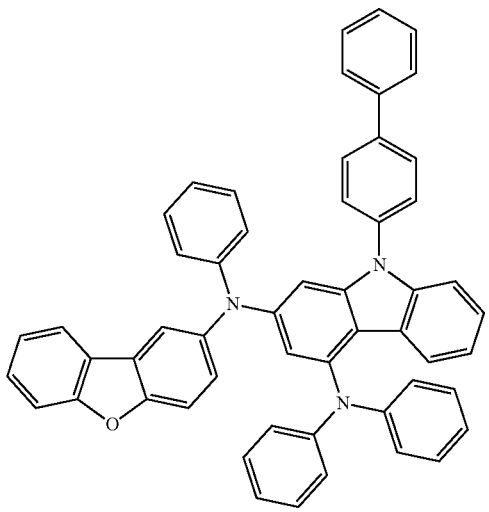
C-256
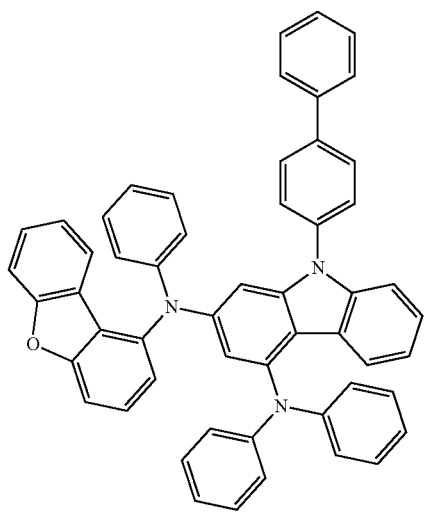
C-257
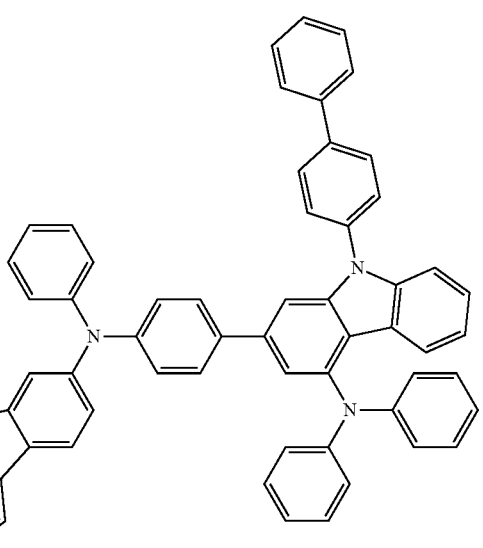

C-258
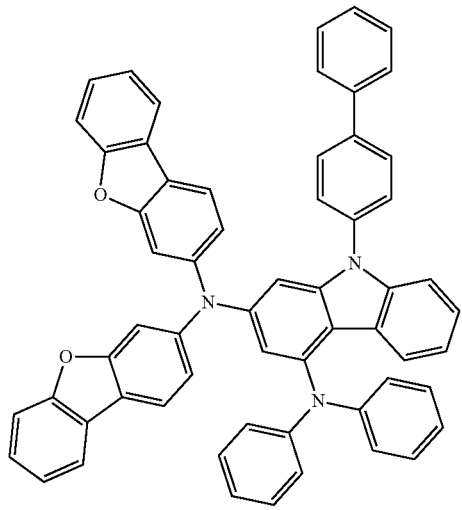
C-261
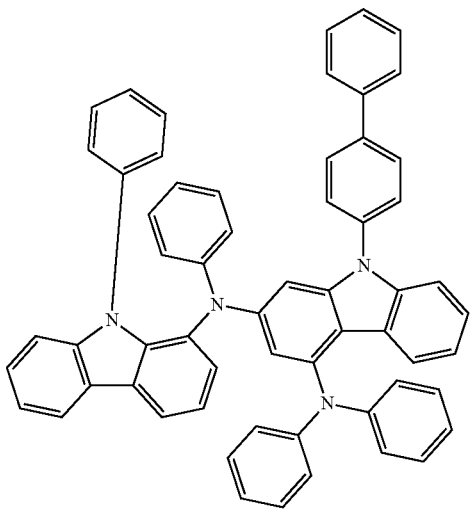
C-259
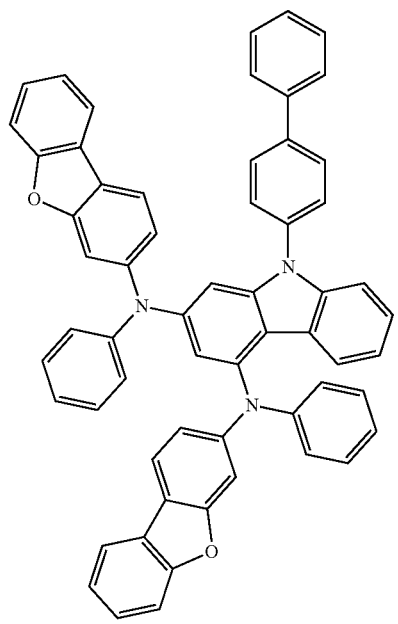
C-262
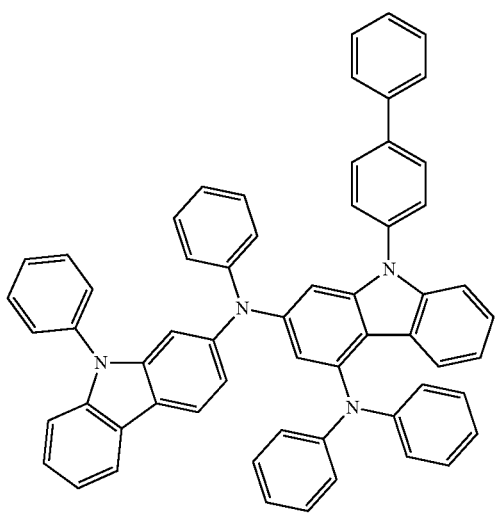
C-260
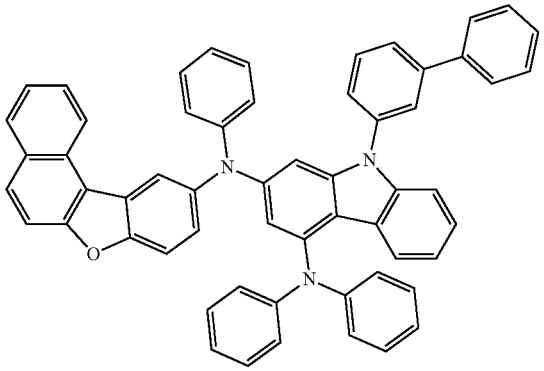
C-263
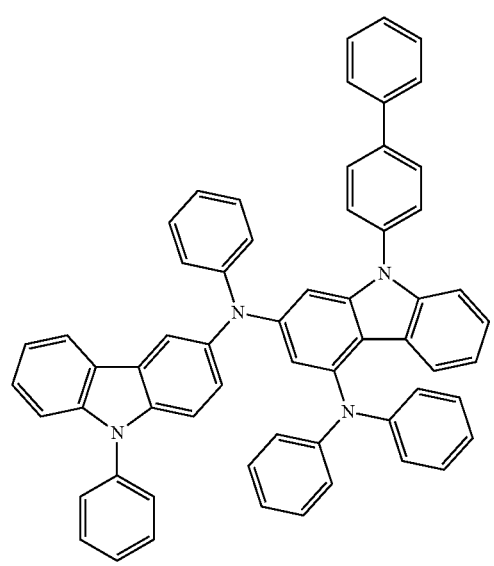

-continued
C-264
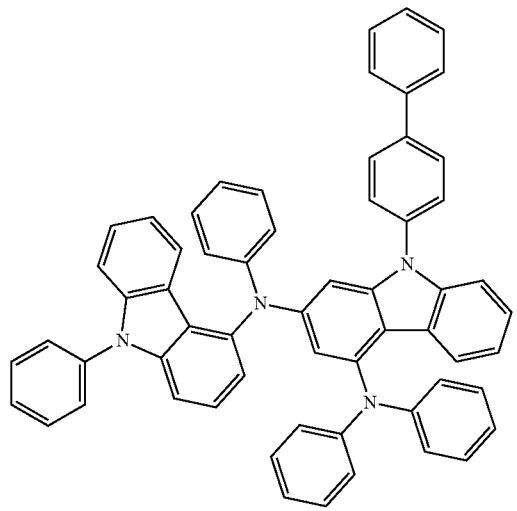
C-265
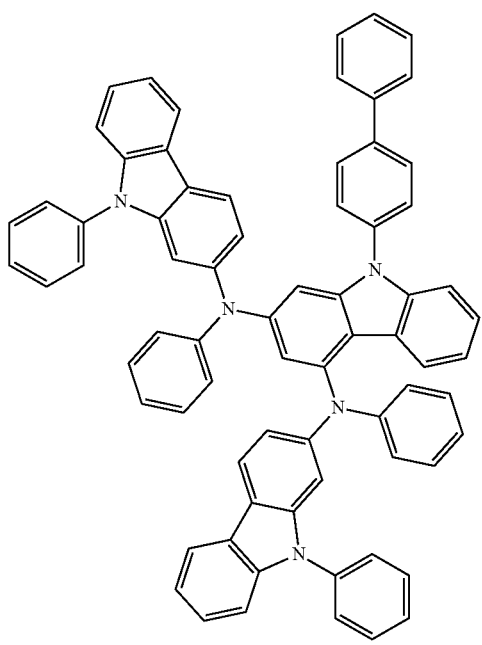
C-266
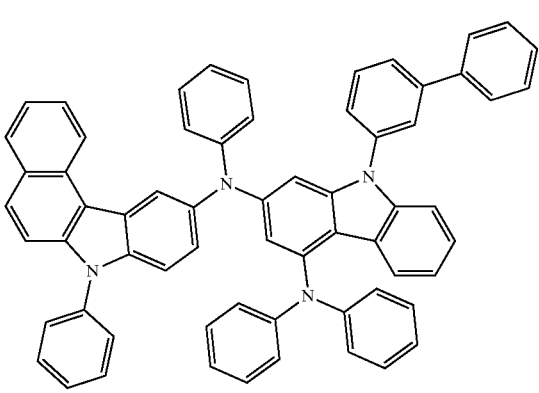
-continued
C-267
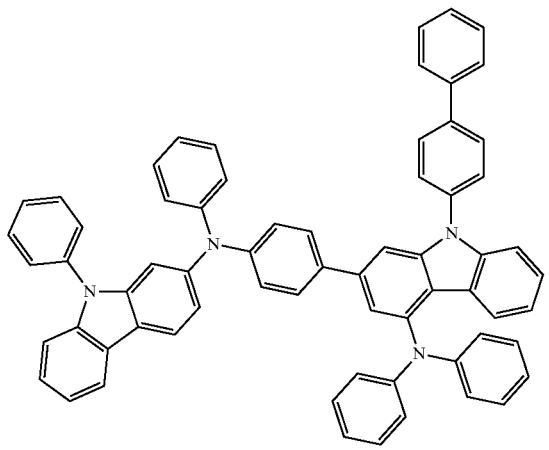
C-268
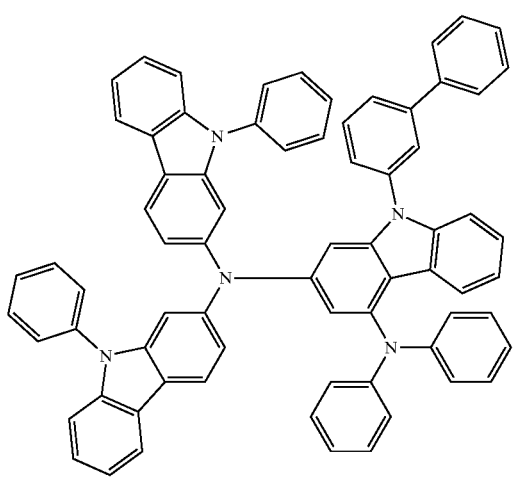
C-269
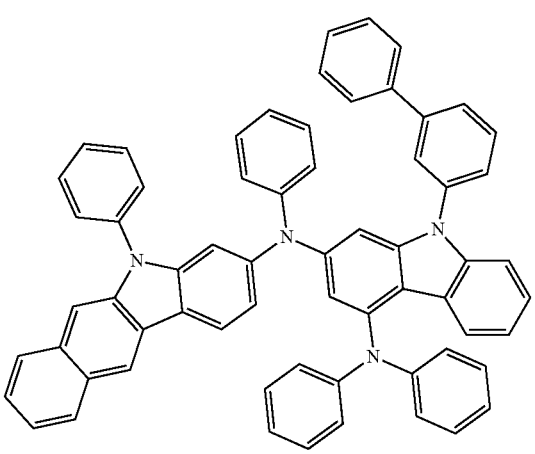

C-270
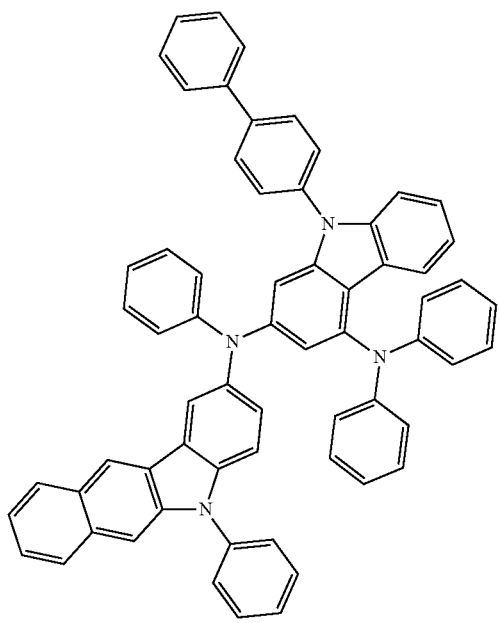
C-273
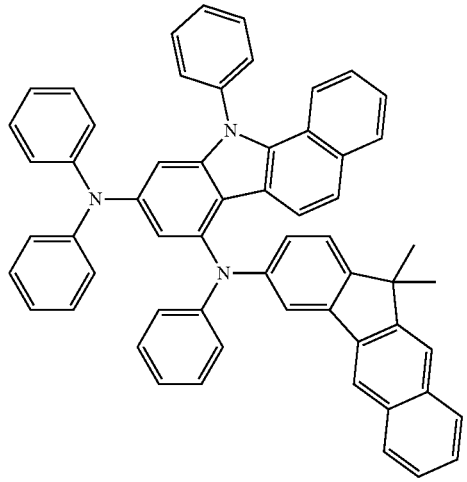
C-271
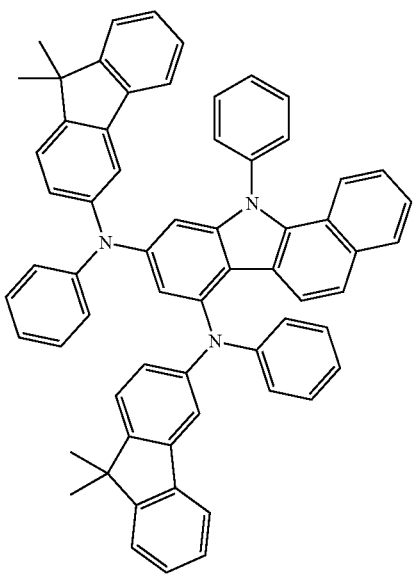
C-274
C-272
C-275
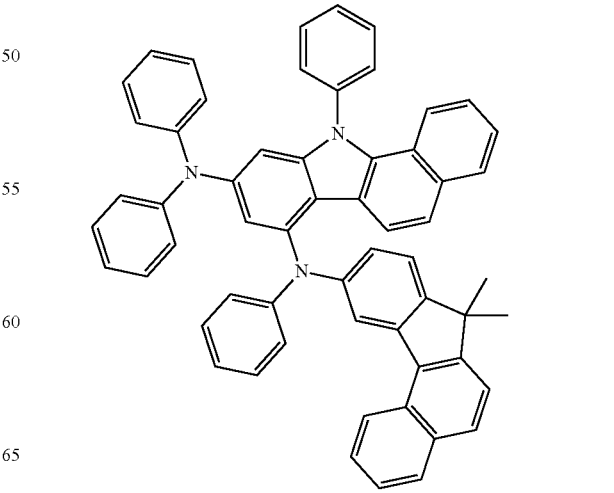

-continued
C-276
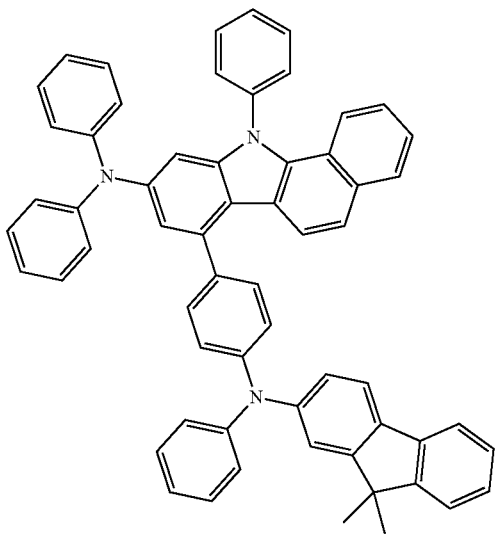
C-277
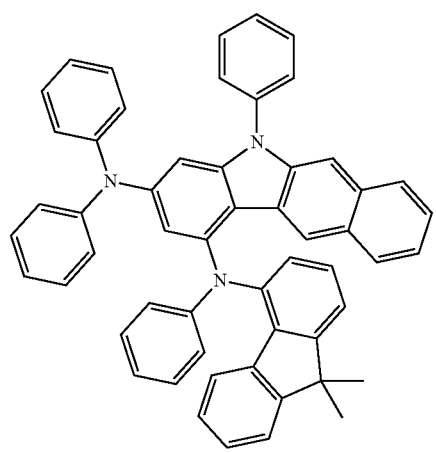
C-278
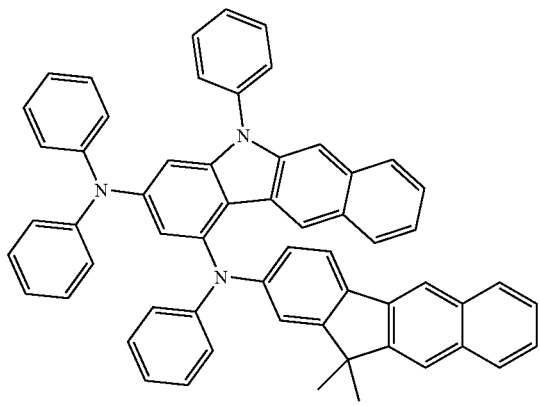
C-279
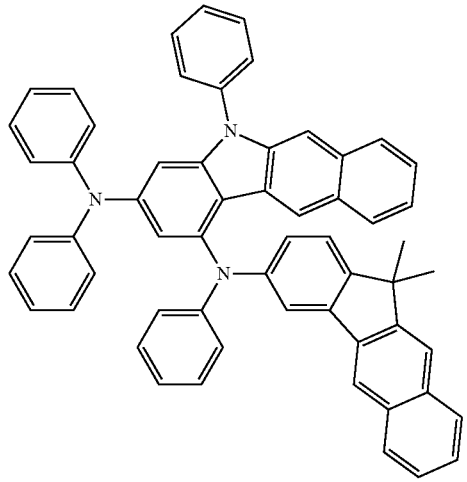
C-280
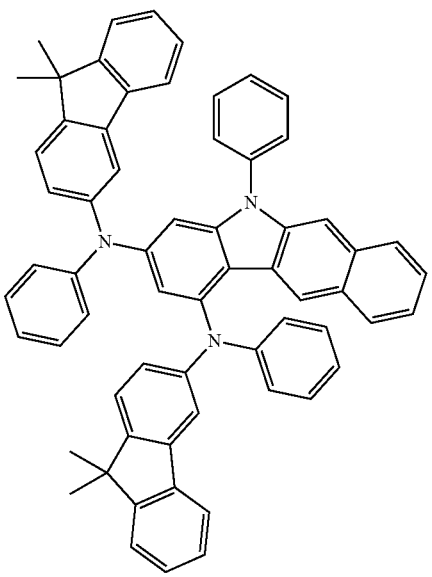
C-281
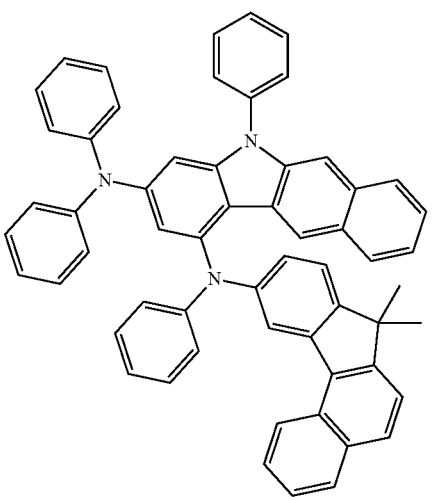

C-282
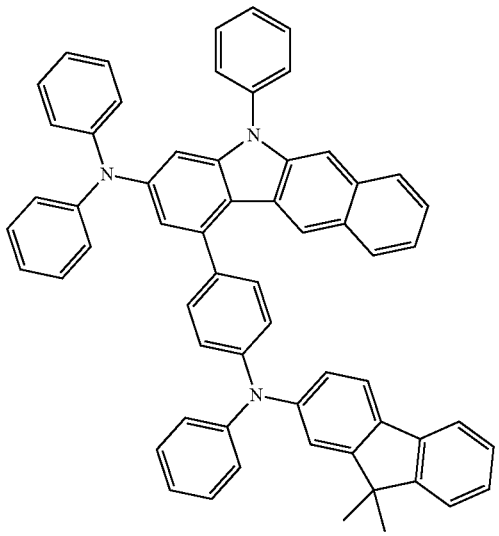
C-283
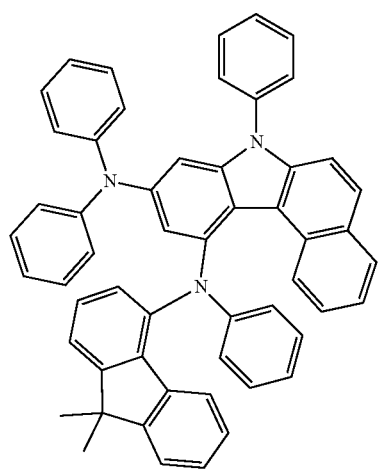
C-284
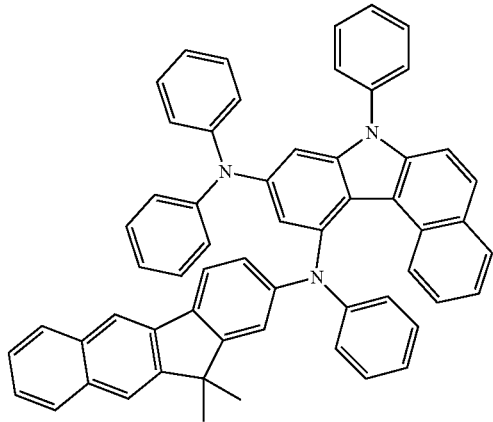
C-285
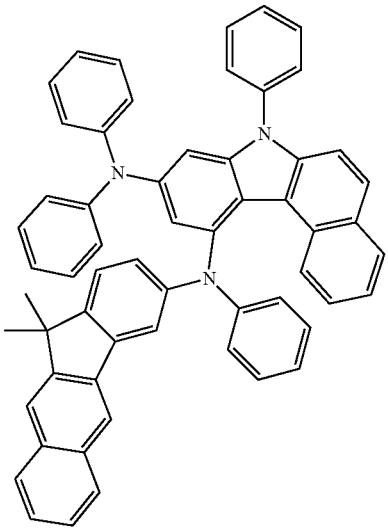
C-286
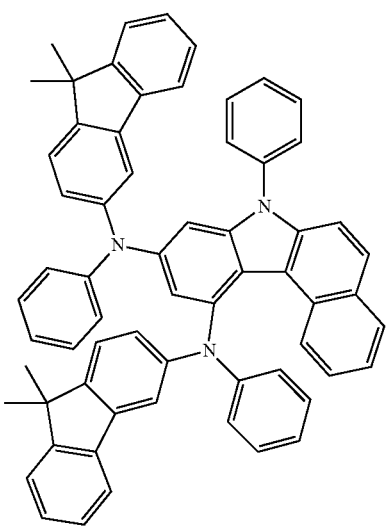
C-287
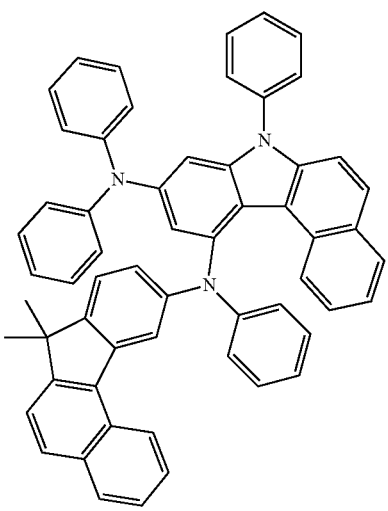

-continued
C-288
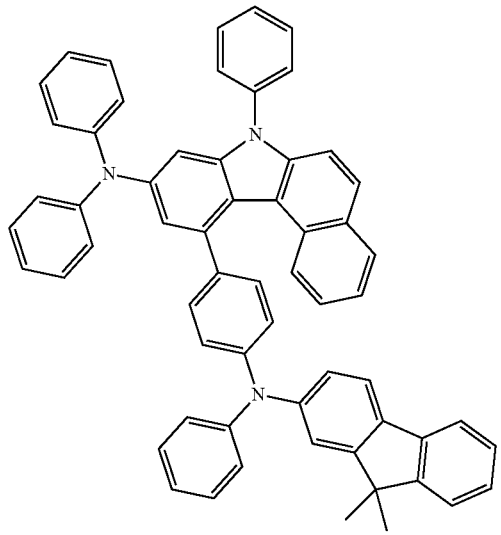
C-289
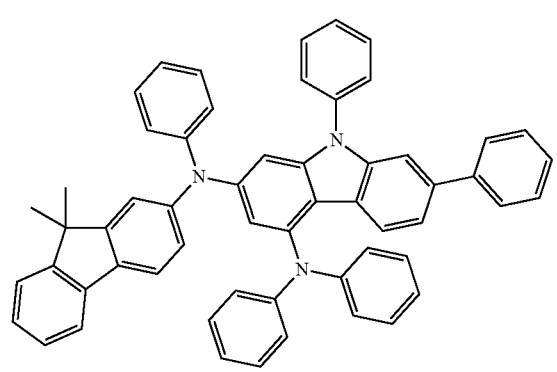
C-290
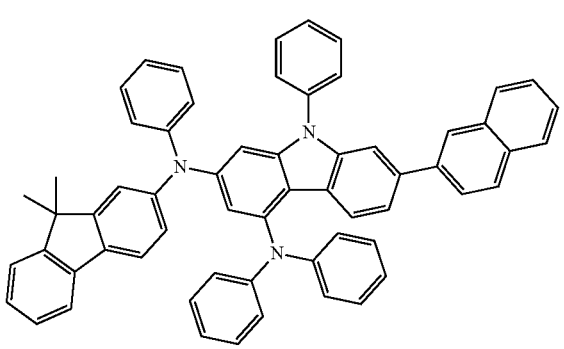
C-291
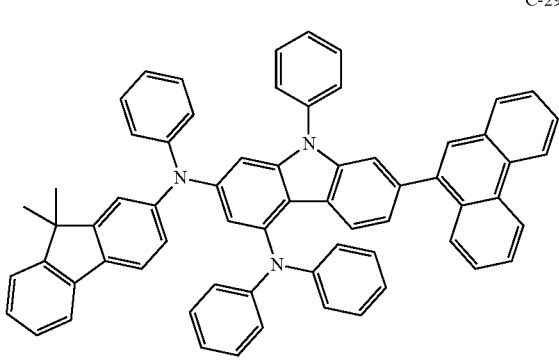
-continued
C-292
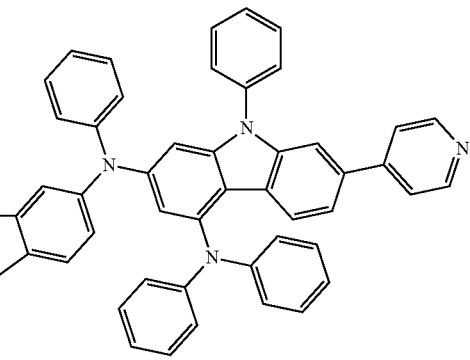
C-293
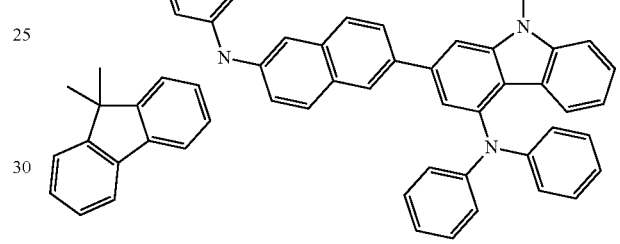
C-294
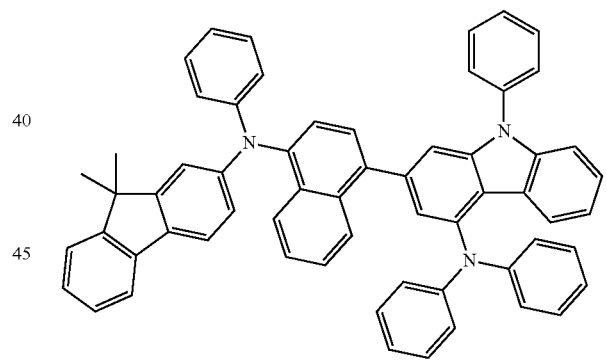
C-295
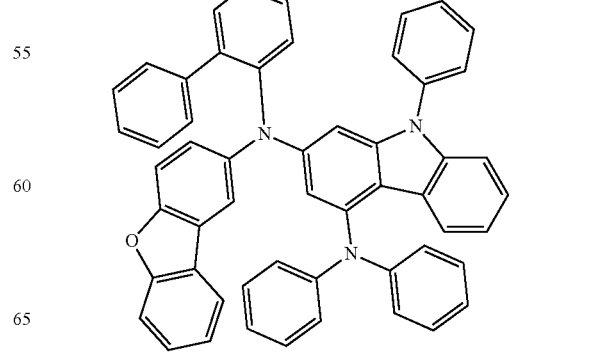

C-296
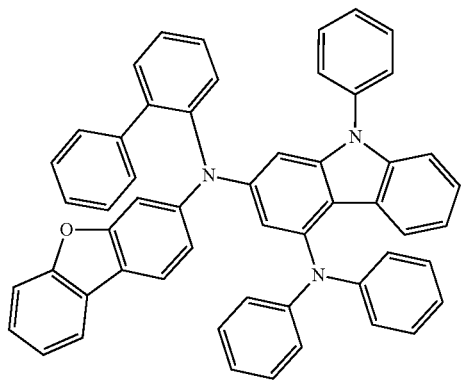
C-297
C-300
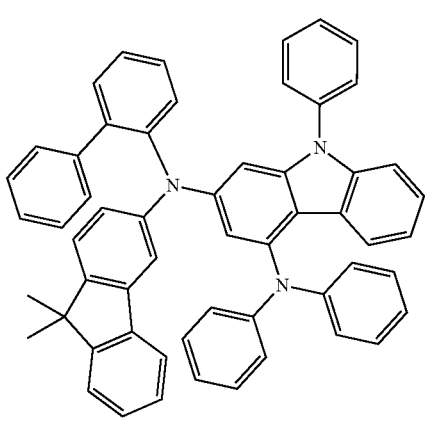
C-301
C-298
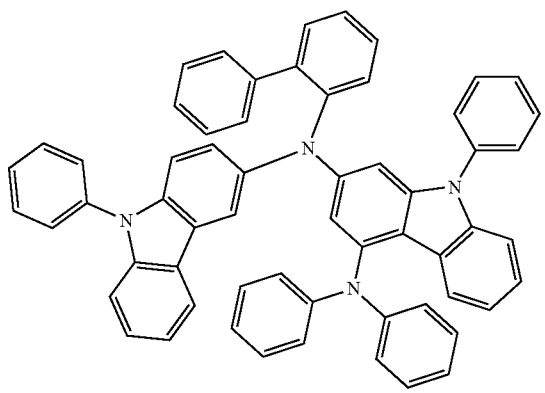
C-299
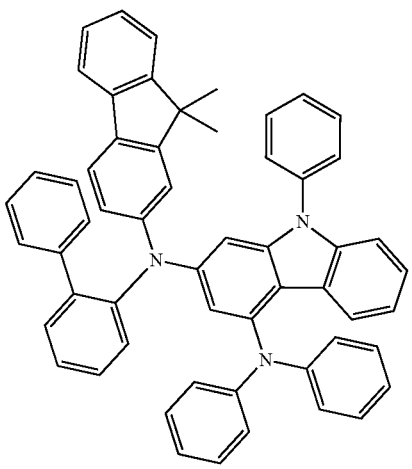
C-302
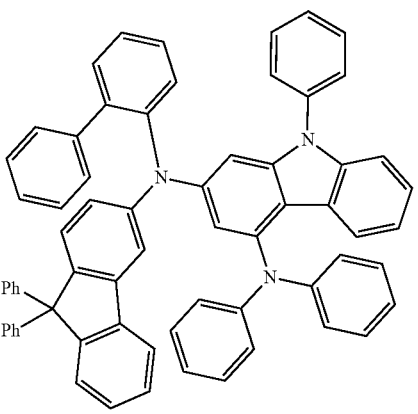

-continued
C-303
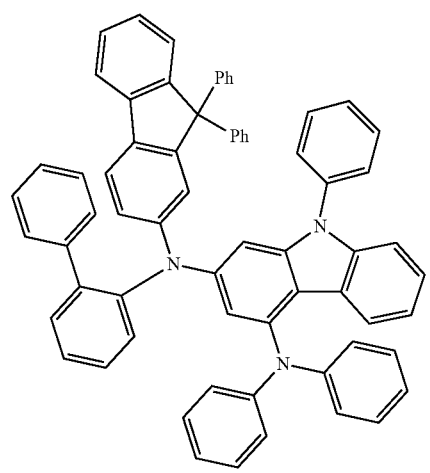
C-304
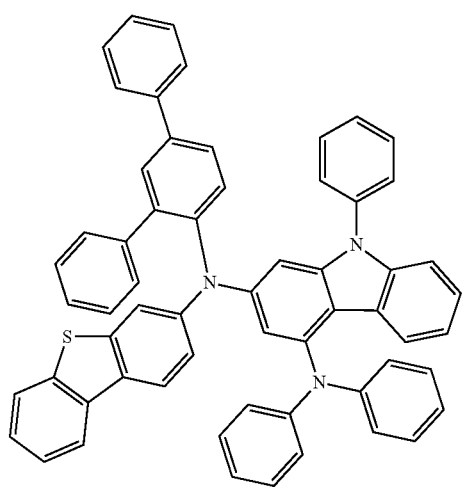
C-305
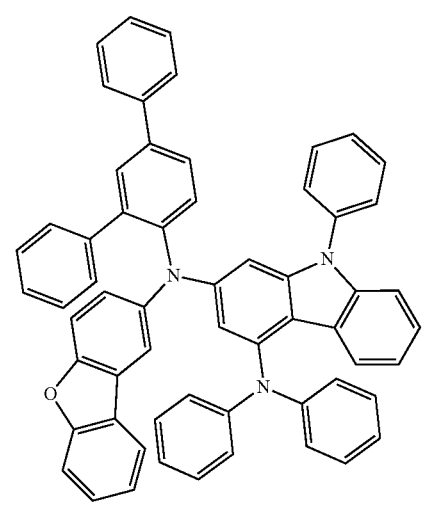
C-306
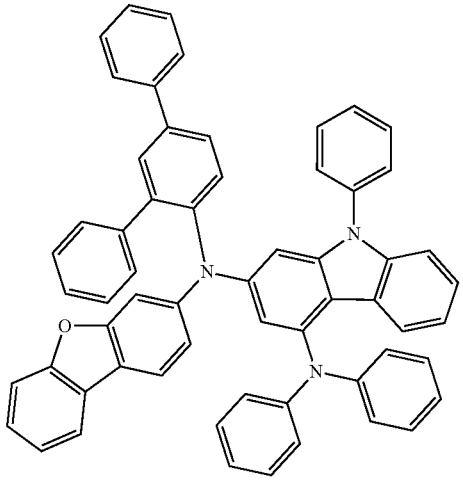
C-307
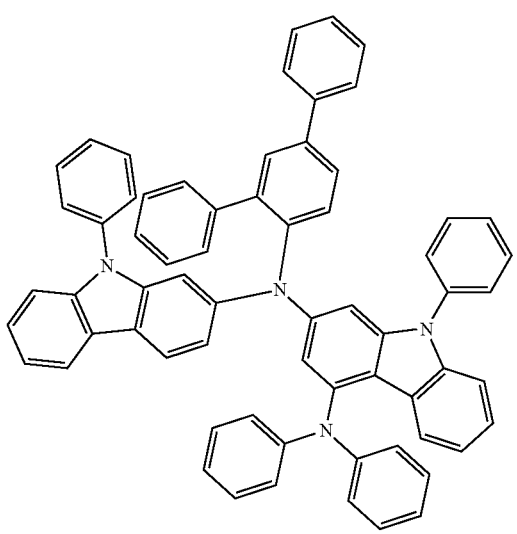
C-308
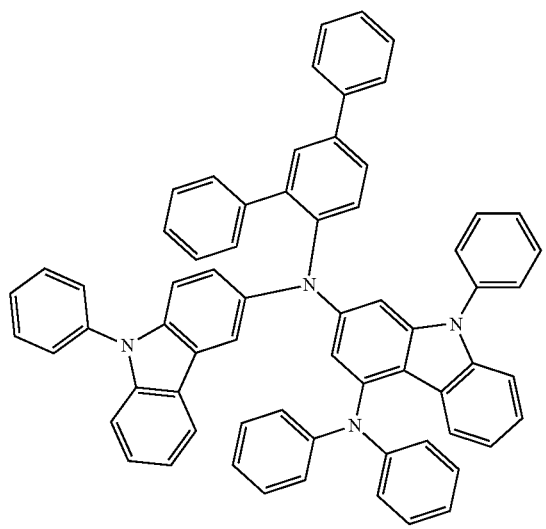

C-309
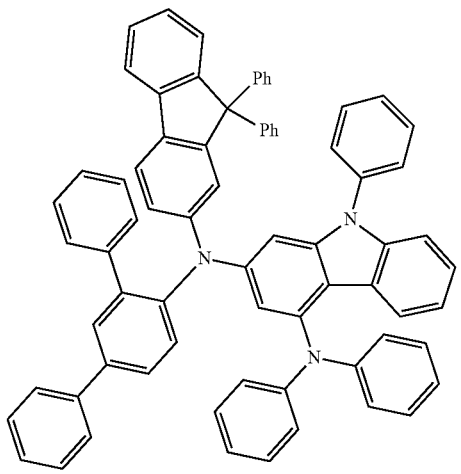
C-312
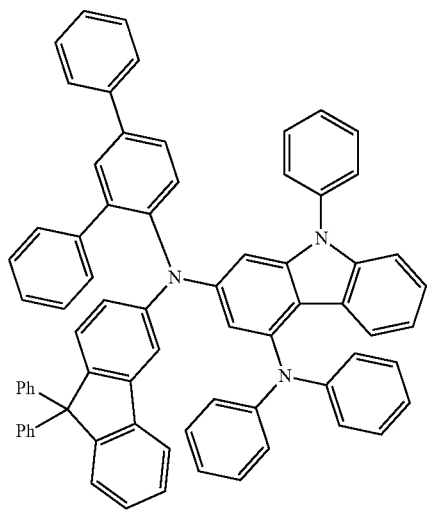
C-310
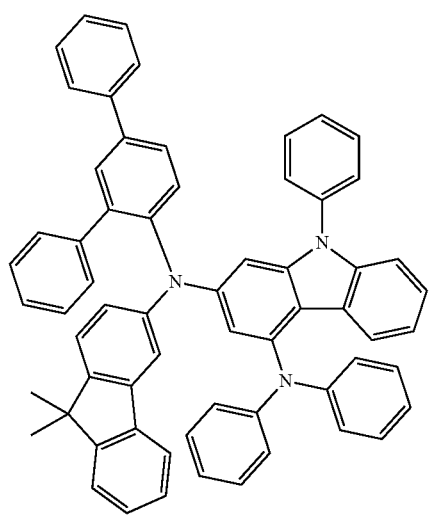
C-313
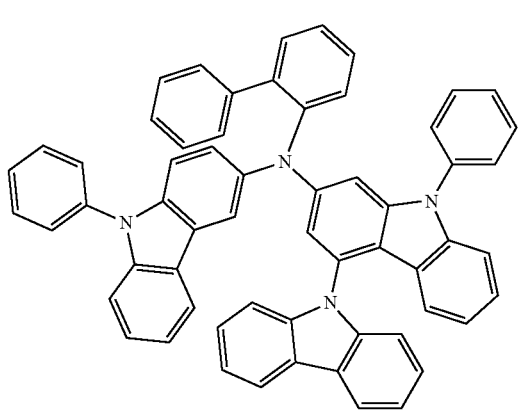
C-311
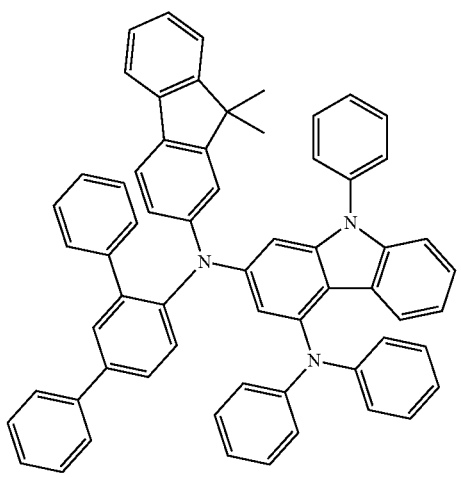
C-314
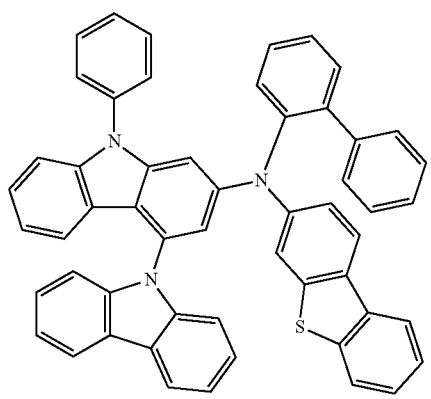

C-315
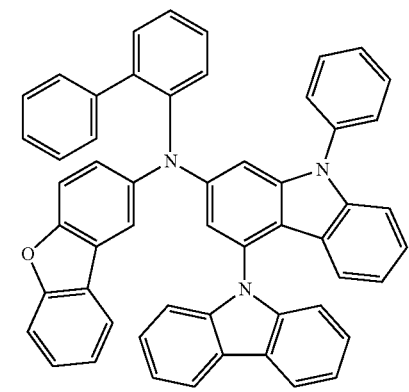
C-316
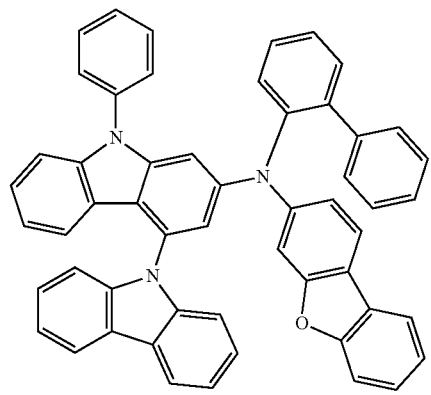
C-317
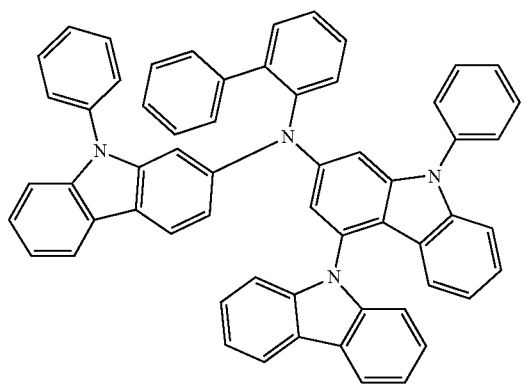
C-318
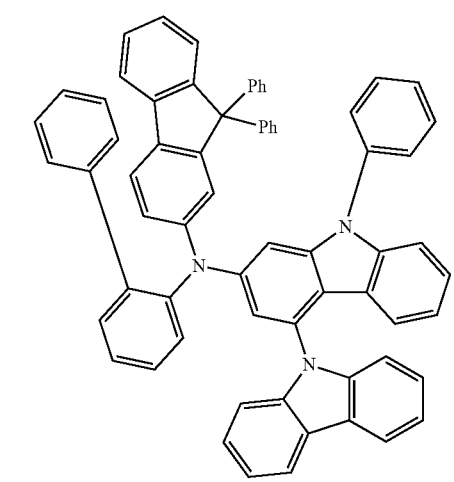
C-319
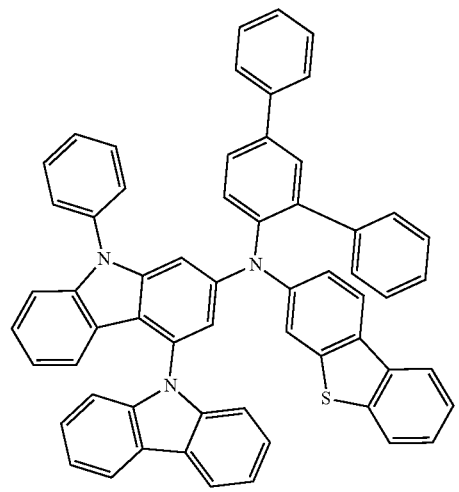
C-320
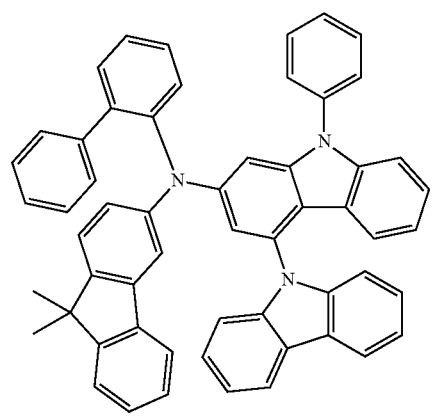
C-321
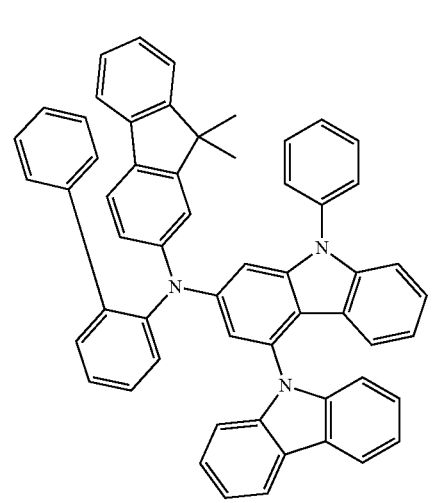

C-322
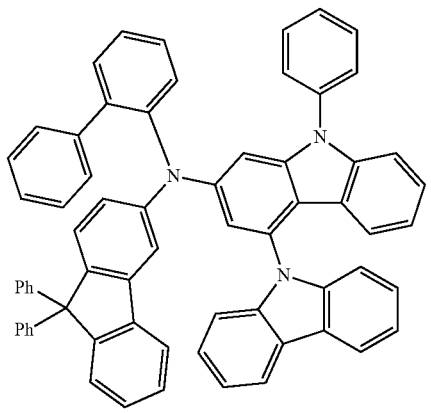
C-325
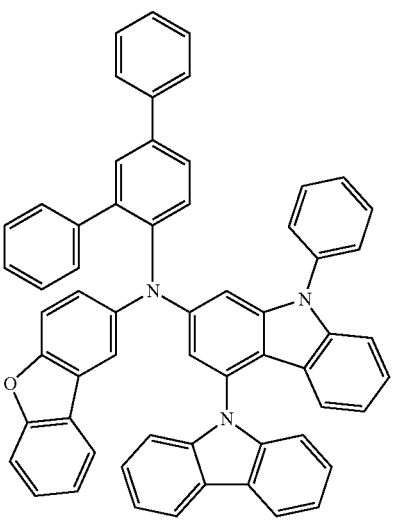
C-323
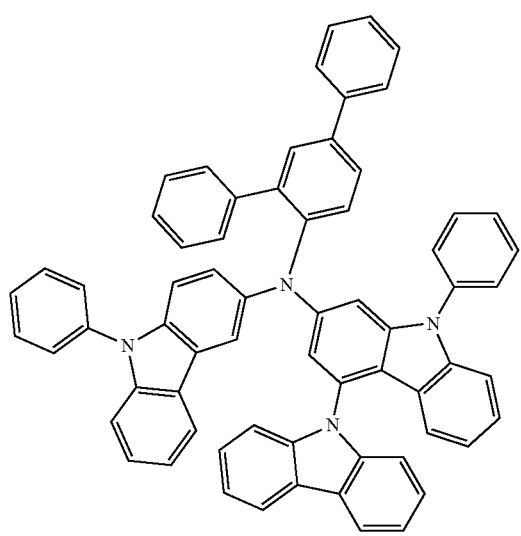
C-326
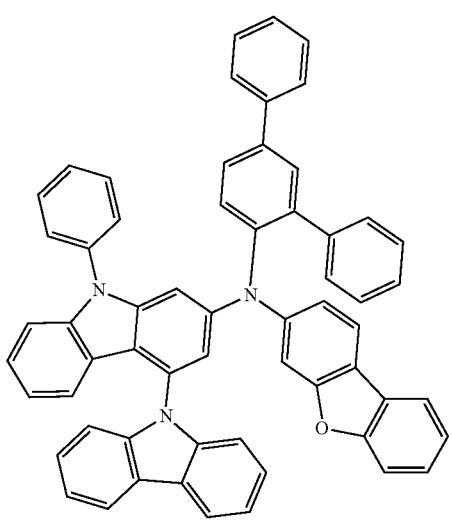
C-324
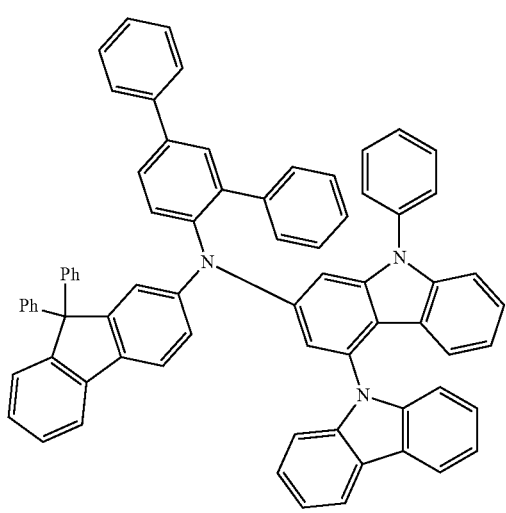
C-327
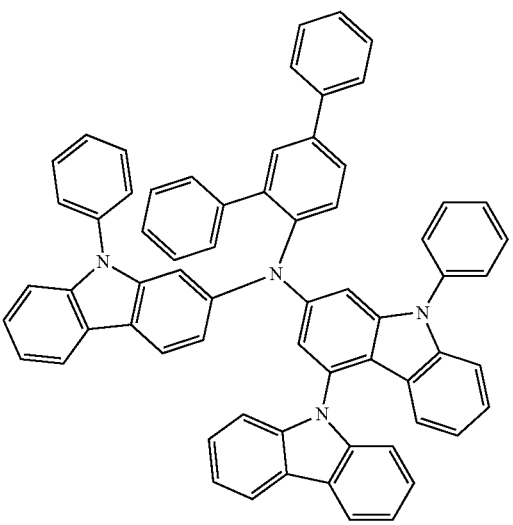

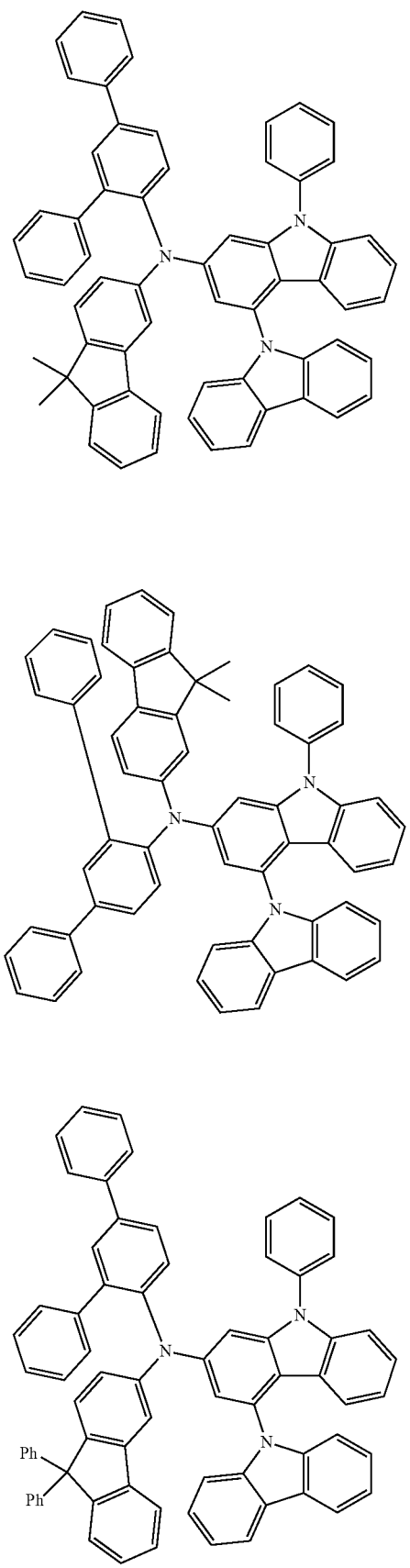
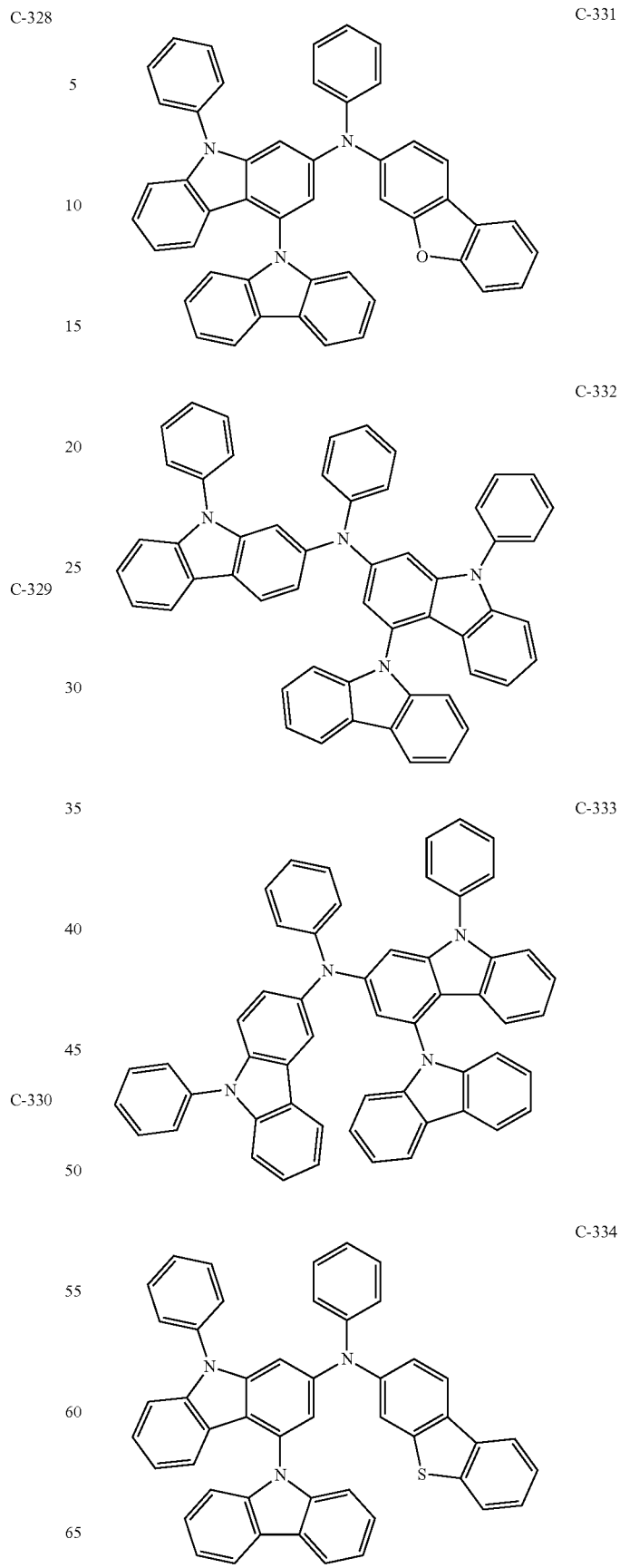

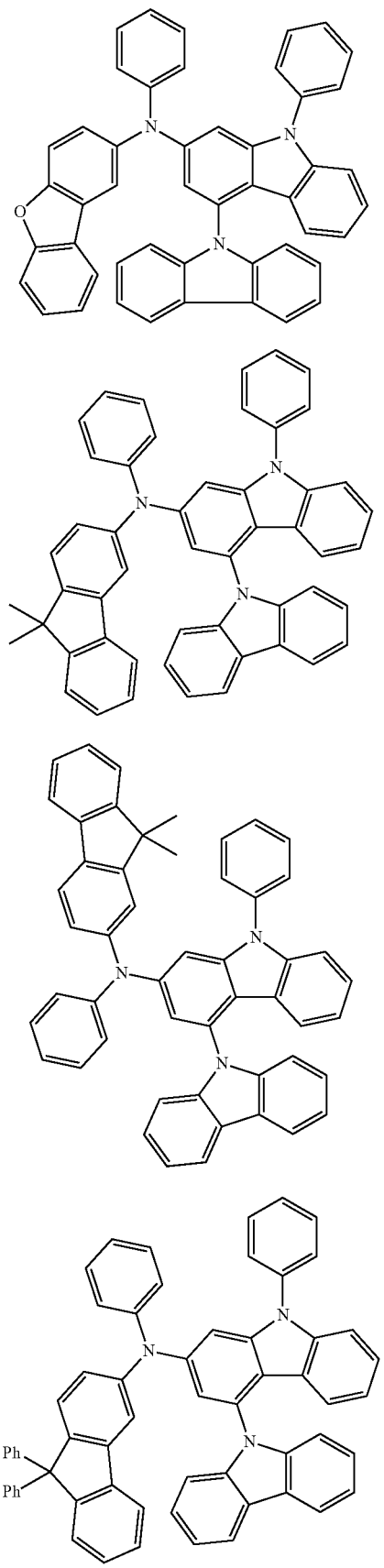
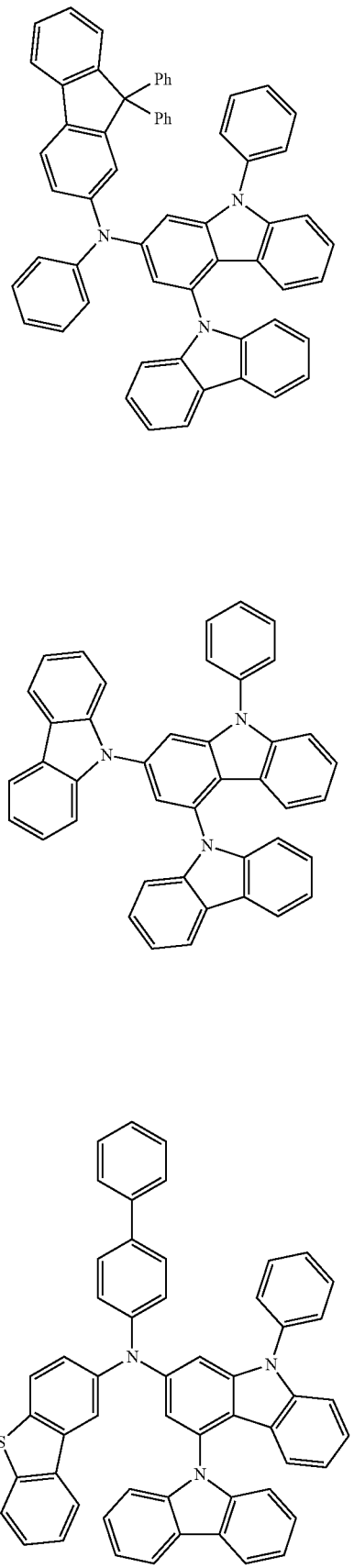

C-342

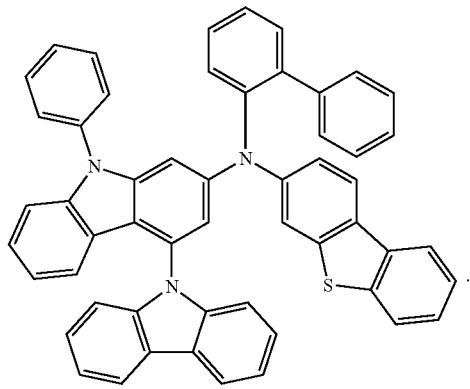

The organic electroluminescent compound of the present disclosure can be prepared by a synthetic method known to a person skilled in the art. For example, it can be prepared according to the following reaction schemes.

[Reaction Scheme 1]

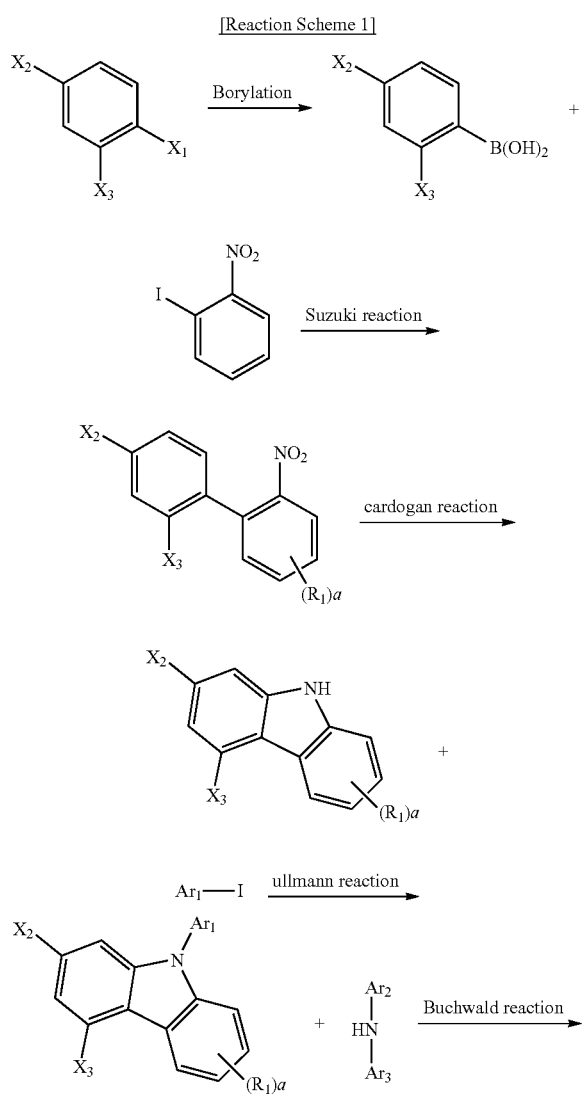

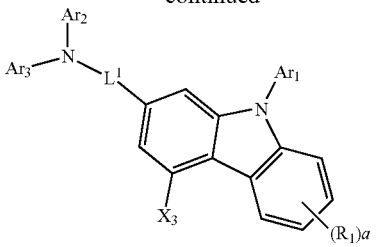

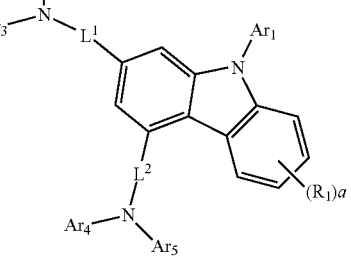

wherein $Ar_1$ to $Ar_5$, $L_1$, $L_2$, $R_1$, and a are as defined in formula 1, and $X_1$ to $X_3$ represent a halogen.

The hole transport zone of the present disclosure may be composed of one or more layers selected from the group consisting of a hole transport layer, a hole injection layer, an electron blocking layer, and a hole auxiliary layer. Each layer may consist of one or more layers.

According to one embodiment of the present disclosure, the hole transport zone comprises a hole transport layer. In addition, the hole transport zone may comprise a hole transport layer and further comprise one or more layers of a hole injection layer, an electron blocking layer, and a hole auxiliary layer.

In addition, the present disclosure provides an organic electroluminescent material comprising the organic electroluminescent compound of formula 1, and an organic electroluminescent device comprising the material.

The above material may be a hole transport material, a hole auxiliary material, or a light-emitting auxiliary material, specifically a hole transport material, a hole auxiliary material, or a light-emitting auxiliary material of an organic electroluminescent device emitting red light. When there are two or more hole transport layers, the material may be a hole transport material (hole auxiliary material) comprised in the hole transport layer adjacent to the light-emitting layer.

The above material can be comprised of the organic electroluminescent compound according to the present disclosure alone, or can further include conventional materials generally used in organic electroluminescent materials.

The organic electroluminescent device according to the present disclosure comprises a first electrode; a second electrode; and at least one organic layer between the first and second electrodes. The organic layer may comprise at least one organic electroluminescent compound of formula 1.

One of the first and second electrodes may be an anode, and the other may be a cathode. The organic layer may comprise a light-emitting layer, and may further comprise at least one layer selected from a hole injection layer, a hole transport layer, a hole auxiliary layer, a light-emitting auxiliary layer, an electron transport layer, an electron buffer layer, an electron injection layer, an interlayer, a hole blocking layer, and an electron blocking layer.

According to one embodiment of the present disclosure, the organic electroluminescent device of the present disclosure may further comprise an azine-based compound as one or more of an electron transport material, an electron injection material, an electron buffer material, and a hole blocking material, besides the organic electroluminescent compound of the present disclosure.

The organic electroluminescent compound of the present disclosure may be comprised in at least one layer of the light-emitting layer, the hole injection layer, the hole transport layer, the hole auxiliary layer, the light-emitting auxiliary layer, the electron transport layer, the electron buffer layer, the electron injection layer, the interlayer, the hole blocking layer, and the electron blocking layer, preferably in at least one layer of the hole transport layer, the hole auxiliary layer, and the light-emitting auxiliary layer. When there are two or more hole transport layers, the organic electroluminescent compound can be used in at least one of the layers. For example, when used in the hole transport layer, the organic electroluminescent compound of the present disclosure may be comprised as a hole transport material.

The light-emitting layer may comprise one or more hosts and one or more dopants. If necessary, the light-emitting layer may comprise a co-host material, i.e., a plurality of host materials of two or more.

The host used in the present disclosure may be a phosphorescent host compound or a fluorescent host compound, and it is not particularly limited.

In another embodiment of the present disclosure, a composition for preparing an organic electroluminescent device is provided. The composition is preferably for preparing a hole transport layer, a hole auxiliary layer, or a light-emitting auxiliary layer of an organic electroluminescent device and comprises the compound of the present disclosure. When there are two or more hole transport layers, the compound of the present disclosure may be comprised in the composition for preparing a hole transport layer (hole auxiliary layer) adjacent to the light-emitting layer.

In addition, the organic electroluminescent device according to the present disclosure comprises a first electrode; a second electrode; and at least one organic layer between the first and second electrodes. The organic layer comprises a hole transport layer, a hole auxiliary layer, or a light-emitting auxiliary layer, and the hole transport layer, the hole auxiliary layer, or the light-emitting auxiliary layer may comprise the composition for preparing the organic electroluminescent device according to the present disclosure.

The organic electroluminescent device according to the present disclosure may further comprise, in addition to the organic electroluminescent compound represented by formula 1, at least one compound selected from the group consisting of arylamine-based compounds and styrylarylamine-based compounds.

In the organic electroluminescent device of the present disclosure, the organic layer may further comprise, besides the organic electroluminescent compound of formula 1, at least one metal selected from the group consisting of metals of Group 1, metals of Group 2, transition metals of the 4$^{th}$ period, transition metals of the 5$^{th}$ period, lanthanides, and organic metals of the d-transition elements of the Periodic Table, or at least one complex compound comprising the metal.

In addition, the organic electroluminescent device of the present disclosure may emit white light by further comprising at least one light-emitting layer, which comprises a blue, a red, or a green electroluminescent compound known in the field, besides the compound of the present disclosure. If necessary, it may further comprise a yellow or an orange light-emitting layer.

In the organic electroluminescent device of the present disclosure, preferably, at least one layer selected from a chalcogenide layer, a metal halide layer, and a metal oxide layer (hereinafter, "a surface layer") may be placed on an inner surface(s) of one or both electrode(s). Specifically, a chalcogenide (includes oxides) layer of silicon or aluminum is preferably placed on an anode surface of an electroluminescent medium layer, and a metal halide layer or a metal oxide layer is preferably placed on a cathode surface of an electroluminescent medium layer. Such a surface layer provides operation stability for the organic electroluminescent device. Preferably, the chalcogenide includes $SiO_x(1 \leq X \leq 2)$, $AlO_x(1 \leq X \leq 1.5)$, SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, an electron blocking layer, or a combination thereof can be used between the anode and the light-emitting layer. The hole injection layer may be multi-layers in order to lower the hole injection barrier (or hole injection voltage) from the anode to the hole transport layer or the electron blocking layer, wherein each of the multi-layers may use two compounds simultaneously. The hole transport layer or the electron blocking layer may also be multi-layers.

An electron buffer layer, a hole blocking layer, an electron transport layer, an electron injection layer, or a combination thereof can be used between the light-emitting layer and the cathode. The electron buffer layer may be multi-layers in order to control the injection of the electron and improve the interfacial properties between the light-emitting layer and the electron injection layer, wherein each of the multi-layers may use two compounds simultaneously. The hole blocking layer or the electron transport layer may also be multi-layers, wherein each of the multi-layers may use a plurality of compounds.

Herein, the hole auxiliary layer or the light-emitting auxiliary layer is placed between the hole transport layer and the light-emitting layer, and may be used for controlling the hole transport speed. The hole auxiliary layer or the light-emitting auxiliary layer may provide an effect of improving the efficiency and lifespan of the organic electroluminescent device.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or hole transport, or for preventing the overflow of electrons. When the light-emitting auxiliary layer is placed between the cathode and the light-emitting layer, it can be used for promoting the electron injection and/or electron transport, or for preventing the overflow of holes. Also, the hole auxiliary layer may be placed between the hole transport layer (or hole injection layer) and the light-emitting layer, and may be effective to promote or block the hole transport rate (or hole injection rate), thereby enabling the charge balance to be controlled. Further, the electron blocking layer may be placed between the hole transport layer (or hole injection layer) and the light-emitting layer, and can confine the excitons within the light-emitting layer by blocking the overflow of electrons from the light-emitting layer to prevent a light-emitting leakage. When an organic electroluminescent device includes two or more hole transport layers, the hole transport layer, which is further included, may be used as a hole auxiliary layer or an electron blocking layer. The hole auxiliary layer and the electron blocking layer may have an effect of improving the efficiency and/or the lifespan of the organic electroluminescent device.

Preferably, in the organic electroluminescent device of the present disclosure, a mixed region of an electron transport compound and a reductive dopant, or a mixed region of a hole transport compound and an oxidative dopant may be placed on at least one surface of a pair of electrodes. In this case, the electron transport compound is reduced to an anion, and thus it becomes easier to inject and transport electrons from the mixed region to the light-emitting medium. Furthermore, the hole transport compound is oxidized to a cation, and thus it becomes easier to inject and transport holes from the mixed region to the light-emitting medium. Preferably, the oxidative dopant includes various Lewis acids and acceptor compounds; and the reductive dopant includes alkali metals, alkali metal compounds, alkaline earth metals, rare-earth metals, and mixtures thereof. The reductive dopant layer may be employed as a charge-generating layer to prepare an organic EL device having two or more light-emitting layers and emitting white light.

In order to form each layer constituting the organic EL device of the present disclosure, dry film-forming methods such as vacuum deposition, sputtering, plasma, ion plating methods, etc., or wet film-forming methods such as spin coating, dip coating, flow coating methods, etc., can be used.

When using a wet film-forming method, a thin film is formed by dissolving or dispersing the material constituting each layer in suitable solvents, such as ethanol, chloroform, tetrahydrofuran, dioxane, etc. The solvents are not specifically limited as long as the material constituting each layer is soluble or dispersible in the solvents, which do not cause any problems in forming a layer.

By using the organic electroluminescent device of the present disclosure, a display system, for example, for smartphones, tablets, notebooks, PCs, TVs, or vehicles, or a lighting system, for example, an indoor or outdoor lighting system, can be produced.

Hereinafter, the preparation method of the organic electroluminescent compounds of the present disclosure, the physical properties of the compounds, and the luminous properties of the organic electroluminescent device comprising the compounds will be explained in detail with reference to the representative compounds of the present disclosure, but not limited thereto.

EXAMPLE 1

Preparation of Compound C-92

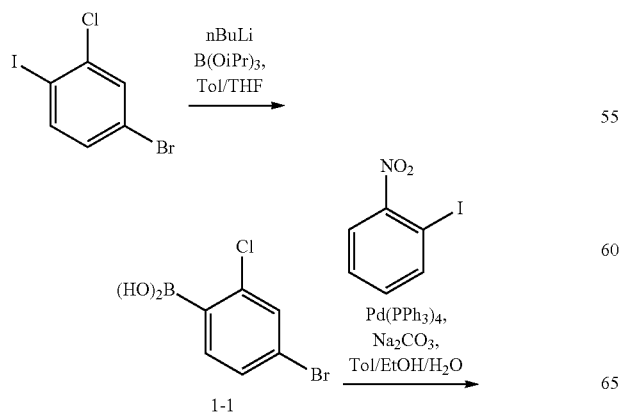

Preparation of Compound 1-1

75 g of 4-bromo-2-chloro-1-iodobenzene (236.3 mmol), 137.0 mL of B(OiPr)$_3$ (590.8 mmol), 880 mL of toluene, and 300 mL of tetrahydrofuran (THF) were introduced into a flask and dissolved, and the mixture was stirred at −78° C. for 20 minutes. 142 mL of nBuLi (354.5 mmol) was slowly introduced thereto at −78° C. and the mixture was stirred for 1 hour and additionally stirred at room temperature for 3 hours. After completion of the reaction, the mixture was extracted with ethyl acetate (EA)/H$_2$O to obtain 35.5 g of compound 1-1 (yield: 64%).

Preparation of Compound 1-2

35.5 g of compound 1-1 (151.0 mmol), 39.5 g of 1-iodo-2-nitrobenzene (159.0 mmol), 8.7 g of Pd(PPh$_3$)$_4$ (7.6 mmol), 40.0 g of Na$_2$CO$_3$ (378.0 mmol), 500 mL of toluene, 125 mL of EtOH, and 125 mL of H$_2$O were introduced into a flask and dissolved, and the mixture was stirred under reflux for 1 hour and 30 minutes. After completion of the reaction, the mixture was extracted with EA/H$_2$O and separated with column chromatography to obtain 47.2 g of compound 1-2 (yield: 100%).

Preparation of Compound 1-3

47.2 g of compound 1-2 (151.0 mmol), 99.0 g of PPh$_3$ (377.5 mmol), and 750 mL of dichlorobenzene (DCB) were introduced into a flask and dissolved, and the mixture was stirred under reflux for 5 hours. After completion of the reaction, the mixture was distilled under reduced pressure and separated with column chromatography to obtain 20.3 g of compound 1-3 (yield: 48%).

Preparation of Compound 1-4

13.2 g of compound 1-3 (47.1 mmol), 10.5 mL of PhI (94.1 mmol), 4.5 g of CuI (23.6 mmol), 6.3 mL of ethylenediamine (EDA) (94.2 mmol), 25.0 g of K$_3$PO$_4$ (117.8 mmol), and 230 mL of toluene were introduced into a flask and dissolved, and the mixture was stirred under reflux for 1 hour and 20 minutes. After completion of the reaction, the mixture was separated with column chromatography to obtain 11.1 g of compound 1-4 (yield: 66%).

Preparation of Compound 1-5

5.3 g of compound 1-4 (14.9 mmol), 4.7 g of 9,9-dimethyl-N-phenyl-9H-fluorene-2-amine (16.3 mmol), 0.1 g of Pd(OAc)$_2$ (0.45 mmol), 0.4 mL of P(tBu)$_3$ (0.89 mmol), 3.6 g of NaOtBu (37.3 mmol), and 80 mL of toluene were introduced into a flask and dissolved, and the mixture was stirred under reflux for 15 minutes. After completion of the reaction, the mixture was extracted with EA/H$_2$O and separated with column chromatography to obtain 6.0 g of compound 1-5 (yield: 80%).

Preparation of Compound C-92

6.0 g of compound 1-5 (10.7 mmol), 2.0 g of diphenylamine (11.8 mmol), 0.49 g of Pd$_2$(dba)$_3$ (0.54 mmol), 0.44 g of 2-dicyclohexylphosphino-2',6'-dimethoxybiphenyl (s-phos) (1.07 mmol), 2.6 g of NaOtBu (26.8 mmol), and 55 mL of toluene were introduced into a flask and dissolved, and the mixture was stirred under reflux for 20 minutes. After completion of the reaction, the mixture was extracted with EA/H$_2$O and separated with column chromatography to obtain 6.4 g of compound C-92 (yield: 86%).

|      | MW     | UV     | PL     | M.P.    |
|------|--------|--------|--------|---------|
| C-92 | 693.88 | 402 nm | 415 nm | 177° C. |

EXAMPLE 2

Preparation of Compound C-102

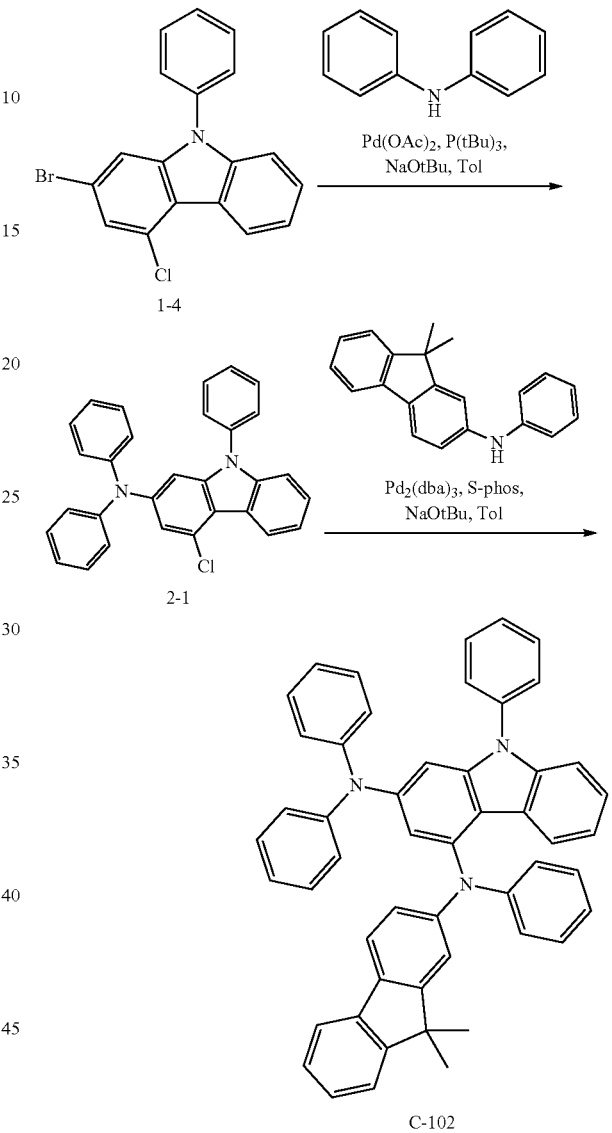

Preparation of Compound 2-1

5.0 g of compound 1-4 (14.0 mmol), 2.6 g of diphenylamine (15.4 mmol), 0.09 g of Pd(OAc)$_2$ (0.42 mmol), 0.4 mL of P(tBu)$_3$ (0.84 mmol), 3.4 g of NaOtBu (35.0 mmol), and 70 mL of toluene were introduced into a flask and dissolved, and the mixture was stirred under reflux for 10 minutes. After completion of the reaction, the mixture was extracted with EA/H$_2$O and separated with column chromatography to obtain 4.6 g of compound 2-1 (yield: 74%).

Preparation of Compound C-102

4.6 g of compound 2-1 (10.3 mmol), 3.3 g of 9,9-dimethyl-N-phenyl-9H-fluorene-2-amine (11.4 mmol), 0.47 g of Pd$_2$(dba)$_3$ (0.52 mmol), 0.42 g of s-phos (1.00 mmol), 2.5 g of NaOtBu (25.8 mmol), and 52 mL of toluene were introduced into a flask and dissolved, and the mixture was stirred under reflux for 20 minutes. After completion of the reaction, the mixture was extracted with EA/H₂O and separated with column chromatography to obtain 6.3 g of compound C-102 (yield: 89%).

|     | MW     | UV     | PL     | M.P.    |
| --- | ------ | ------ | ------ | ------- |
| C-102 | 693.88 | 384 nm | 409 nm | 223° C. |

EXAMPLE 3

Preparation of Compound C-1

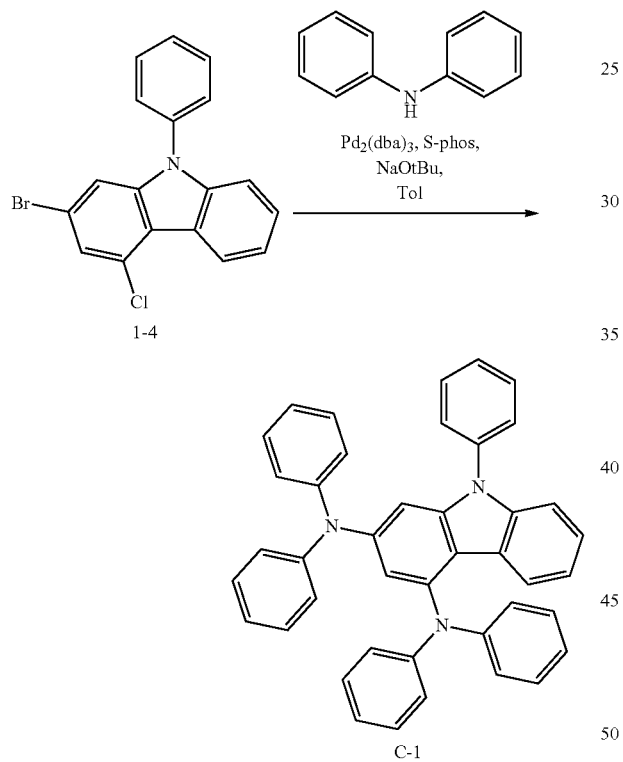

3.0 g of compound 1-4 (8.41 mmol), 2.9 g of diphenylamine (17.2 mmol), 0.39 g of Pd₂(dba)₃ (0.42 mmol), 0.35 g of s-phos (0.84 mmol), 2.4 g of NaOtBu (25.2 mmol), and 42 mL of toluene were introduced into a flask and dissolved, and the mixture was stirred under reflux for 1 hour. After completion of the reaction, the mixture was extracted with EA/H₂O and separated with column chromatography to obtain 3.6 g of compound C-1 (yield: 74%).

|     | MW     | UV     | PL     | M.P.    |
| --- | ------ | ------ | ------ | ------- |
| C-1 | 577.72 | 388 nm | 403 nm | 207° C. |

EXAMPLE 4

Preparation of Compound C-63

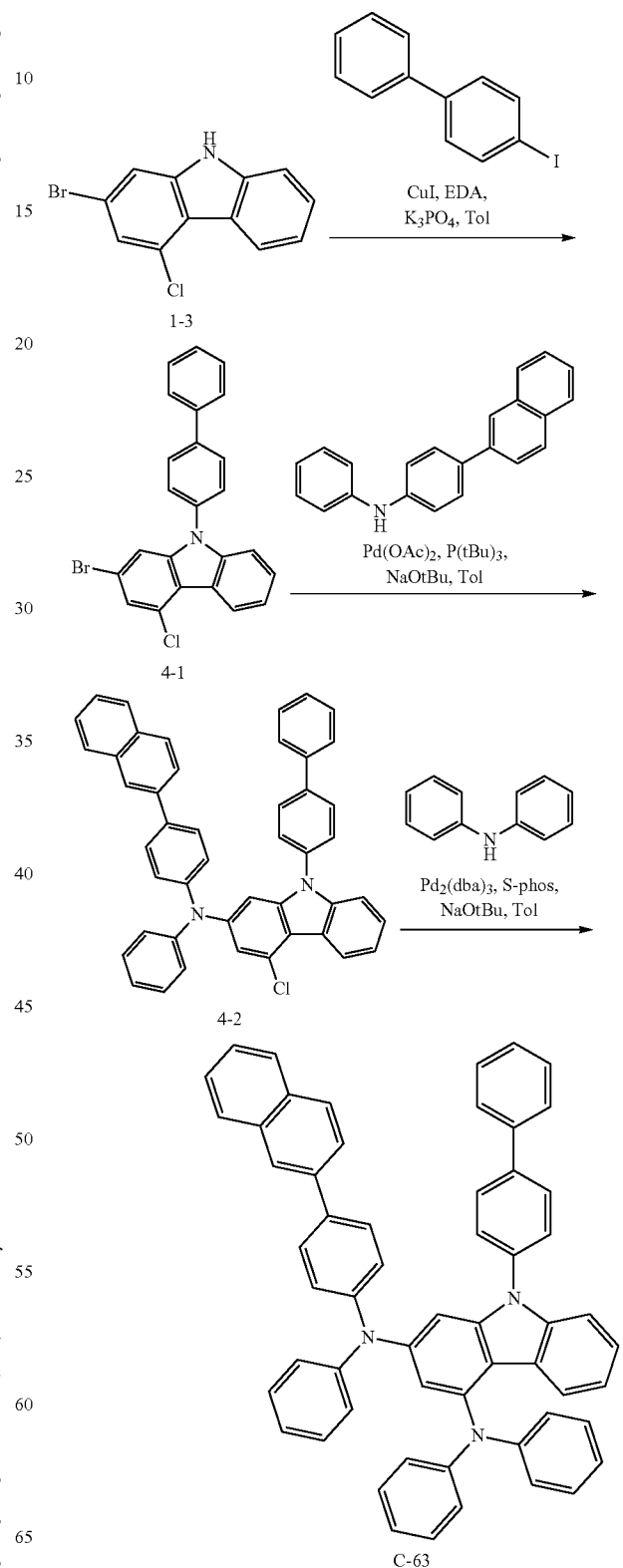

Preparation of Compound 4-1

20.0 g of compound 1-3 (71.3 mmol), 40.0 g of 4-iodo-1,1'-biphenyl (142.6 mmol), 6.8 g of CuI (35.7 mmol), 9.6 mL of EDA (142.6 mmol), 75.7 g of $K_3PO_4$ (356.5 mmol), and 360 mL of toluene were introduced into a flask and dissolved, and the mixture was stirred under reflux for 1 hour and 20 minutes. After completion of the reaction, the mixture was separated with column chromatography to obtain 16.0 g of compound 4-1 (yield: 56%).

Preparation of Compound 4-2

7.0 g of compound 4-1 (16.2 mmol), 5.3 g of 4-(naphthalen-2-yl)-N-phenylaniline (17.8 mmol), 0.1 g of $Pd(OAc)_2$ (0.49 mmol), 0.5 mL of $P(tBu)_3$ (0.97 mmol), 3.9 g of NaOtBu (40.5 mmol), and 81 mL of toluene were introduced into a flask and dissolved, and the mixture was stirred under reflux for 30 minutes. After completion of the reaction, the mixture was extracted with $EA/H_2O$ and separated with column chromatography to obtain 6.3 g of compound 4-2 (yield: 60%).

Preparation of Compound C-63

6.3 g of compound 4-2 (9.7 mmol), 1.8 g of diphenylamine (10.7 mmol), 0.45 g of $Pd_2(dba)_3$ (0.48 mmol), 0.40 g of s-phos (1.00 mmol), 2.4 g of NaOtBu (24.4 mmol), and 50 mL of toluene were introduced into a flask and dissolved, and the mixture was stirred under reflux for 30 minutes. After completion of the reaction, the mixture was extracted with $EA/H_2O$ and separated with column chromatography to obtain 6.1 g of compound C-63 (yield: 80%).

|  | MW | UV | PL | M.P. |
|---|---|---|---|---|
| C-63 | 779.99 | 406 nm | 451 nm | 180° C. |

EXAMPLE 5

Preparation of Compound C-61

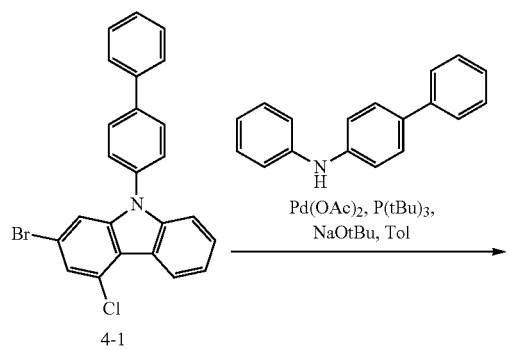

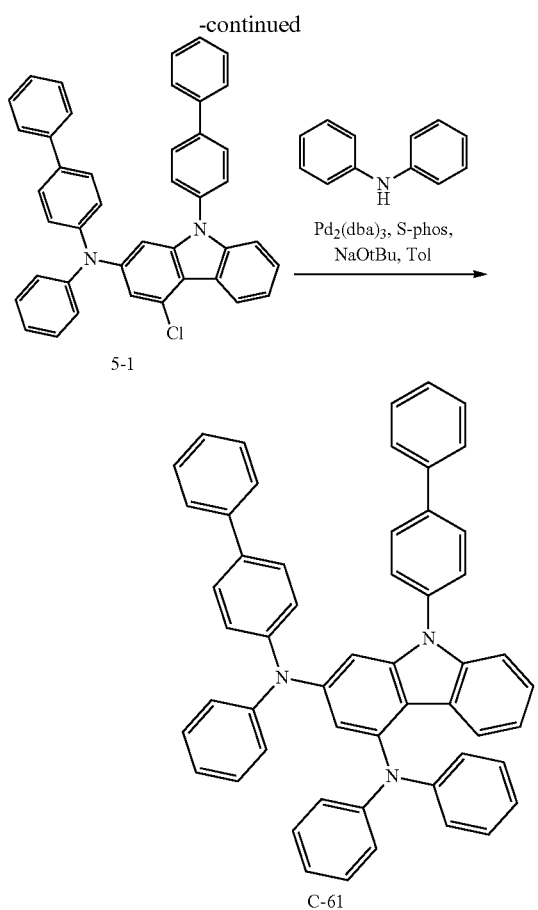

Preparation of Compound 5-1

6.5 g of compound 4-1 (15.0 mmol), 4.1 g of N-phenyl-[1,1'-biphenyl]-4-amine (16.5 mmol), 0.1 g of $Pd(OAc)_2$ (0.45 mmol), 0.5 mL of $P(tBu)_3$ (0.90 mmol), 3.6 g of NaOtBu (37.5 mmol), and 75 mL of toluene were introduced into a flask and dissolved, and the mixture was stirred under reflux for 15 minutes. After completion of the reaction, the mixture was extracted with $EA/H_2O$ and separated with column chromatography to obtain 7.6 g of compound 5-1 (yield: 84%).

Preparation of Compound C-61

7.6 g of compound 5-1 (12.7 mmol), 2.4 g of diphenylamine (14.0 mmol), 0.58 g of $Pd_2(dba)_3$ (0.64 mmol), 0.52 g of s-phos (1.30 mmol), 3.1 g of NaOtBu (31.8 mmol), and 64 mL of toluene were introduced into a flask and dissolved, and the mixture was stirred under reflux for 20 minutes. After completion of the reaction, the mixture was extracted with $EA/H_2O$ and separated with column chromatography to obtain 6.6 g of compound C-61 (yield: 71%).

|  | MW | UV | PL | M.P. |
|---|---|---|---|---|
| C-61 | 729.91 | 396 nm | 413 nm | 215° C. |

EXAMPLE 6

Preparation of Compound C-152

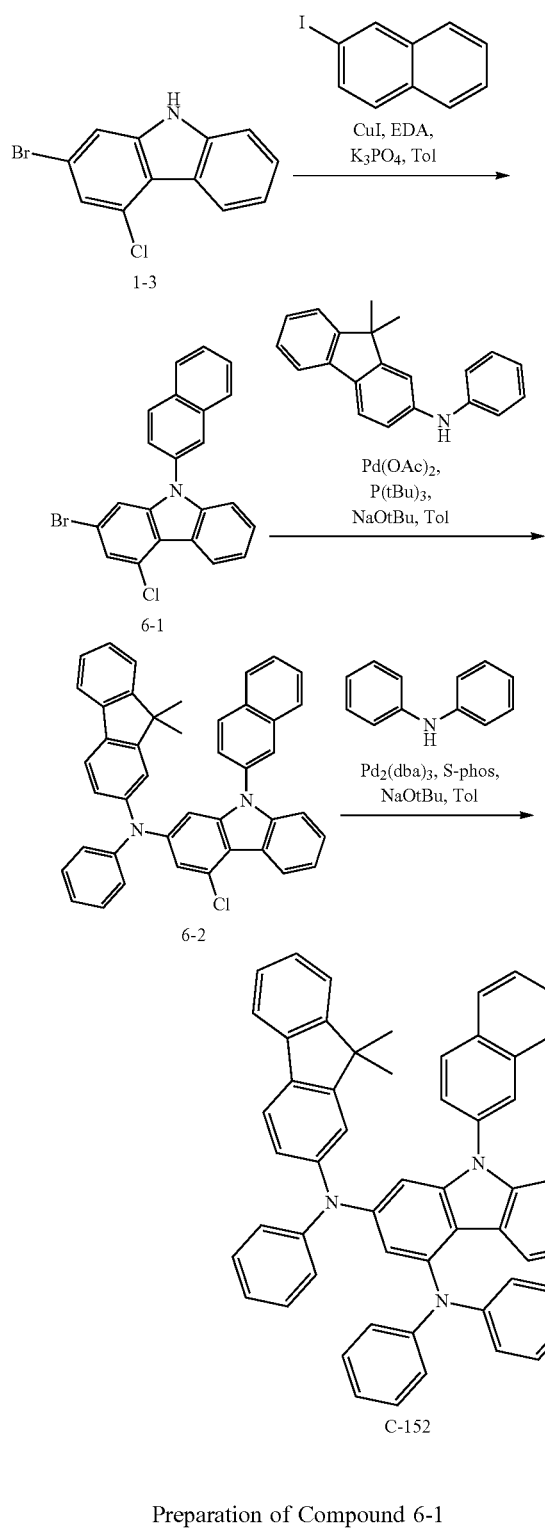

Preparation of Compound 6-1

15.0 g of compound 1-3 (53.5 mmol), 27.2 g of 2-iodonaphthalene (106.9 mmol), 5.1 g of CuI (26.8 mmol), 7.2 mL of EDA (107.0 mmol), 28.4 g of K$_3$PO$_4$ (133.8 mmol), and 270 mL of toluene were introduced into a flask and dissolved, and the mixture was stirred under reflux for 50 minutes. After completion of the reaction, the mixture was separated with column chromatography to obtain 13.4 g of compound 6-1 (yield: 62%).

Preparation of Compound 6-2

6.5 g of compound 6-1 (14.8 mmol), 4.6 g of 9,9-dimethyl-N-phenyl-9H-fluorene-2-amine (16.2 mmol), 0.1 g of Pd(OAc)$_2$ (0.44 mmol), 0.4 mL of P(tBu)$_3$ (0.89 mmol), 3.6 g of NaOtBu (37.0 mmol), and 74 mL of toluene were introduced into a flask and dissolved, and the mixture was stirred under reflux for 17 minutes. After completion of the reaction, the mixture was separated with column chromatography to obtain 5.6 g of compound 6-2 (yield: 62%).

Preparation of Compound C-152

5.6 g of compound 6-2 (9.2 mmol), 1.6 g of diphenylamine (9.6 mmol), 0.42 g of Pd$_2$(dba)$_3$ (0.46 mmol), 0.38 g of s-phos (0.92 mmol), 2.2 g of NaOtBu (23.0 mmol), and 46 mL of toluene were introduced into a flask and dissolved, and the mixture was stirred under reflux for 40 minutes. After completion of the reaction, the mixture was extracted with EA/H$_2$O and separated with column chromatography to obtain 6.0 g of compound C-152 (yield: 88%).

|       | MW     | UV     | PL     | M.P.   |
|-------|--------|--------|--------|--------|
| C-152 | 743.93 | 398 nm | 413 nm | 176° C. |

EXAMPLE 7

Preparation of Compound C-212

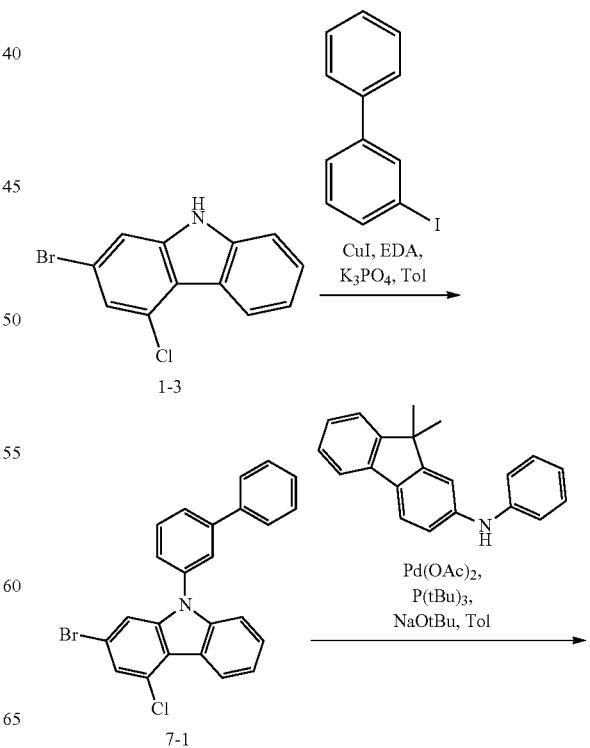

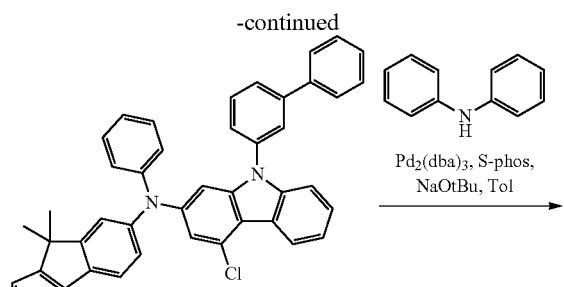

7-2

| | MW | M.P. |
|---|---|---|
| C-212 | 769.97 | 150° C. |

EXAMPLE 8

Preparation of Compound C-98

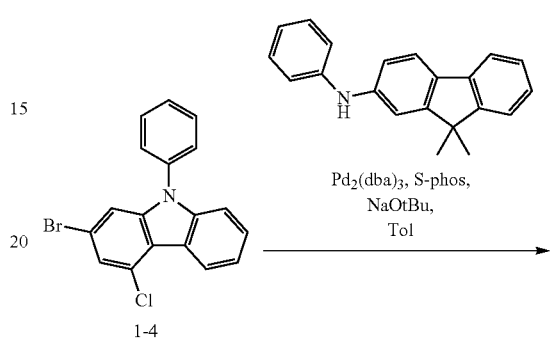

1-4

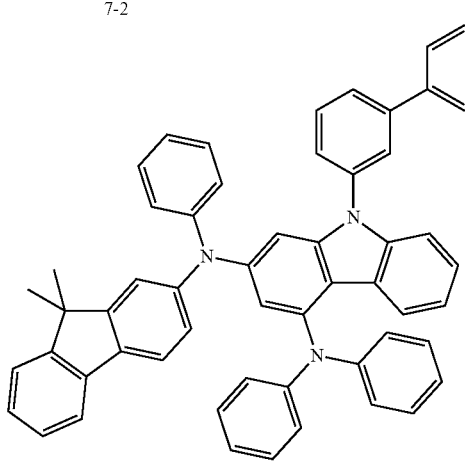

C-212

Preparation of Compound 7-1

15.0 g of compound 1-3 (53.5 mmol), 30.0 g of 3-iodo-1,1'-biphenyl (107.0 mmol), 5.1 g of CuI (26.8 mmol), 7.2 mL of EDA (107.0 mmol), 28.4 g of $K_3PO_4$ (133.8 mmol), and 270 mL of toluene were introduced into a flask and dissolved, and the mixture was stirred under reflux for 40 minutes. After completion of the reaction, the mixture was separated with column chromatography to obtain 15.8 g of compound 7-1 (yield: 68%).

Preparation of Compound 7-2

7.3 g of compound 7-1 (16.9 mmol), 5.3 g of 9,9-dimethyl-N-phenyl-9H-fluorene-2-amine (18.6 mmol), 0.1 g of $Pd(OAc)_2$ (0.51 mmol), 0.5 mL of $P(tBu)_3$ (1.01 mmol), 4.0 g of NaOtBu (42.3 mmol), and 85 mL of toluene were introduced into a flask and dissolved, and the mixture was stirred under reflux for 15 minutes. After completion of the reaction, the mixture was extracted with $EA/H_2O$ and separated with column chromatography to obtain 6.8 g of compound 7-2 (yield: 63%).

Preparation of Compound C-212

6.8 g of compound 7-2 (10.7 mmol), 1.8 g of diphenylamine (10.7 mmol), 0.49 g of $Pd_2(dba)_3$ (0.54 mmol), 0.44 g of s-phos (1.10 mmol), 2.1 g of NaOtBu (21.4 mmol), and 54 mL of toluene were introduced into a flask and dissolved, and the mixture was stirred under reflux for 20 minutes. After completion of the reaction, the mixture was extracted with $EA/H_2O$ and separated with column chromatography to obtain 6.4 g of compound C-212 (yield: 86%).

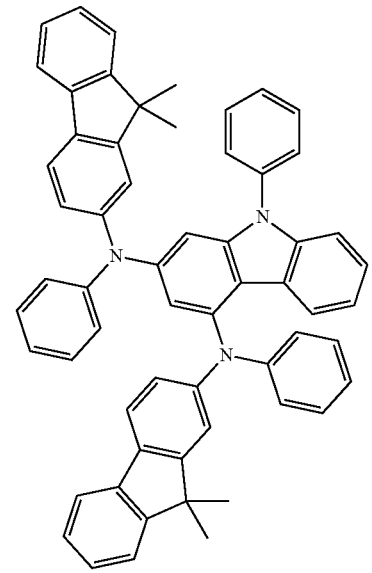

C-98

4.0 g of compound 1-4 (11.2 mmol), 7.1 g of 9,9-dimethyl-N-phenyl-9H-fluorene-2-amine (24.7 mmol), 1.0 g of $Pd_2(dba)_3$ (1.12 mmol), 0.92 g of s-phos (2.24 mmol), 4.3 g of NaOtBu (44.8 mmol), and 60 mL of toluene were introduced into a flask and dissolved, and the mixture was stirred under reflux for 50 minutes. After completion of the reaction, the mixture was extracted with $EA/H_2O$ and separated with column chromatography to obtain 6.5 g of compound C-98 (yield: 71%).

| | MW | M.P. |
|---|---|---|
| C-98 | 810.06 | 162° C. |

Device Examples 1 to 7: Production of an OLED Device According to the Present Disclosure An OLED device comprising the organic electroluminescent compound of the present disclosure was produced as follows. A transparent electrode indium tin oxide (ITO) thin film (10 Ω/sq) on a glass substrate for an organic light-emitting diode (OLED) device (Geomatec, Japan) was subjected to an ultrasonic washing with acetone, ethanol, and distilled water, sequentially, and was then stored in isopropyl alcohol. Next, the ITO substrate was mounted on a substrate holder of a vacuum vapor depositing apparatus. Compound HI-1 was introduced into a cell of said vacuum vapor depositing apparatus, and then the pressure in the chamber of said apparatus was controlled to $10^{-6}$ torr. Thereafter, an electric current was applied to the cell to evaporate the above-introduced material, thereby forming a first hole injection layer having a thickness of 80 nm on the ITO substrate. Compound HI-2 was then introduced into another cell of said vacuum vapor depositing apparatus, and was evaporated by applying an electric current to the cell, thereby forming a second hole injection layer having a thickness of 3 nm on the first hole injection layer. Compound HT-1 was introduced into another cell of said vacuum vapor depositing apparatus, and was evaporated by applying an electric current to the cell, thereby forming a first hole transport layer having a thickness of 10 nm on the second hole injection layer. The second hole transport layer compounds listed in Table 1 below were introduced into another cell of said vacuum vapor depositing apparatus, and was evaporated by applying an electric current to the cell, thereby forming a second hole transport layer (or hole auxiliary layer) having a thickness of 30 nm on the first hole transport layer. After forming the hole injection layers and the hole transport layers (or hole auxiliary layer), a light-emitting layer was then deposited as follows. Compound B-176 as below was introduced into one cell of the vacuum vapor depositing apparatus as a host, and compound D-1 was introduced into another cell as a dopant. The two materials were evaporated at different rates and were deposited in a doping amount of 10 wt % (the amount of dopant) based on the total amount of the dopant and host to form a light-emitting layer having a thickness of 40 nm on the second hole transport layer. Compound ET-1 and compound EI-1 were then introduced into another two cells, evaporated at the rate of 1:1, and deposited to form an electron transport layer having a thickness of 35 nm on the light-emitting layer. Next, after depositing compound EI-1 as an electron injection layer having a thickness of 2 nm on the electron transport layer, an Al cathode having a thickness of 80 nm was deposited by another vacuum vapor deposition apparatus on the electron injection layer. Thus, an OLED device was produced.

Comparative Examples 1 and 2: Production of an OLED Device not According to the Present Disclosure OLED devices were produced in the same manner as in Device Examples 1 to 7, except for using the compounds shown in Table 1 below for the second hole transport layer.

The driving voltage, luminous efficiency, and CIE color coordinate at a luminance of 1,000 nit, and the time taken for the luminance to decrease from 100% to 97% at a luminance of 15,000 nit (T97) of the OLED devices produced in Device Examples 1 to 7 and Comparative Examples 1 and 2 are provided in Table 1 below.

TABLE 1

| | Second hole transport layer | Voltage (V) | Efficiency (cd/A) | Color coordinate (x) | Color coordinate (y) | Lifespan (T97) (hr) |
|---|---|---|---|---|---|---|
| Device Example 1 | C-92 | 2.7 | 44.8 | 0.305 | 0.669 | 34 |
| Device Example 2 | C-102 | 3.1 | 49.1 | 0.305 | 0.669 | 29 |
| Device Example 3 | C-1 | 3.2 | 53.1 | 0.304 | 0.670 | 17 |
| Device Example 4 | C-341 | 2.7 | 55.9 | 0.309 | 0.669 | — |
| Device Example 5 | C-332 | 2.7 | 54.3 | 0.307 | 0.670 | — |
| Device Example 6 | C-342 | 2.7 | 56.5 | 0.306 | 0.670 | — |
| Device Example 7 | C-340 | 5.2 | 57.7 | 0.304 | 0.671 | — |
| Comparative Example 1 | Compound X | 3.8 | 36.0 | 0.304 | 0.669 | 0.3 |
| Comparative Example 2 | Compound Y | 3.0 | 49.4 | 0.305 | 0.668 | 0.1 |

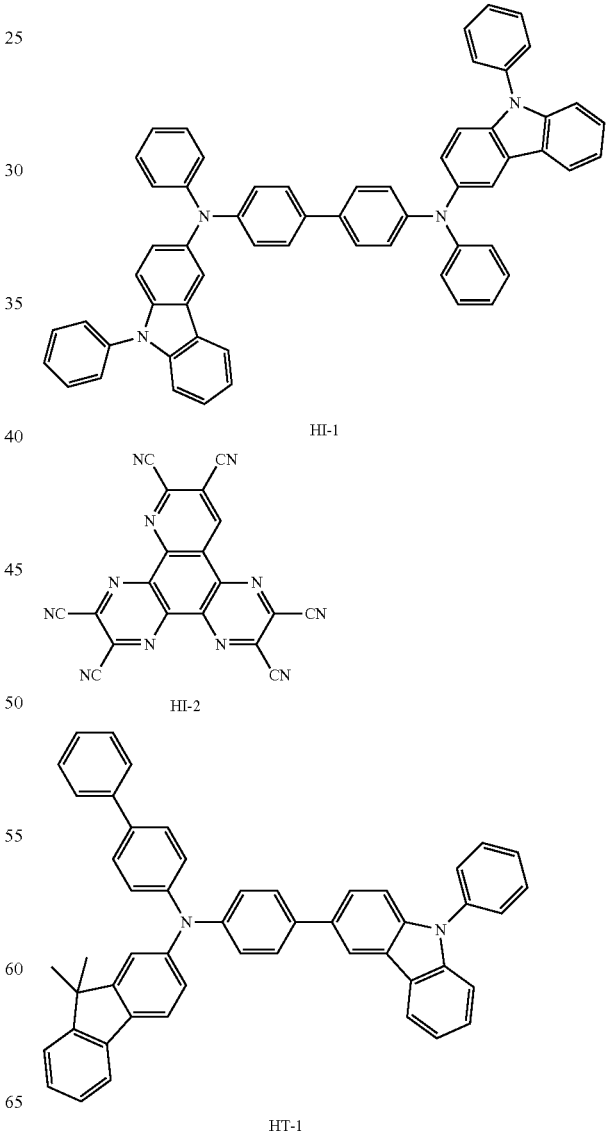

HI-1

HI-2

HT-1

TABLE 1-continued
| Second hole transport layer | Voltage (V) | Efficiency (cd/A) | Color coordinate (x) | Color co-ordinate (y) | Life-span (T97) (hr) |
|---|---|---|---|---|---|
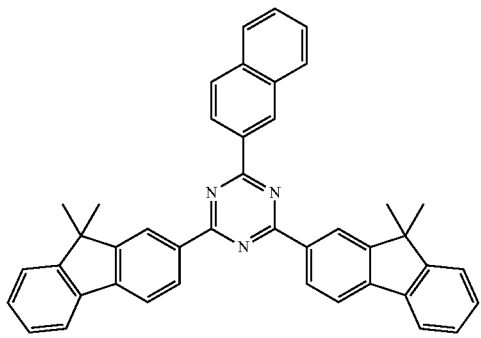
ET-1
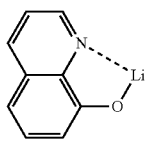
EI-1
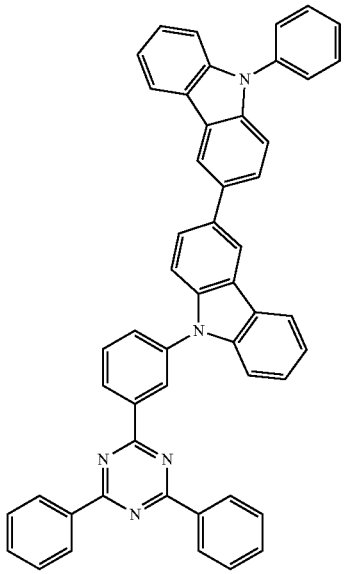
B-176
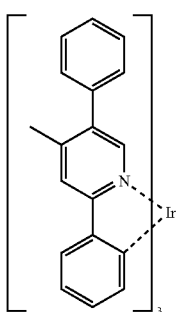
D-1
TABLE 1-continued
| Second hole transport layer | Voltage (V) | Efficiency (cd/A) | Color coordinate (x) | Color co-ordinate (y) | Life-span (T97) (hr) |
|---|---|---|---|---|---|
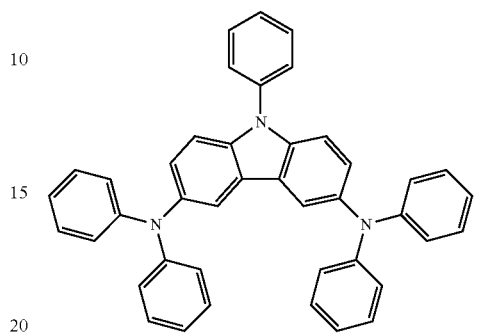
Compound X
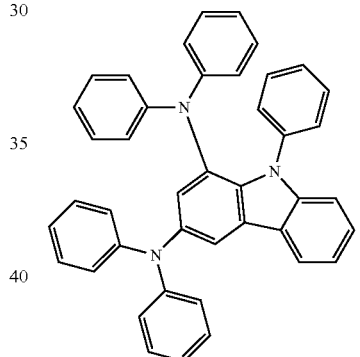
Compound Y
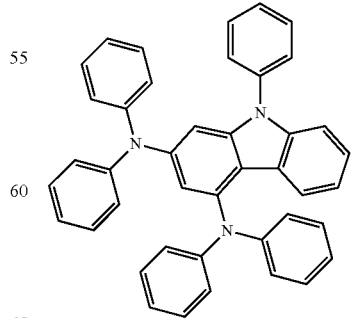
C-1

TABLE 1-continued

| Second hole transport layer | Voltage (V) | Efficiency (cd/A) | Color coordinate (x) | Color co-ordinate (y) | Life-span (T97) (hr) |
|---|---|---|---|---|---|

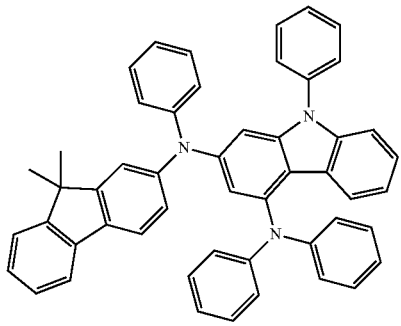

C-92

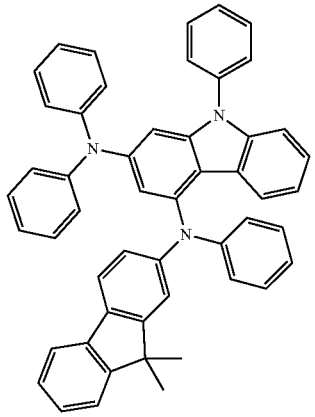

C-102

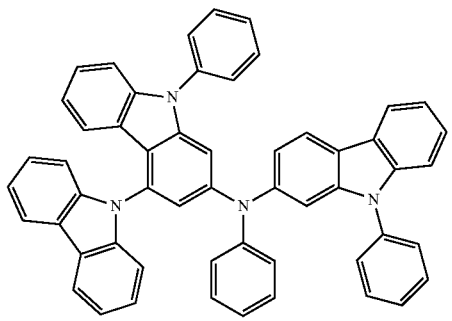

C-332

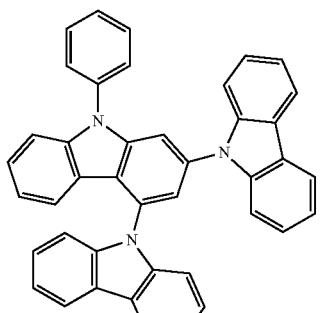

C-340

TABLE 1-continued

| Second hole transport layer | Voltage (V) | Efficiency (cd/A) | Color coordinate (x) | Color co-ordinate (y) | Life-span (T97) (hr) |
|---|---|---|---|---|---|

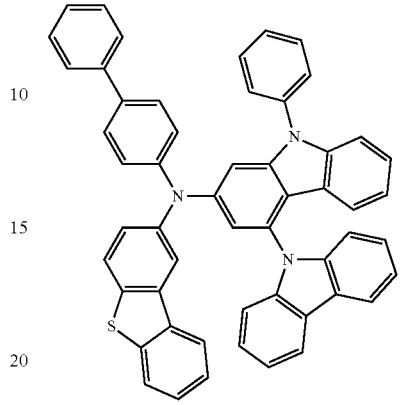

C-341

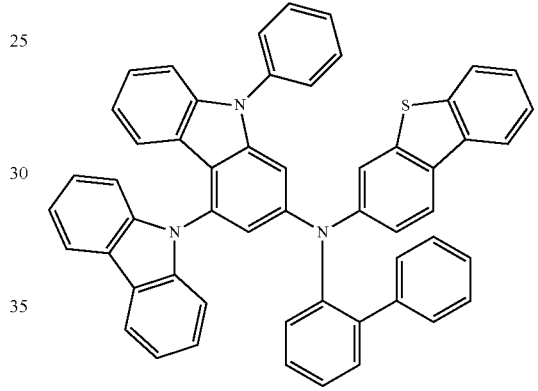

C-342

Upon comparison of the organic electroluminescent compound of the present disclosure with the conventional materials, at least one of the properties of voltage, efficiency, and lifespan was superior, and particularly, an organic electroluminescent device having excellent lifespan characteristic was provided.

The invention claimed is:

1. An organic electroluminescent compound represented by the following formula 1:

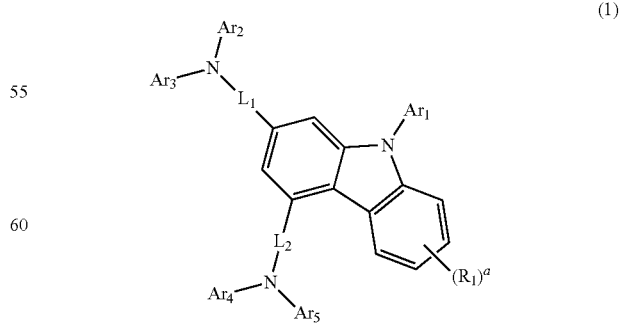

(1)

wherein $Ar_1$ to $Ar_5$ each independently represent hydrogen, deuterium, a substituted or unsubstituted (C1-C30)alkyl, a substituted or unsubstituted (C6-C30)aryl, a substituted or unsubstituted (3- to 30-membered)heteroaryl, a substituted or unsubstituted mono- or di-(C1-C30)alkylamino, a substituted or unsubstituted mono- or di-(C6-C30)arylamino, or a substituted or unsubstituted (C1-C30)alkyl(C6-C30)arylamino, or $Ar_2$ and $Ar_3$, and $Ar_4$ and $Ar_5$ may independently be linked to form a ring;

$L_1$ and $L_2$ each independently represent a single bond, a substituted or unsubstituted (C6-C30)arylene, or a substituted or unsubstituted (3- to 30-membered)heteroarylene;

$R_1$ represents hydrogen, deuterium, a halogen, a cyano, a substituted or unsubstituted (C1-C30)alkyl, a substituted or unsubstituted (C6-C30)aryl, a substituted or unsubstituted (3- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30) arylsilyl, a substituted or unsubstituted tri(C6-C30) arylsilyl, a substituted or unsubstituted mono- or di- (C1-C30)alkylamino, a substituted or unsubstituted mono- or di-(C6-C30)arylamino, or a substituted or unsubstituted (C1-C30)alkyl(C6-C30)arylamino; or may be linked to each other to form a ring; and a represents an integer of 1 to 4, where a is 2 or more, each of $R_1$ may be the same or different.

2. The organic electroluminescent compound according to claim 1, wherein formula 1 is represented by the following formula 2 or 3:

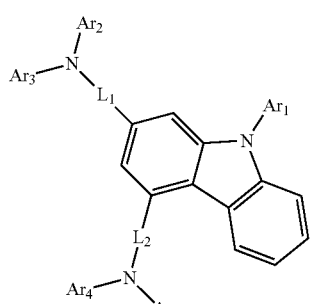

(2)

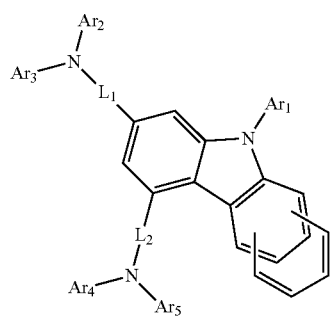

(3)

wherein $Ar_1$ to $Ar_5$, $L_1$, and $L_2$ are as defined in claim 1.

3. The organic electroluminescent compound according to claim 1, wherein the substituents of the substituted alkyl, the substituted aryl(ene), the substituted heteroaryl(ene), the substituted cycloalkyl, the substituted alkoxy, the substituted trialkylsilyl, the substituted dialkylarylsilyl, the substituted alkyldiarylsilyl, the substituted triarylsilyl, the substituted mono- or di- alkylamino, the substituted mono- or di- arylamino, and the substituted alkylarylamino in $Ar_1$ to $Ar_5$, $L_1$, $L_2$, and $R_1$ each independently are at least one selected from the group consisting of deuterium, a halogen, a cyano, a carboxyl, a nitro, a hydroxyl, a (C1-C30)alkyl, a halo(C1-C30)alkyl, a (C2-C30) alkenyl, a (C2-C30) alkynyl, a (C1-C30)alkoxy, a (C1-C30)alkylthio, a (C3-C30)cycloalkyl, a (C3-C30)cycloalkenyl, a (3- to 7-membered)heterocycloalkyl, a (C6-C30)aryloxy, a (C6-C30)arylthio, a (3- to 30-membered)heteroaryl unsubstituted or substituted with a (C6-C30)aryl, a (C6-C30)aryl unsubstituted or substituted with a (3- to 30-membered)heteroaryl, a tri(C1-C30)alkylsilyl, a tri(C6-C30)arylsilyl, a di(C1-C30)alkyl(C6-C30)arylsilyl, a (01-C30)alkyldi(C6-C30)arylsilyl, an amino, a mono- or di-(C1-C30)alkylamino, a mono- or di-(C6-C30) arylamino, a (C1-C30)alkyl(C6-C30)arylamino, a (C1-C30) alkylcarbonyl, a (C1-C30)alkoxycarbonyl, a (C6-C30)arylcarbonyl, a di(C6-C30)arylboronyl, a di(C1-C30) alkylboronyl, a (C1-C30)alkyl(C6-C30)arylboronyl, a (C6-C30)aryl(C1-C30)alkyl, and a (C1-C30)alkyl(C6-C30)aryl.

4. The organic electroluminescent compound according to claim 1, wherein $Ar_1$ to $Ar_5$ each independently represent a substituted or unsubstituted (C6-C30)aryl, or a substituted or unsubstituted (5- to 20-membered)heteroaryl, or $Ar_2$ and $Ar_3$, and $Ar_4$ and $Ar_5$ may independently be linked to form a ring;

$L_1$ and $L_2$ each independently represent a single bond, or a substituted or unsubstituted (C6-C12)arylene;

$R_1$ represents hydrogen, a substituted or unsubstituted (C6-C20)aryl, or a substituted or unsubstituted (5- to 15-membered)heteroaryl, or may be linked to each other to form a ring; and a represents 1 or 2.

5. The organic electroluminescent compound according to claim 1, wherein $Ar_1$ to $Ar_5$ each independently represent a (C6-C30)aryl unsubstituted or substituted with one or more of a (C1-C6)alkyl or a (C6-C12)aryl, or a (5- to 20-membered)heteroaryl unsubstituted or substituted with a (C6-C12)aryl, or $Ar_2$ and $Ar_3$, and $Ar_4$ and $Ar_5$ may independently be linked to form a ring;

$L_1$ and $L_2$ each independently represent a single bond, or an unsubstituted (C6-C12)arylene;

$R_1$ represents hydrogen, an unsubstituted (C6-C20)aryl, or an unsubstituted (5- to 15-membered)heteroaryl, or two Ri's may be linked to each other to form a ring; and a represents 1 or 2.

6. The organic electroluminescent compound according to claim 1, wherein the compound represented by formula 1 is selected from the group consisting of:

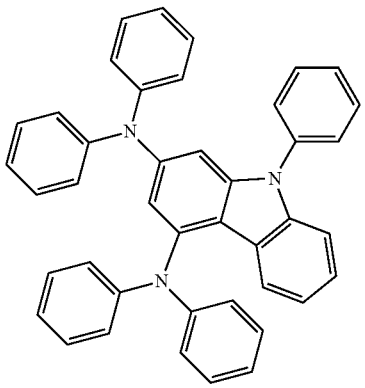

C-1

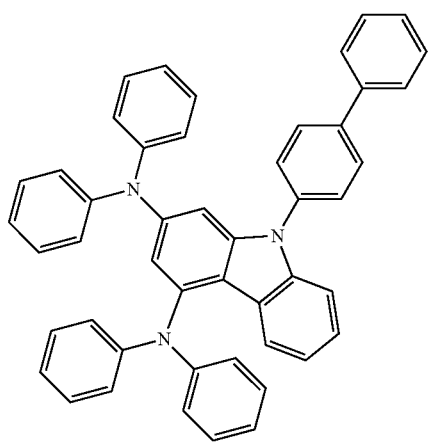
C-2
C-3
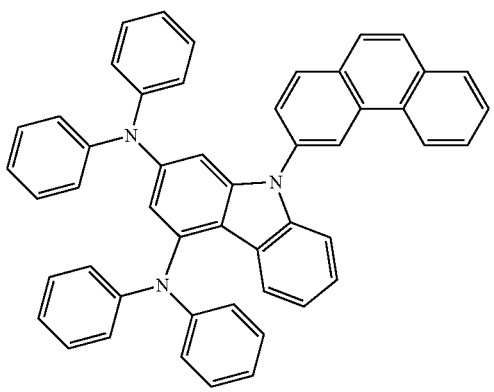
C-5
C-6
C-4
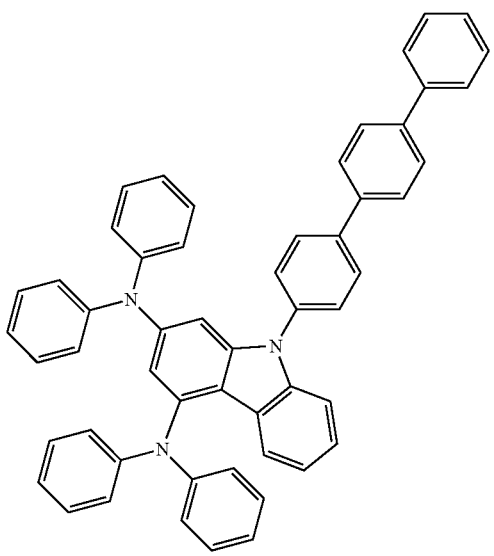
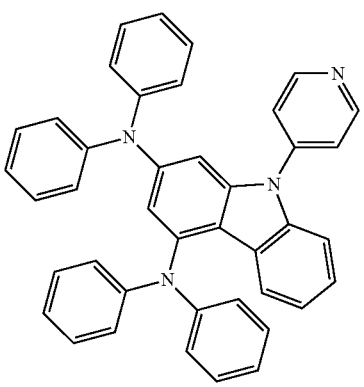
C-7

C-8
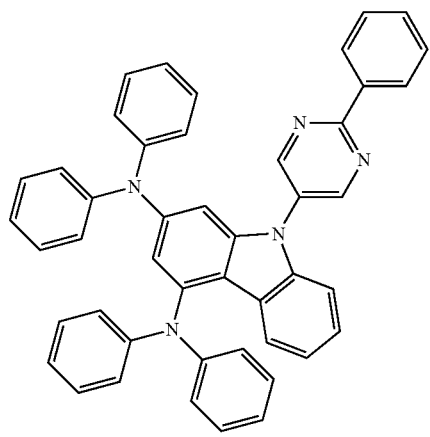
C-9
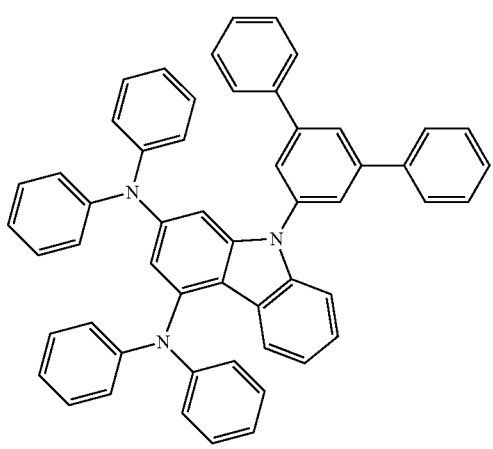
C-10
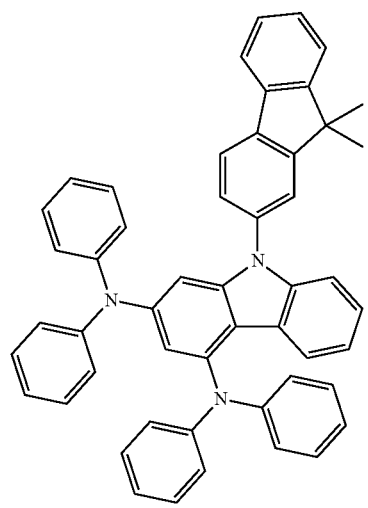
C-11
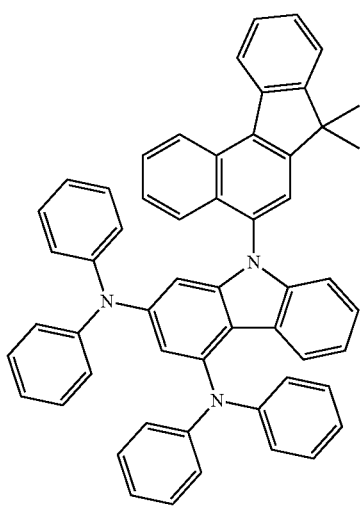
C-12
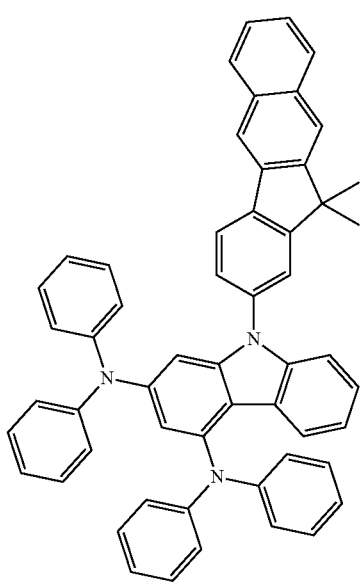
C-13
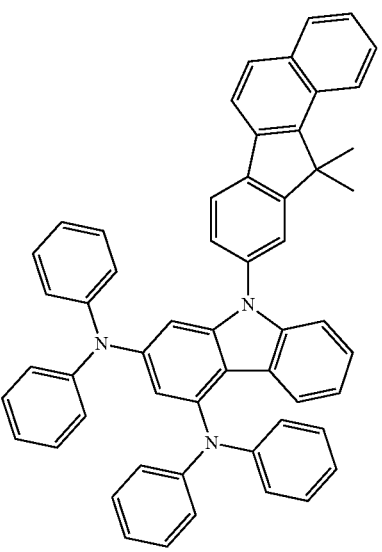

C-14
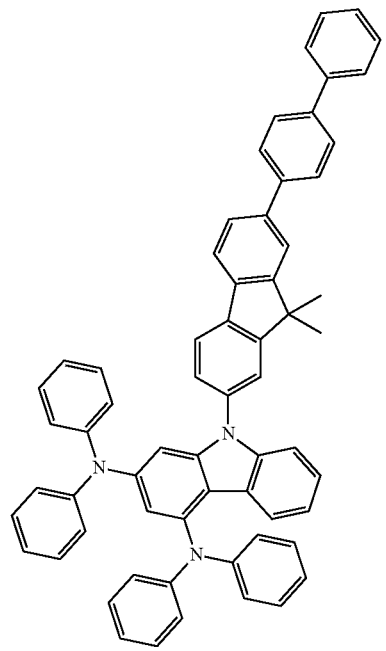
C-15
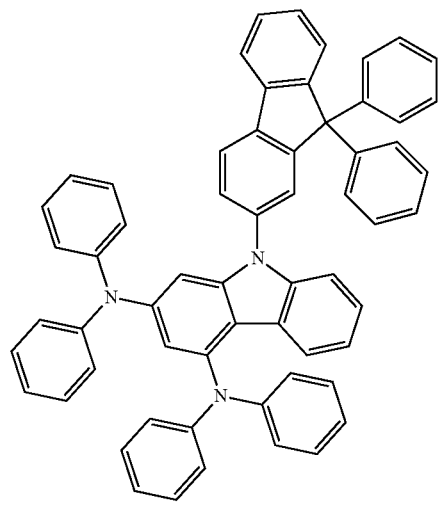
C-16
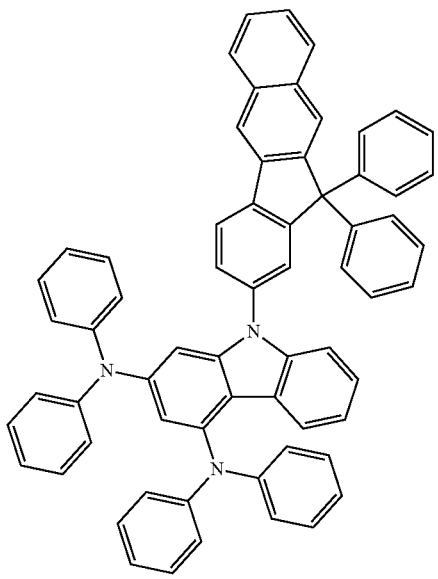
C-17
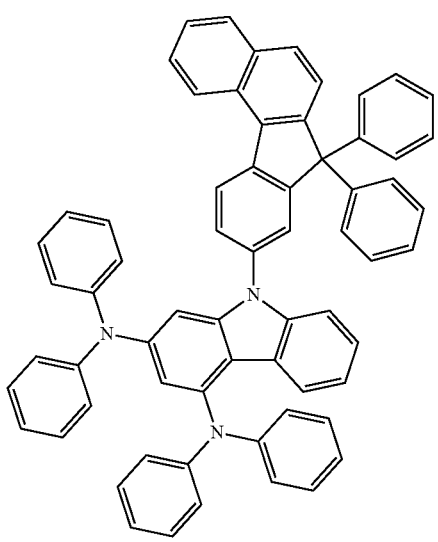
C-18
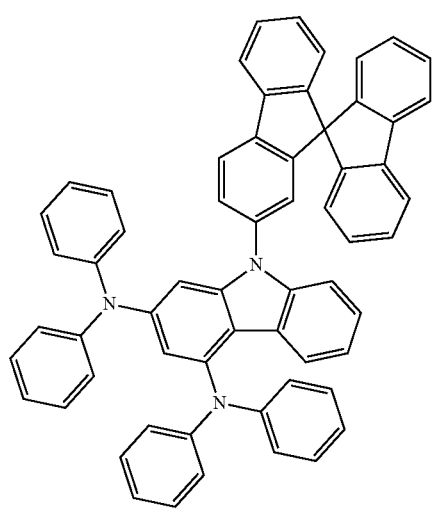

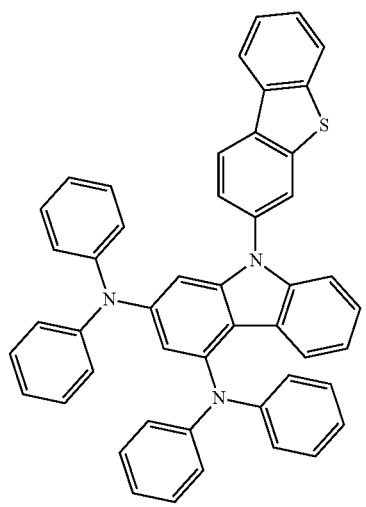
C-19
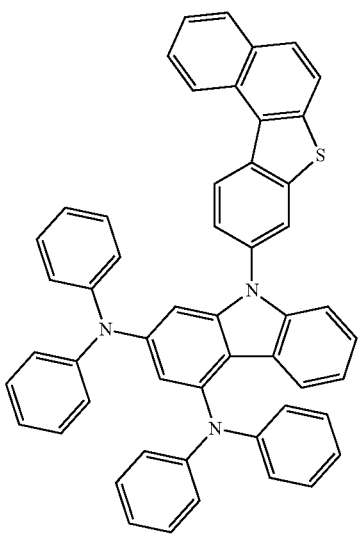
C-22
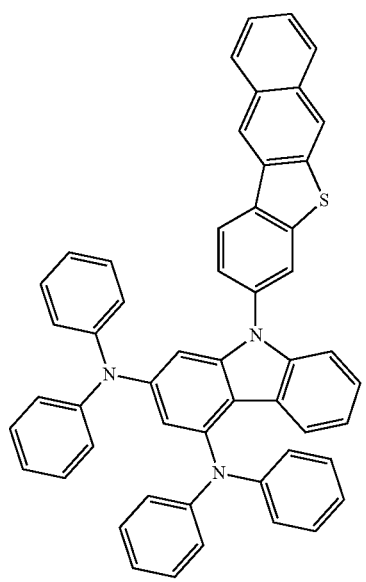
C-20
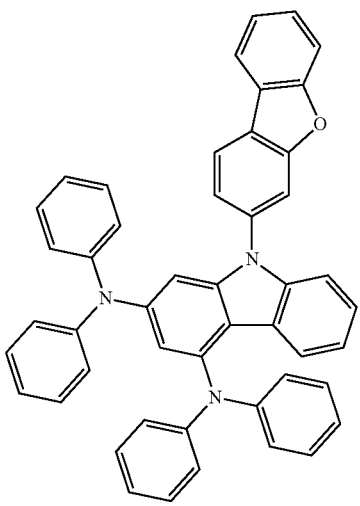
C-23
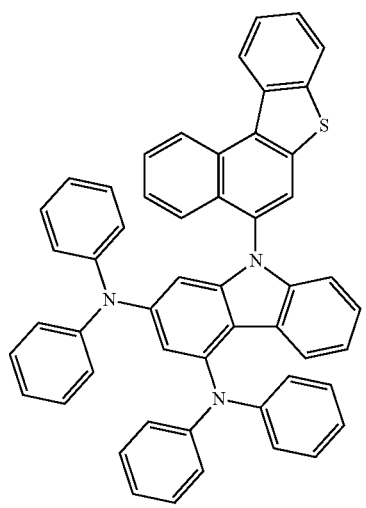
C-21
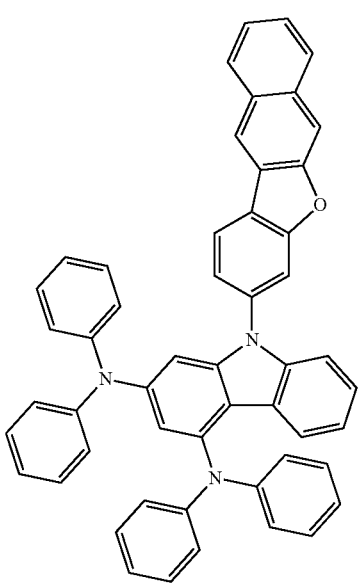
C-24

-continued
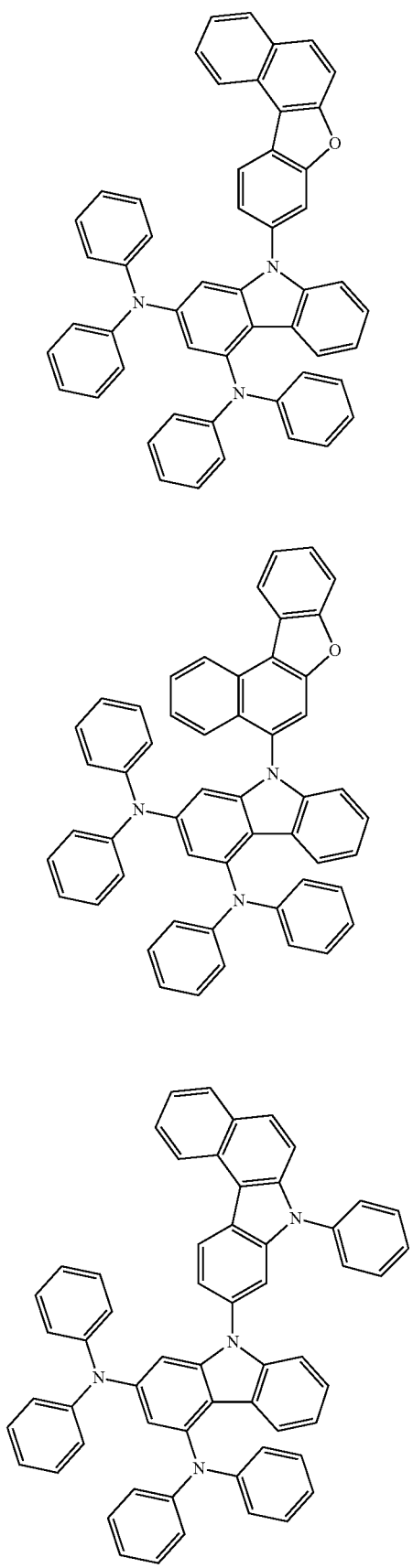
C-25
C-26
C-27
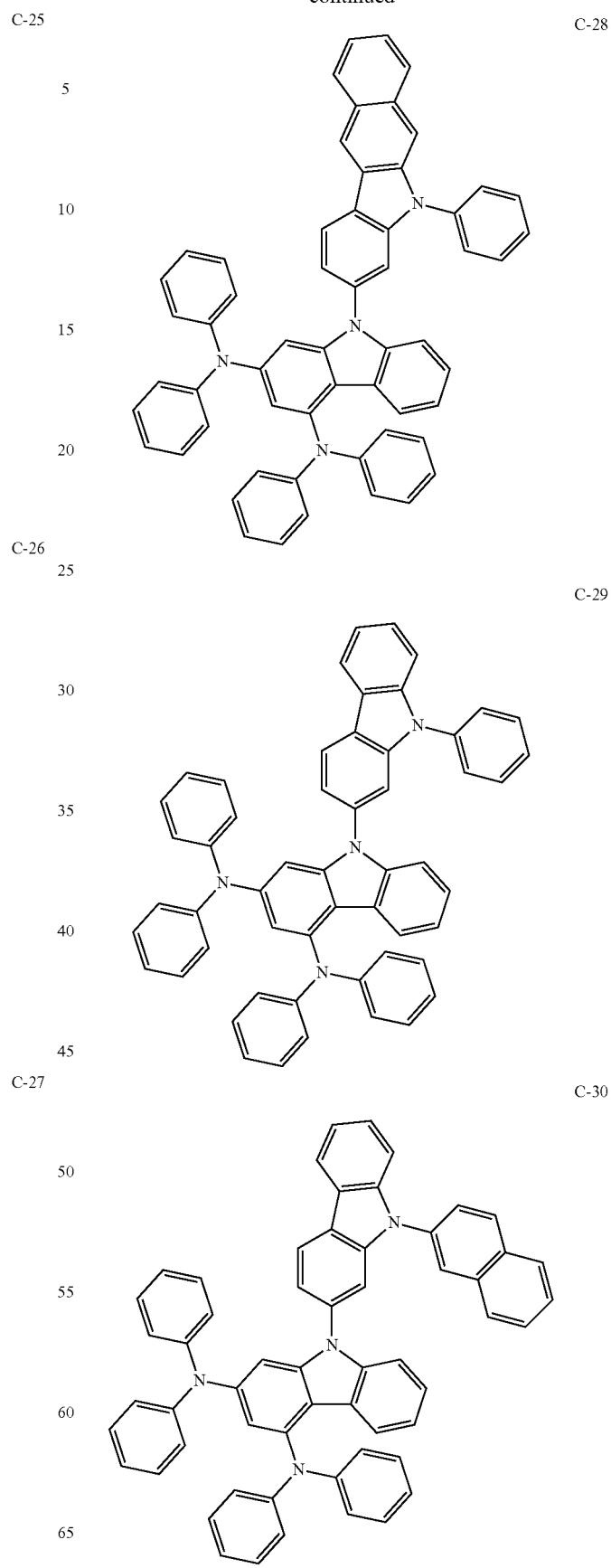
C-28
C-29
C-30

-continued
C-31
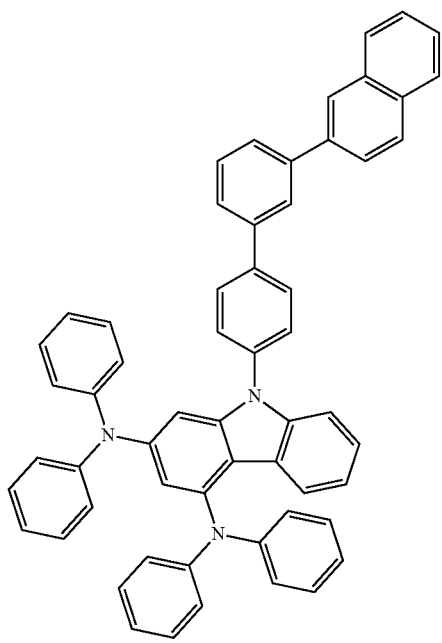
C-32
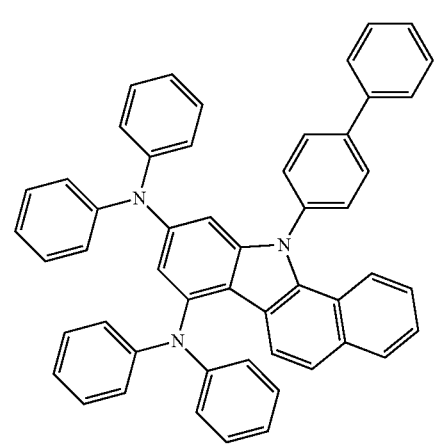
C-33
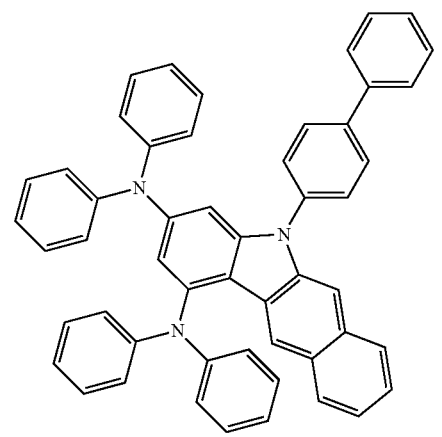
-continued
C-34
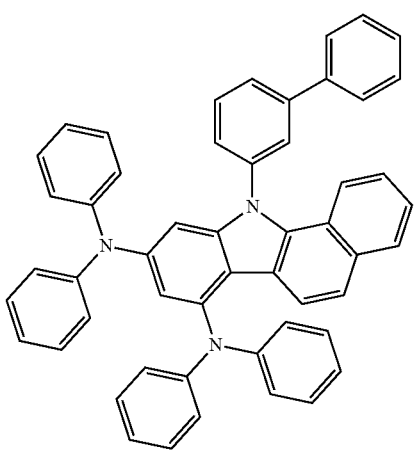
C-35
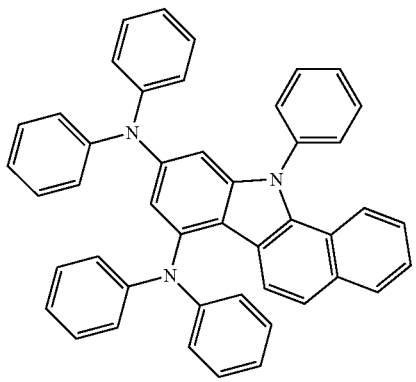
C-36
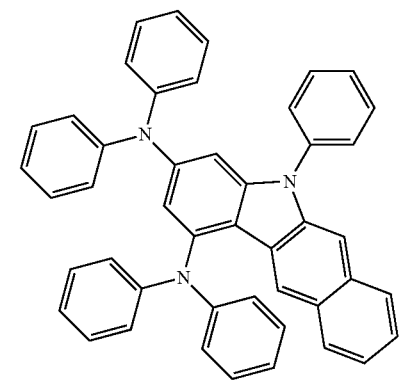

C-37
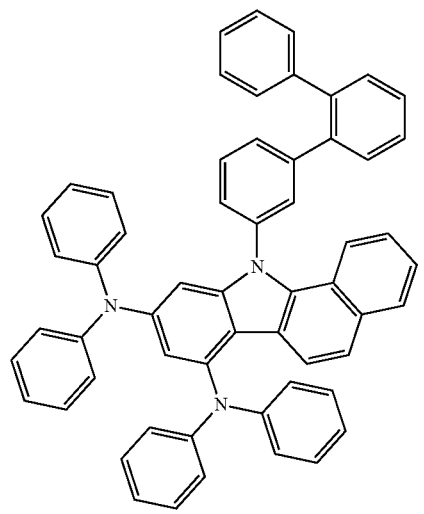
C-38
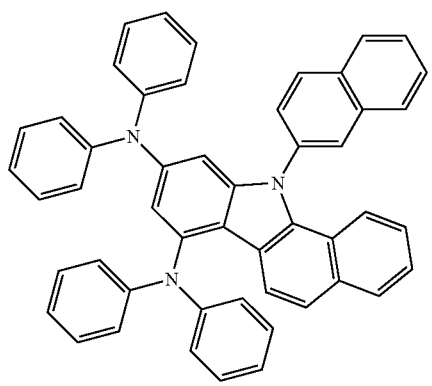
C-39
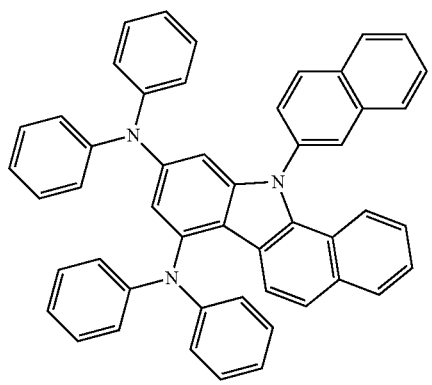
C-40
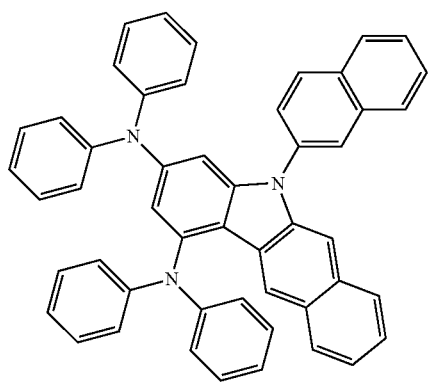
C-41
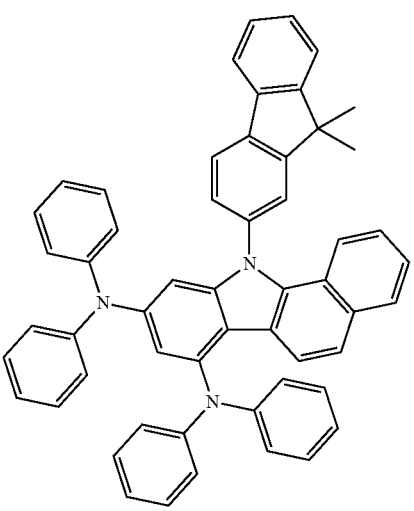
C-42
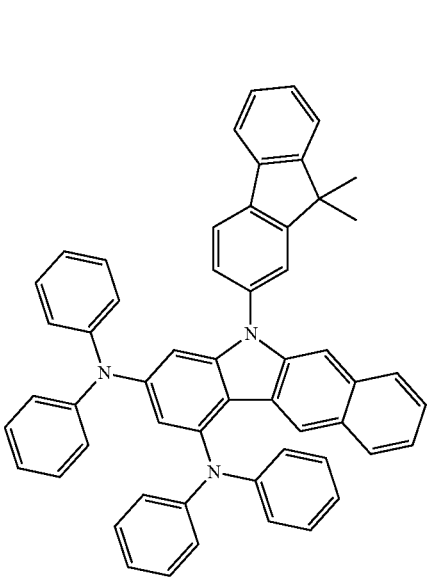
C-43
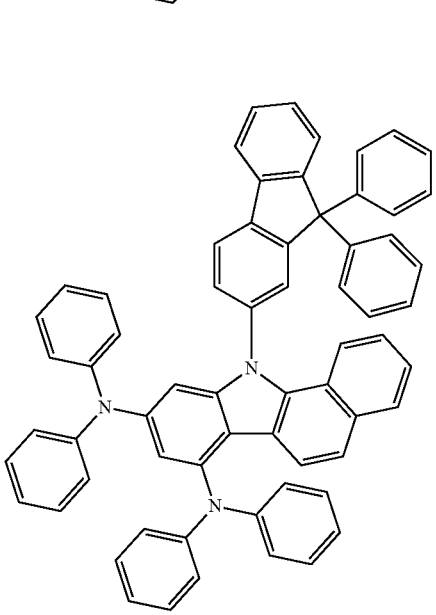

C-44
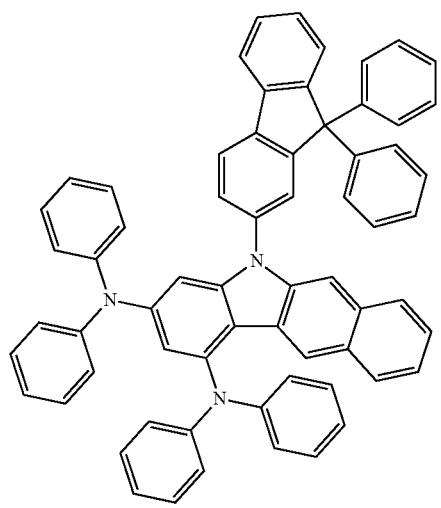
C-45
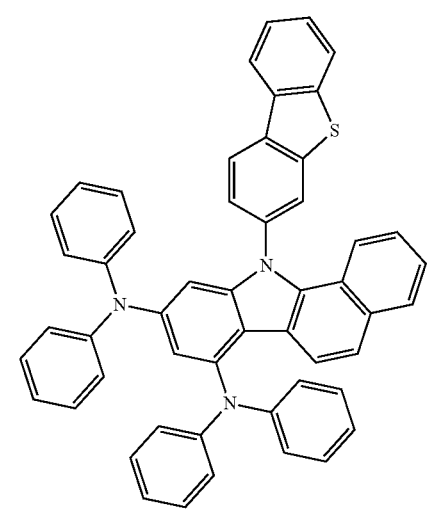
C-46
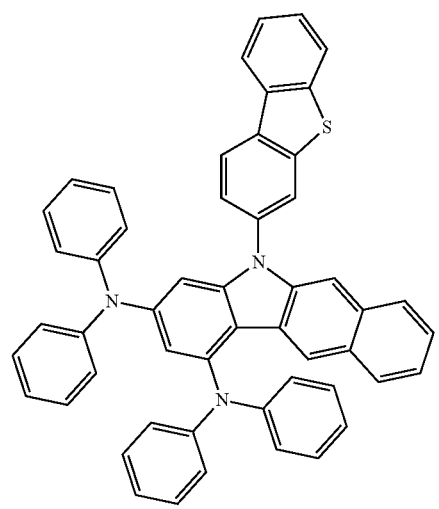
C-47
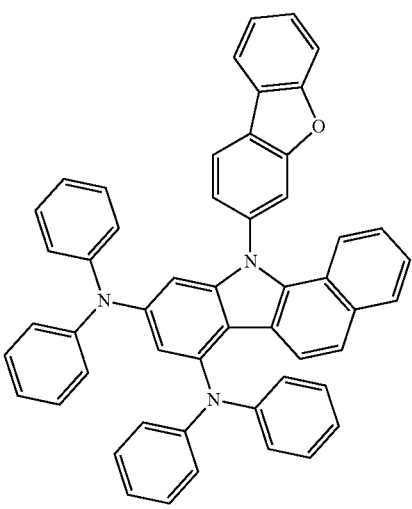
C-48
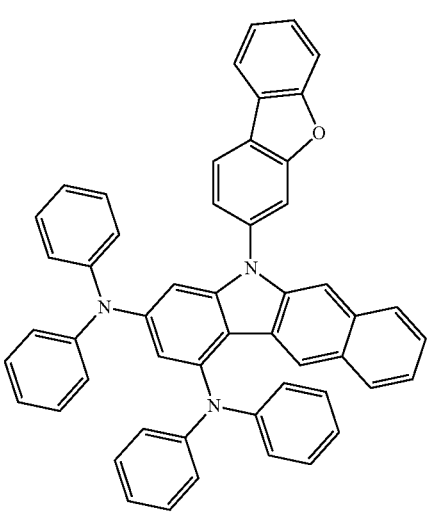
C-49
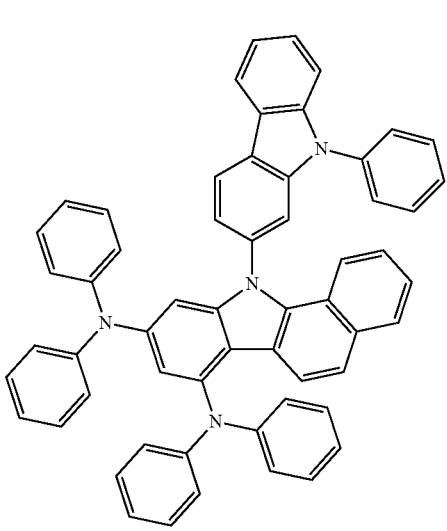

C-50
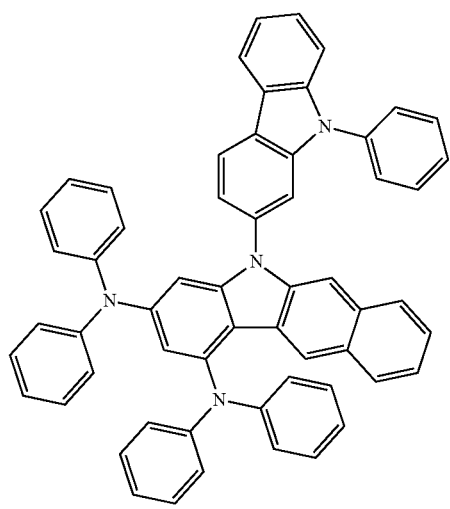
C-51
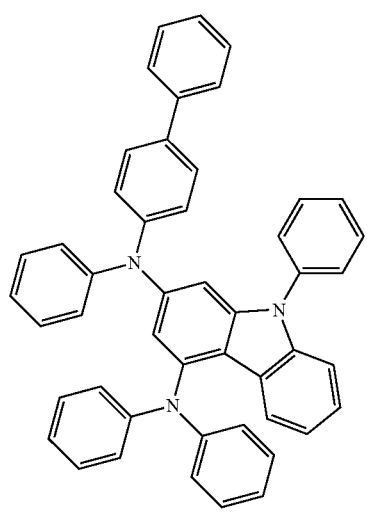
C-52
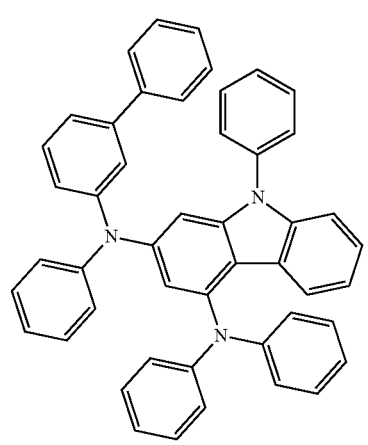
C-53
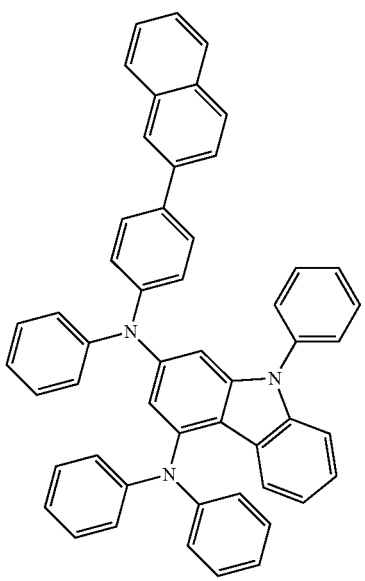
C-54
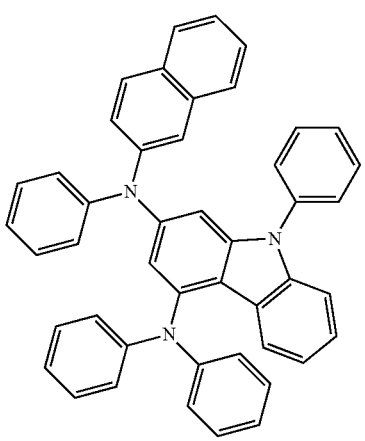
C-55
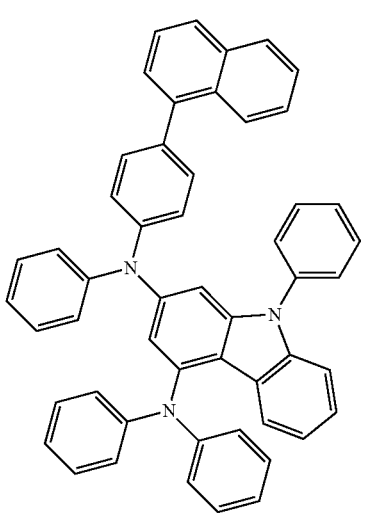

C-56
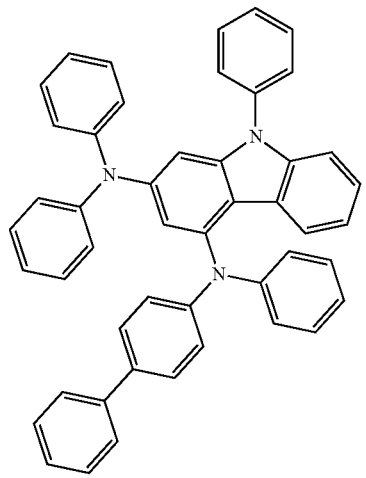
C-59
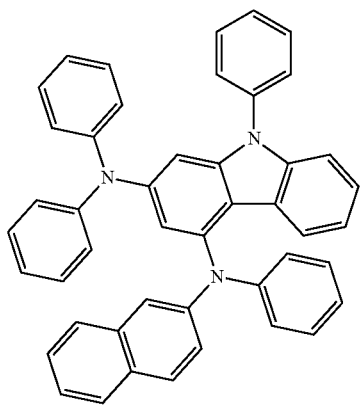
C-57
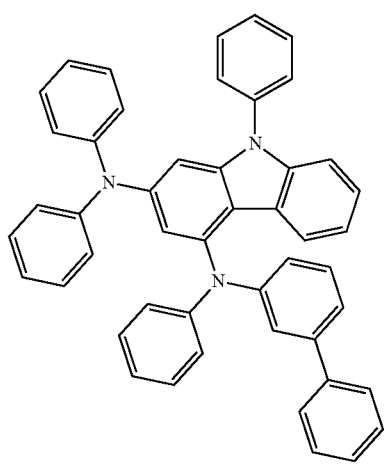
C-60
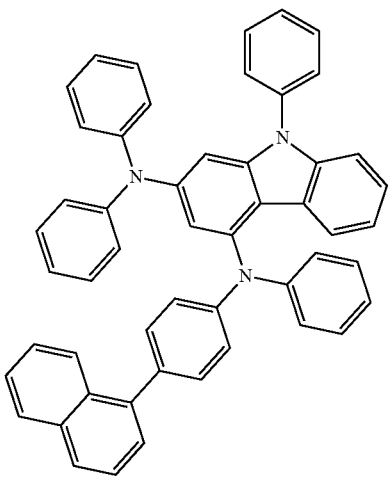
C-58
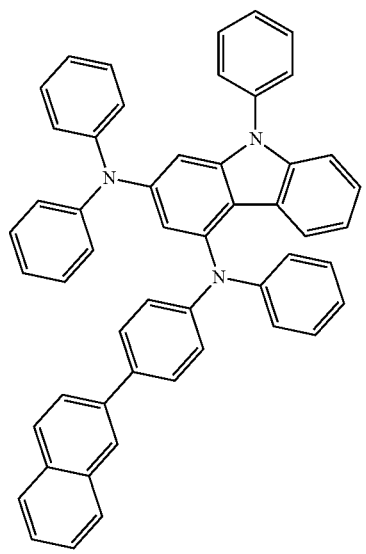
C-61
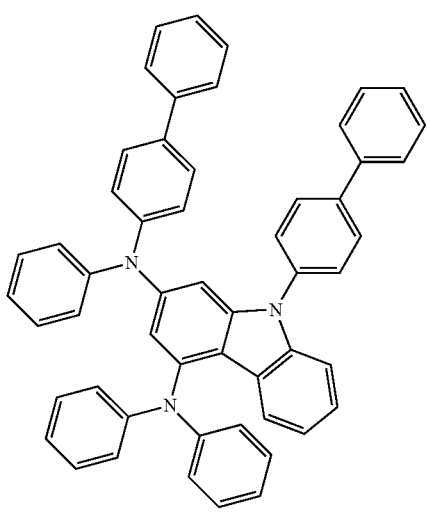

C-62
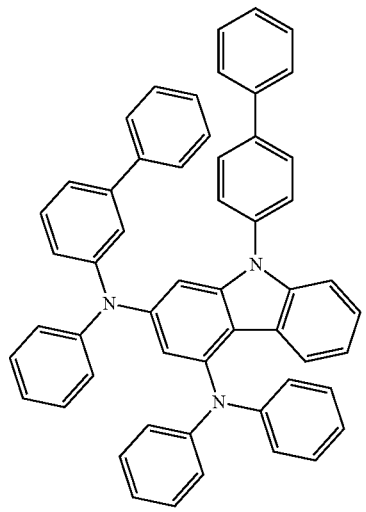
C-65
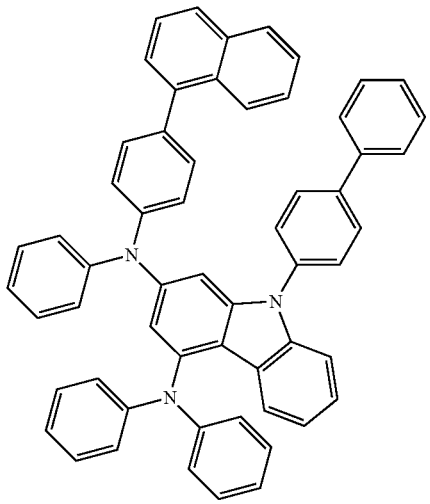
C-63
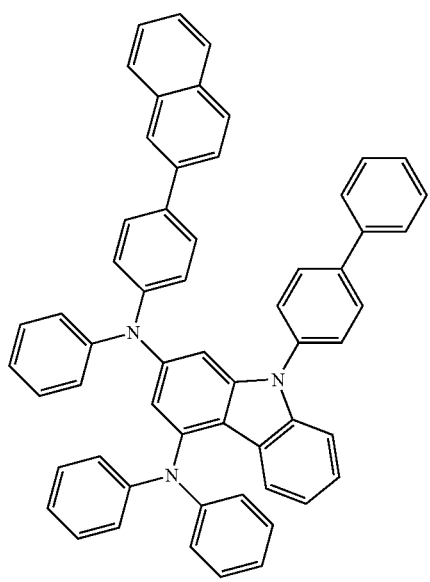
C-64
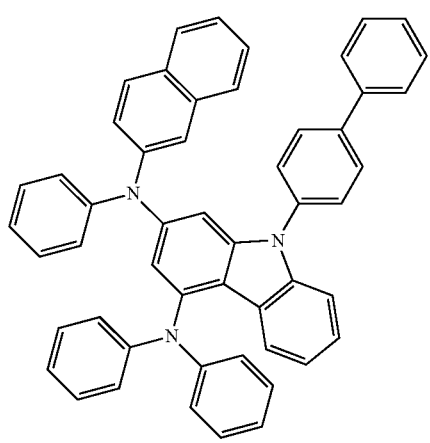
C-66
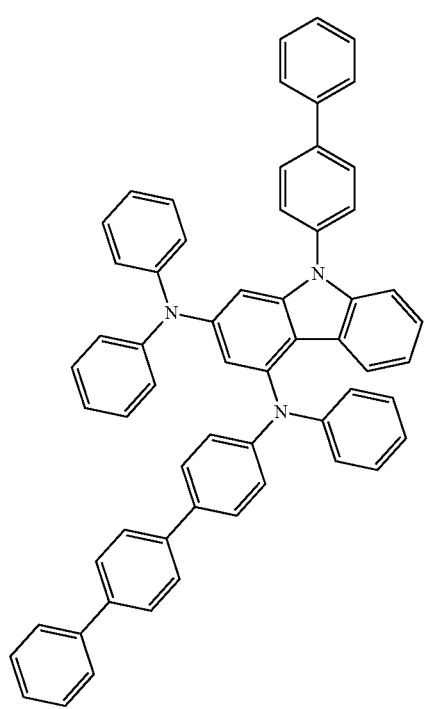

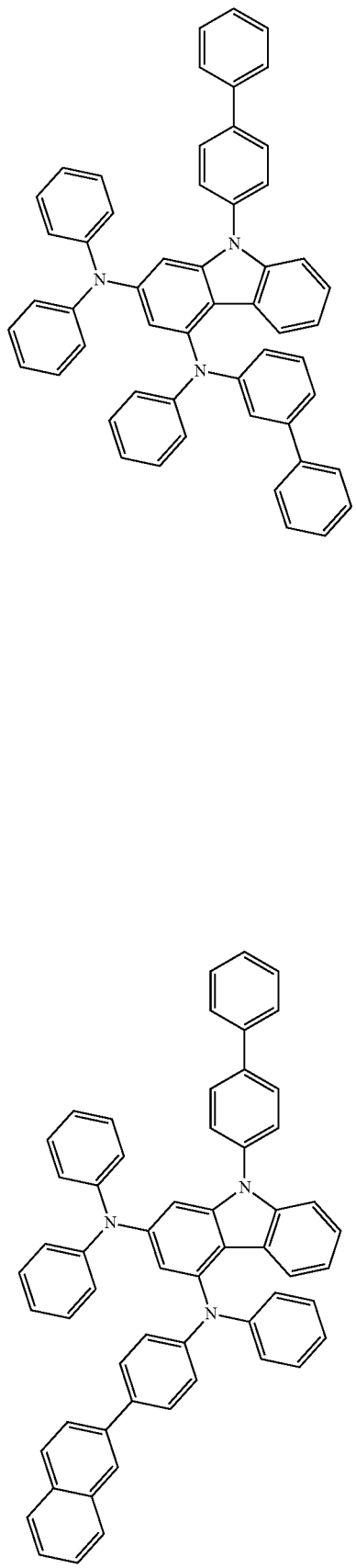
C-67
C-68
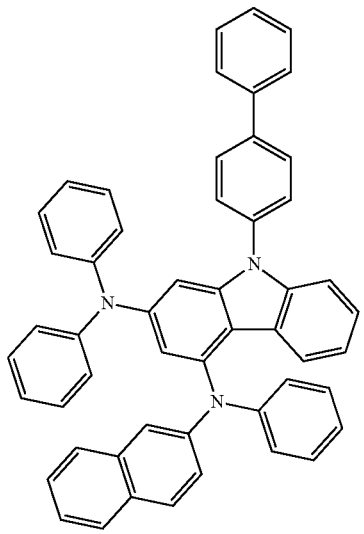
C-69
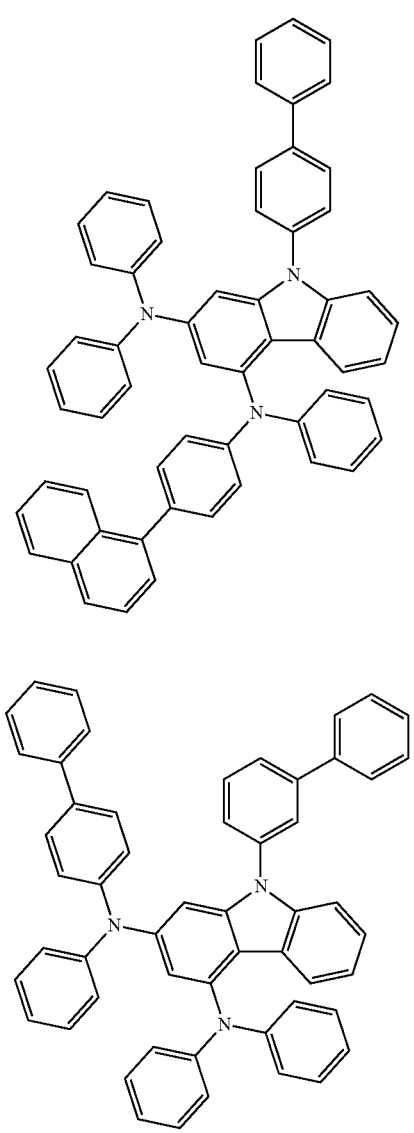
C-70
C-71

C-72
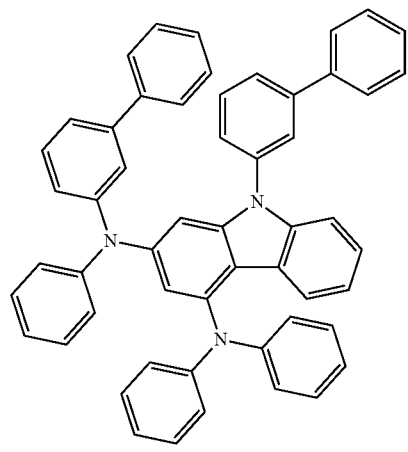
C-73
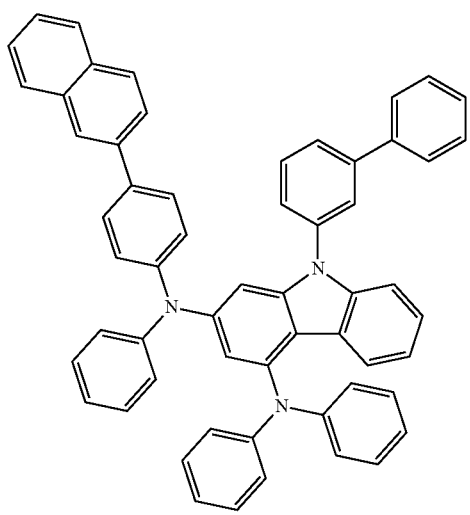
C-74
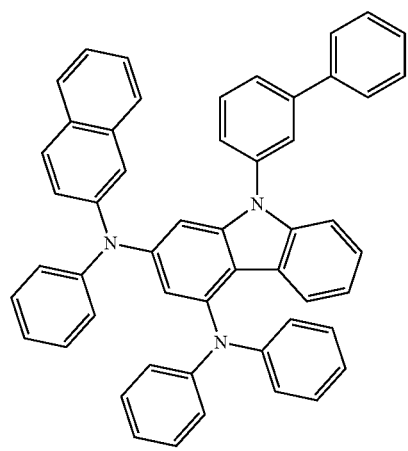
C-75
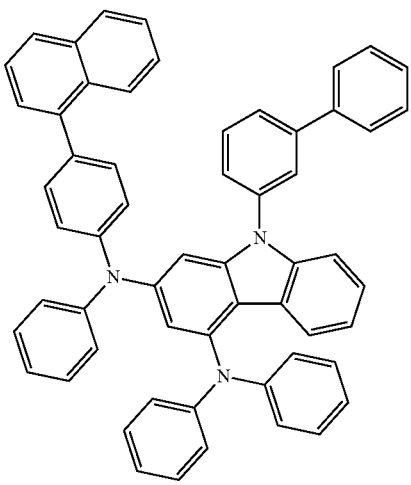
C-76
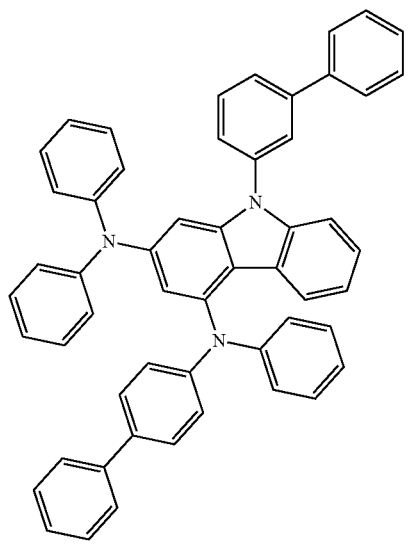
C-77
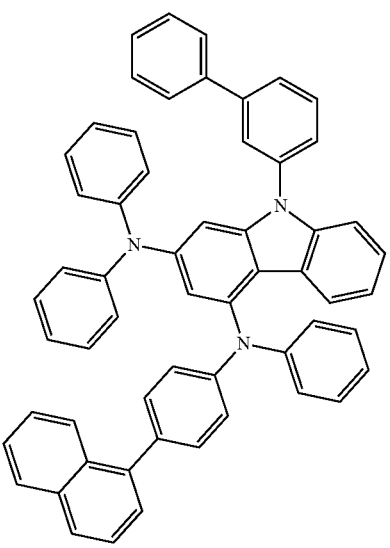

C-78
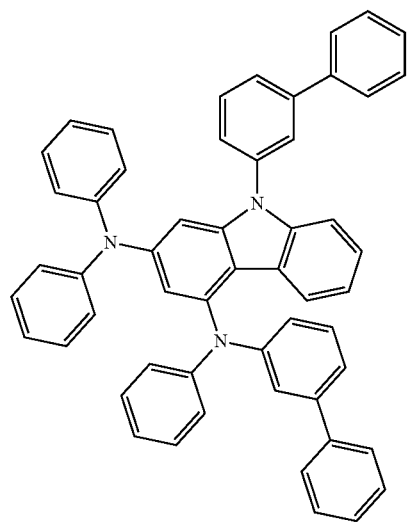
C-79
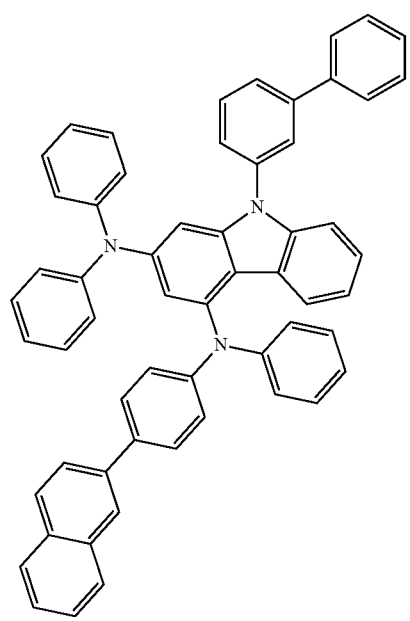
C-80
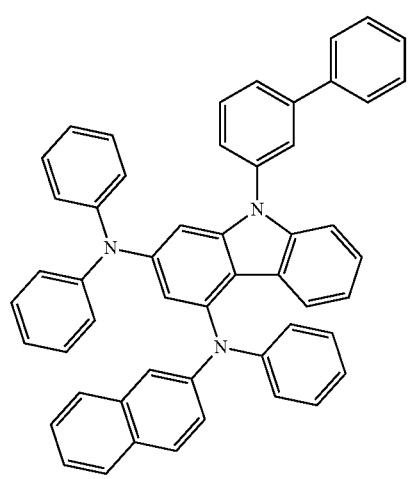
C-81
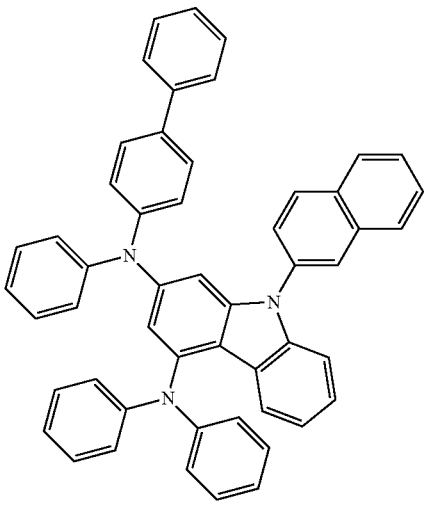
C-82
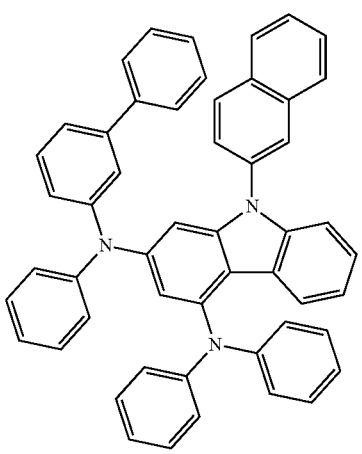
C-83
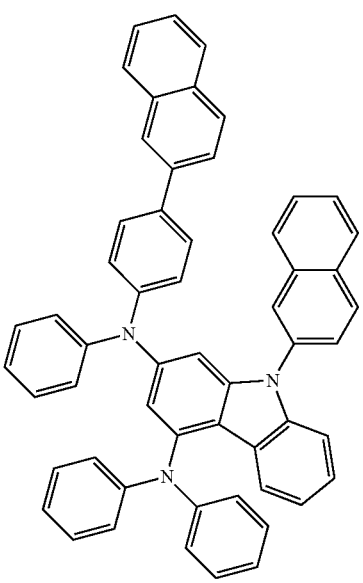

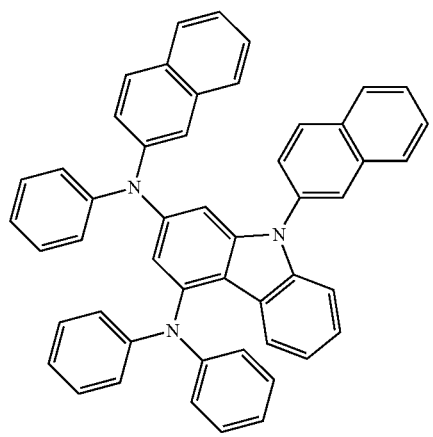
C-84
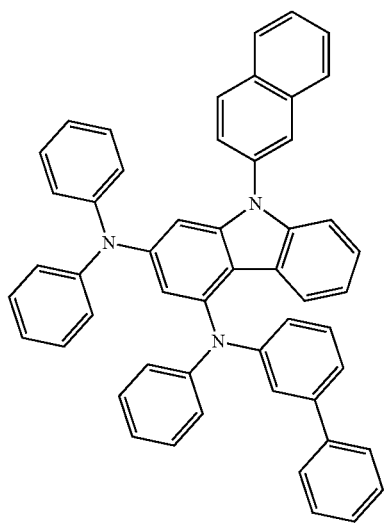
C-85
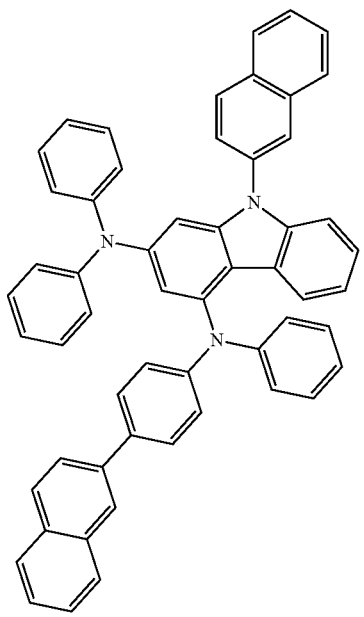
C-86
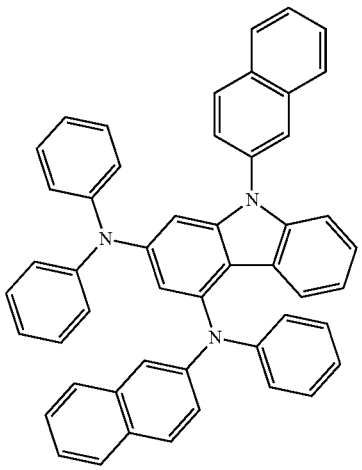
C-87
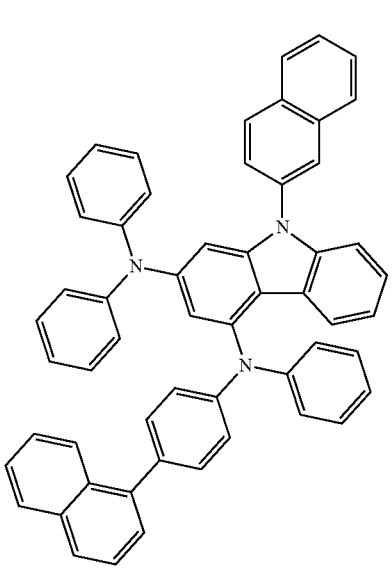
C-88
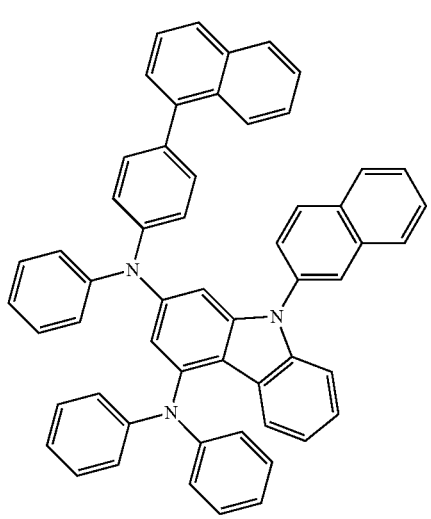
C-89

C-90
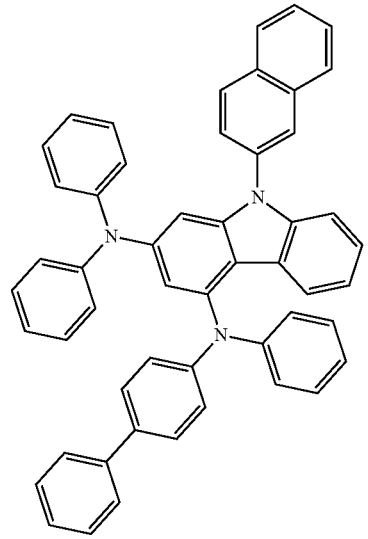
C-91
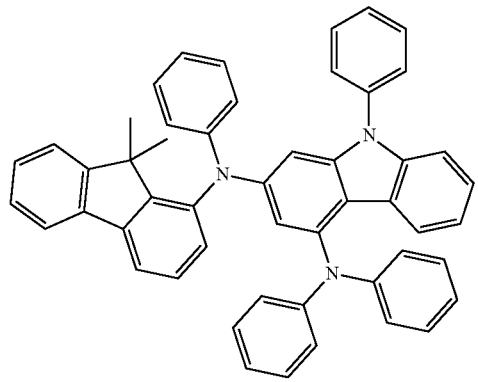
C-92
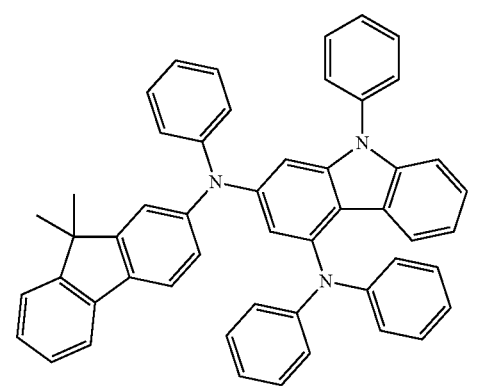
C-93
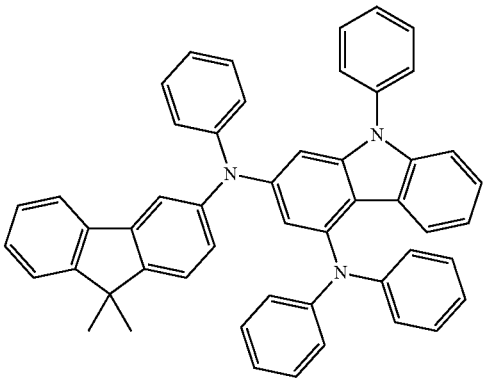
C-94
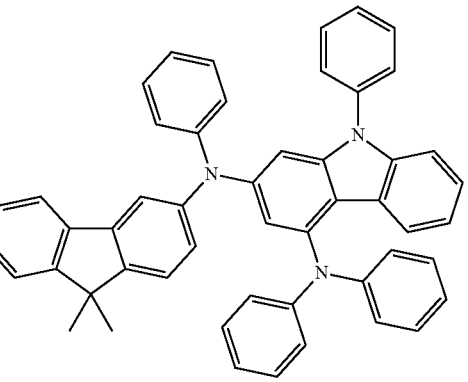
C-95
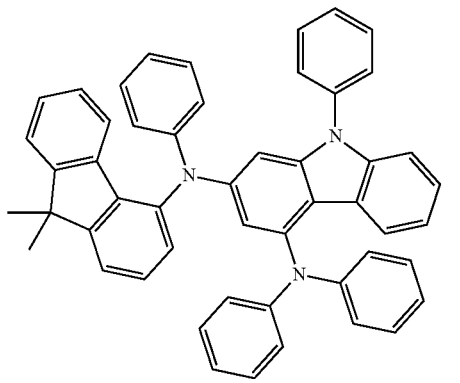
C-96
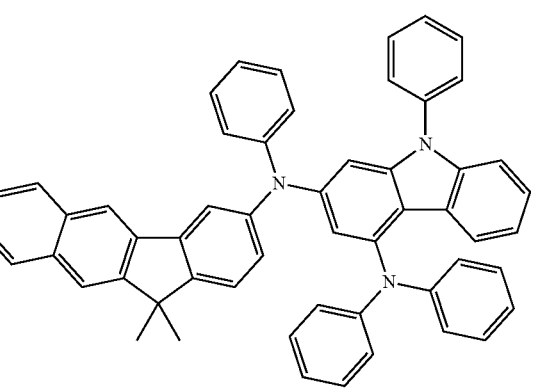

C-97
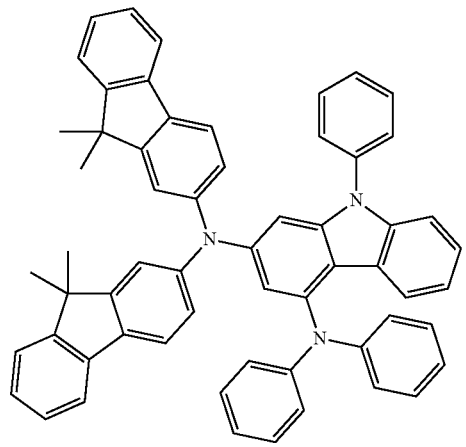
C-100
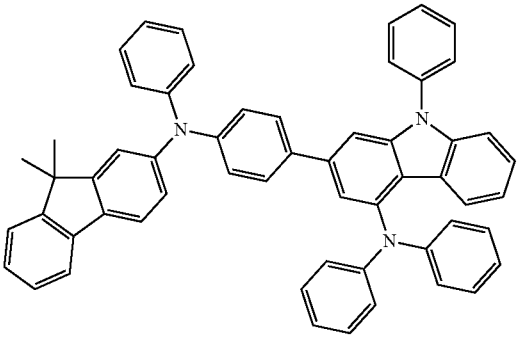
C-98
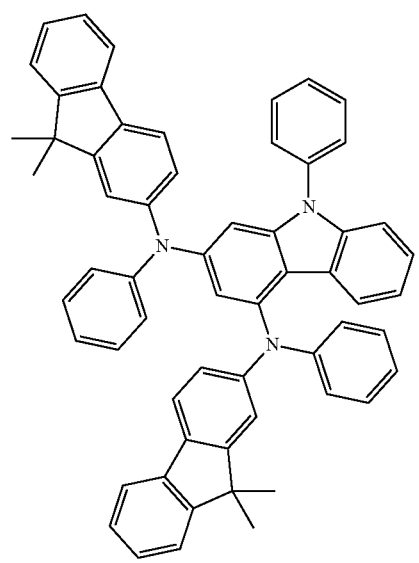
C-101
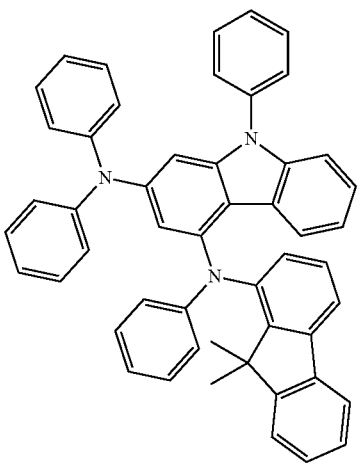
C-99
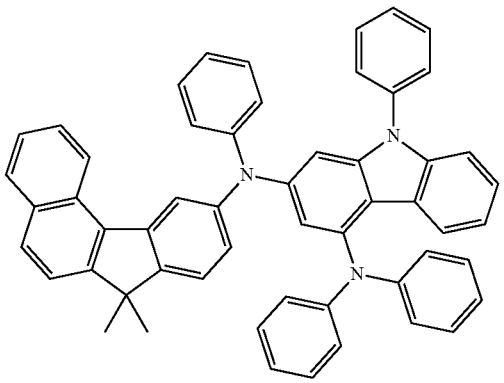
C-102
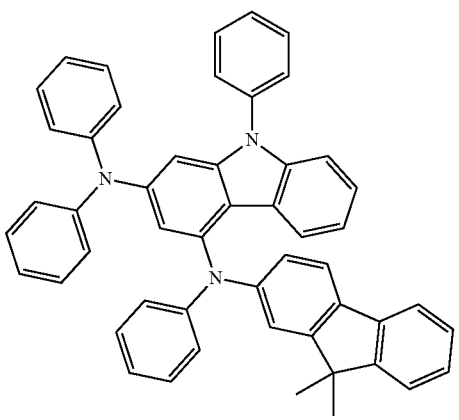

-continued
C-103
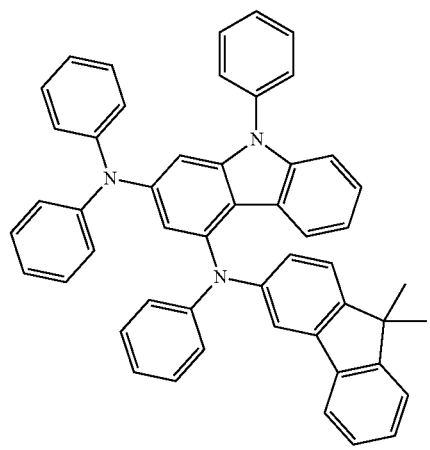
C-104
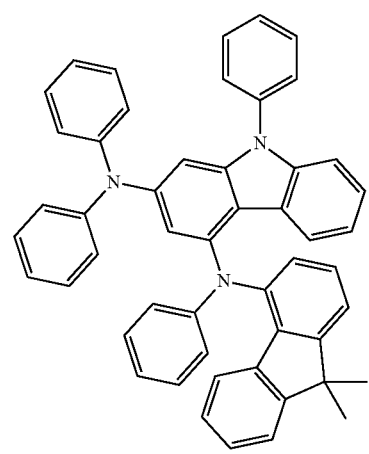
C-105
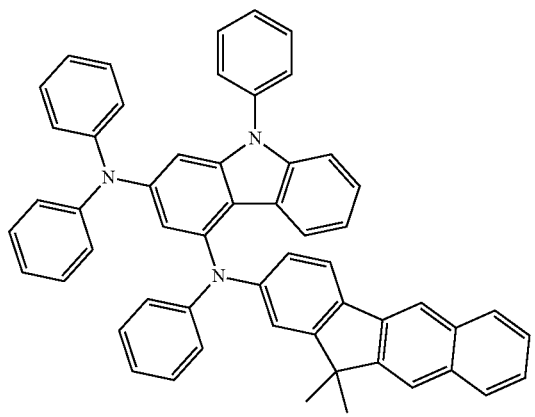
-continued
C-106
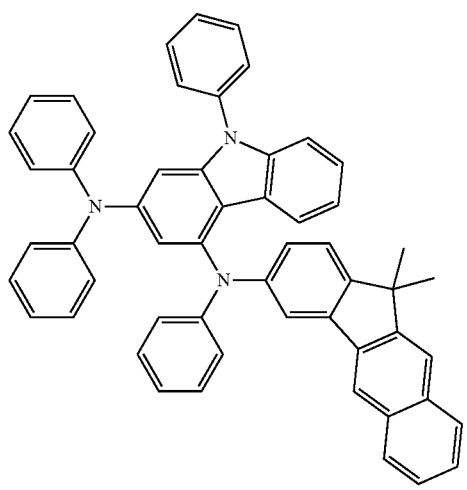
C-107
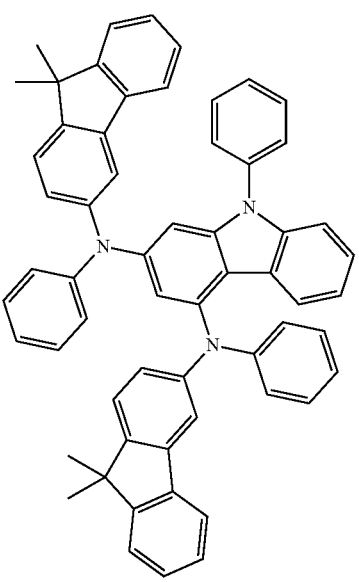
C-108
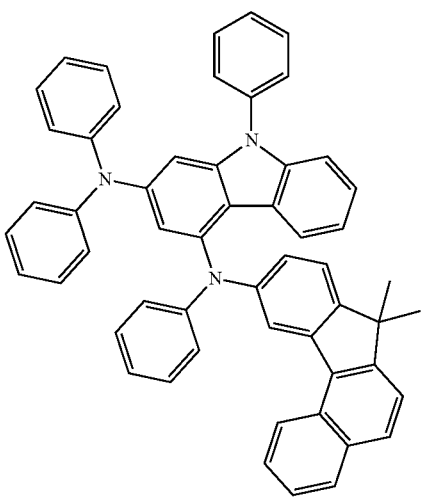

C-109
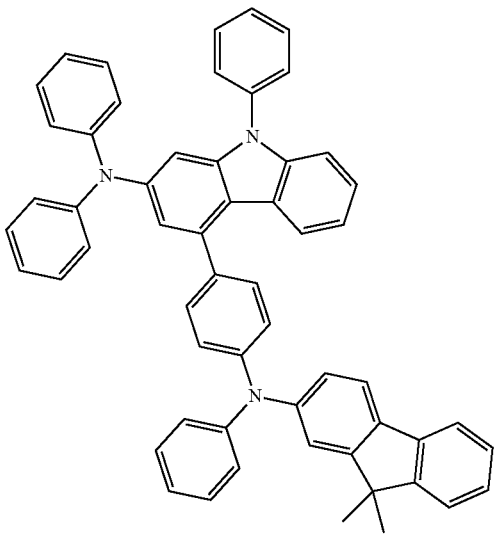
C-112
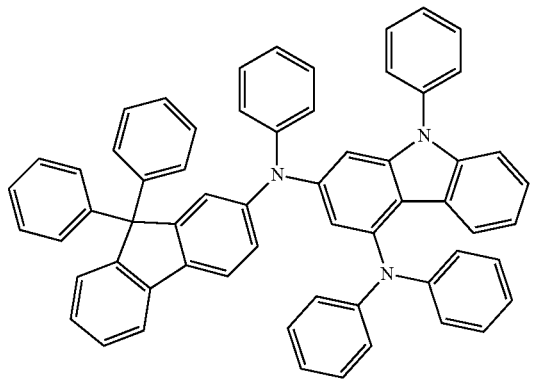
C-110
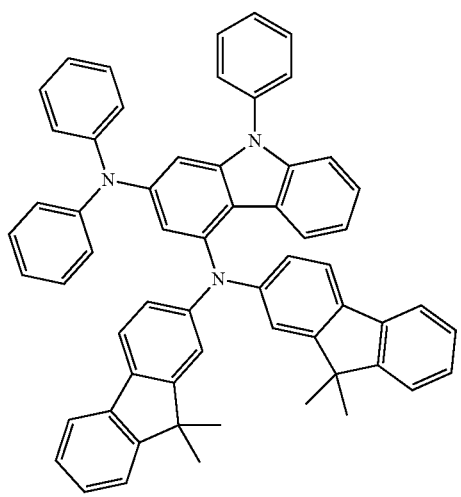
C-113
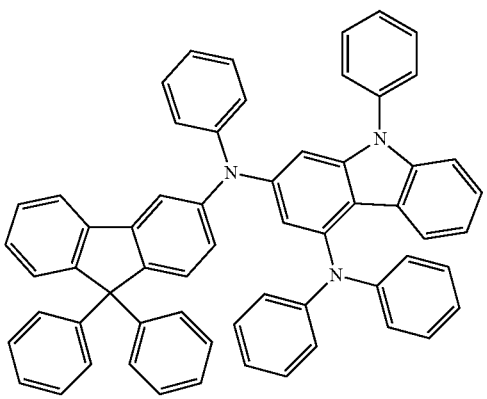
C-111
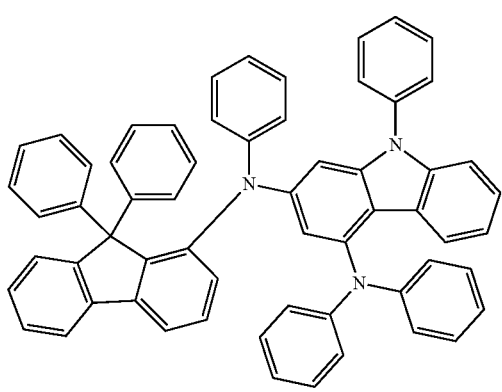
C-114
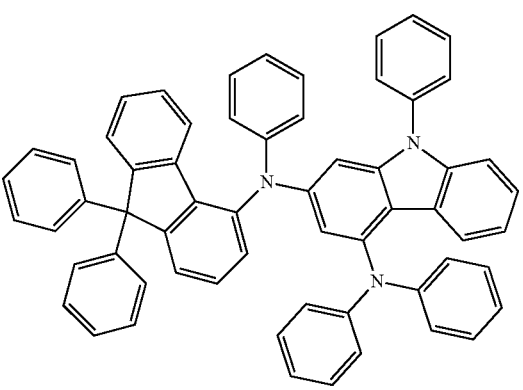

C-115
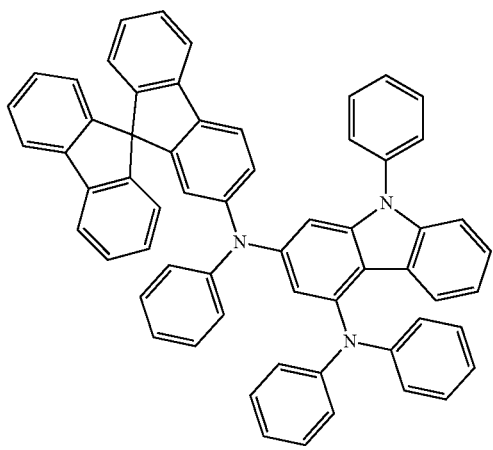
C-116
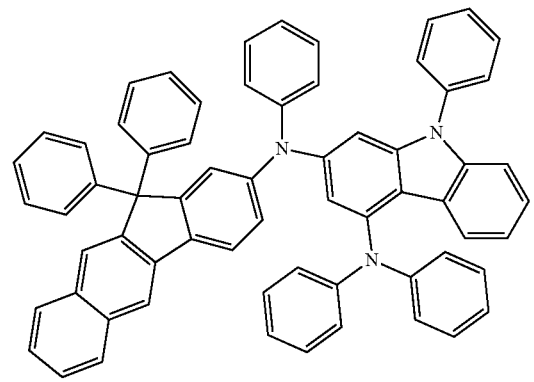
C-117
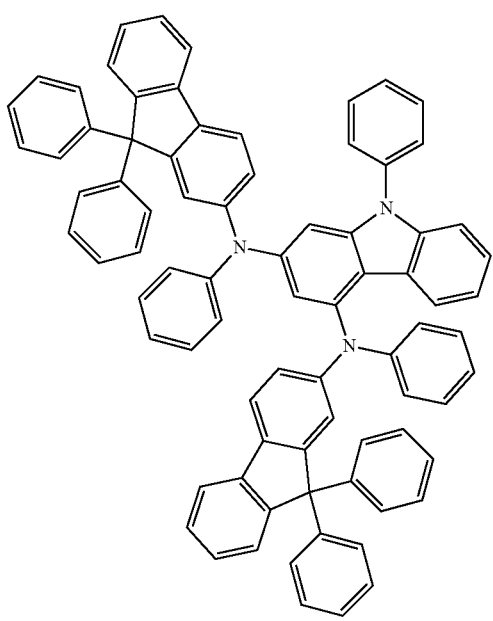
C-118
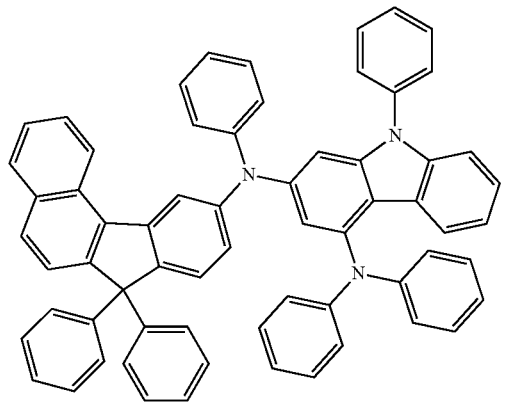
C-119
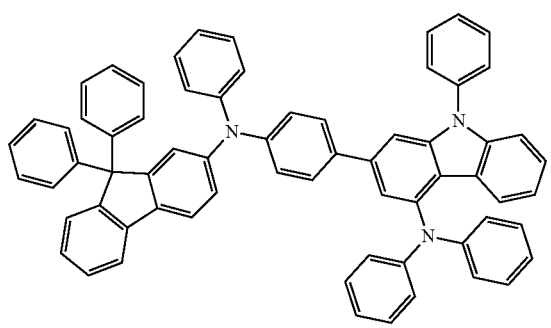
C-120
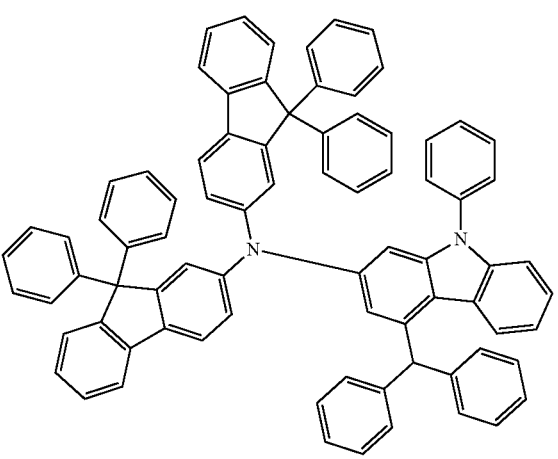
C-121
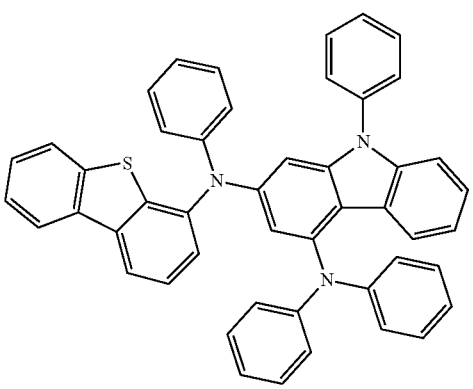

C-122
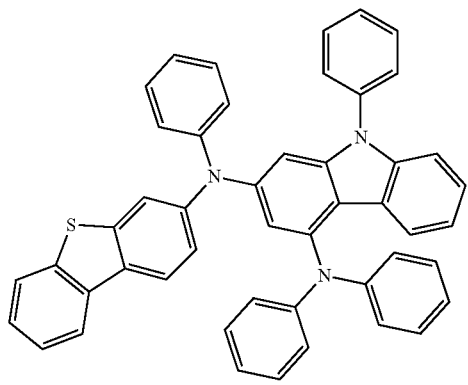
C-123
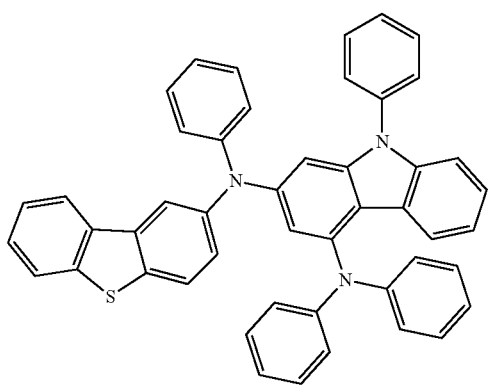
C-124
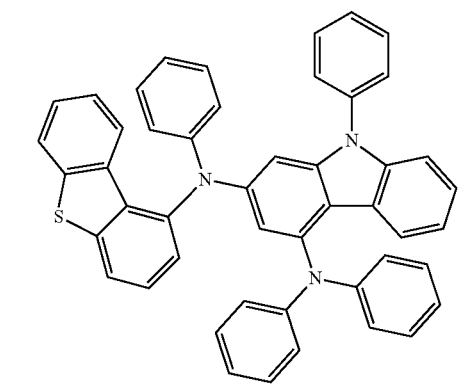
C-125
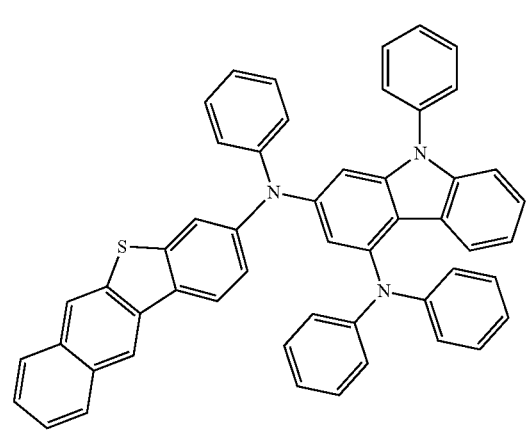
C-126
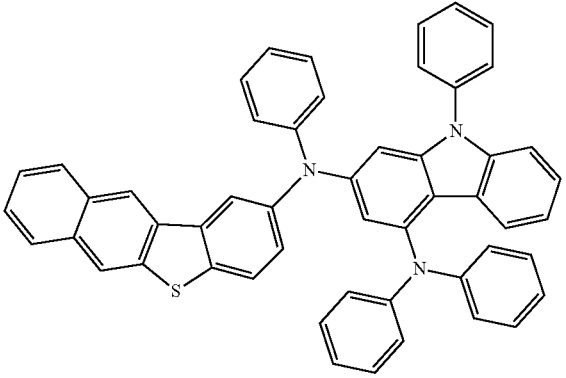
C-127
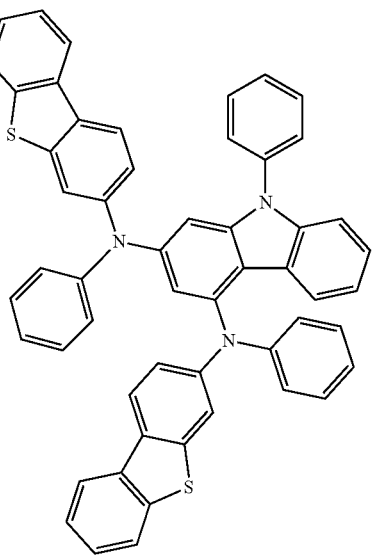
C-128
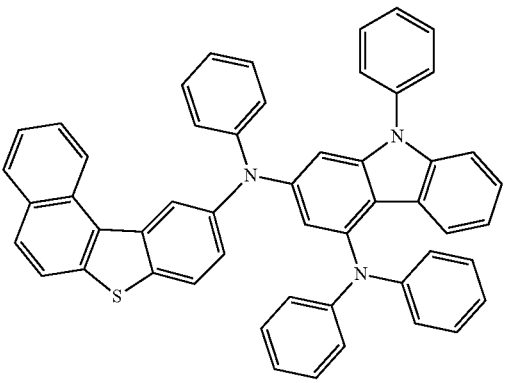

C-129
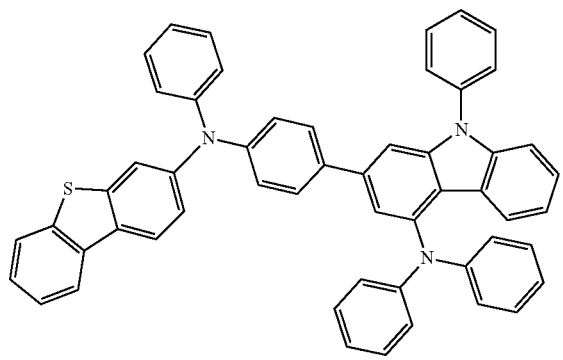
C-130
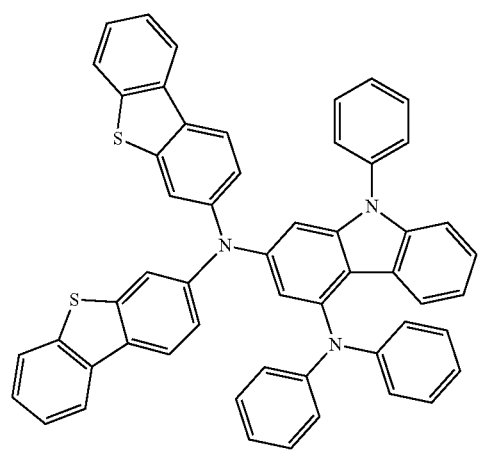
C-131
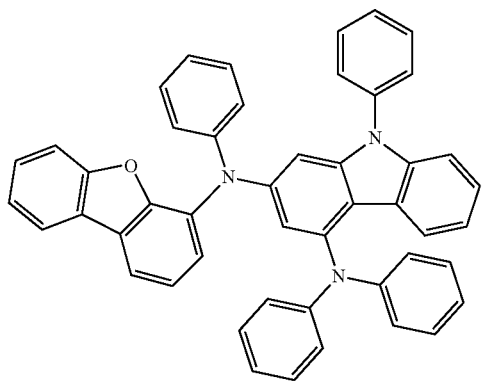
C-132
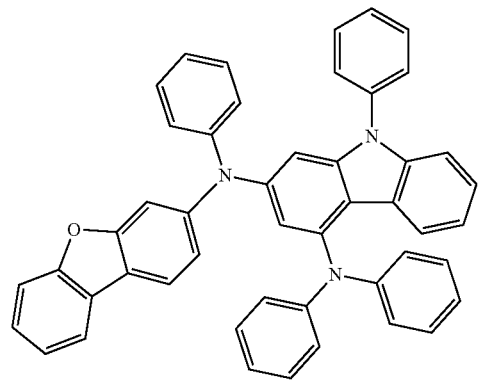
C-133
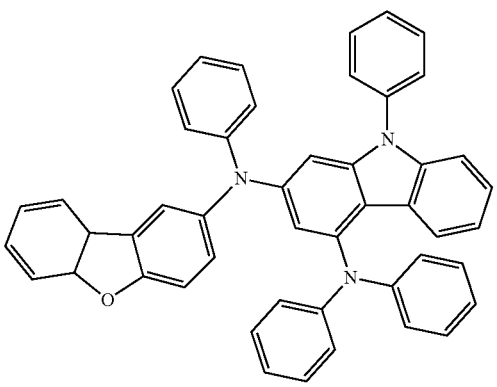
C-134
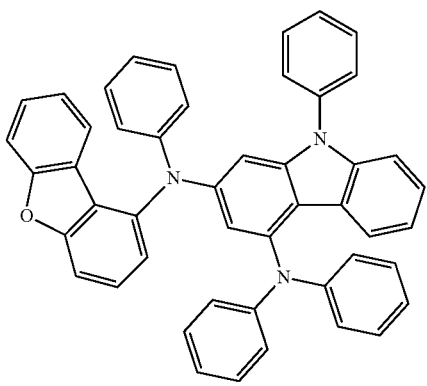
C-135
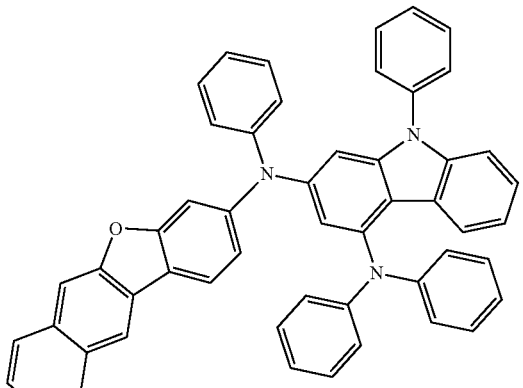
C-136
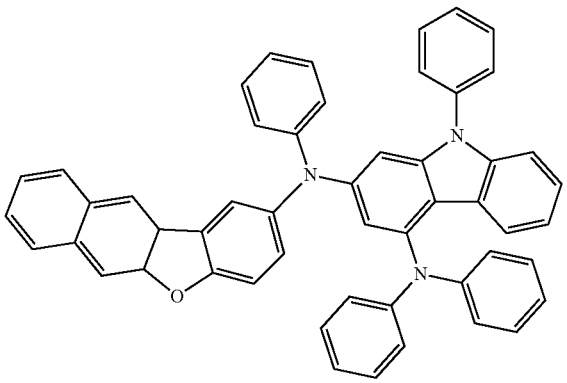

C-137
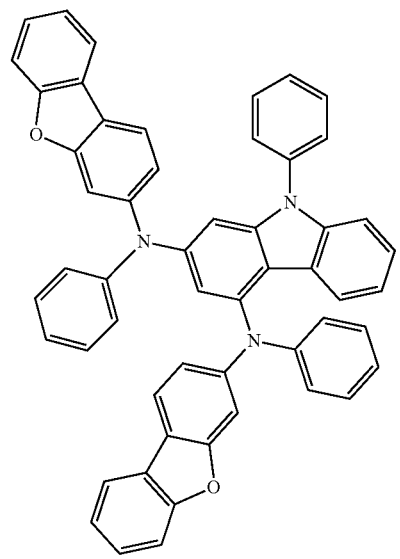
C-138
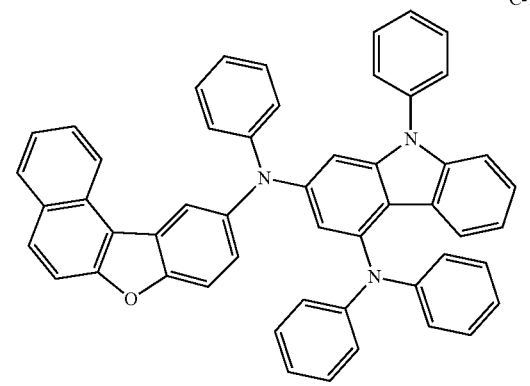
C-139
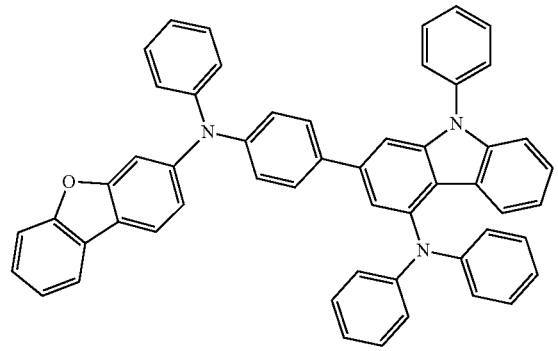
C-140
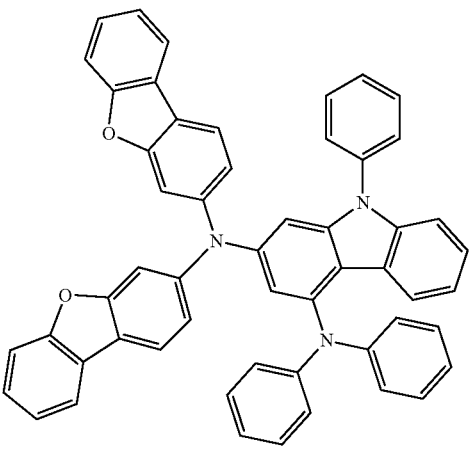
C-141
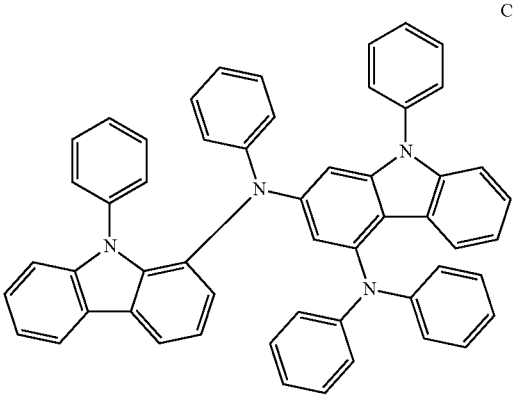
C-142
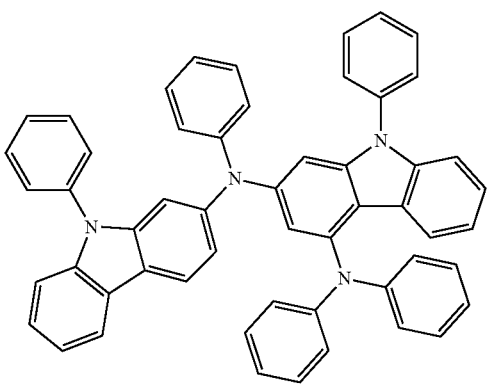
C-143
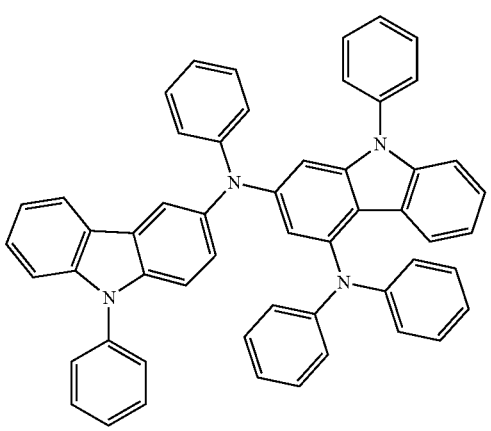

C-144
C-145
C-146
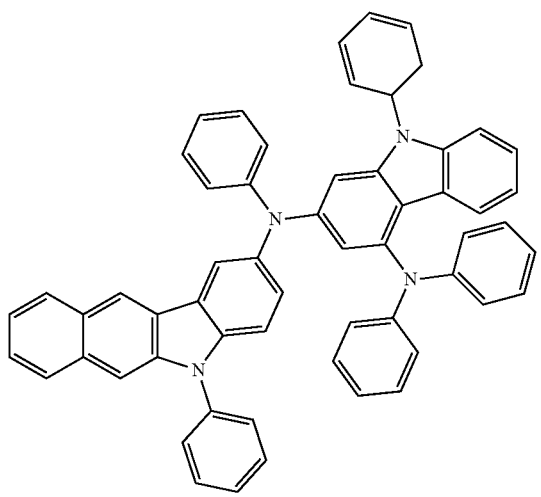
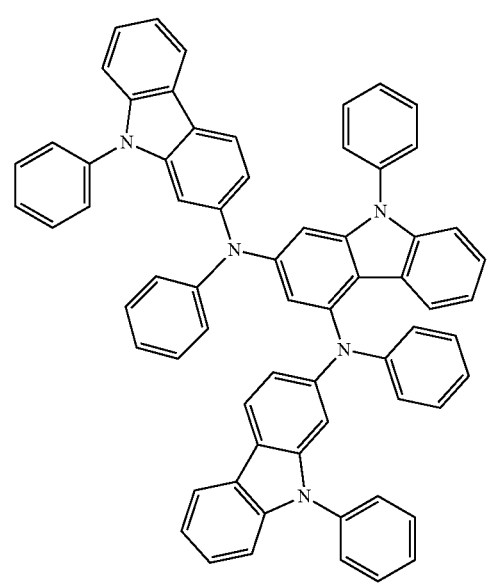
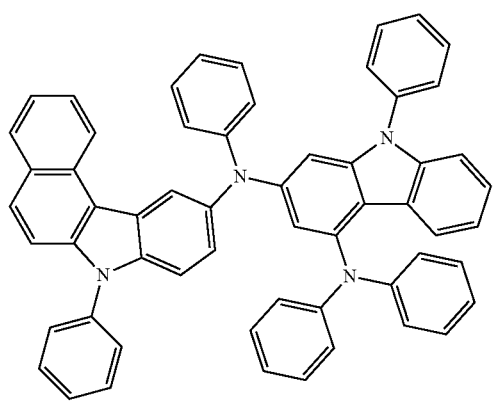
C-147
C-148
C-149
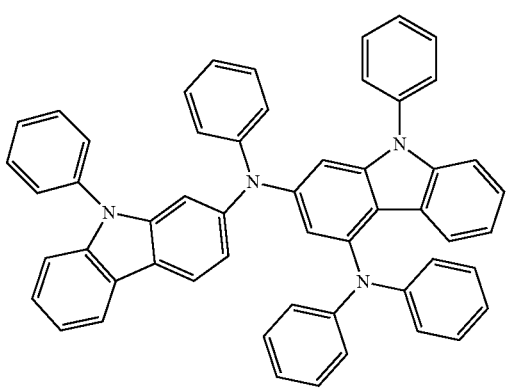

C-150
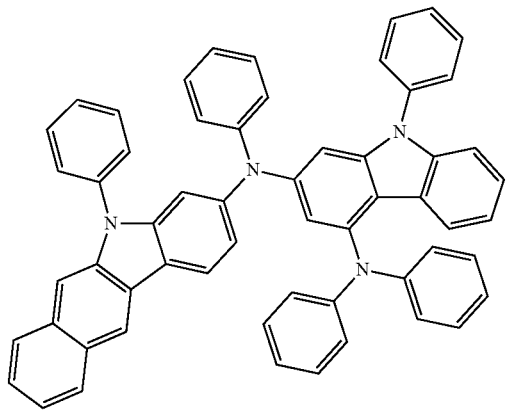
C-153
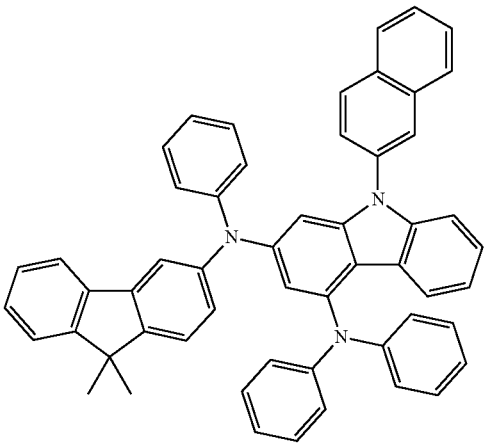
C-151
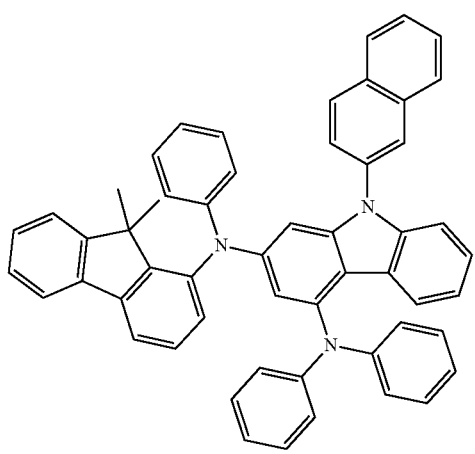
C-154
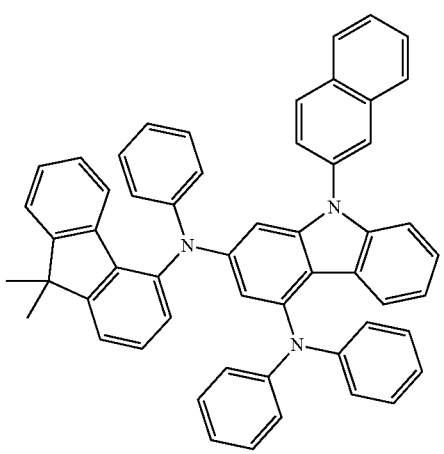
C-152
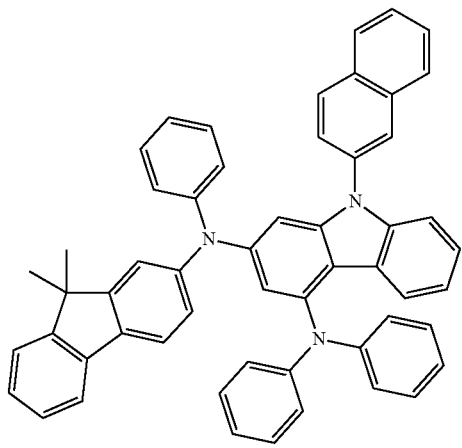
C-155
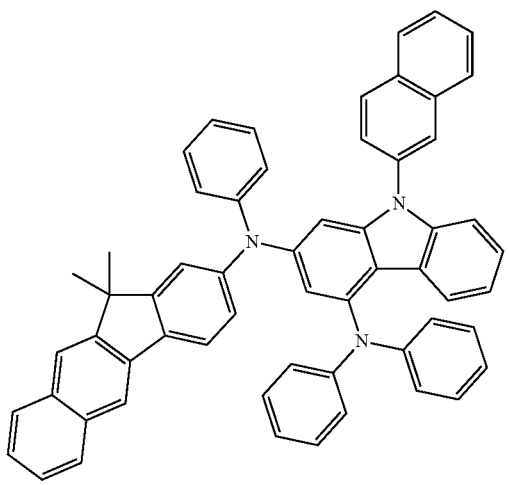

C-156
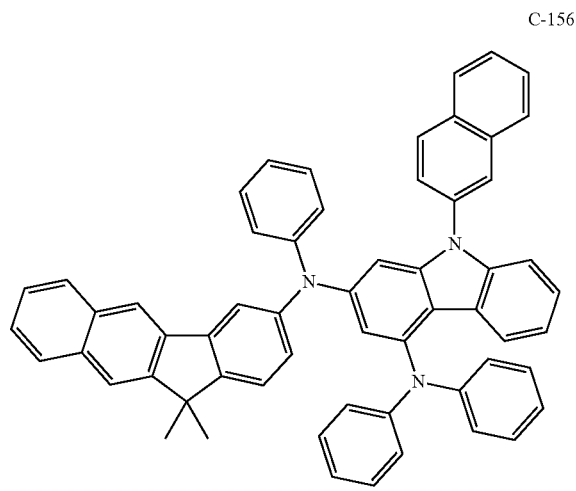
C-159
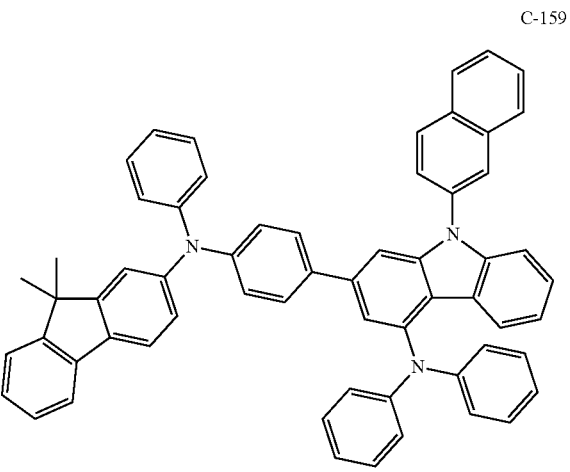
C-157
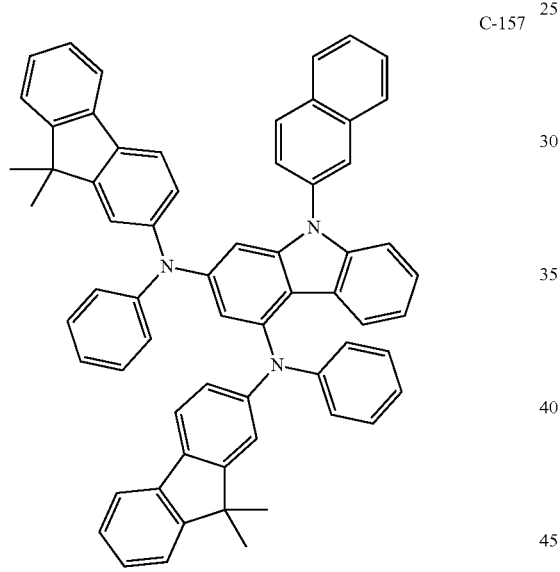
C-160
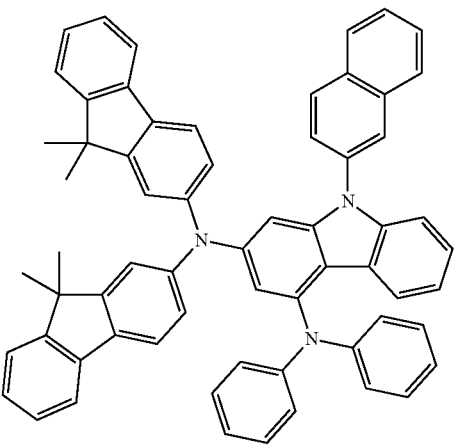
C-158
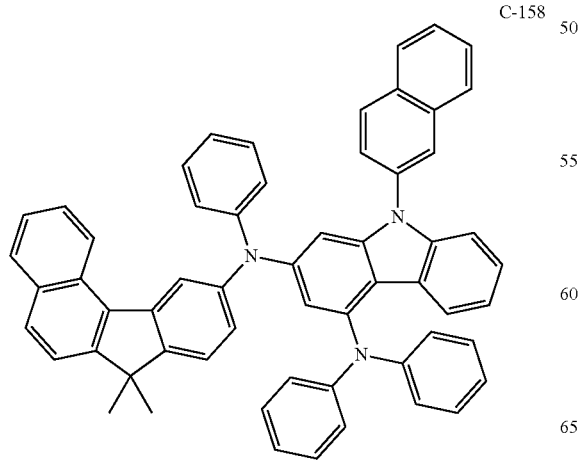
C-161
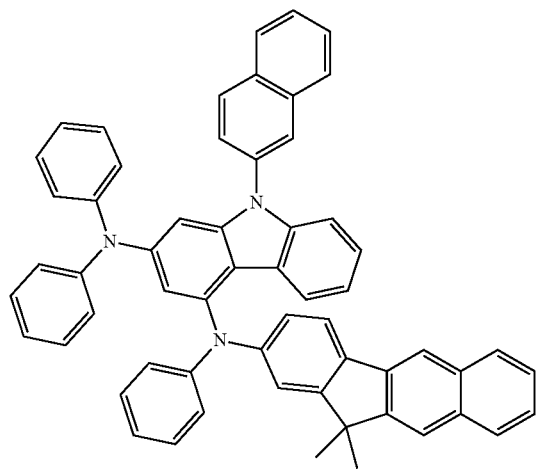

-continued
C-162
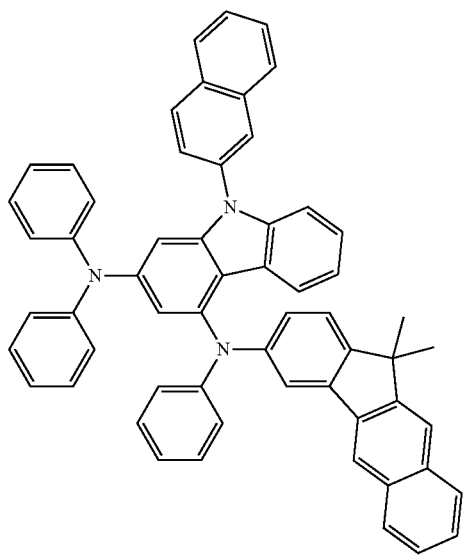
C-163
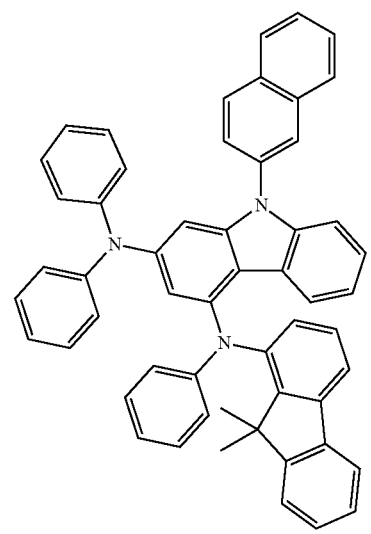
C-164
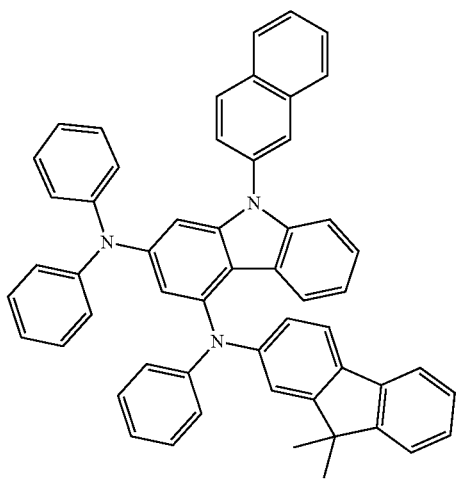
C-165
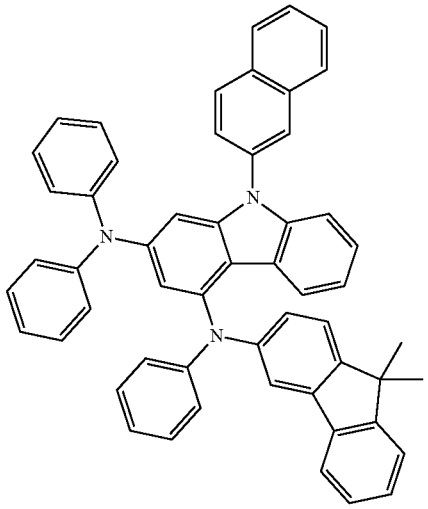
C-166
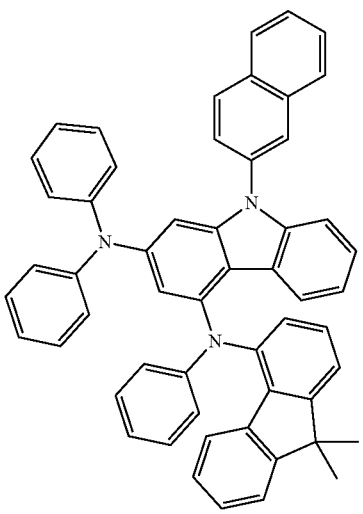
C-167
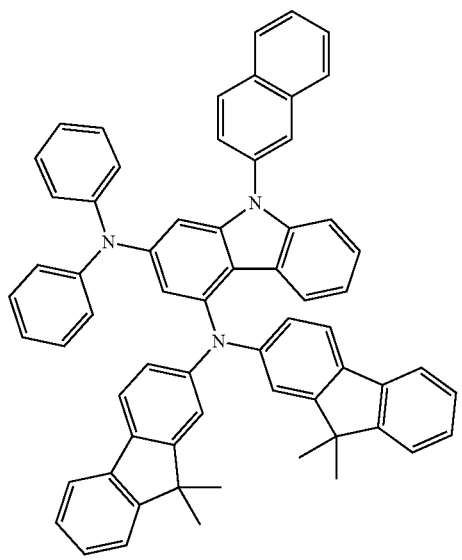

C-168
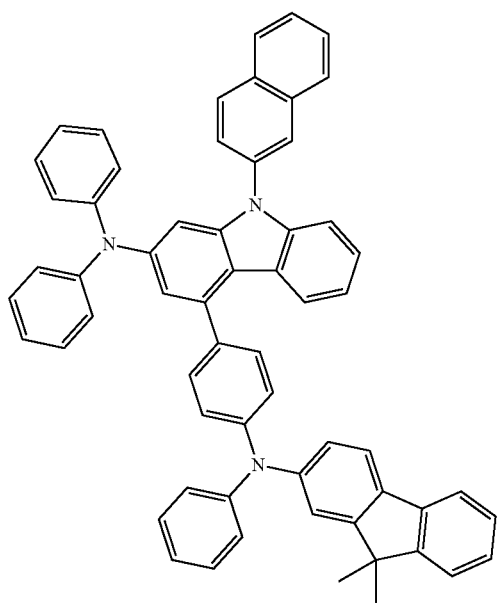
C-169
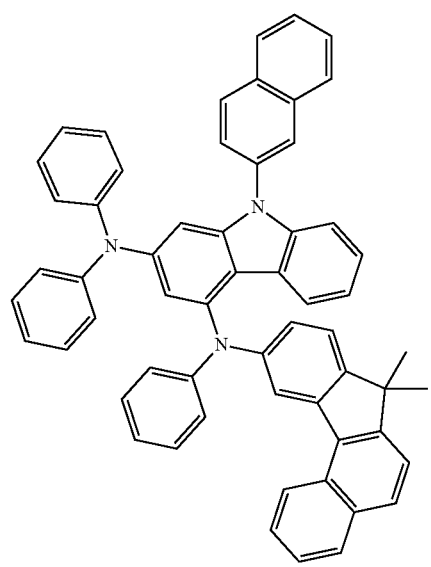
C-170
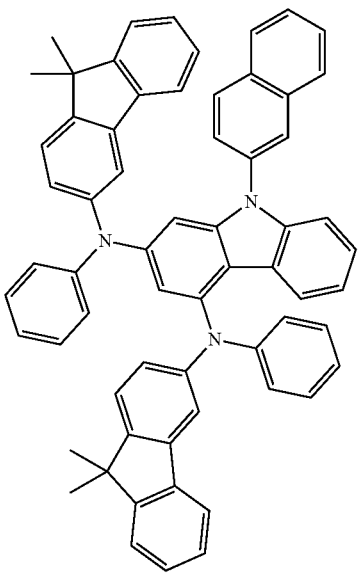
C-171
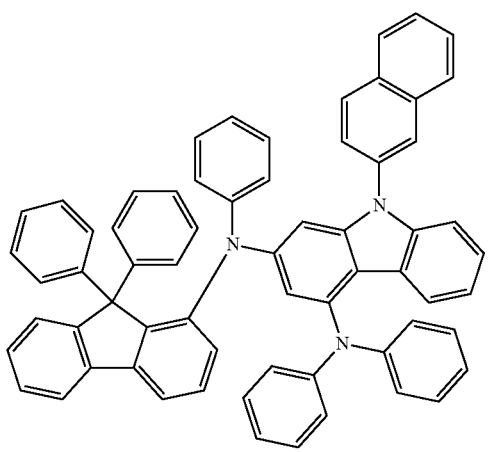
C-172

C-173
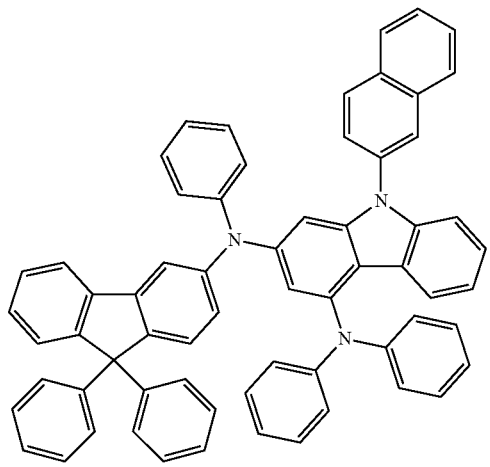
C-174
C-175
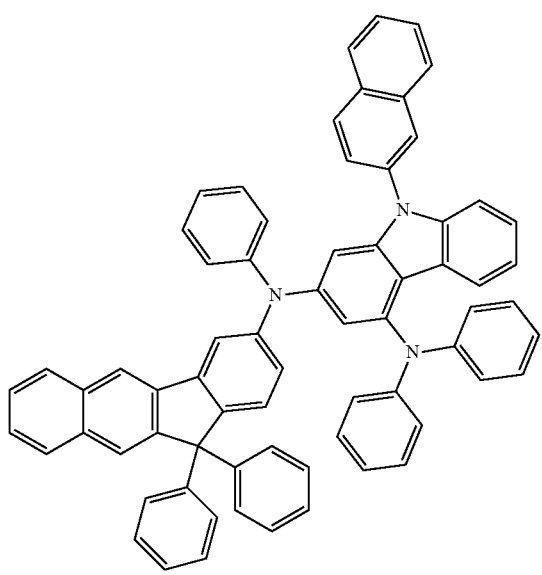
C-176
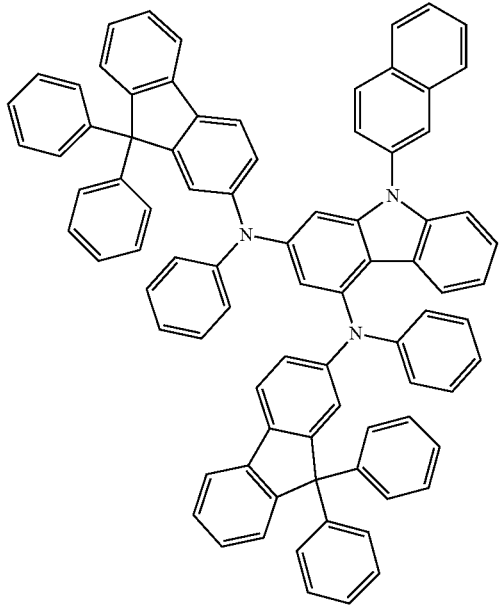
C-177
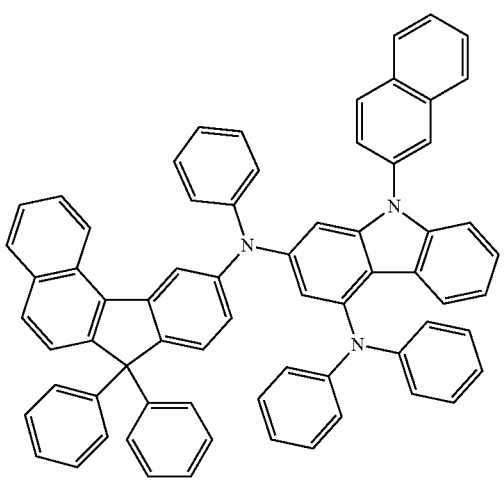
C-178

C-179
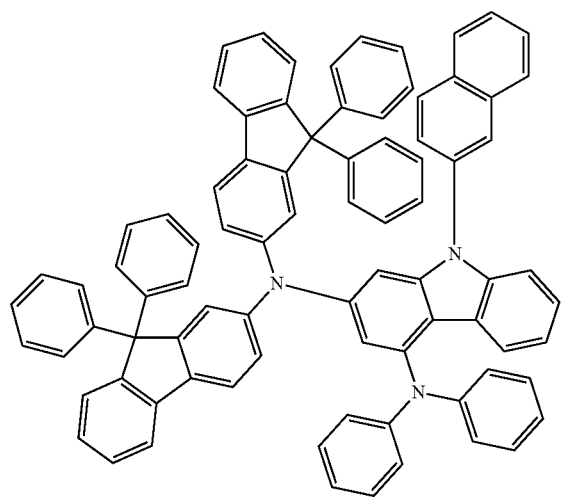
C-180
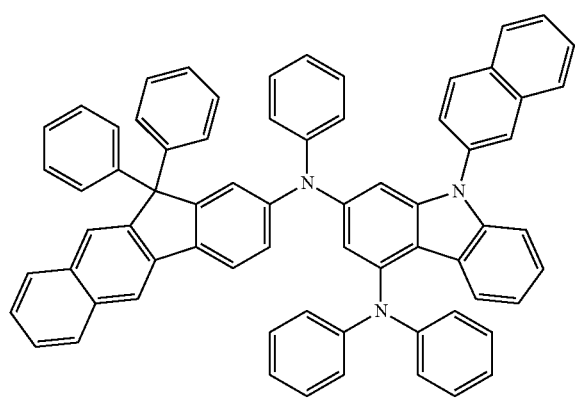
C-181
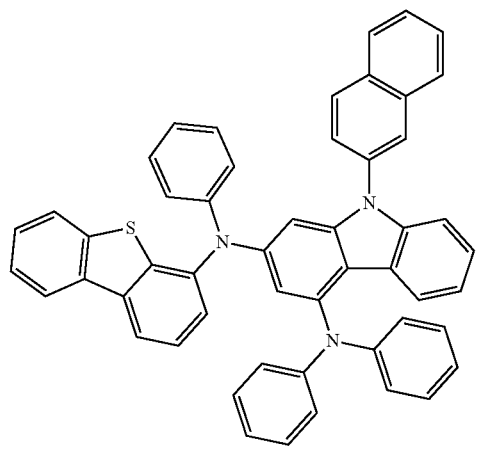
C-182
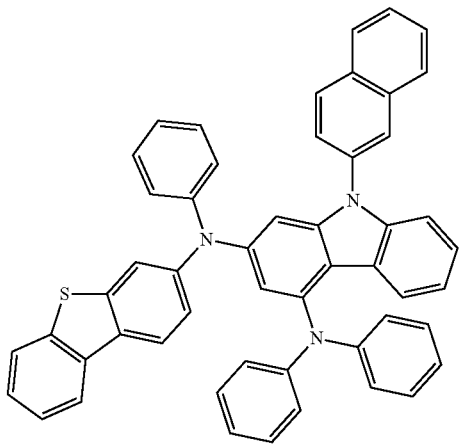
C-183
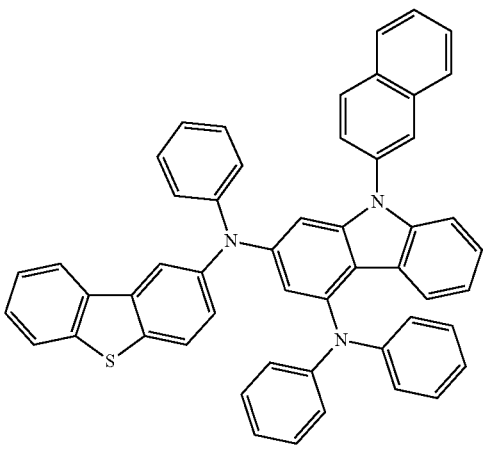
C-184

C-185
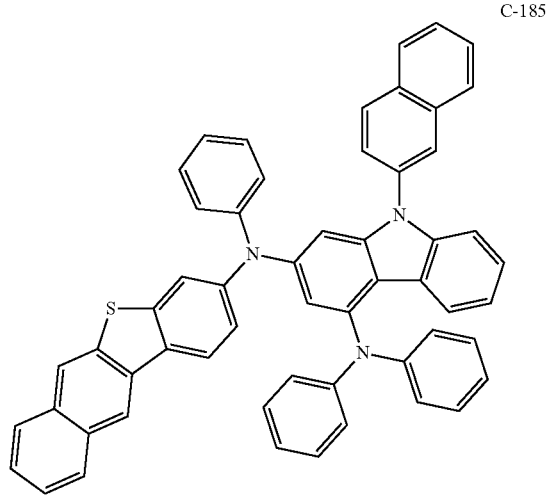
C-188
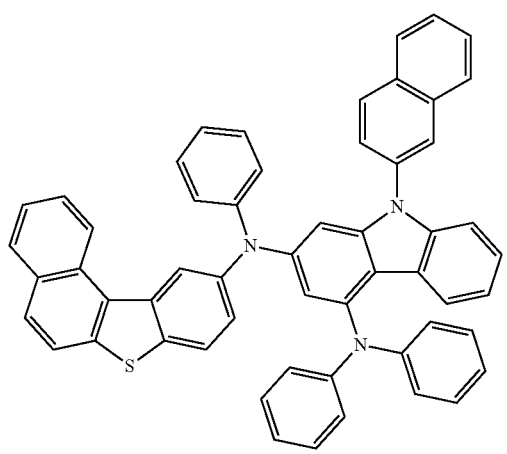
C-186
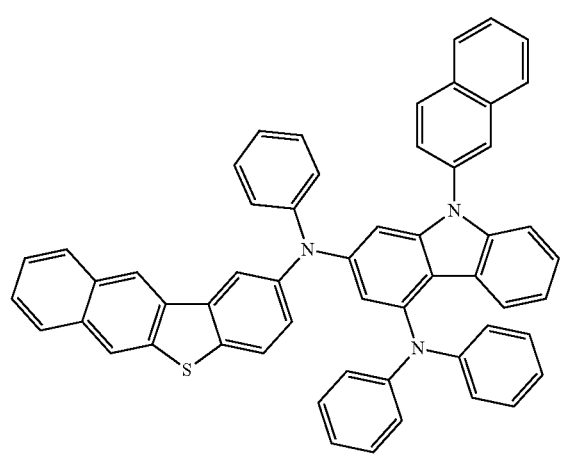
C-189
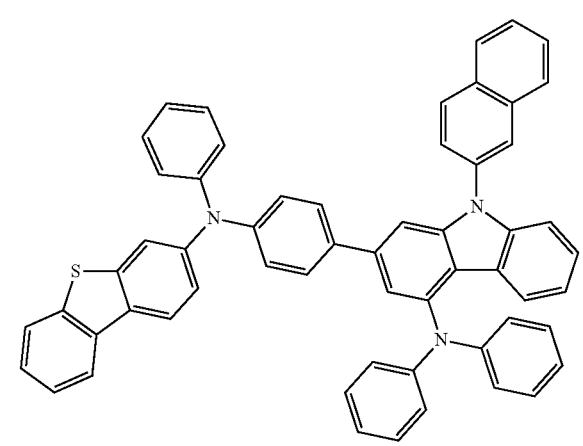
C-187
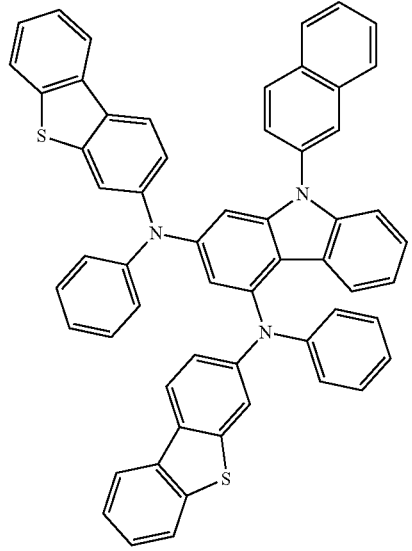
C-190
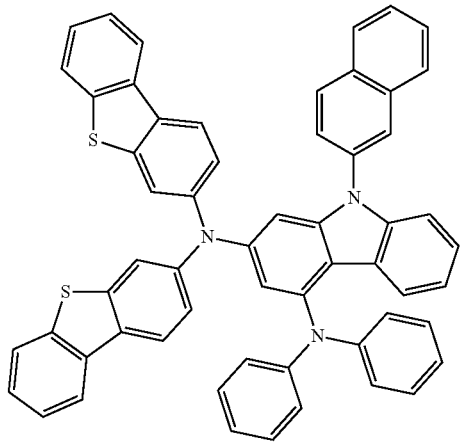

C-191
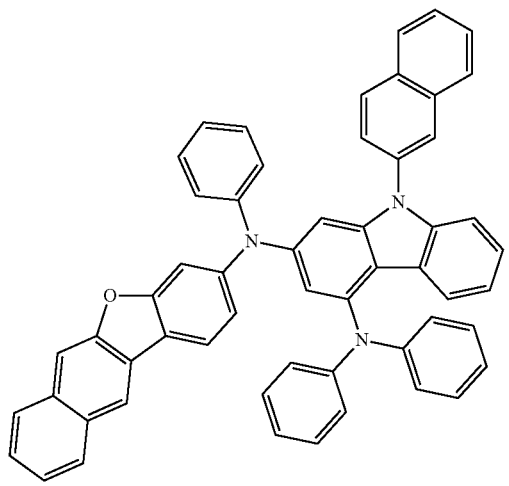
C-192
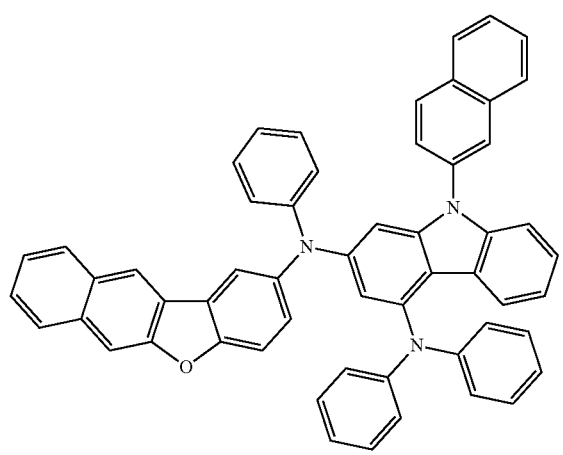
C-193
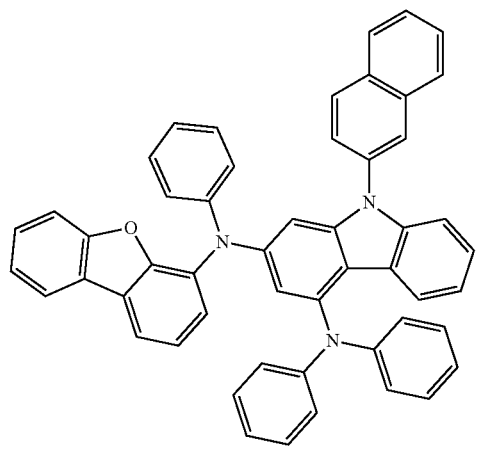
C-194
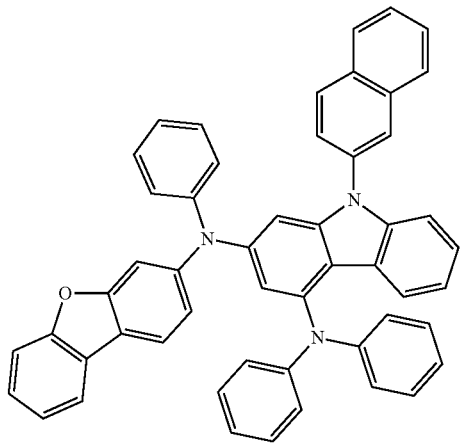
C-195
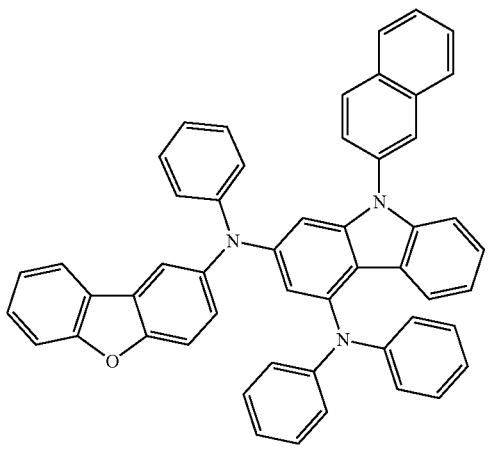
C-196
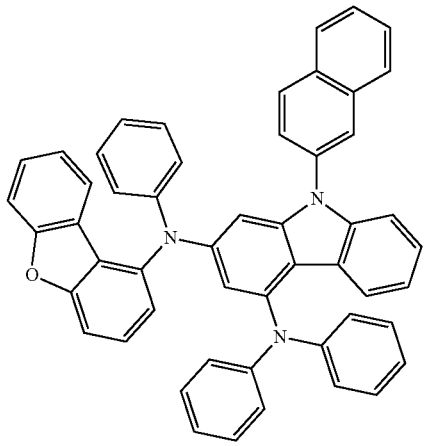

C-197
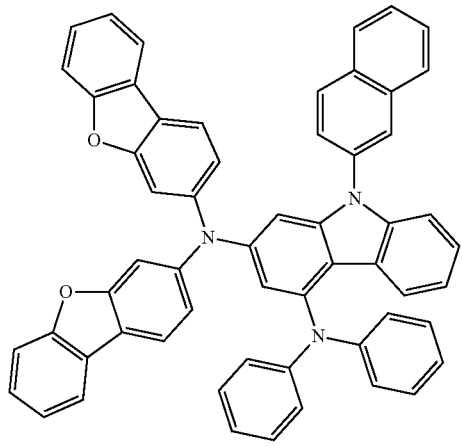
C-198
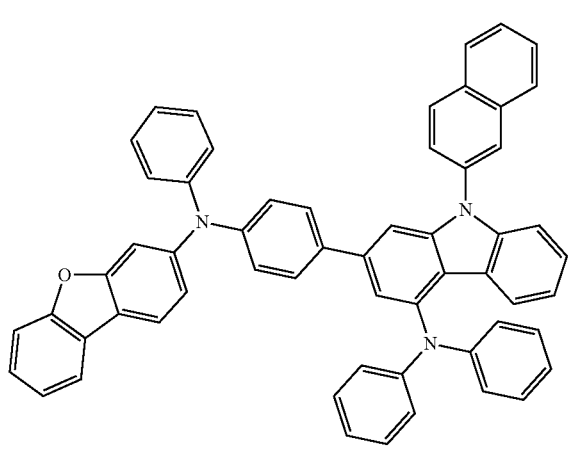
C-199
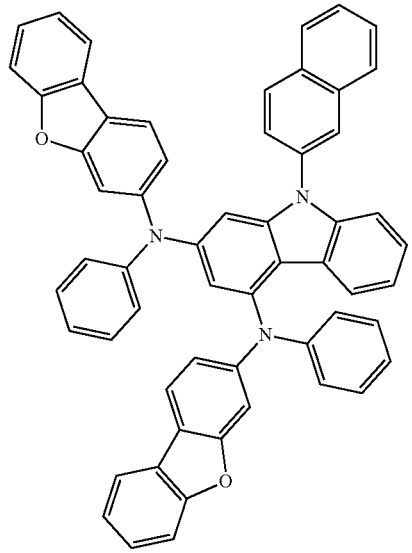
C-200
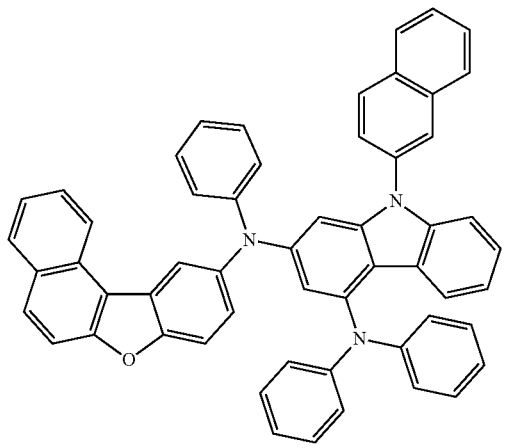
C-201
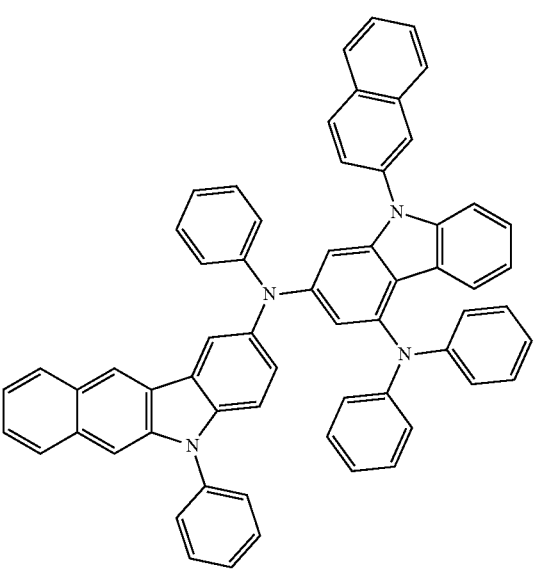
C-202
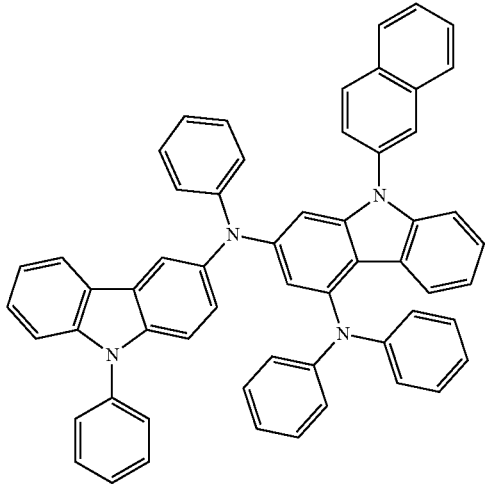

C-203
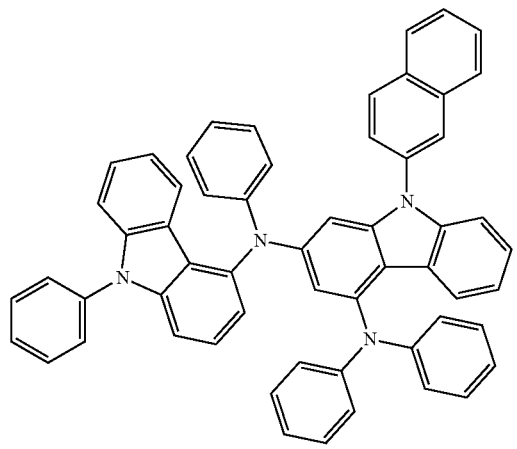
C-206
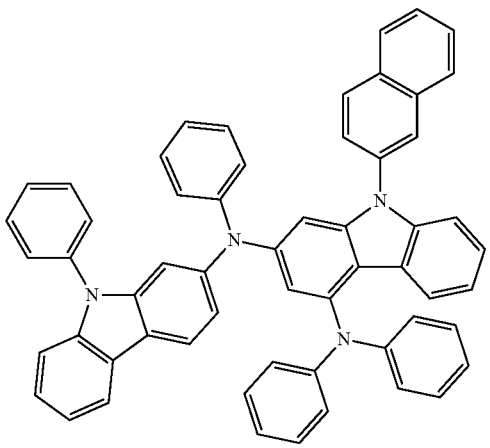
C-204
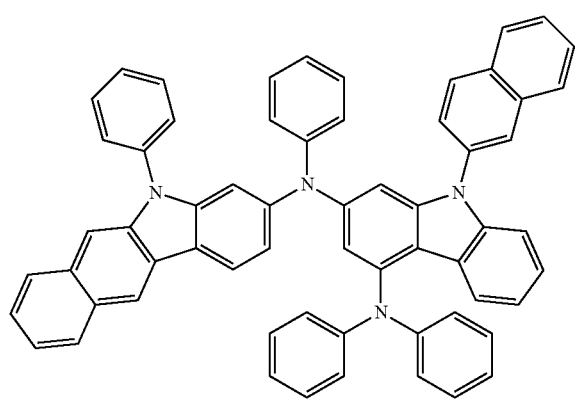
C-207
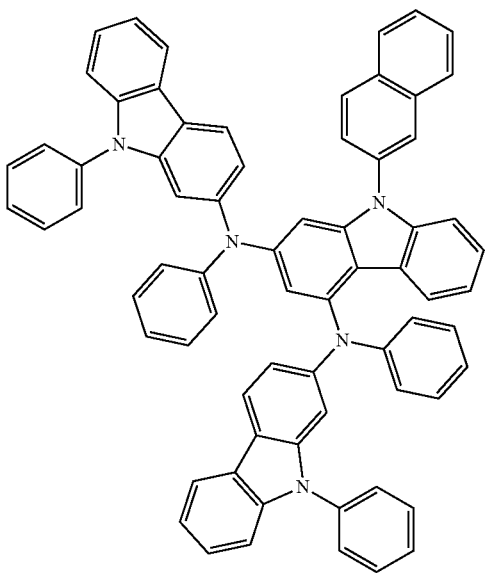
C-205
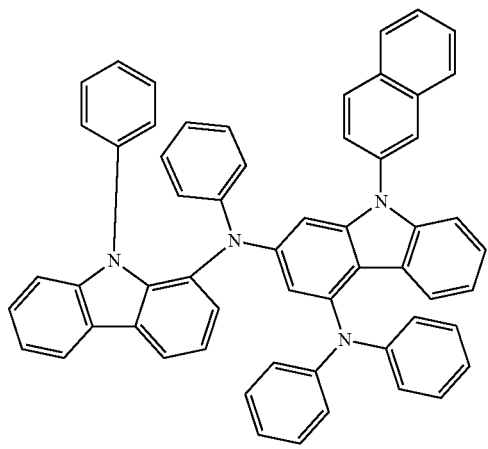
C-208
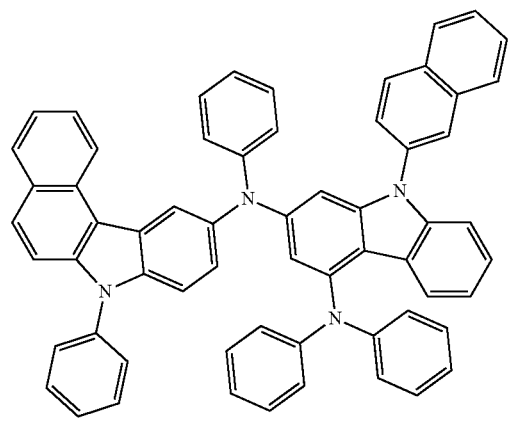

C-209
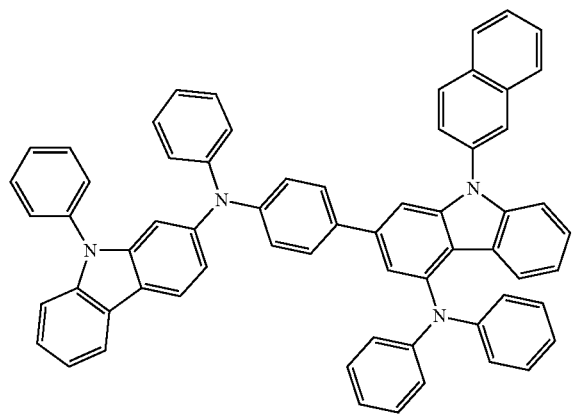
C-212
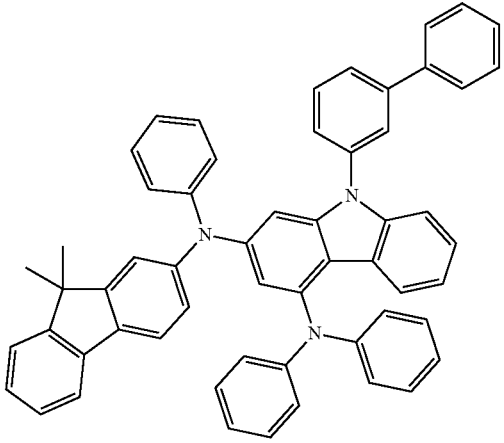
C-210
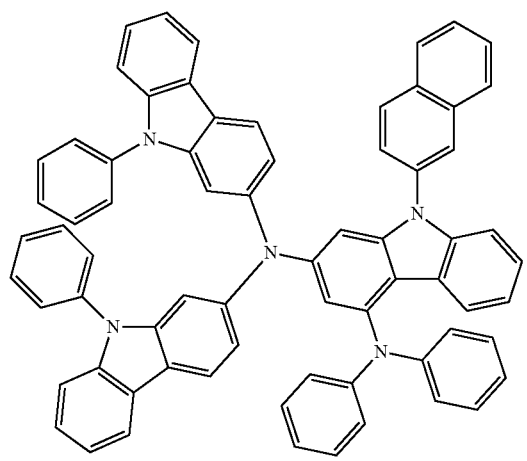
C-213
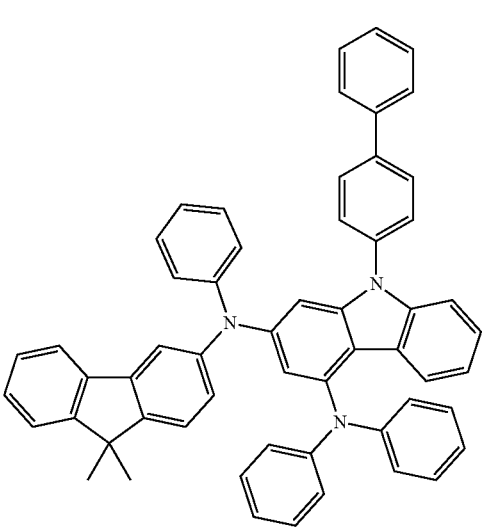
C-211
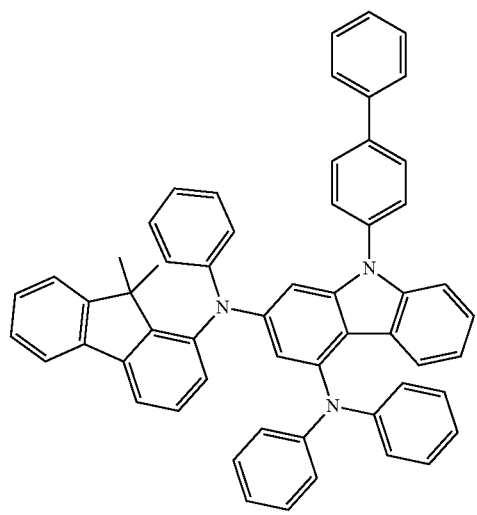
C-214
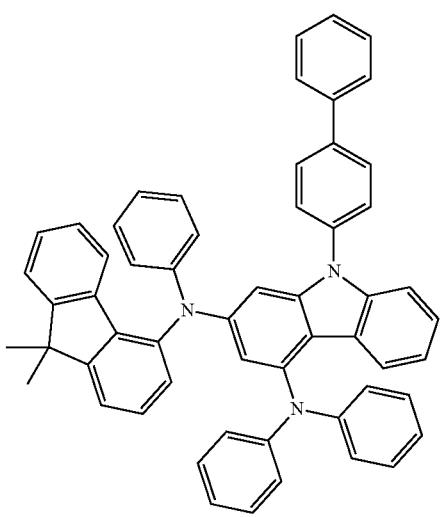

C-215
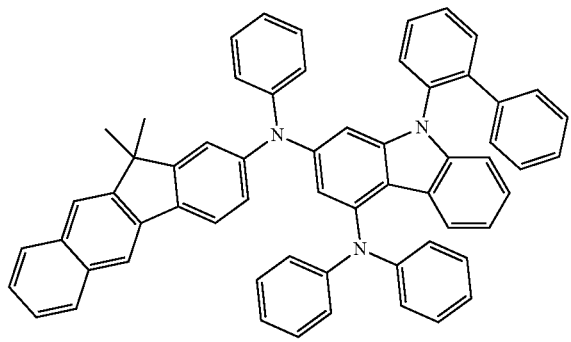
C-216
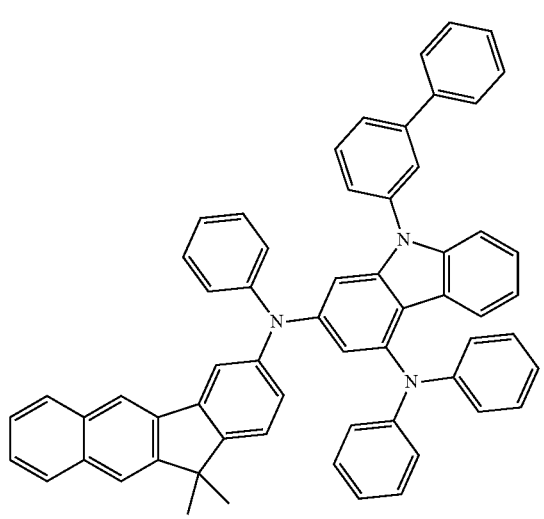
C-217
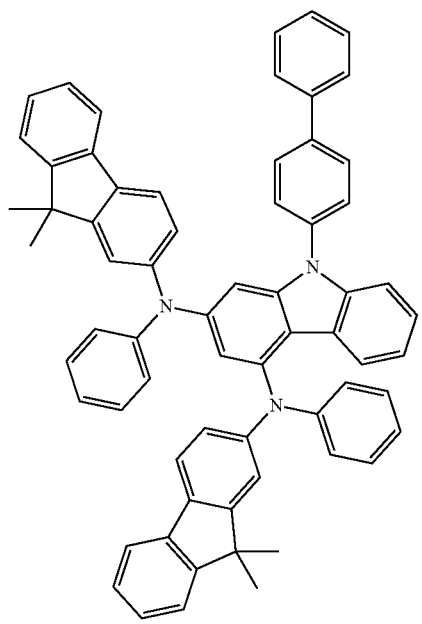
C-218
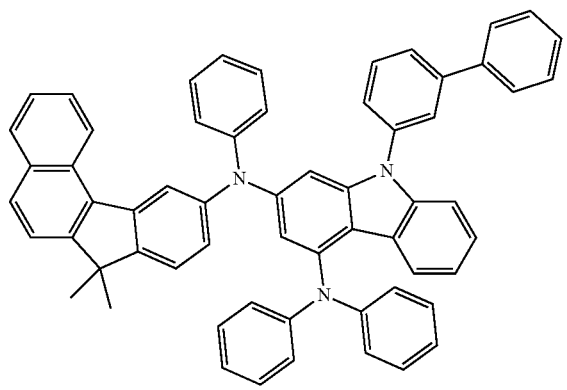
C-219
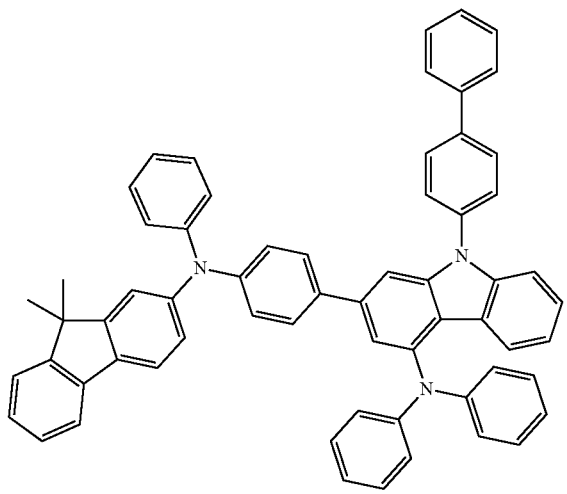
C-220
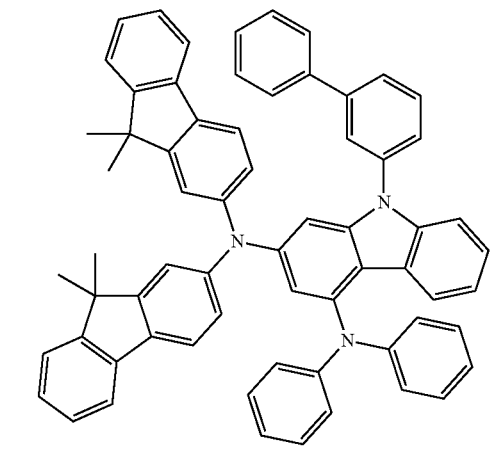

C-221
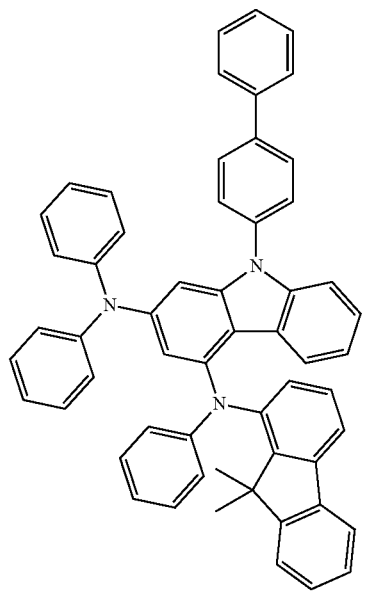
C-222
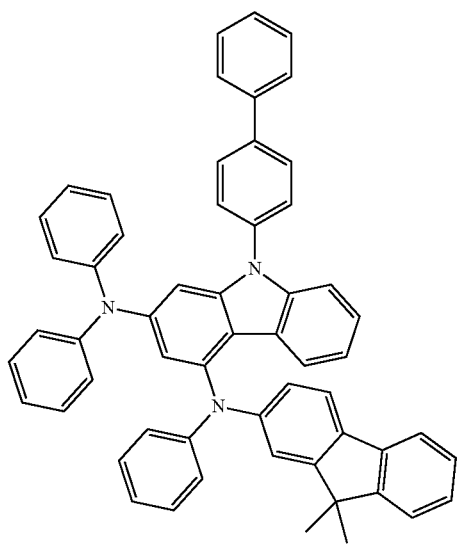
C-223
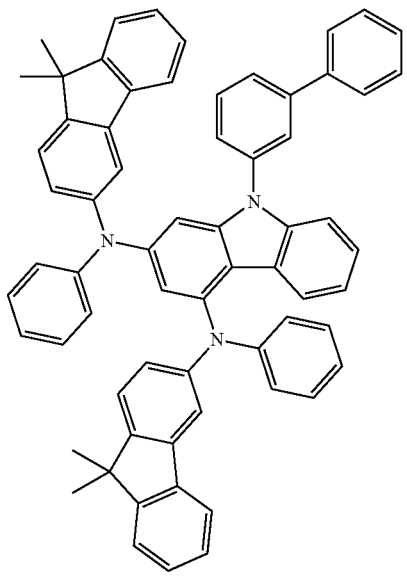
C-224
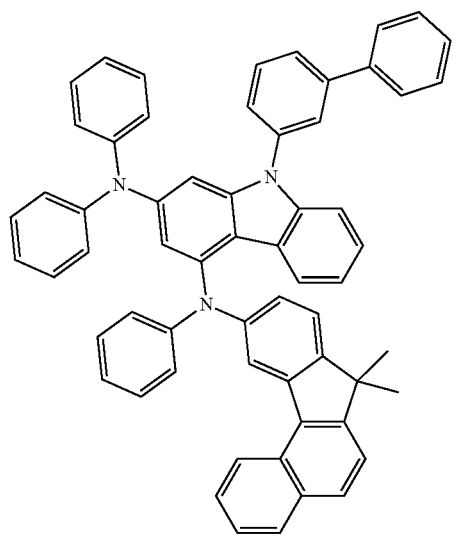

C-225
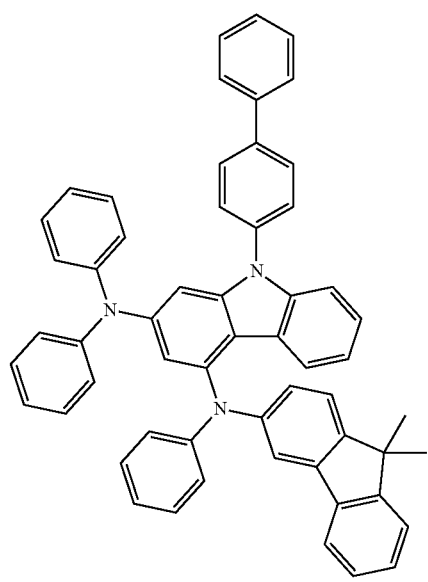
C-226
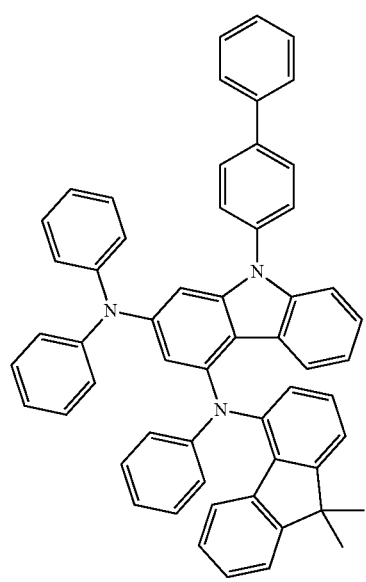
C-227
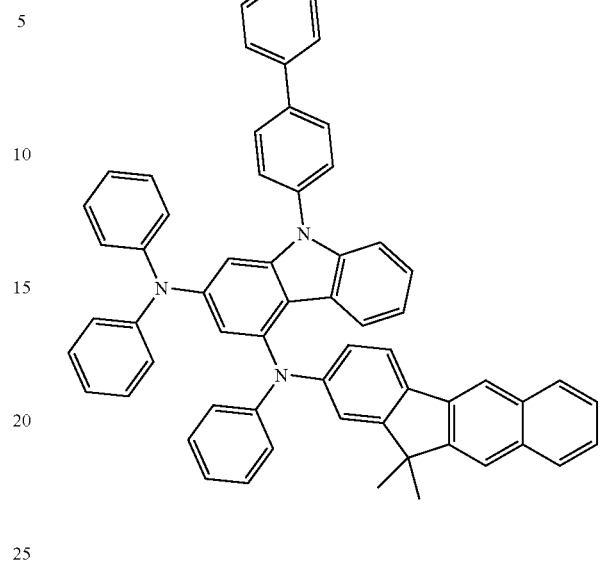
C-228
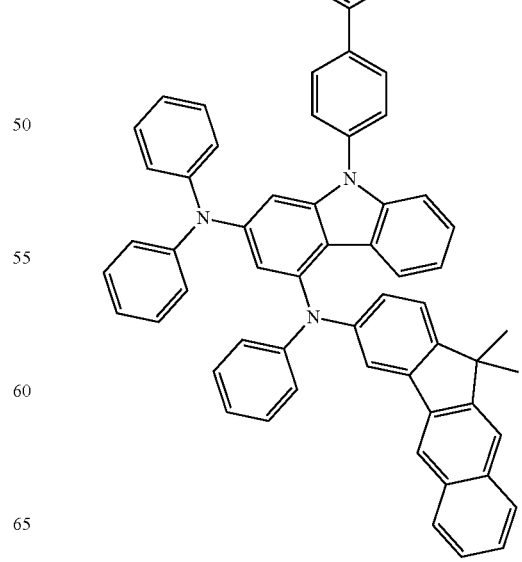

C-229
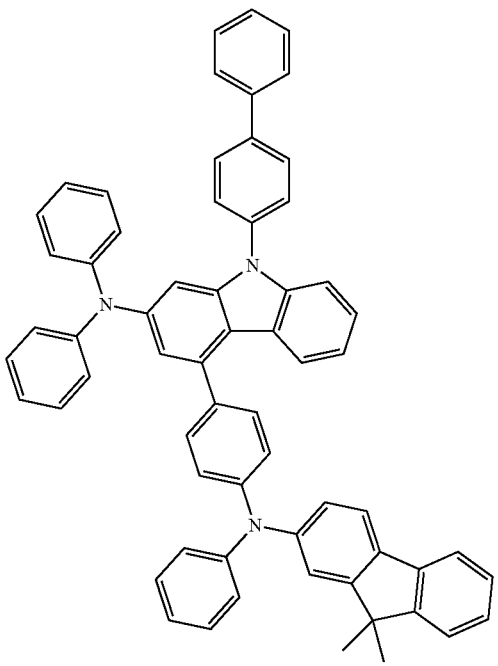
C-231
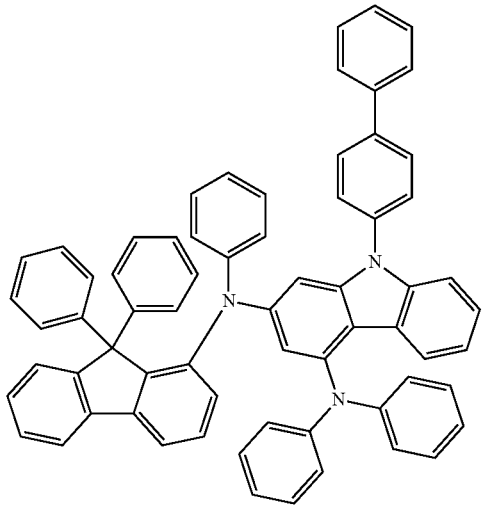
C-232
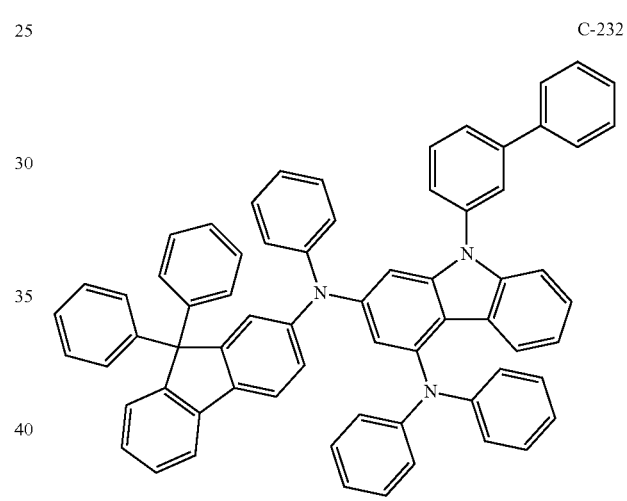
C-230
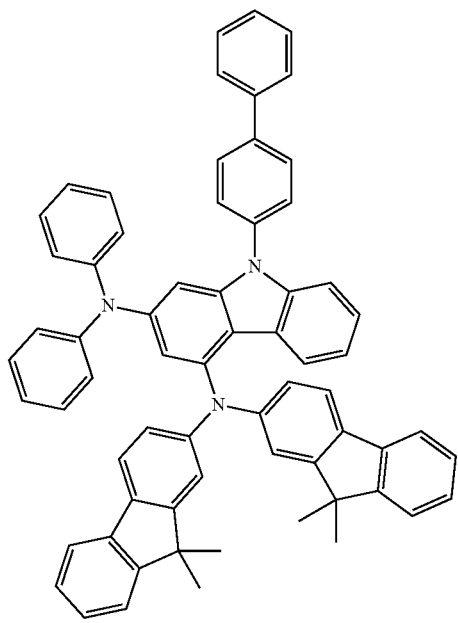
C-233
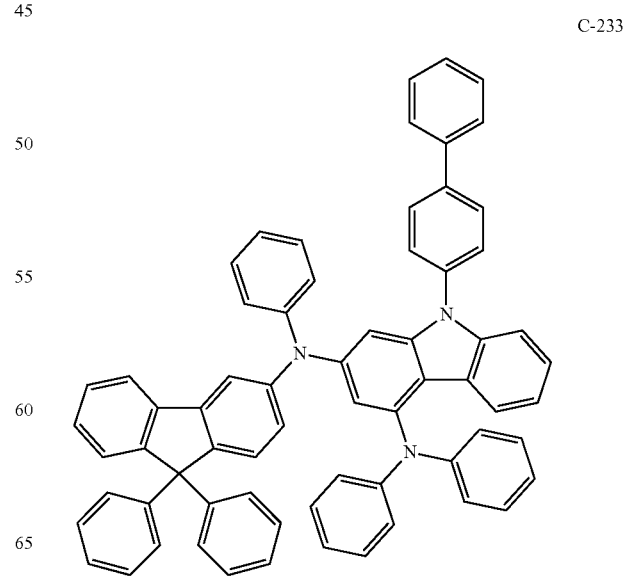

-continued
C-234
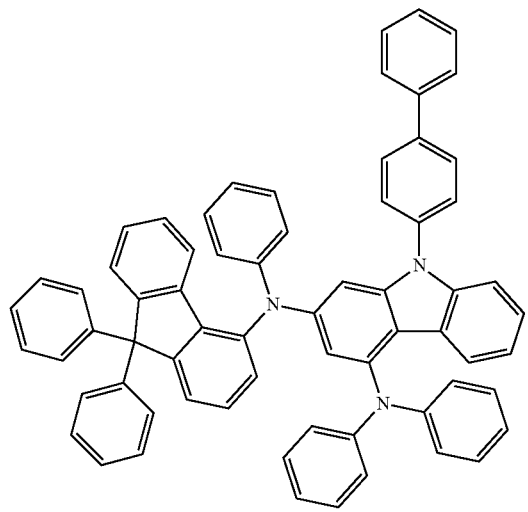
C-235
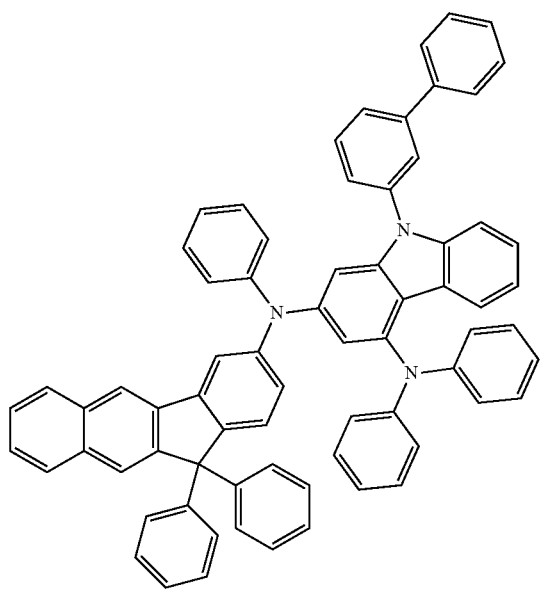
C-236
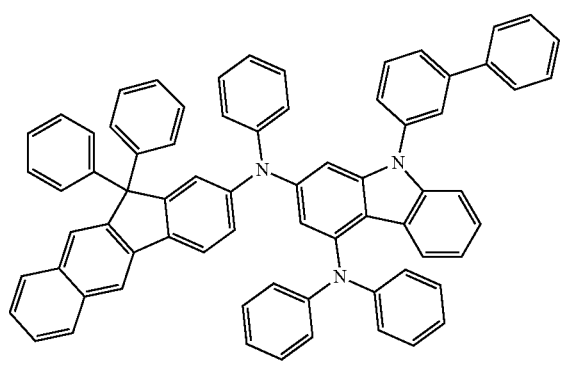
-continued
C-237
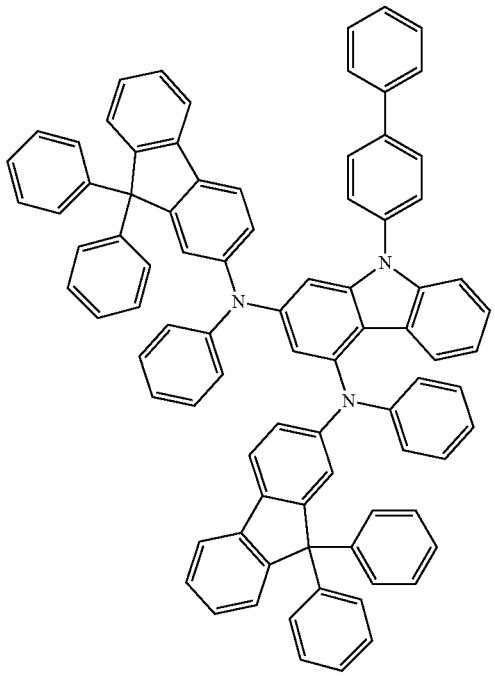
C-238
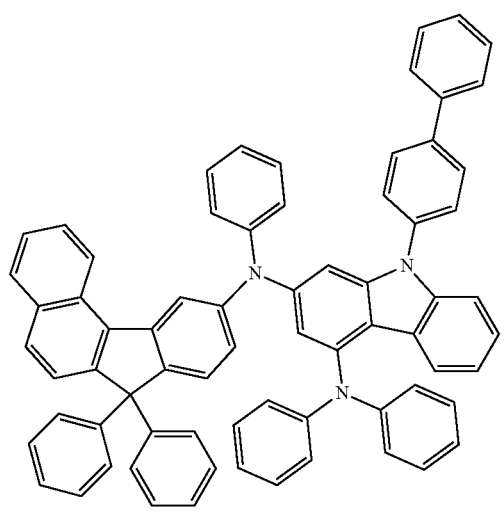
C-239
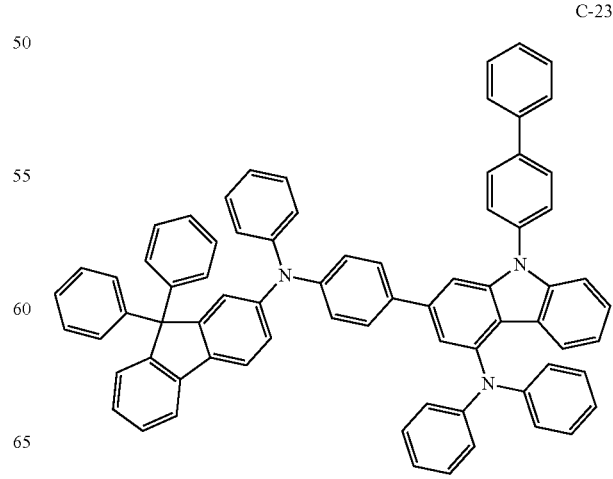

C-240
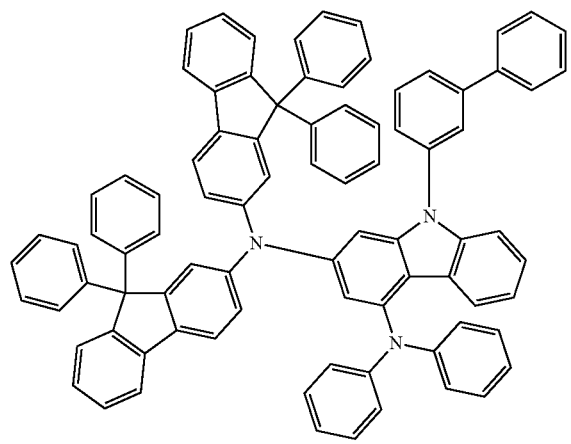
C-243
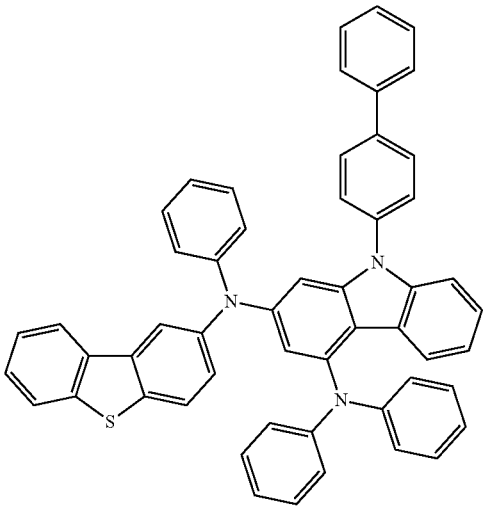
C-241
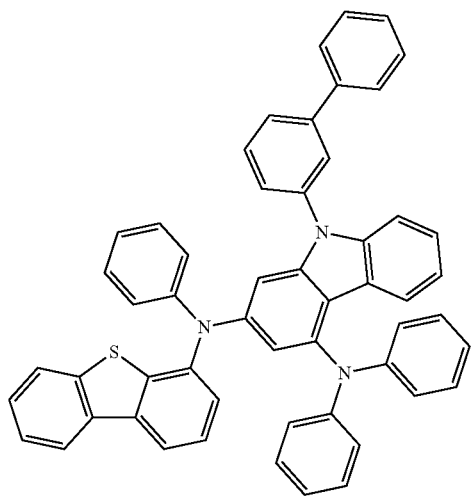
C-244
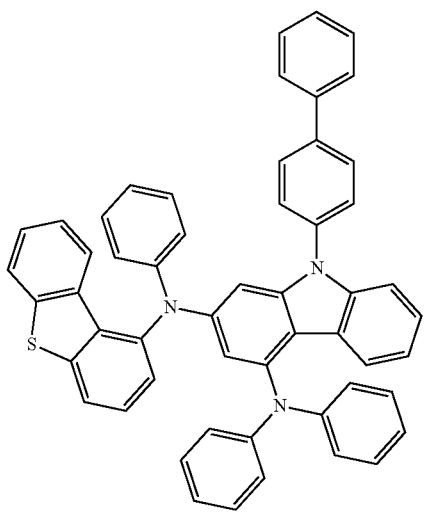
C-242
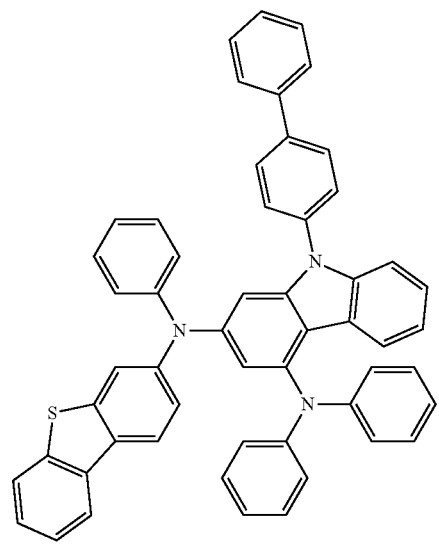
C-245
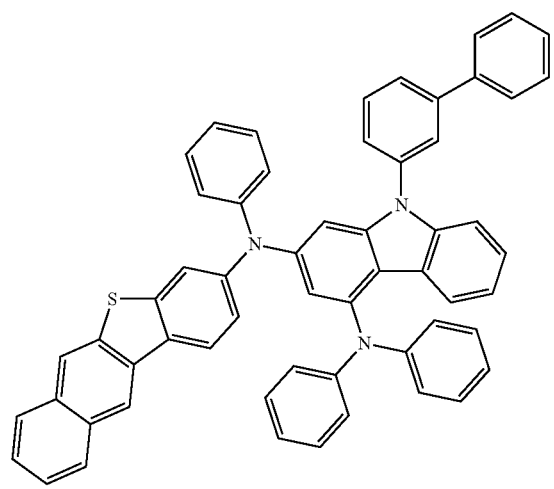

-continued
C-246
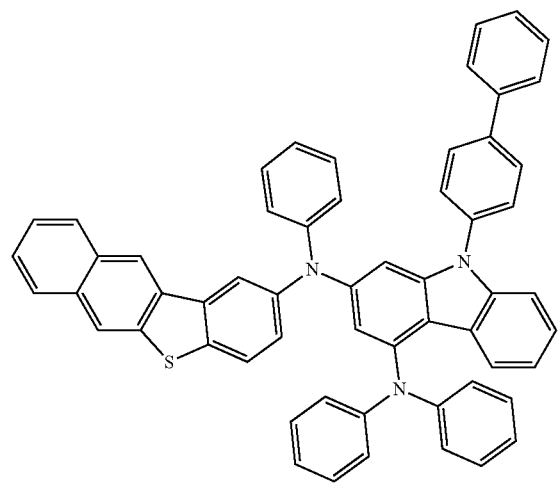
C-247
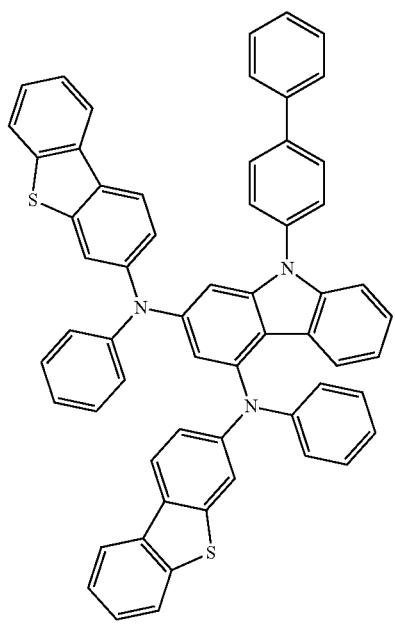
C-248
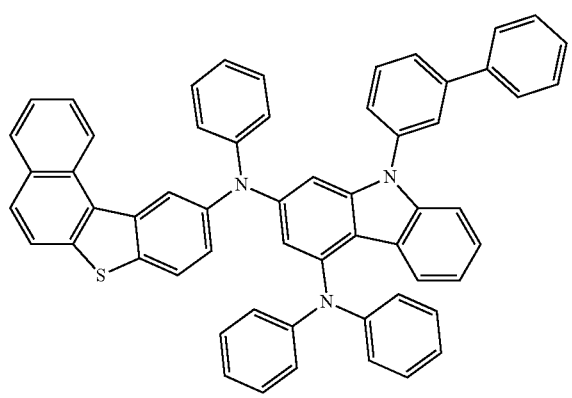
-continued
C-249
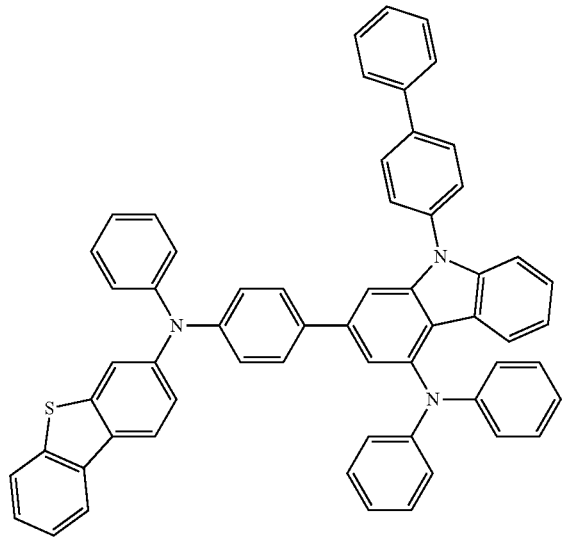
C-250
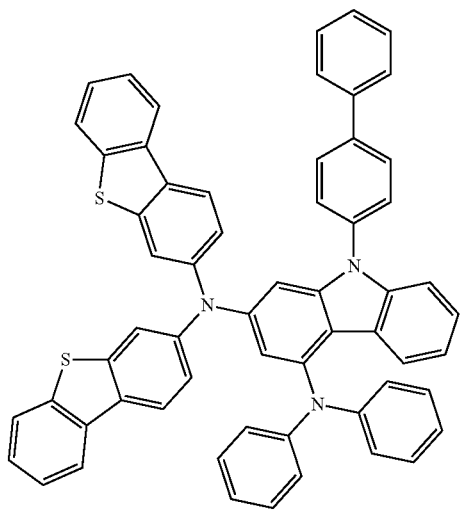
C-251
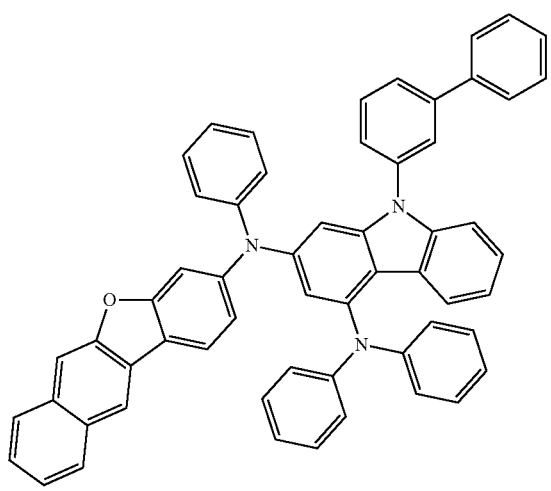

C-252
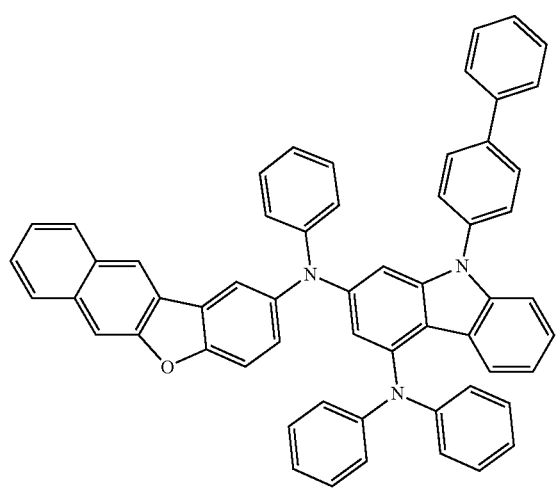
C-253
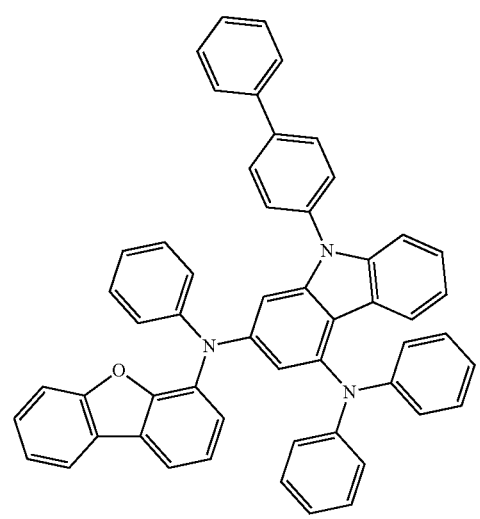
C-254
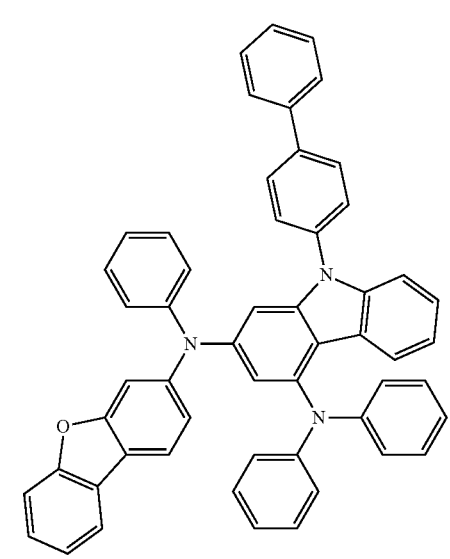
C-255
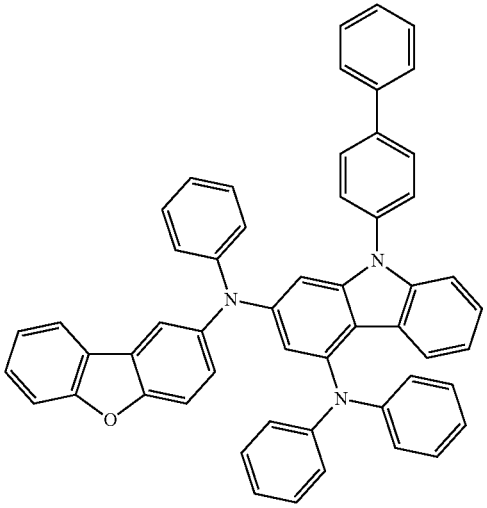
C-256
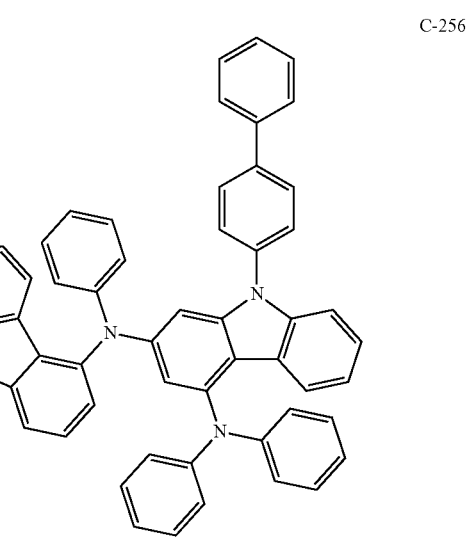
C-257
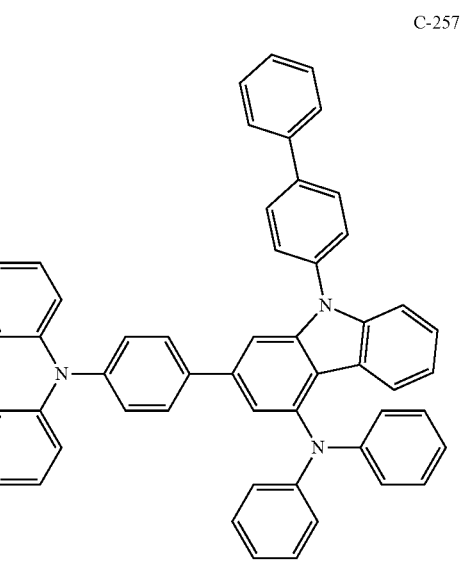

C-258
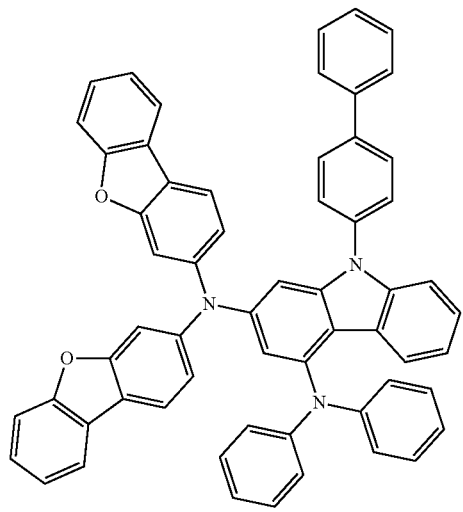
C-259
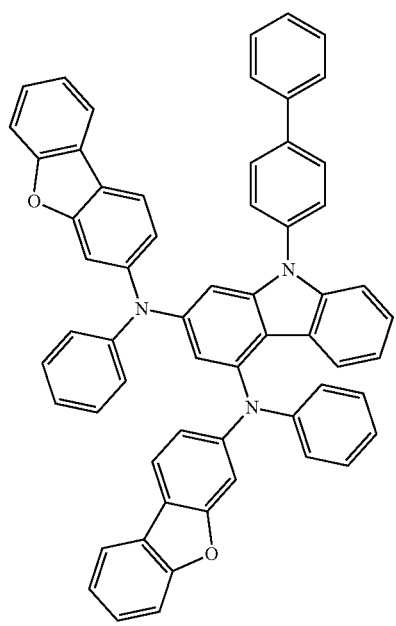
C-260
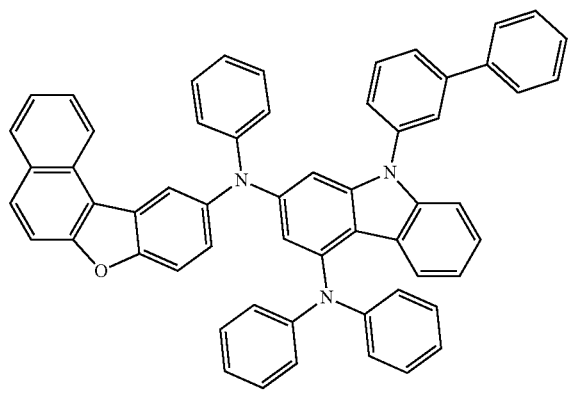
C-261
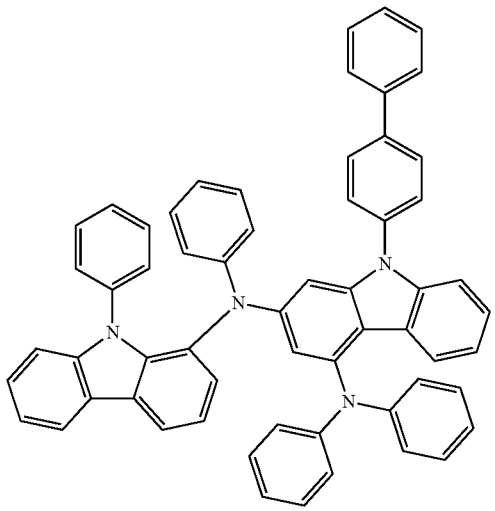
C-262
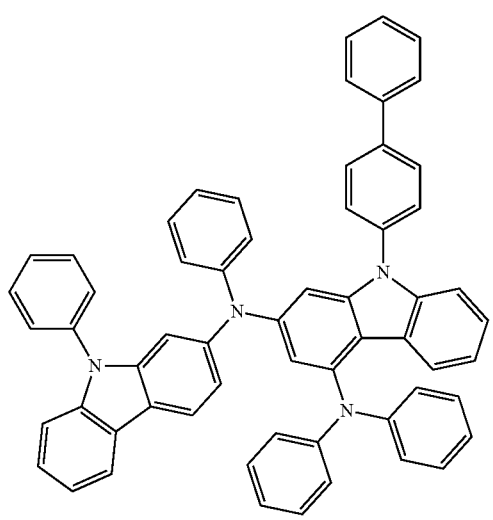
C-263
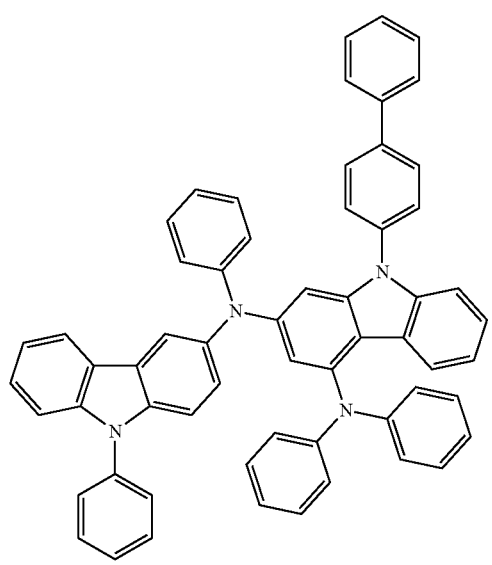

C-264
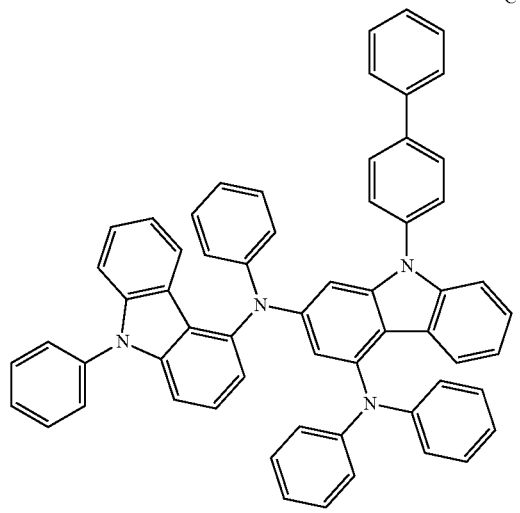
C-267
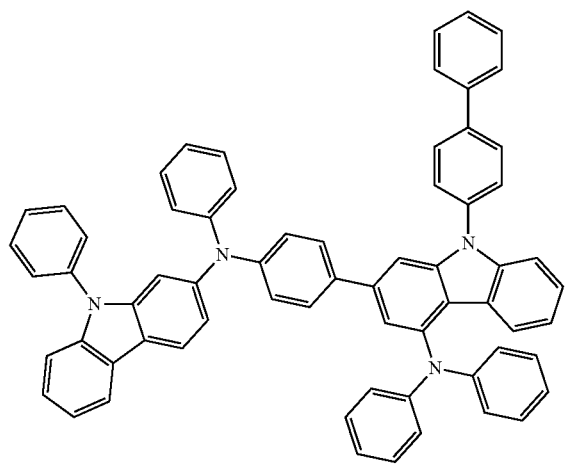
C-265
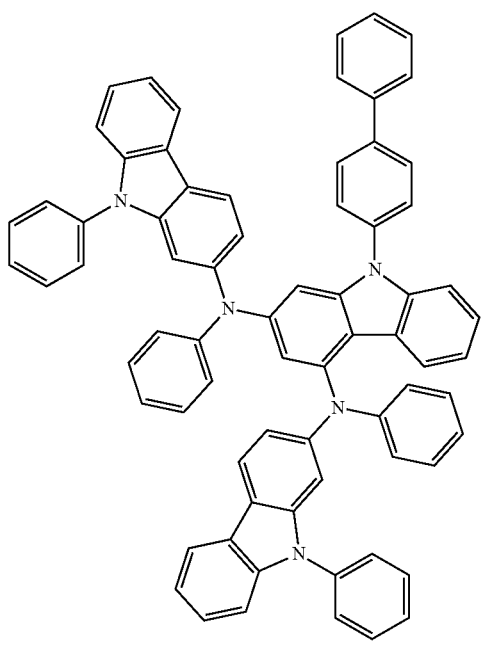
C-268
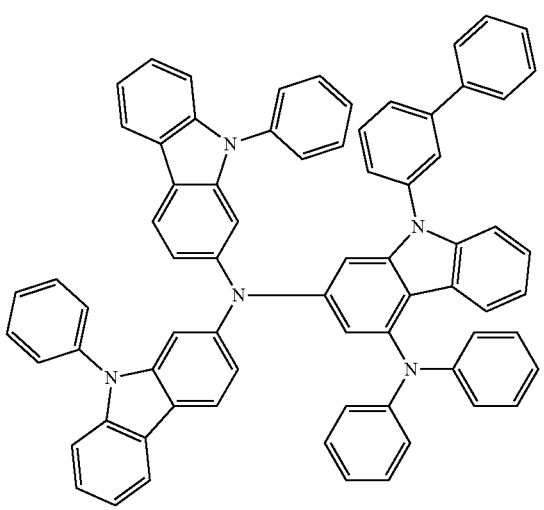
C-266
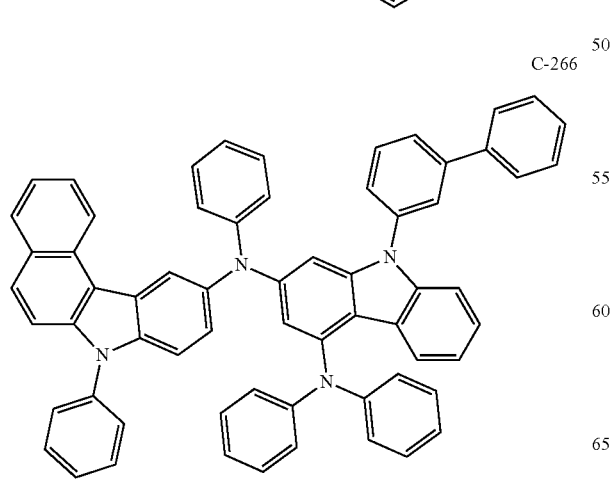
C-269
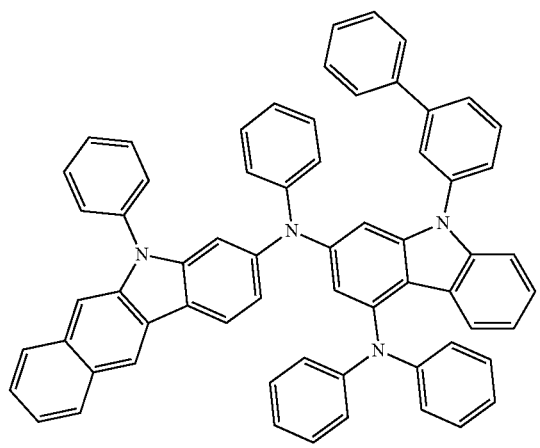

C-270
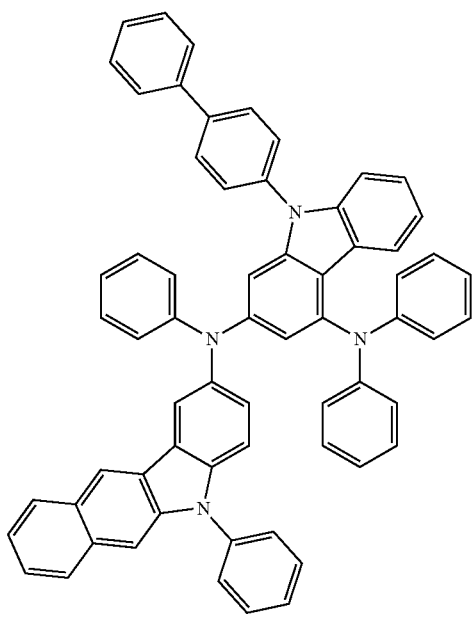
C-271
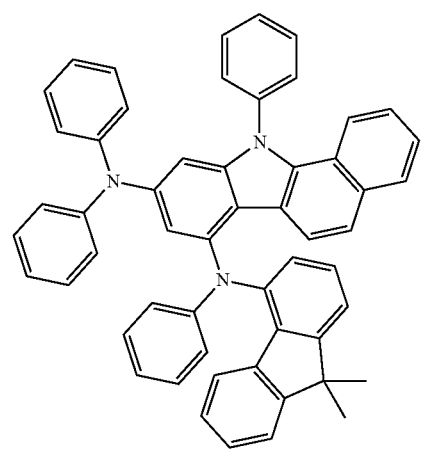
C-272
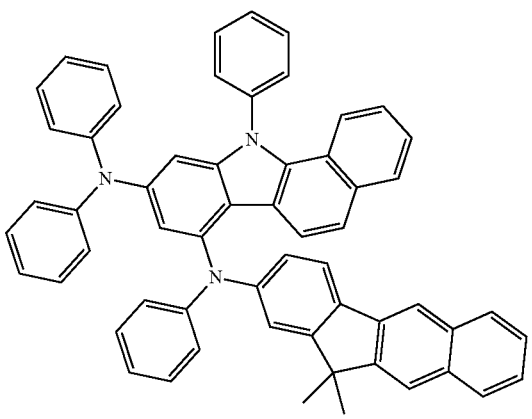
C-273
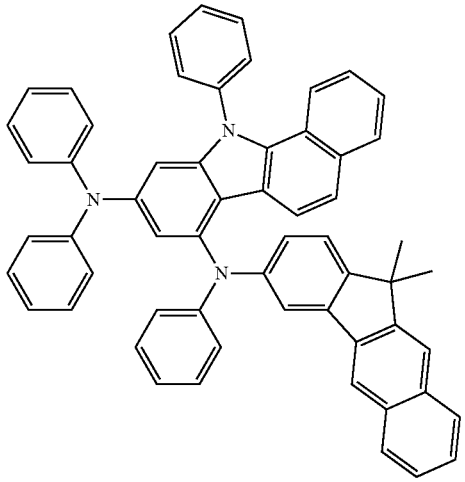
C-274
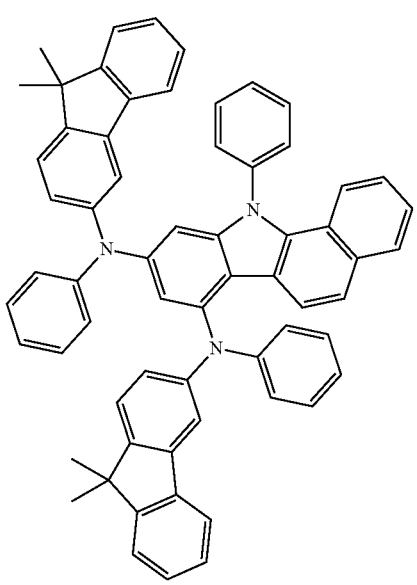
C-275
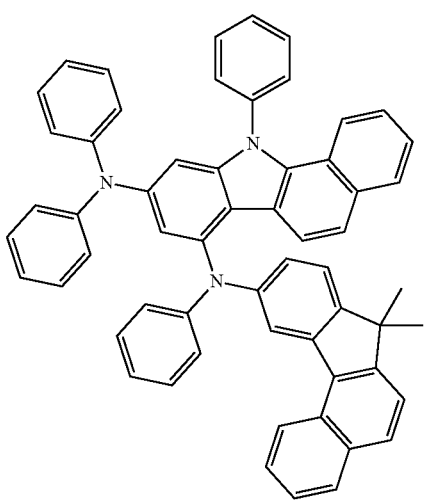

C-276
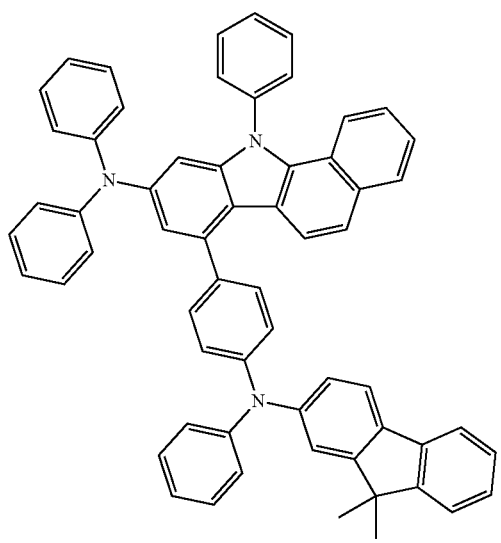
C-277
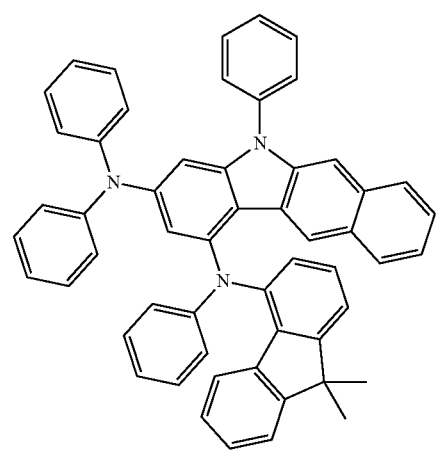
C-278
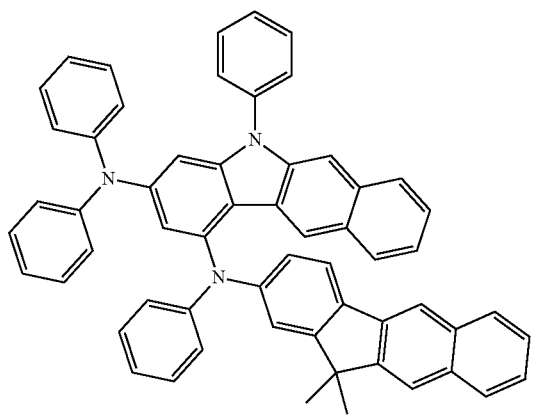
C-279
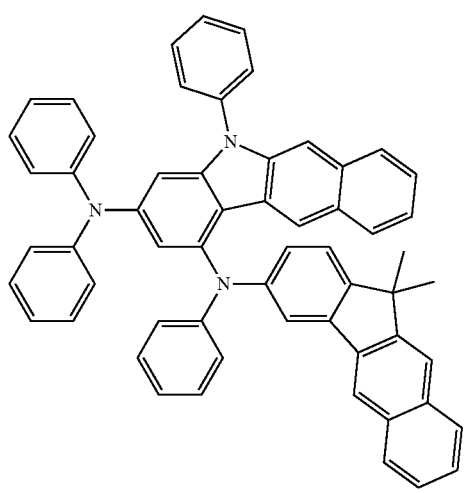
C-280
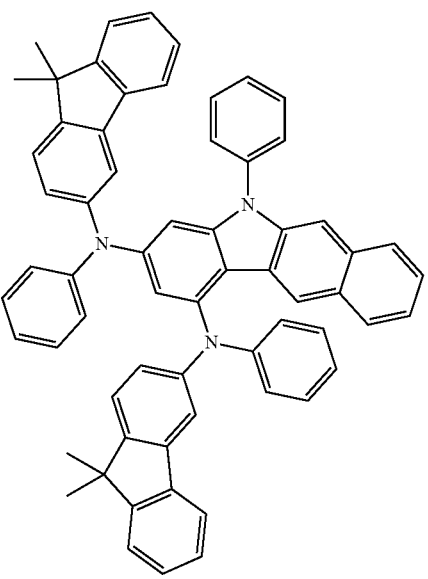
C-281
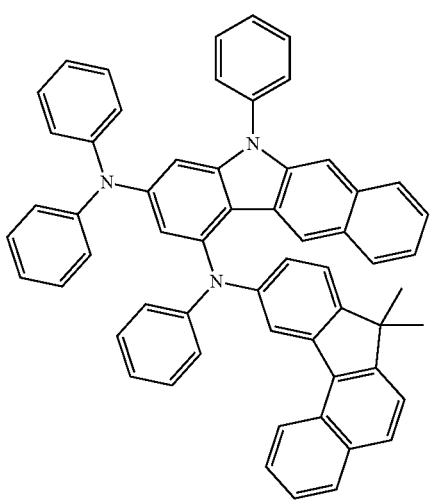

C-282
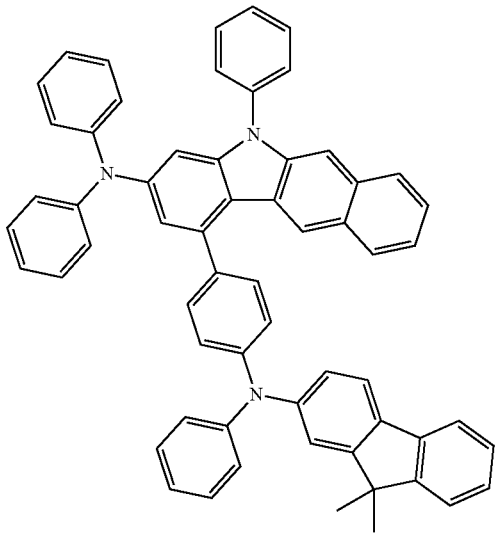
C-285
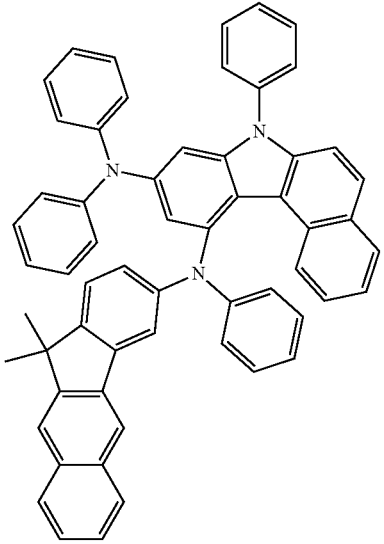
C-283
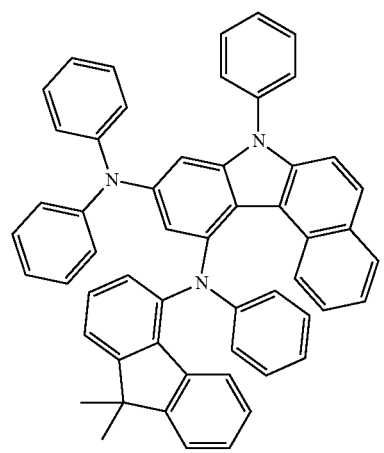
C-286
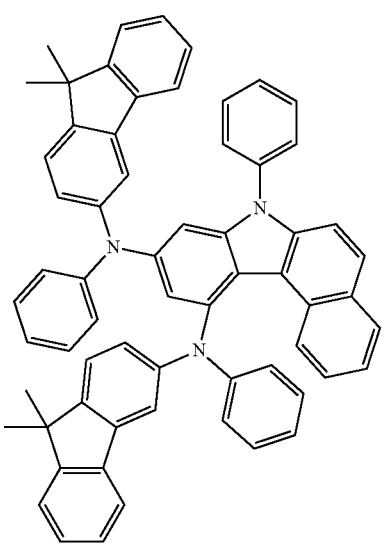
C-284
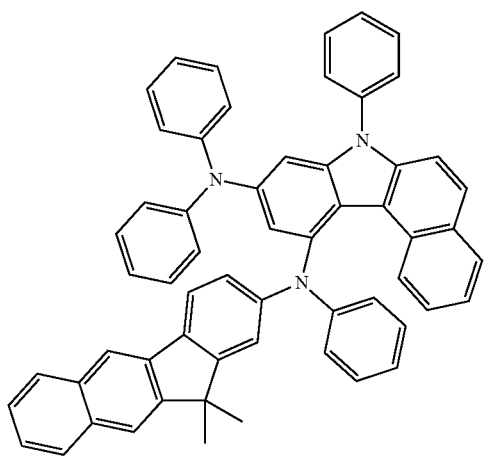
C-287
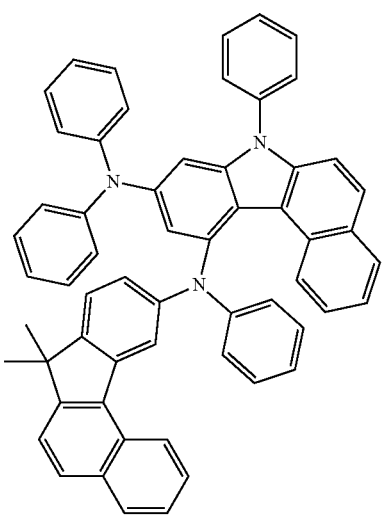

C-288
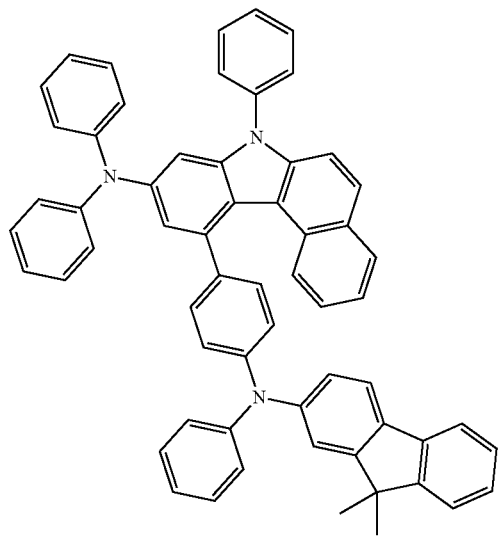
C-291
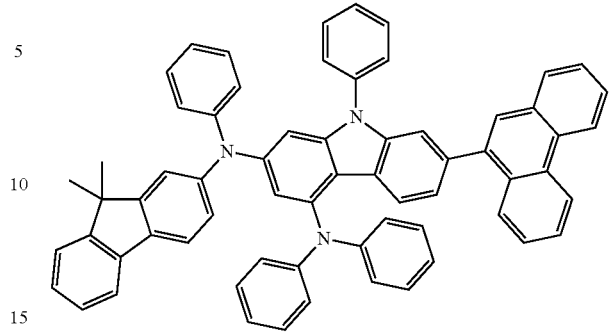
C-292
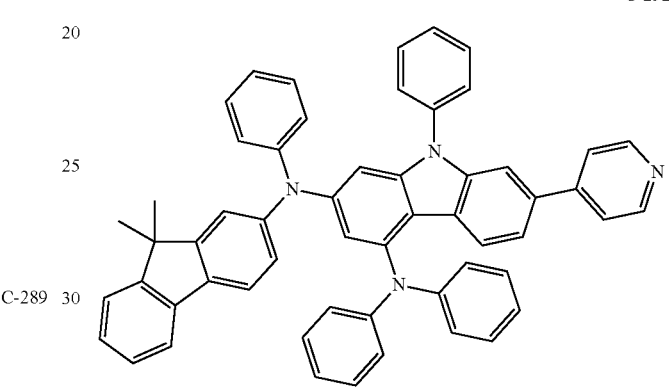
C-289
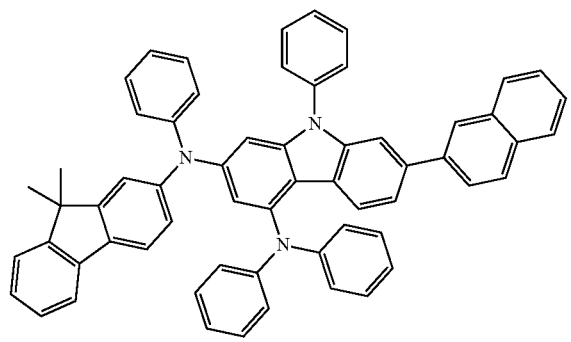
C-293
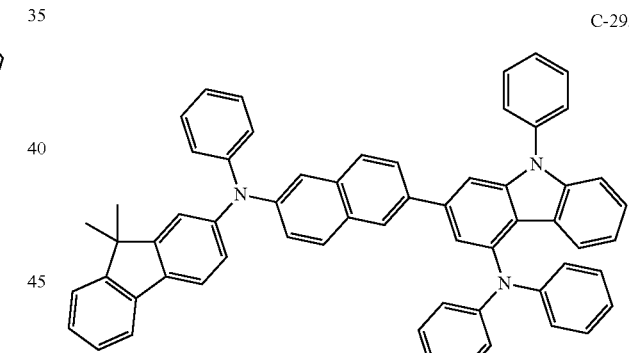
C-290
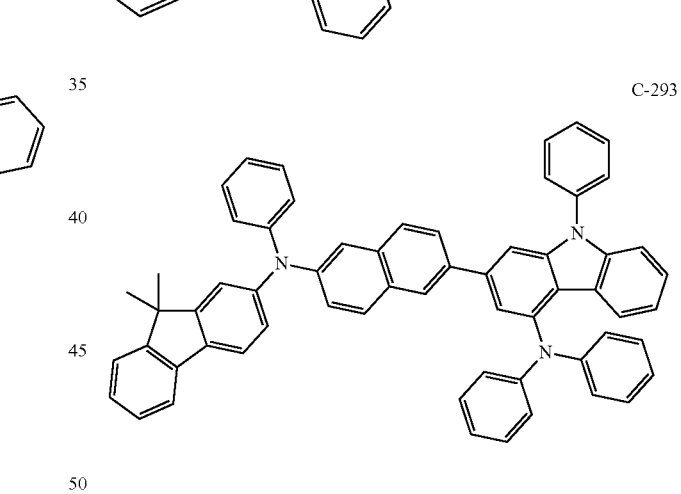
C-294
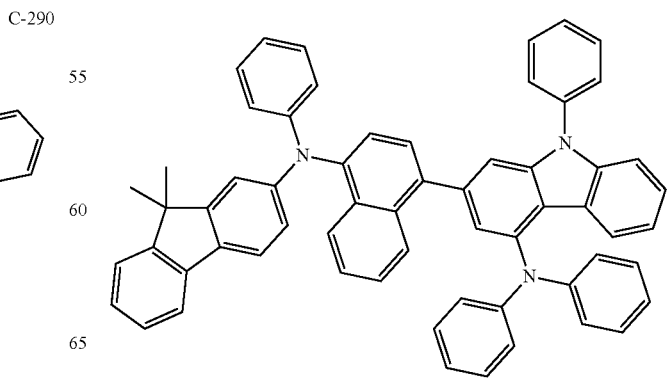

C-295
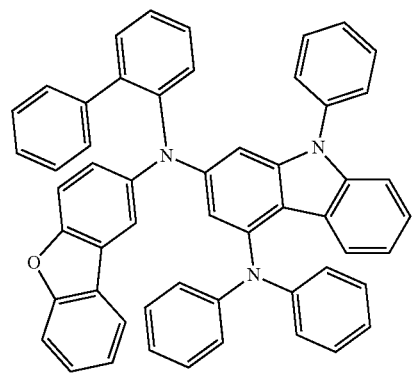
C-296
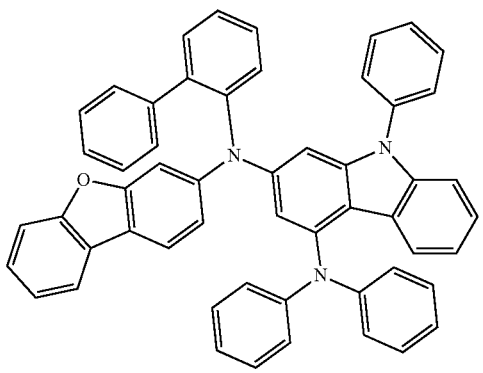
C-297
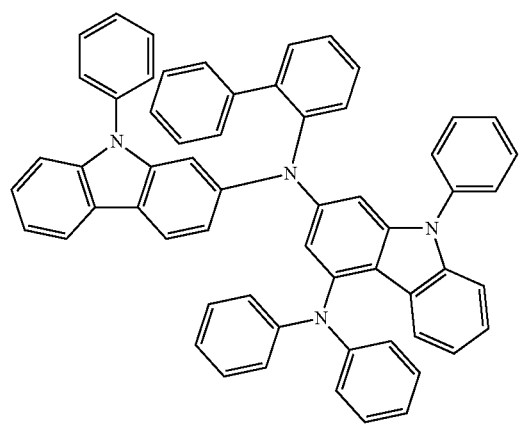
C-298
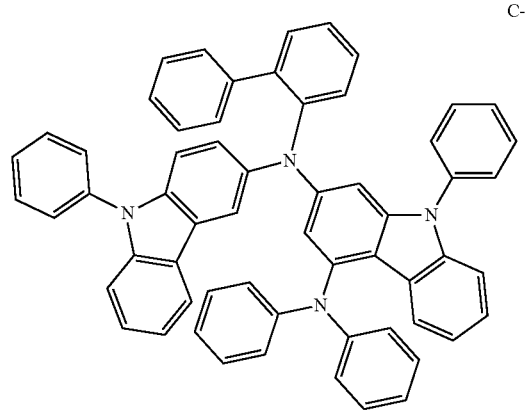
C-299
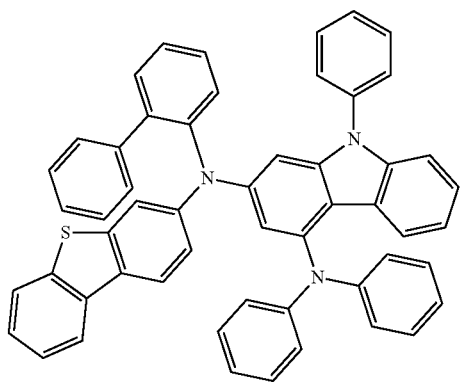
C-300
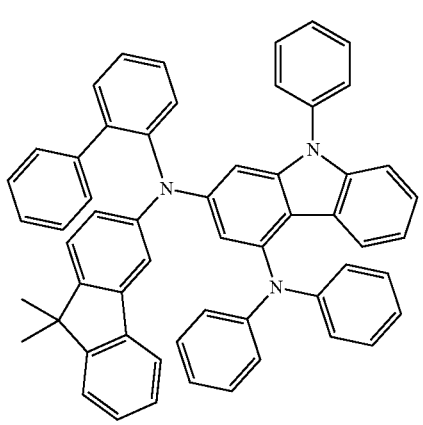
C-301
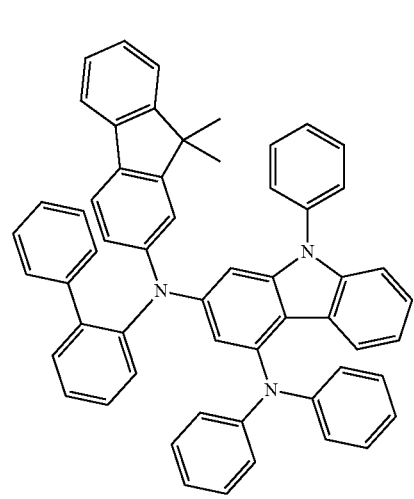

C-302
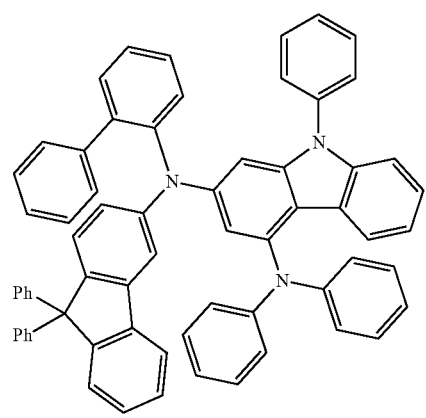
C-305
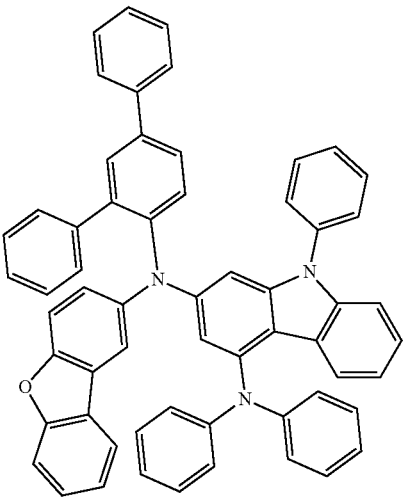
C-303
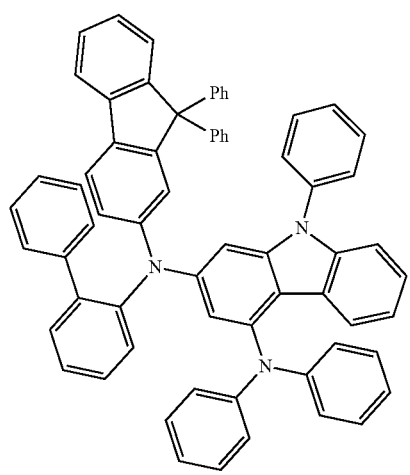
C-306
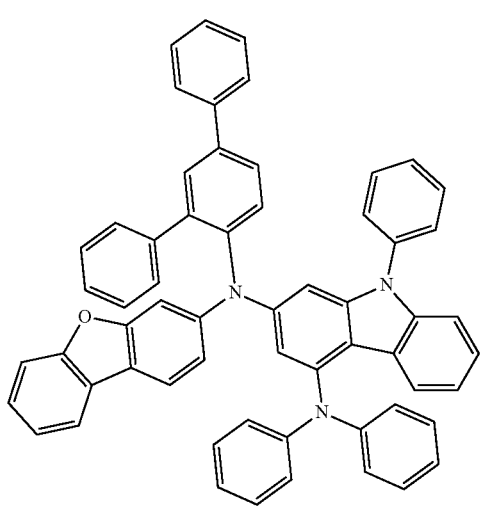
C-304
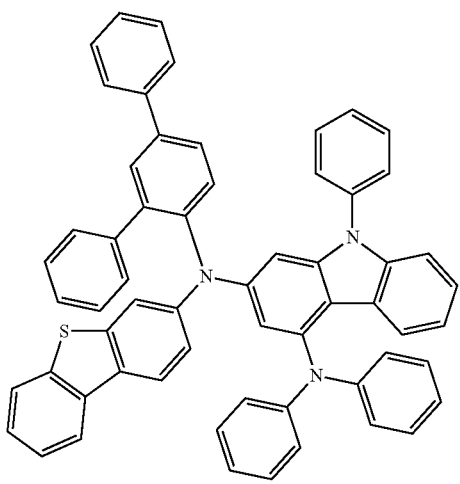
C-307
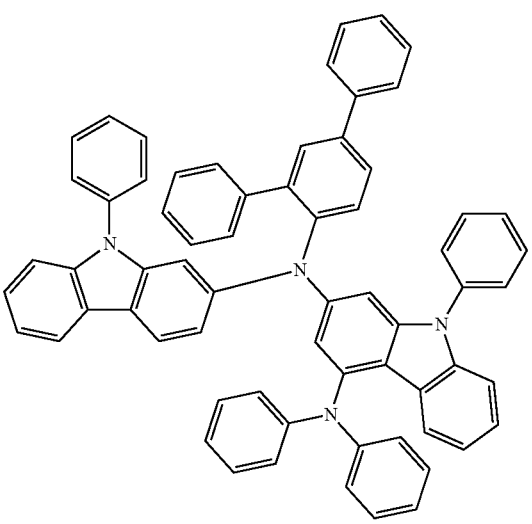

C-308
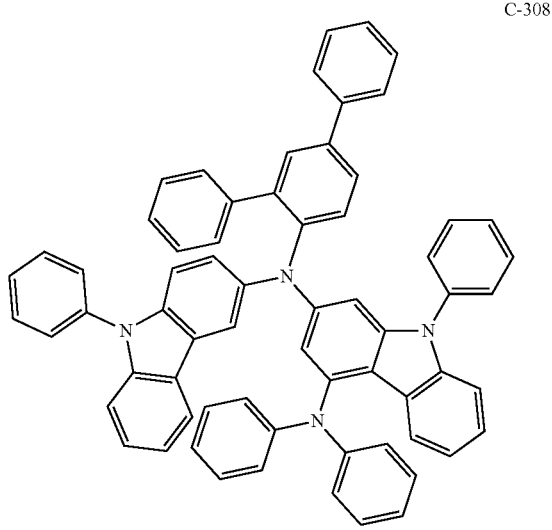
C-311
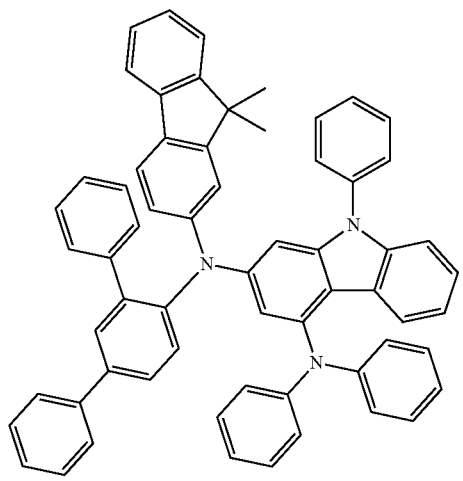
C-309
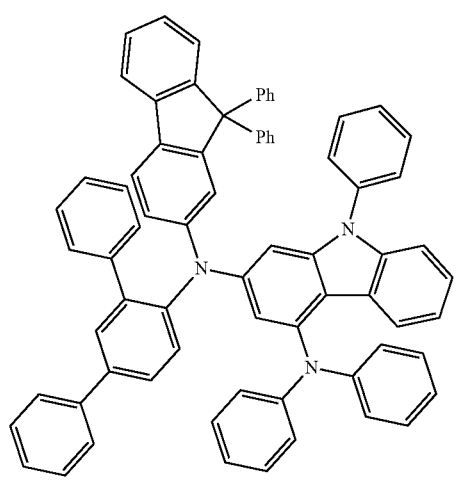
C-312
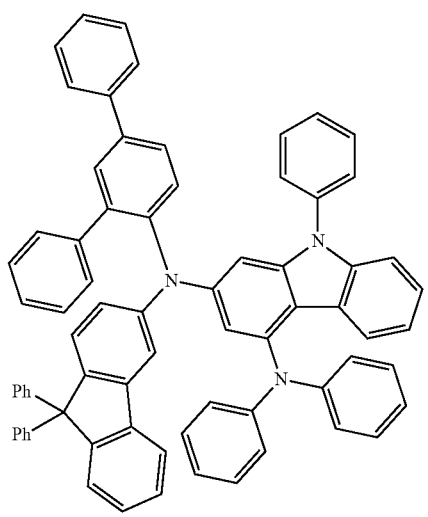
C-310
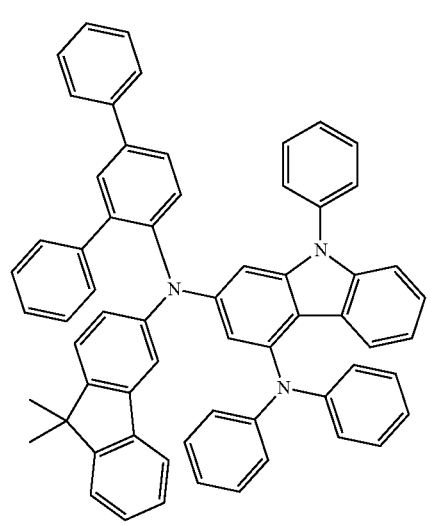
C-313
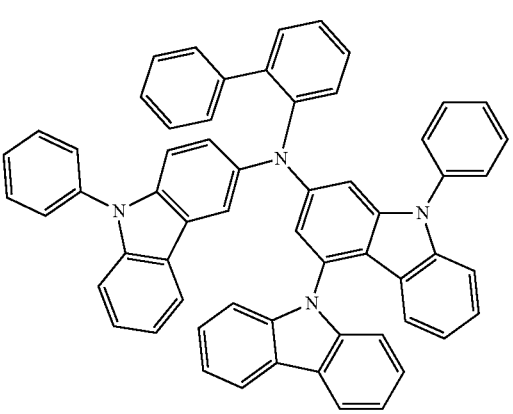

C-314
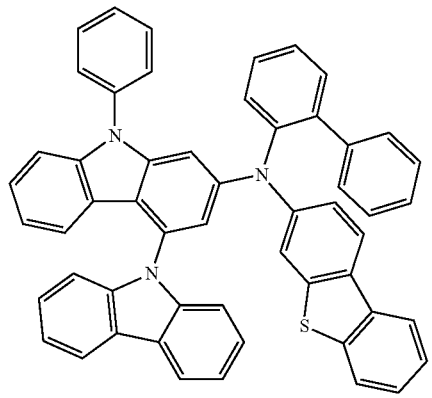
C-315
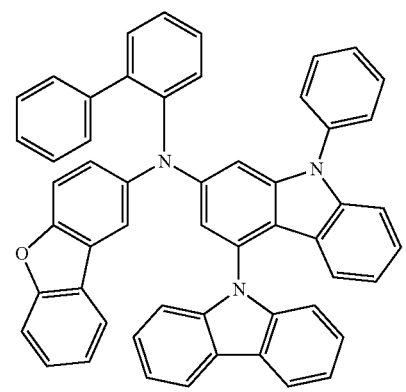
C-316
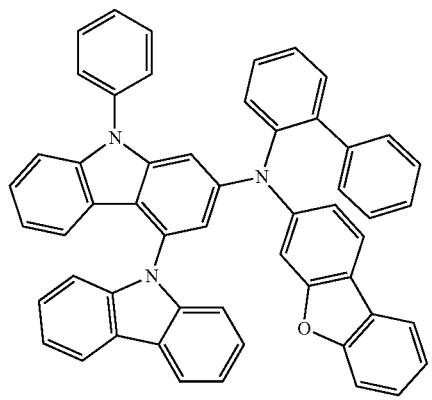
C-317
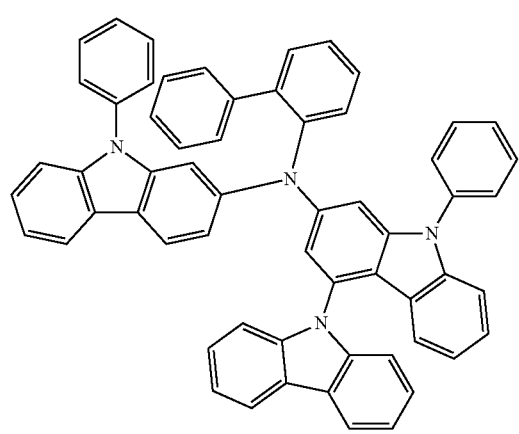
C-318
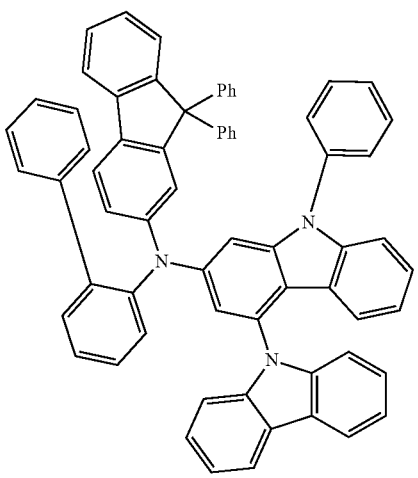
C-319
C-320
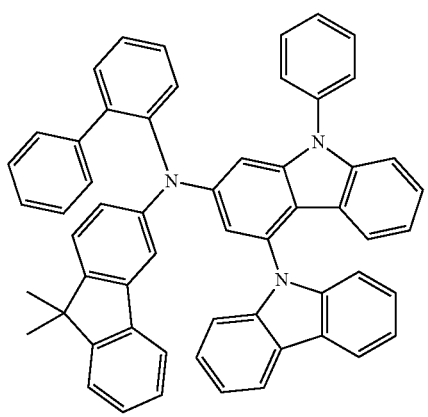

C-321
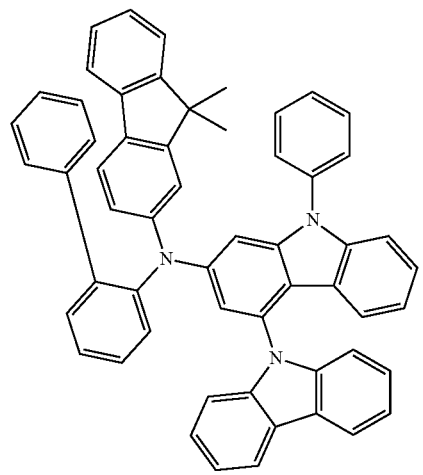
C-324
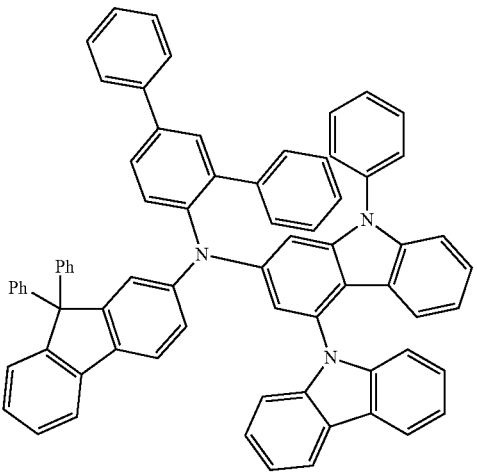
C-322
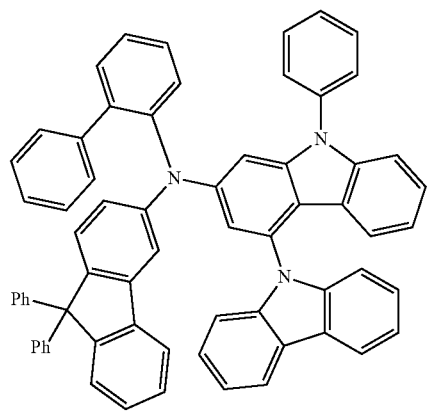
C-325
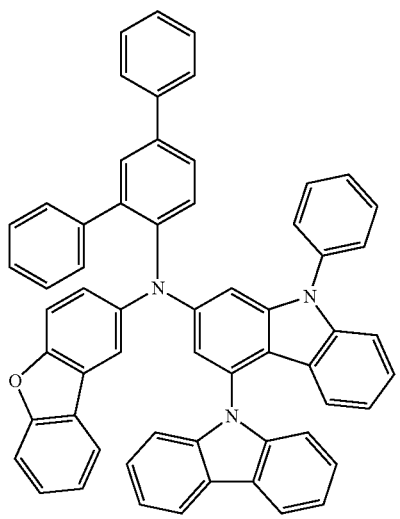
C-323
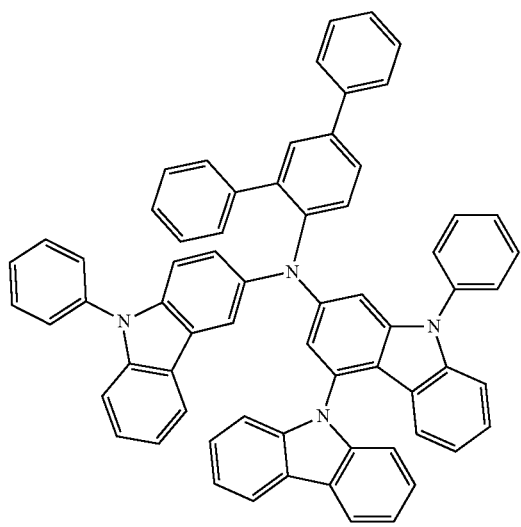
C-326
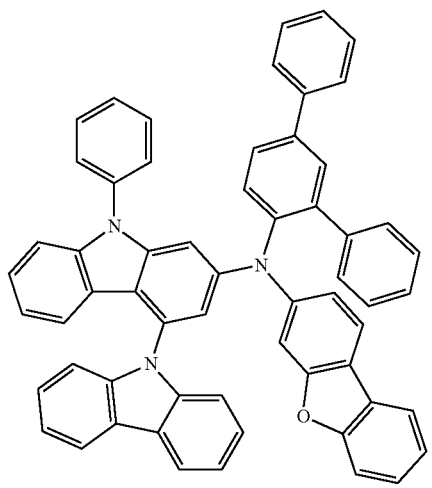

-continued
C-327
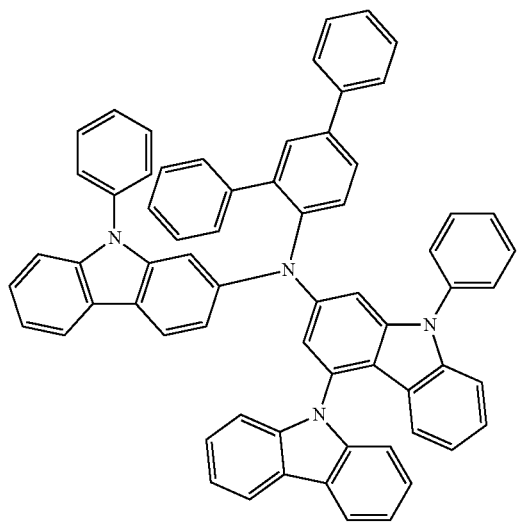
C-328
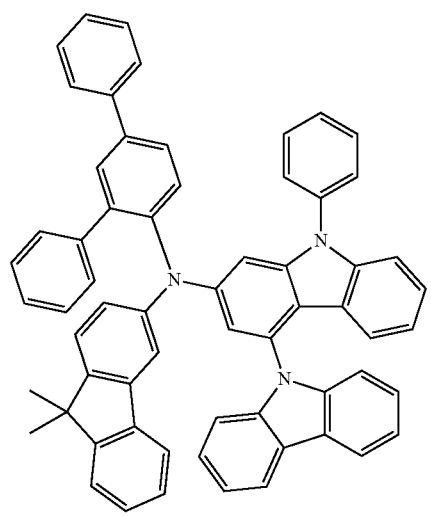
C-329
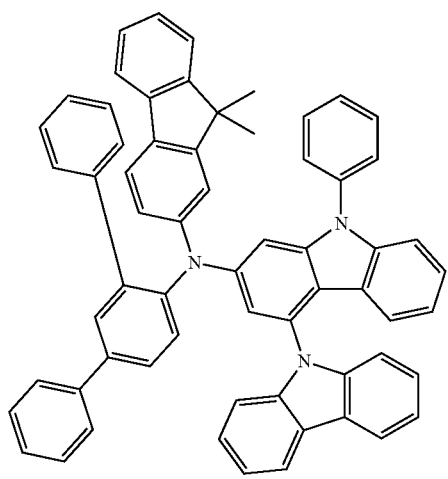
C-330
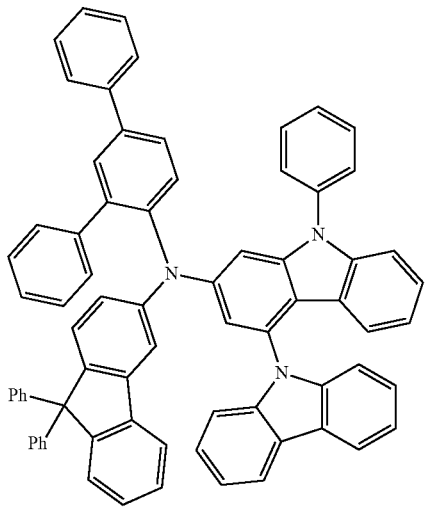
C-331
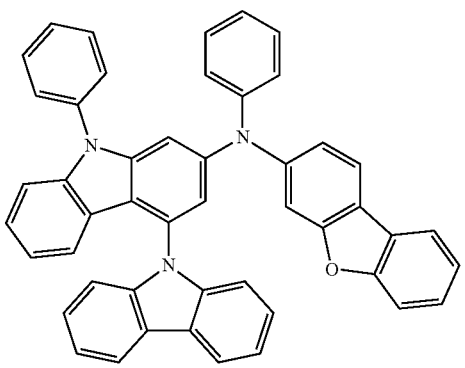
C-332
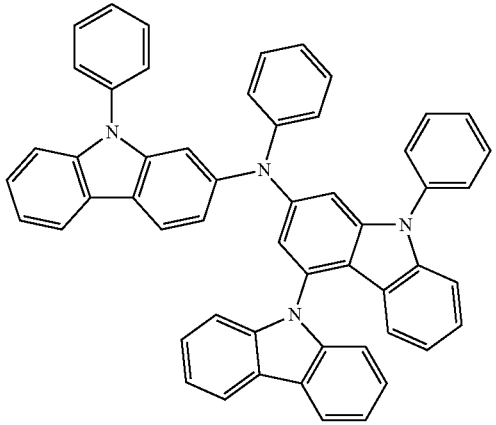

-continued
C-333
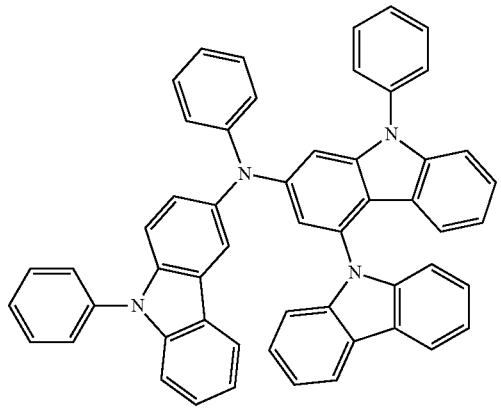
C-334
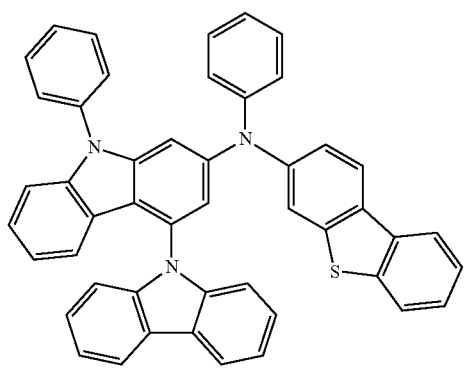
C-335
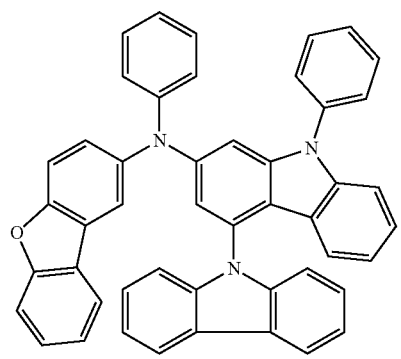
C-336
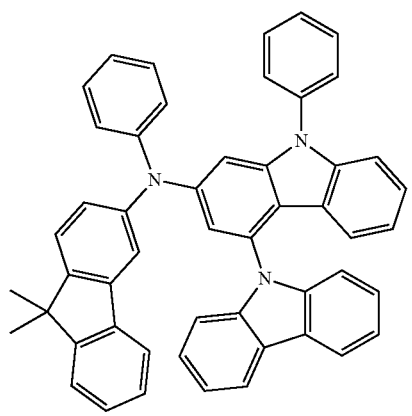
-continued
C-337
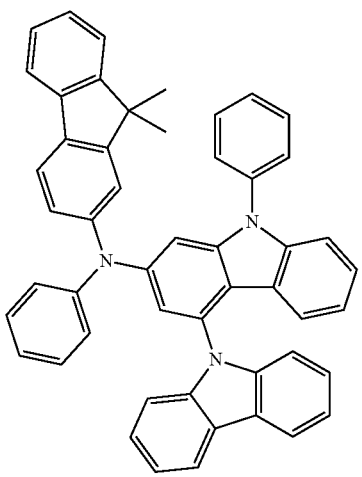
C-338
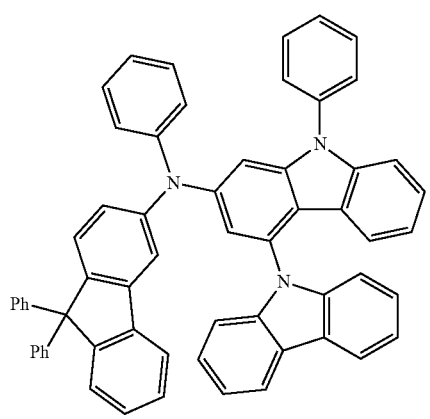
C-339
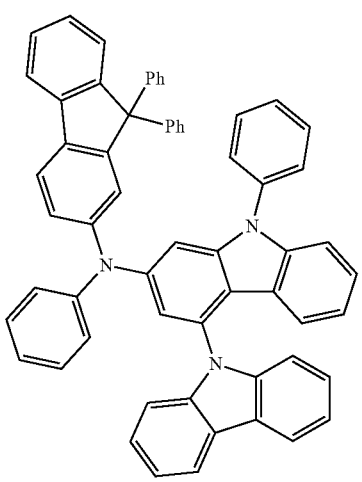

C-340

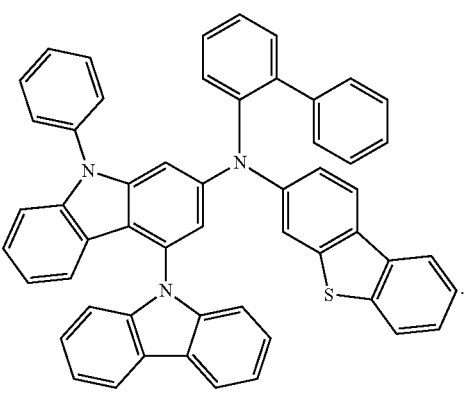

C-341

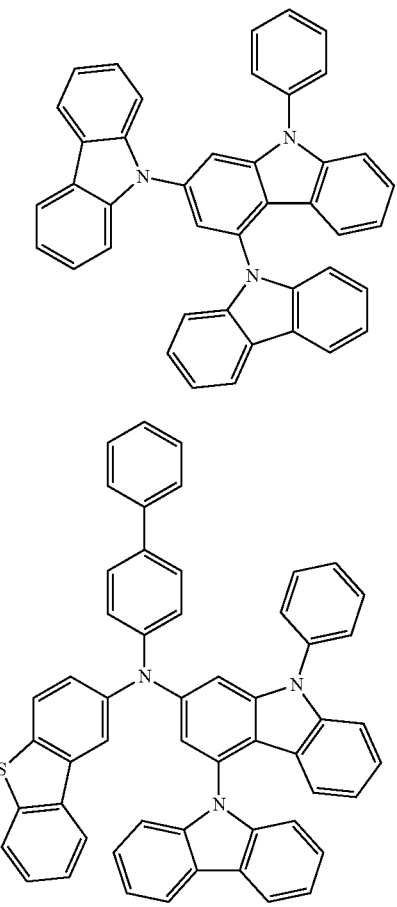
and

C-342

7. An organic electroluminescent material comprising the organic electroluminescent compound according to claim 1.

8. An organic electroluminescent device comprising the organic electroluminescent compound according to claim 1.

9. The organic electroluminescent device according to claim 8, wherein the organic electroluminescent compound is comprised in a hole transport zone.

10. A display device comprising the organic electroluminescent compound according to claim 1.

* * * * *

UNITED STATES PATENT AND TRADEMARK OFFICE
CERTIFICATE OF CORRECTION

| | | |
|---|---|---|
| PATENT NO. | : 11,450,814 B2 | |
| APPLICATION NO. | : 16/640425 | |
| DATED | : September 20, 2022 | |
| INVENTOR(S) | : Jin-Ri Hong | |

It is certified that error appears in the above-identified patent and that said Letters Patent is hereby corrected as shown below:

In the Claims

In Claim 5, at Column 142, Line 45:
"two Ri's" should be "two $R_1$'s"

Signed and Sealed this
Eighth Day of November, 2022

Katherine Kelly Vidal
*Director of the United States Patent and Trademark Office*